US011662351B2

(12) United States Patent
Boniface et al.

(10) Patent No.: US 11,662,351 B2
(45) Date of Patent: May 30, 2023

(54) PREGNANCY CLOCK PROTEINS FOR PREDICTING DUE DATE AND TIME TO BIRTH

(71) Applicant: Sera Prognostics, Inc., Salt Lake City, UT (US)

(72) Inventors: John Jay Boniface, Salt Lake City, UT (US); Paul Edward Kearney, Seattle, WA (US); Julja Burchard, Holladay, UT (US); Gregory Charles Critchfield, Holladay, UT (US); Durlin Edward Hickok, Seattle, WA (US); Tracey Cristine Fleischer, Sandy, UT (US); Ashoka Dharmapriya Polpitiya, Sandy, UT (US)

(73) Assignee: Sera Prognostics, Inc., Salt Lake City, UT (US)

( * ) Notice: Subject to any disclaimer, the term of this patent is extended or adjusted under 35 U.S.C. 154(b) by 691 days.

(21) Appl. No.: 15/999,333

(22) Filed: Aug. 17, 2018

(65) Prior Publication Data
US 2019/0234954 A1 Aug. 1, 2019

Related U.S. Application Data

(60) Provisional application No. 62/547,676, filed on Aug. 18, 2017.

(51) Int. Cl.
*G01N 33/53* (2006.01)
*G01N 33/68* (2006.01)
*C12Q 1/68* (2018.01)

(52) U.S. Cl.
CPC ............. *G01N 33/689* (2013.01); *C12Q 1/68* (2013.01); *G01N 33/6848* (2013.01); *G01N 2800/368* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,130,238 A | 7/1992 | Malek et al. | |
| 5,270,184 A | 12/1993 | Walker et al. | |
| 5,399,491 A | 3/1995 | Kacian et al. | |
| 5,455,166 A | 10/1995 | Walker | |
| 5,480,784 A | 1/1996 | Kacian et al. | |
| 7,091,316 B2 | 8/2006 | Uchida et al. | |
| 7,191,068 B2 | 3/2007 | Rosenfeld et al. | |
| 7,323,346 B2 | 1/2008 | Thadhani et al. | |
| 7,425,419 B2 | 9/2008 | Poston et al. | |
| 7,435,419 B2 | 10/2008 | Karumanchi et al. | |
| 7,790,463 B2 | 9/2010 | Mor et al. | |
| 10,392,665 B2 | 8/2019 | Boniface et al. | |
| 10,961,584 B2 | 3/2021 | Boniface et al. | |
| 2002/0137086 A1 | 9/2002 | Olek et al. | |
| 2003/0105731 A1 | 6/2003 | Lapointe et al. | |
| 2004/0197930 A1 | 10/2004 | Rosenfeld et al. | |
| 2004/0203023 A1 | 10/2004 | Chandrasiri-Herath | |
| 2005/0043640 A1 | 2/2005 | Chang | |
| 2005/0059013 A1 | 3/2005 | Kokudo | |
| 2005/0074746 A1 | 4/2005 | Mor et al. | |
| 2005/0148023 A1 | 7/2005 | Thadhani et al. | |
| 2005/0148040 A1 | 7/2005 | Thadhani et al. | |
| 2005/0233400 A1 | 10/2005 | Weiner et al. | |
| 2006/0046265 A1 | 3/2006 | Becker et al. | |
| 2006/0094039 A1 | 5/2006 | Rosenfeld et al. | |
| 2006/0127962 A1 | 6/2006 | Buhimschi et al. | |
| 2006/0166242 A1 | 7/2006 | Pennell et al. | |
| 2006/0166280 A1 | 7/2006 | Strauss et al. | |
| 2007/0054329 A1 | 3/2007 | Fung et al. | |
| 2007/0111326 A1 | 5/2007 | Sogin et al. | |
| 2007/0141055 A1 | 6/2007 | Kajander et al. | |
| 2007/0161125 A1 | 7/2007 | Rosenfeld et al. | |
| 2007/0178605 A1 | 8/2007 | Mor et al. | |
| 2008/0090759 A1 | 4/2008 | Kokenyesi et al. | |
| 2008/0187929 A1 | 8/2008 | Meiri et al. | |
| 2008/0213794 A1 | 9/2008 | Thadhani et al. | |
| 2008/0233583 A1 | 9/2008 | Fisher et al. | |
| 2008/0274481 A1 | 11/2008 | Fung et al. | |
| 2009/0018778 A1 | 1/2009 | Nation et al. | |

(Continued)

FOREIGN PATENT DOCUMENTS

| | | |
|---|---|---|
| CA | 2629451 | 5/2007 |
| EA | 002520 | 6/2002 |

(Continued)

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, , 2014, pp. 1-7. (Year: 2014).*
Smith et al., Maternal and biochemical predictors of spontaneous preterm birth among nulliparous women: a systematic analysis in relation to the degree of prematurity, International Journal of Epidemiology, 2006, 35, pp. 1169-1177. (Year: 2006).*
SRMAtlas, retrieved from http://www.srmatlas.org/on May 25, 2021. 1 page.
Alcaraz et al., "Tenascin-X promotes epithelial-to-mesenchymal transition by activating latent TGF-β," *J. Cell Biol.*, 205(3):409-428 (2014).

(Continued)

*Primary Examiner* — Gary Counts
(74) *Attorney, Agent, or Firm* — Greenberg Traurig, LLP

(57) ABSTRACT

Compositions and methods for predicting due date and time to birth for a pregnancy with significantly higher accuracy than current clinical methods. The compositions and methods for predicting due date and time to birth for a pregnancy can also identify those pregnancies that will deliver earlier than the due date derived from Last Menstrual Period (LMP) and/or obstetric ultrasonography (US) dating.

13 Claims, 2 Drawing Sheets

Specification includes a Sequence Listing.

(56) References Cited

U.S. PATENT DOCUMENTS

| | | |
|---|---|---|
| 2010/0016173 A1 | 1/2010 | Nagalla et al. |
| 2010/0017143 A1 | 1/2010 | Nagalla et al. |
| 2010/0035284 A1 | 2/2010 | Buhimschi et al. |
| 2010/0062471 A1 | 3/2010 | Kantor |
| 2010/0113286 A1 | 5/2010 | Lajoie et al. |
| 2010/0143949 A1 | 6/2010 | Petricoin |
| 2010/0163721 A1 | 7/2010 | Graves et al. |
| 2010/0167267 A1 | 7/2010 | Schulzknappe et al. |
| 2010/0173317 A1 | 7/2010 | Nakamura et al. |
| 2010/0173786 A1 | 7/2010 | Brun et al. |
| 2010/0216250 A1 | 8/2010 | Lopez et al. |
| 2010/0291612 A1 | 11/2010 | Luider et al. |
| 2010/0297679 A1 | 11/2010 | Graves et al. |
| 2011/0008805 A1 | 1/2011 | Urdea |
| 2011/0165554 A1 | 7/2011 | Levin et al. |
| 2011/0171645 A1 | 7/2011 | McManus et al. |
| 2011/0195478 A1 | 8/2011 | Chen et al. |
| 2011/0247404 A1 | 10/2011 | Graves et al. |
| 2011/0256560 A1 | 10/2011 | Diamandis |
| 2012/0046261 A1 | 2/2012 | Manuck et al. |
| 2012/0149041 A1 | 6/2012 | Graves et al. |
| 2012/0190561 A1 | 7/2012 | Wildt et al. |
| 2012/0315630 A1 | 12/2012 | Gong et al. |
| 2013/0040844 A1 | 2/2013 | Wyss-Coray |
| 2013/0130278 A1 | 5/2013 | Gruslin et al. |
| 2013/0137595 A1 | 5/2013 | Zangar et al. |
| 2013/0296198 A1 | 11/2013 | Gordon et al. |
| 2014/0287947 A1 | 9/2014 | Boniface et al. |
| 2014/0287948 A1 | 9/2014 | Boniface et al. |
| 2014/0287950 A1 | 9/2014 | Hickok et al. |
| 2014/0296108 A1 | 10/2014 | Hickok et al. |
| 2016/0003837 A1 | 1/2016 | Murtha et al. |
| 2016/0154003 A1 | 6/2016 | Boniface et al. |
| 2017/0022565 A1 | 1/2017 | Boniface et al. |
| 2017/0146548 A1 | 5/2017 | Hickok et al. |
| 2018/0143202 A1 | 5/2018 | Boniface et al. |
| 2018/0172696 A1 | 6/2018 | Boniface et al. |
| 2018/0172698 A1 | 6/2018 | Boniface et al. |
| 2019/0187145 A1 | 6/2019 | Hickok et al. |
| 2019/0219588 A1 | 7/2019 | Boniface et al. |
| 2019/0317107 A1 | 10/2019 | Boniface et al. |
| 2019/0369109 A1 | 12/2019 | Boniface et al. |
| 2019/0376978 A1 | 12/2019 | Hickok et al. |
| 2020/0071761 A1 | 3/2020 | Boniface et al. |
| 2021/0156870 A1 | 5/2021 | Hickok et al. |
| 2021/0180135 A1 | 6/2021 | Boniface et al. |
| 2021/0190792 A1 | 6/2021 | Boniface et al. |

FOREIGN PATENT DOCUMENTS

| | | |
|---|---|---|
| EP | 0684315 | 11/1995 |
| EP | 1914548 | 4/2008 |
| EP | 1914552 | 4/2008 |
| EP | 1914553 | 4/2008 |
| WO | WO 1991/016633 A1 | 10/1991 |
| WO | WO 1993/009438 A1 | 5/1993 |
| WO | WO 2002/070742 A1 | 9/2002 |
| WO | WO 2004/088324 A2 | 10/2004 |
| WO | WO 2005/014635 A2 | 2/2005 |
| WO | WO 2005/031364 A1 | 4/2005 |
| WO | WO 2006/029838 A2 | 3/2006 |
| WO | WO 2006/034427 A2 | 3/2006 |
| WO | WO 2006/074360 A2 | 7/2006 |
| WO | WO 2007/022248 A2 | 2/2007 |
| WO | WO 2007/051069 A2 | 5/2007 |
| WO | WO 2007/092353 A2 | 8/2007 |
| WO | WO 2007/110625 A2 | 10/2007 |
| WO | WO 2008/046160 A1 | 4/2008 |
| WO | WO 2008/054764 A2 | 5/2008 |
| WO | WO 2008/063369 A2 | 5/2008 |
| WO | WO 2009/014987 A2 | 1/2009 |
| WO | WO 2009/158423 A1 | 12/2009 |
| WO | WO 2011/022526 A1 | 2/2011 |
| WO | WO 2011/077129 A1 | 6/2011 |
| WO | WO 2011/100792 A1 | 8/2011 |
| WO | WO 2012/017071 A1 | 2/2012 |
| WO | WO 2012/170711 A1 | 12/2012 |
| WO | WO 2014/066568 A1 | 5/2014 |
| WO | WO 2014/089124 A1 | 6/2014 |
| WO | WO 2014/143977 A2 | 9/2014 |
| WO | WO 2014/144129 A2 | 9/2014 |
| WO | WO 2016/205723 A2 | 12/2016 |
| WO | WO 2017/096405 A1 | 6/2017 |
| WO | WO 2018/027160 A1 | 2/2018 |
| WO | WO 2018/027171 A1 | 2/2018 |
| WO | WO 2019/036032 A1 | 2/2019 |

OTHER PUBLICATIONS

Ananth et al., "Association of Temporal Changes in Gestational Age With Perinatal Mortality in the United States, 2007-2015," *JAMA Pediatr.*, 172(7):627-634 (2018).

Anderson et al., "Quantitative mass spectrometric multiple reaction monitoring assays for major plasma proteins," *Mol. Cell. Proteomics*, 5(4):573 (2006).

Anderson, "Sex-hormone-binding globulin," *Clin. Endocrinol (Oxf)*,3(1):69-96 (1974).

Bamber, "The area above the ordinal dominance graph and the area below the receiver operating characteristic graph," *J. Math. Psychol.*, 12(4):387-415 (1975).

Banaem et al., "Maternal serum C-reactive protein in early pregnancy and occurrence of preterm premature rupture of membranes and preterm birth," *J. Obstet. Gynaecol. Res.*, 38(5):780-786 (2012).

Behrman et al. eds., "Preterm Birth: Causes, Consequences, and Prevention," Institute of Medicine (US) Committee on Understanding Premature Birth and Assuring Healthy Outcomes, National Academies Press, Washington DC, 791 pages (2007).

Belfiore et al., "Insulin receptor and cancer," *Endocr. Relat. Cancer*, 18:R125-R147 (2011).

Berkley et al., "Multiple Marker Screen for Preeclampsia," *Am. J. Obstet. Gynecol.*, 197(6):S142 (2007).

Beta et al., Prediction of spontaneous preterm delivery from maternal factors, obstetric history and placental perfusion and function at 11-13 weeks, *Prenat. Diagn.*, 31(1):75-83 (2011).

Bezold et al., "The genomics of preterm birth: from animal models to human studies," *Genome Med.*, 5(4):34 (2013).

Biemann, "Sequencing of peptides by tandem mass spectrometry and high-energy collision-induced dissociation," *Methods Enzymol.*, 193:455-479 (1990).

Blencowe et al., "National, regional and worldwide estimates of preterm birth." *Lancet*, 9; 379(9832):2162-2172 (2012).

Box et al., "An analysis of transformations," *Royal Stat. Soc. Series B*, 26:211-246 (1964).

Breiman, "Random Forests," *Mach. Learn.*, 45:5-32 (2001).

Brody et al., "Life's simple measures: unlocking the proteome," *J. Mol. Biol.*, 422(5):595-606 (2012).

Brown et al., "Interval estimation for a binomial proportion.," *Statistical Science*, 16(2):101-133 (2001).

Carty et al., "Novel Biomarkers for Predicting Preeclampsia," *Trends Cardiovasc. Med.*, 15(5):186-194 (2008).

Catov et al., "Activation of the Fibrinolytic Cascade Early in Pregnancy Among Women with Spontaneous Preterm Birth," *Obstet. Gynecol.*, 112(5):1116-1122 (2008).

Chen et al., "Lysophosphatidic acid up-regulates expression of growth-regulated oncogene-alpha, interleukin-8, and monocyte chemoattractant protein-1 in human first-trimester trophoblasts: possible roles in angiogenesis and immune regulation," *Endocrinology*, 151(1):369-379 (2010).

Chim et al., "Systematic identification of spontaneous preterm birth-associated RNA transcripts in maternal plasma," *PLoS One*, 7(4):e34328 (2012).

Cozens et al., "DNA sequences of two expressed nuclear genes for human mitochondrial ADP/ATP translocase," *J. Mol. Biol.*, 206(2):261-280 (1989).

Craig et al., "Tandem: matching proteins with tandem mass Spectra," *Bioinformatics*, 20:1466-1467 (2004).

(56) References Cited

OTHER PUBLICATIONS

Crosley et al., "IGFBP-4 and -5 are expressed in first-trimester villi and differentially regulate the migration of HTR-8/SVneo cells," *Reprod. Biol. Endocrinol.*, 12(1):123 (2014).
Cunningham et al., "The complete amino acid sequence of beta 2-microglobulin," *Biochemistry*, 12(24):4811-4822 (1973).
Damsky et al., "Distribution patterns of extracellular matrix components and adhesion receptors are intricately modulated during first trimester cytotrophoblast differentiation along the invasive pathway, in vivo," *J. Clin. Invest.*, 89(1):210-222 (1992).
Dasari et al., "Comprehensive proteomic analysis of human cervical-vaginal fluid," *J. Proteome Res.*, 6(4):1258-1268 (2007).
De Groot et al., "Specific Peptides Identified by Mass Spectometry in Placental Tissue from Pregnancies Attained by Laser Capture Dissection," *Protemics Clin. Appl.*, 1(3):325-335 (2007).
Demetriou et al., "Paternally expressed, imprinted insulin-like growth factor-2 in chorionic villi correlates significantly with birth weight," *PLoS One*, 9(1):e85454 (2014).
Dmitrienko et al., "Key multiplicity issues in clinical drug development," *Stat Med.*, 32(7):1079-1111 (2012).
Domanski et al., "MRM-Based Multiplexed Quantification of 67 Putative Cardiovascular Disease Biomarkers in Human Plasma," *Proteomics*, 12:1222-1243 (2012).
Eastaugh et al., "Comparison of Neural Networks and Statistical Models to Predict Gestational Age at Birth," *Neural Comput. Applic.*, 6(3):158-164 (1997).
Efron et al., "Least angle regression," *Annals Statistics*, 32:407-451 (2004).
Endo et al., "Primary structure and gene localization of human prolidase," *J. Biol. Chem.*, 264(8):4476-4481 (1989).
Eng et al., "An Approach to Correlate Tandem Mass Spectral Data of Peptides with Amino Acid Sequences in a Protein Database," *J. Am. Soc. Mass Spectrom*, 5:976-989 (1994).
Enquobahrie et al., "Early pregnancy peripheral blood gene expression and risk of preterm delivery: a nested case control study," *BMC Pregnancy Childbirth*, 9(1):56 (2009).
Erez et al., "High Tissue Factor Activity and Low Tissue Factor Pathway Inhibitor Concentrations in Patients with Preterm Labor," *J. Matern. Fetal Neonatal Med.*, 23(1):23-33 (2010).
Esplin et al., "Proteomic identification of serum peptides predicting subsequent spontaneous preterm birth," *Am. J. Obstet. Gynecol.*, 204(5):391e1-8 (2010).
Flick et al., "Mechanistic insights from serum proteomic biomarkers predictive of spontaneous preterm birth," *Am. J. Obstet. Gynecol.*, Abstract No. 253, S148-S149 (2016).
Forbes et al., "Insulin-like growth factor I and II regulate the life cycle of trophoblast in the developing human placenta," *Am. J Physiol. Cell Physiol.*, 294(6):C1313-1322 (2008).
Fullerton et al., "Sequence polymorphism at the human apolipoprotein AII gene (APOA2): unexpected deficit of variation in an African-American sample," *Hum. Genet.*, 111(1):75-87 (2002).
Fullerton et al., "The effects of scale: variation in the APOA1/C3/A4/A5 gene cluster," *Hum. Genet.*, 115(1):36-56 (2004).
Geisert et al., "Expression of an inter-alpha-trypsin inhibitor heavy chain-like protein in the pig endometrium during the oestrous cycle and early pregnancy," *J. Reprod. Fertility*, 114(1):35-43 (1998).
Geman et al., "Classifying gene expression profiles from pair wise mRNA comparisons," *Stat. Appl. Genet. Mol. Biol.*, 3(1):Article19 (2004).
Gershagen et al., "A cDNA coding for human sex hormone binding globulin," *FEBS Lett.*, 220(1):129-135 (1987).
Goldenberg et al., "Epidemiology and causes of preterm birth," *Lancet*, 371(9606):75-84 (2008).
Goldenberg et al., "The Preterm Prediction Study: Cervical lactoferrin concentration, other markers of lower genital tract infection, and preterm birth," *Am. J. Obstet. Gynecol.*, 182(3):631-635 (2000).
Goldenberg et al., "The preterm prediction study: the value of new vs standard risk factors in predicting early and all spontaneous preterm births," *Am. J. Public Health*, 88(2):233-238 (1998).
Gomez-Lopez et al., "Immune cells in term and preterm labor.," *Cell Mol. Immunol.*, 11(6):571-581 (2014).
Gravett et al., "Diagnosis of intra-amniotic infection by proteomic profiling and identification of novel biomarkers," *JAMA*, 292(4):462-469 (2004).
Gravett et al., "Proteomic analysis of cervical-vaginal fluid: identification of novel biomarkers for detection of intra-amniotic infection," *J. Proteome Res.*, 6(1):89-96 (2007).
Greene, "Choices in Managing Full-Term Pregnancy," *N. Engl. J. Med.*, 379(6):580-581 (2018).
Grobman et al., "Labor Induction versus Expectant Management in Low-Risk Nulliparous Women," *N. Engl. J. Med.*, 379(6):513-523 (2018).
Grobman, "A randomized trial of elective induction of labor at 39 weeks compared with expectant management of low-risk nulliparous women," *Am. J. Obst. Gyn.*, 218(1):S601 (2018).
Grundmann et al., "Complete cDNA sequence encoding the B subunit of human factor XIII," *Nucleic Acids Res.*, 18(9):2817-2818 (1990).
Guatelli et al., "Isothermal, in vitro amplification of nucleic acids by a multienzyme reaction modeled after retroviral replication," *Proc. Natl. Acad. Sci. USA*, 87:1874-1878 (1990).
Haataja et al., "Mapping a new spontaneous preterm birth susceptibility gene, IGF1R, using linkage, haplotype sharing, and association analysis," *PLoS Genet.*, 7(2):e1001293 (2011).
Haefliger et al., "Structural and Functional Characterization of Complement C8γ, A Member of the Lipocalin Protein Family," *Mol. Immunol.*, 28(1-2):123-131 (1991).
Hammond, "Diverse roles for sex hormone-binding globulin in reproduction," *Biol. Reprod.*, 85(3):431-441 (2011).
Hassan et al. "Vaginal progesterone reduces the rate of preterm birth in women with a sonographic short cervix: a multicenter, randomized, double-blind, placebo-controlled trial," *Ultrasound Obstet. Gynecol.*, 38(1):18-31 (2011).
Haviland et al., "Complete cDNA sequence of human complement pro-C5. Evidence of truncated transcripts derived from a single copy gene," *J. Immunol.*, 146(1):362-368 (1991).
Heitner et al., "Differneitiation of HELLP patients from healthy pregnant women by proteome analysis—On the way towards a clinical marker set," *J. Chromatog. B*, 840(1):10-19 (2006).
Hobel et al., "Maternal plasma corticotropin-releasing hormone associated with stress at 20 weeks gestation in pregnancies ending in preterm delivery," *Am. J. Obstet. Gynecol.*, 180(1):5257-5263 (1999).
Howard et al., "Complementary DNA and derived amino acid sequence of the beta subunit of human complement protein C8: identification of a close structural and ancestral relationship to the alpha subunit and C9," *Biochemistry*, 26(12):3565-3570 (1987).
Howson et al. eds., "Born too soon: The Global Action Report on Preterm Birth," World Health Organization, Geneva, 126 pages (2012).
Huang et al., "Tree-structured supervised learning and the genetics of hypertension," *Proc. Nat. Acad. Sci. U.S.A.*, 101:10529-10534 (2004).
Huynh et al., "Low pregnancy-associated plasma protein a level in the first trimester," *Can. Fam. Physician*, 60(10):899-903 (2014).
Iams et al., "The length of the cervix and the risk of spontaneous premature delivery," *N. Engl. J. Med.*, 334(9):567-572 (1996).
Katayama et al., "Application of serum proteomics to the Women's Health Initiative conjugated equine estrogens trial reveals a multitude of effects relevant to clinical findings," *Genome Med.*, 1:47 (2009).
Keller et al., "Empirical Stat istical Model to Estimate the Accuracy of Peptide Identificat ions Made by MS/MS and Database Search," *Anal. Chem*, 74:5383-5392 (2002).
Kenny et al., "Novel biomarkers for pre-eclampsia detected using metabolomics and machine learning," *Metabolomics*, 1(3):227-234 (2005).
Khan et al., "Delineation and synthesis of the membrane receptor-binding domain of sex hormone-binding globulin," *J. Biolog. Chem.*, 265(30):18362-18365 (1990).

(56) References Cited

OTHER PUBLICATIONS

Kim et al., "ITI-H4, as a biomarker in the serum of recurrent pregnancy loss (RPL) patients," *Mol. Biosyst.*, 7(5):1430-1440 (2011).

Klee et al., "Strategy for the development of a mass spectrometry assay for measuring sex hormone binding globulin (SHBG) in human serum," *Clinical Chemistry*, Poster B-103, 58(S10):A1-A77 (2012).

Knott et al., "Complete protein sequence and identification of structural domains of human apolipoprotein B," *Nature*, 323:734-738 (1986).

Kuhn et al., "Quantification of C-reactive protein in the serum of patients with rheumatoid arthritis using multiple reaction monitoring mass spectrometry and 13C-labeled peptide standards," *Proteomics*, 4:1175-1186 (2004).

Kwoh et al., "Transcription-based amplification system and detection of amplified human immunodeficiency virus type 1 with a bead-based sandwich hybridization format," *Proc. Natl. Acad. Sci. USA*, 86:1173-1177 (1989).

Larrea et al. "Evidence that human placenta is a site of sex hormone-binding globulin gene expression," *J. Steroid Biochem. Mol. Biol.*, 46(4):497-505 (1993).

Li et al., "A blood-based proteomic classifier for the molecular characterization of pulmonary nodules," *Sci. Transl. Med.*, 5(207):ra142 (2013).

Li et al., "An integrated quantification method to increase the precision, robustness, and resolution of protein measurement in human plasma samples," *Clin. Proteomics*, 12(1):3 (2015).

Lin et al., "Simple and Rapid Sample Preparation Methods for Whole Blood and Blood Plasma," *Diagnostic Molecular Microbiology, Principles and Applications*, Persing et al., eds., Rochester, MN, pp. 605-616 (1993).

Lindström et al. "The role of nuclear factor kappa B in human labour," *Reproduction*, 130(5):569-581 (2005).

Ling et al. "Multiplexing molecular diagnostics and immunoassays using emerging microarray technologies" *Expert Rev. Mol. Diagn.*, 7:87-98 (2007).

Liu et al., "Recent developments in protein and cell-targeted aptamer selection and applications," *Curr. Med. Chem.*, 18(27):4117-4125 (2011).

Lizardi et al., "Exponential amplification of recombinant-RNA hybridization probes," *BioTechnol.*, 6:1197-1202 (1988).

Lukanova et al., "Body mass index, circulating levels of sex-steroid hormones, IGF-I and IGF-binding protein-3: a cross-sectional study in healthy women," *Eur. J Endocrinol.*, 150(2):161-171 (2004).

MacDorman et al., "Fetal and Perinatal Mortality: United States, 2013," *Natl. Vital. Stat. Rep.*, 64(8):1-24 (2015).

MacKinnon et al., "Molecular cloning of cDNA for human complement component C1s. The complete amino acid sequence," *Eur. J. Biochem.*, 169(3):547-553 (1987).

Martin et al., "Births: Final Data for 2012," *Natl. Vital Stat. Rep.*, 64(1):1-65 (2015).

Martin et al., "Births: Final Data for 2016," *Natl. Vital Stat. Rep.*, 67(1):1-55 (2018).

Martin et al., "Deaths: Final Data for 2012," *Natl. Vital Stat. Rep.*, 63(9):1-86 (2015).

Mason et al., "Areas beneath the relative operating characteristics (ROC) and relative operating levels (ROL) curves: Statistical significance and interpretation," *QJR Meteorol. Soc.*, 128(584):2145-2166 (2002).

Mayo Clinic, "Researchers Discover Link Between High Levels of HtrA1 Protein and Preeclampsia, a Complication of Pregnancy," URL: http://www.mayoclinic.org/news2006-rst/3234.html, Publication Date: Feb. 1, 2006.

McElroy et al., "Maternal coding variants in complement receptor 1 and spontaneous idiopathic preterm birth," *Hum. Genet.*, 132(8):935-942 (2013).

McLean et al., "Effect of Collision Energy Optimization on the Measurement of Peptides by Selected Reaction Monitoring (SRM) Mass Spectrometry," *Anal. Chem.*, 82(24):10116-10124 (2010).

McLean et al., "Skyline: an open source document editor for creating and analyzing targeted proteomics experiments," *Bioinformatics*, 26(7):966-968 (2010).

Mendelson, "Minireview: fetal-maternal hormonal signaling in pregnancy and labor," *Mol Endocrinol.*, 23(7):947-954 (2009).

Menon et al., "Amniotic fluid metabolomic analysis in spontaneous preterm birth," *Reprod. Sci.*, 21(6):791-803 (2014).

Menon et al., "Genetic regulation of amniotic fluid TNF-alpha and soluble TNF receptor concentrations affected by race and preterm birth," *Human Genet.*, 124(3):243-253 (2008).

Middleton et al., "Induction of labour for improving birth outcomes for women at or beyond term," *Cochrane Database Syst. Rev.*, 5:CD004945 (2018).

Moore et al., "Pregnancy-specific glycoproteins: complex gene families regulating maternal-fetal interactions," *Int. J Dev. Biol.*, 58:273-280 (2014).

Morisaki et al., "Risk factors for spontaneous and provider-initiated preterm delivery in high and low Human Development Index countries: a secondary analysis of the World Health Organization Multicountry Survey on Maternal and Newborn Health," *BJOG*, 121(Supp. 1):101-109 (2014).

Moutquin, "Classification and heterogeneity of preterm birth," *BJOG*, 110 (Suppl 20):30-33 (2003).

Murata et al., "Molecular cloning and expression of the human interleukin 5 receptor," *J. Exp. Med.*, 175(2):341-351 (1992).

Nakajima et al., "Elevated vasoinhibin derived from prolactin and cathepsin D activities in sera of patients with preeclampsia," *Hypertens. Res.*, 38:899-901 (2015).

Nielsen et al., "Multiplexed sandwich assays in microarray format" *J. Immunol. Methods*, 290:107-120 (2004).

O'Leary et al., "Longitudinal assessment of changes in reproductive hormones during normal pregnancy," *Clin. Chem.*, 37(5):667-672 (1991).

Oliveira et al., "Primary Structure of Human C-reactive Protein," *J. Biol. Chem.*, 254(2):489-502 (1979).

Pal et al., "Fetuin-A acts as an endogenous ligand of TLR4 to promote lipid-induced insulin resistance," *Nature Med.*, 18(8):1279-1285 (2012).

Pereira et al., "Identification of novel protein biomarkers of preterm birth in human cervical-vaginal fluid," *J. Proteome Res.*, 6(4):1269-1276 (2007).

Pereira et al., "Insights into the multifactorial nature of preterm birth: proteomic profiling of the maternal serum glycoproteome and maternal serum peptidome among women in preterm labor," *Am. J. Obstet. Gynecol.*, 202(6):555.e1-10 (2010).

Petersen et al., "Characterization of the gene for human plasminogen, a key proenzyme in the fibrinolytic system," *J. Biol. Chem.*, 265(11):6104-6111 (1990).

Petrini et al. "Estimated effect of 17 alpha-hydroxyprogesterone caproate on preterm birth in the United States," *Obstet Gynecol.*, 105(2):267-272 (2005).

Poirier et al., "Obesity and cardiovascular disease: pathophysiology, evaluation, and effect of weight loss: an update of the 1997 American Heart Association Scientific Statement on Obesity and Heart Disease from the Obesity Committee of the Council on Nutrition, Physical Activity, and Metabolism," *Circulation*, 113:898-918 (2006).

Polpitiya et al., "DAnTE: a statistical tool for quantitative analysis of -omics data," *Bioinformatics*, 24:1556-1558 (2008).

Powe et al., "First Trimester Vitamin D, Vitamin D Binding Protein, and Subsequent Preeclampsia," *Hypertension*, 56(4):758-763 (2010).

Price et al., "Highly accurate two-gene classifier for differentiating gastrointestinal stromal tumors and leiomyosarcomas," *Proc. Natl. Acad. Sci. USA*, 104(9):3414-3419 (2007).

Qiu et al., "Significance of IGFBP-4 in the development of fetal growth restriction," *J. Clin. Endocrinol. Metab.*, 97(8):E1429-1439 (2012).

Rasanen et al., "First Trimester Maternal Serum Biomarkers for Prediction of Preeclampsia," *Am. J. Obstet. Gynecol.*, 197(6):S10 (2007).

Rask et al., "Structural and functional studies of vitamin A-binding proteins," *Ann. N. Y. Acad. Sci.*, 359:79-90 (1981).

(56) References Cited

OTHER PUBLICATIONS

Red-Horse et al., "Trophoblast differentiation during embryo implantation and formation of the maternal-fetal interface," *J. Clin. Invest.*, 114:744-754 (2004).
Reid, "Complete Amino Acid Sequences of the Three Collagen-Like Regions present in Subcomponent Clq of the First Component of Human Complement," *Biochem. J.*, 179(2):367-371 (1979).
Romero et al., "Identification of fetal and maternal single nucleotide polymorphisms in candidate genes that predispose to spontaneous preterm labor with intact membranes," *Am. J. Obstet. Gynecol.*, 202(5):431.e1-34 (2010).
Ruczinski et al., "Logic Regression," *J. Comput. Graph. Stat.*, 12(3):475-511 (2003).
Saade et al., "Development and validation of a spontaneous preterm delivery predictor in asymptomatic women," *Am. J. Obstet. Gynecol.*, 214(5): 633.e1-633.e24 (2016).
Salier et al., "The inter-alpha-inhibitor family: from structure to regulation," *Biochem. J.*, 315:1-9 (1996).
Sambrook et al., "Analysis of RNA," *Molecular Cloning, a laboratory Manual*, Cold Spring Harbor Laboratory Press, Plainview, NY, pp. 7.37-7.57 (1989).
Scholl et al., "Anemia, Iron and Pregnancy Outcome," *J. Nutrition*, 130(2S):443S-447S (2000).
Schumann et al., "Structure and Function of Lipopolysaccharide Binding Protein," *Science*, 249(4975):1429-1431 (1990).
Seegar et al., "Tie1-Tie2 interactions mediate functional differences between angiopoietin ligands," *Mol. Cell.*, 37(5):643-655 (2010).
Selby et al., "Analysis of a Major Human Chorionic Somatomammotropin Gene," *J. Biol. Chem.*, 259(21):13131-13138 (1984).
Self et al., "Advances in immunoassay technology" *Curr. Opin. Biotechnol.*, 7:60-65 (1996).
Sera Prognostics, Inc., "Proteomic Assessment of Preterm Birth (PAPR)," ClinicalTrials.gov archive, pp. 1-6 (Apr. 18, 2019). Retrieved from the Internet: https://clinicaltrials.gov/ct2/show/NCT01371019, on Apr. 18, 2019.
Shi et al., "IgY14 and SuperMix immunoaffinity separations coupled with liquid chromatography—mass spectrometry for human plasma proteomics biomarker discovery," *Methods*, 56(2):246-253 (2012).
Sibai, "Preeclampsia and Hypertensive Disorders," *Obstetrics: Normal and Problem Pregnancies*, 7th ed., Gabbe et al. eds., Elsevier, Philadelphia, PA, pp. 661-705, 2017.
Simó et al. "Novel insights in SHBG regulation and clinical implications," *Trends Endocrinol. Metab.*, 26(7):376-383 (2015).
Sing et al., "ROCR: visualizing classifier performance in R," *Bioinformatics*, 21(20):3940-3941.
Smets et al., "Novel Biomarkers in Preeclampsia," *Clinica Chimica Acta*, 364:22-32 (2006).
Son et al., "Multiple FAS1 domains and the RGD motif of TGFBI act cooperatively to bind αvβ3 integrin, leading to anti-angiogenic and anti-tumor effects," *Biochim. Biophys. Acta*, 1833(10) 2378-2388 (2013).
Song et al., "Quantification of fragments of human serum inter-alpha-trypsin inhibitor heavy chain 4 by a surface-enhanced laser desorption/ionization-based immunoassay," *Clin. Chem.*, 52(6):1045-1053 (2006).
Spencer et al., "First trimester sex hormone-binding globulin and subsequent development of preeclampsia or other adverse pregnancy outcomes," *Hypertens. Pregnancy*, 24(3):303-311 (2005).
Stagnaro-Green et al., "Thyroid disorders in pregnancy," *Nat. Rev. Endocrinol.*, 8(11):650-658 (2012).
Stella et al., "Preterm labor biomarker discovery in serum using 3 proteomic profiling methodologies," *Am. J. Obstet. Gynecol.*, 387:e1-e13 (2009).
Swaggart et al., "Genomics of preterm birth," *Cold Spring Harb Perspect Med.*, 5(2):a023127 (2015).
Thompson et al., "Identification and confirmation of a module of coexpressed genes," *Genome Res.*, 12(10):1517-1522 (2002).
Tibshirani et al., "Diagnosis of multiple cancer types by shrunken centroids of gene expression," *Proc. Natl. Acad. Sci. USA*, 99:6567-6572 (2002).
Traboni et al., "Sequence of a full length cDNA coding for human protein HC (alpha 1 microglobulin)," *Nucleic Acids Res.*, 14(15):6340 (1986).
Tusher et al., "Significance analysis of microarrays applied to the ionizing radiation response," *Proc. Natl. Acad. Sci. USA*, 98:5116-5121 (2001).
Underwood et al., "The association of the angiotensinogen gene with insulin sensitivity in humans: a tagging single nucleotide polymorphism and haplotype approach," *Metabolism*, 60(8):1150-1157 (2011).
UniProt, P02753—RET4_Human, UniProtKB, 2002, 1.
Vascotto et al., "Oxidized Tmasthyretin in Amniotic Fluid as an Early Marker of Preeclampsia," *J. Proteome Res.*, 6:160-170 (2006).
Villanueva et al., "Automated serum peptide profiling," *Nat. Protoc.*, 1(2):880-891 (2006).
Walker et al., "Isothermal in vitro amplification of DNA by a restriction enzyme/DNA polymerase system," *Proc. Natl. Acad. Sci. USA*, 89:392-396 (1992).
Walker et al., "Randomized Trial of Labor Induction in Women 35 Years of Age or Older," *N. Engl. J. Med.*, 374(9):813-822 (2016).
Walz et al., "Amino acid sequence of human prothrombin fragments 1 and 2," *Proc. Natl. Acad. Sci. U.S.A.*, 74(5):1969-1972 (1977).
Wang et al., "LRG1 promotes angiogenesis by modulating endothelial TGF-β signaling," *Nature* 499:306-311 (2013).
Watanabe et al., "Proteome Analysis Reveals Elevated Serum Levels of Clusterin in Patients with Preeclampsia," 4:537-543 (2004).
Watt et al., "Amino Acid Sequence of the ß Chain of Human Fibrinogen," *Biochemistry*, 18(1):68-76 (1979).
Weiner et al., "Human effector/initiator gene sets that regulate myometrial contractility during term and preterm labor," *Am. J. Obstet. Gynecol.*, 202(5):474.e1-20 (2010).
Weiss, "Hot prospect for new gene amplifier," *Science*, 254:1292-1293 (1991).
Xu et al., "ECE-1: a membrane-bound metalloprotease that catalyzes the proteolytic activation of big endothelin-1," *Cell*, 78(3):473-485 (1994).
Yocum et al., "Current affairs in quantitative targeted proteomics: multiple reaction monitoring-mass spectrometry," *Brief Funct. Genomic Proteomic.*, 8(2):145-157 (2009).

* cited by examiner

PREGNANCY CLOCK PROTEINS FOR PREDICTING DUE DATE AND TIME TO BIRTH

This application claims the benefit of U.S. Provisional Application No. 62/547,676, filed Aug. 18, 2017, the entire contents of which is incorporated by reference.

SEQUENCE LISTING

The present specification is being filed with a computer readable form (CRF) copy of the Sequence Listing in ASCII text format submitted via EFS-Web. The CRF copy of the Sequence Listing, entitled 13271-026-999_Substitute_Sequence_Listing, which was created on May 19, 2021 and is 28,870 bytes in size, is incorporated herein by reference in its entirety.

BACKGROUND

Accurately assigning Estimated Due Date (EDD) and/or Time To Birth (TTB) early in prenatal care is among the most important results of evaluation and history taking. This information is vital for timing of appropriate obstetric care; scheduling and interpretation of certain antepartum tests; determining the appropriateness of fetal growth; and designing interventions to prevent preterm births, postterm births, and related morbidities. A consistent and exacting approach to accurate dating is also a research and public health imperative because of the influence of dating on investigational protocols and vital statistics.

Traditionally, determining the first day of the Last Menstrual Period (LMP) is the first step in establishing the EDD. By convention, the EDD is 280 days after the first day of the LMP. Because this practice assumes a regular menstrual cycle of 28 days, with ovulation occurring on the 14th day after the beginning of the menstrual cycle, its accuracy is affected by factors that include inaccurate recall of the LMP, irregularities in cycle length, or variability in the timing of ovulation. Obstetric ultrasonography (US) is routinely used to determine fetal gestational age and aid in assigning EDD. If the patient is unsure of her LMP, dating of EDD based on first trimester US considered more reliable than second trimester or third semester US.

Both LMP and/or ultrasound are population-based estimates for a normal pregnancy and the accuracy of these methods varies significantly. Current clinical practice utilizing these methods is accurate in making a due date prediction that falls within plus or minus five days of the actual due date for term deliveries only about 35% of the time. In addition, 15% of predictions made under current clinical practice fall on or outside of 14 days before or after the actual due date for term deliveries. More accurate dating of pregnancy is needed to improve outcomes and is a research and public health imperative. The present invention addresses this need by providing an Estimated Due Date (EDD) molecular predictor (EDDmp) and/or Time To Birth (TTB) molecular predictor (TTBmp) that incorporates molecular information from proteins listed in Tables 1-27 into the estimation of pregnancy due date and/or time to birth with much higher accuracy than methods utilized as part of current clinical practice. Related advantages are provided as well.

SUMMARY

The present invention provides compositions and methods for due date and time to birth prediction for a pregnancy with significantly higher accuracy than current clinical methods. The compositions and methods for due date and time to birth prediction for a pregnancy can also identify those pregnancies, with high accuracy, that will deliver earlier than the official EDD as derived from LMP and/or US dating. Accordingly, the present invention provides an improved process that applies the discoveries described herein to enable, inter alia, a new and useful process for estimating the due date of a pregnant female, subsequently referred to as the Estimated Due Date (EDD) and/or estimating time to birth (TTB) with much higher accuracy than currently practiced clinical methods.

Each of the proteins, peptides and clinical variables disclosed herein as components of pairs, ratios and/or reversal pairs serve as biomarkers for determining the EDD, predicting gestational age at birth (GAB), predicting time to birth (TTB), either individually, in ratios, reversal pairs or in panels of biomarkers/reversal pairs.

The utility of the biomarker pairs, ratios and/or reversal pairs as "clock proteins" to accurately date a pregnancy, i.e. accurately estimate gestational age (GA), is essential to the quality of obstetric care and maternal-fetal health. The utility of the clock proteins of the invention to date a pregnancy with significantly higher accuracy than can be achieved with current clinical extends to every prognostic, diagnostic or other clinical assessment of the pregnant female and fetus that relies on accurately estimating GA for its own accuracy.

In one embodiment, the present invention provides a composition comprising a pair of isolated biomarkers selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), FETUA_FSVVYAK (SEQ ID NO:50) and IBP4_Q.CHPALDGQR (SEQ ID NO:111), ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), CRIS3_YEDLYSNCK (SEQ ID NO:70) and TETN_LDTLAQEVALLK (SEQ ID NO:106), B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), CHL1_VIAVNEVGR (SEQ ID NO:66) and IGF2_GIVEECCFR (SEQ ID NO:68), wherein said pair of biomarkers exhibits a change in reversal value between pregnant females that deliver before 270 days relative to pregnant females that deliver on or after 280 days. In some embodiments, the composition further comprises AACT_EIGELYLPK (SEQ ID NO:129).

In one embodiment, the present invention provides a composition comprising a pair of isolated biomarkers selected from the group consisting of ADA12_FGFGGSTDSGPIR (SEQ ID NO:84) and PAEP_HLWYLLDLK (SEQ ID NO:116), PAE- P_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), FETUA_FSVVYAK (SEQ ID NO:50) and IBP4_Q.CHPALDGQR (SEQ ID NO:111), ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), CRIS3_YEDLYSNCK (SEQ ID NO:70) and TETN_LDTLAQEVALLK (SEQ ID NO:106), B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), wherein said pair of biomarkers exhibits a change between pregnant females that deliver before 270 days relative to pregnant females that deliver on or after 280 days. In some embodiments, the composition further comprises AACT_EIGELYLPK (SEQ ID NO:129).

In one embodiment, the present invention provides a method of determining the estimated due date (EDD) for a pregnant female, the method comprising measuring in a biological sample obtained from said pregnant female a reversal value for a pair of biomarkers selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), and FETUA_FSVVYAK (SEQ ID NO:50) and IBP4_Q.CHPALDGQR (SEQ ID NO:111), to determine the EDD for said pregnant female. In some embodiments, the pregnant female is nulliparous. In additional embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the estimated due date (EDD) for a pregnant female, the method comprising measuring in a biological sample obtained from said pregnant female a pair of biomarkers selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), and FETUA_FSVVYAK (SEQ ID NO:50) and IBP4_Q.CHPALDGQR (SEQ ID NO:111), to determine the EDD for said pregnant female. In some embodiments, the pregnant female is nulliparous. In additional embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the time to birth (TTB) for a pregnant female, the method comprising measuring in a biological sample obtained from said pregnant female a reversal value for a pair of biomarkers selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), and FETUA_FSVVYAK (SEQ ID NO:50) and IBP4_Q.CHPALDGQR (SEQ ID NO:111), to determine the TTB for said pregnant female. In some embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the time to birth (TTB) for a pregnant female, the method comprising measuring in a biological sample obtained from said pregnant female a pair of biomarkers selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), and FETUA_FSVVYAK (SEQ ID NO:50) and IBP4_Q.CHPALDGQR (SEQ ID NO:111), to determine the TTB for said pregnant female. In some embodiments, the pregnant female is nulliparous. In additional embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method for separating a pregnancy that delivers before 270 days from a pregnancy that delivers on or after 280 days comprising measuring a change in a reversal value of a biomarker pair selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), and FETUA_FSVVYAK (SEQ ID NO:50) and IBP4_Q.CHPALDGQR (SEQ ID NO:111), wherein said pair of biomarkers exhibits a change in a reversal value between pregnant females that deliver before 270 days relative to pregnant females that deliver on or after 280 days. In some embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method for separating a pregnancy that delivers before 270 days from a pregnancy that delivers on or after 280 days comprising measuring a change in a biomarker pair selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), and FETUA_FSVVYAK (SEQ ID NO:50) and IBP4_Q.CHPALDGQR (SEQ ID NO:111), wherein said pair of biomarkers exhibits a change between pregnant females that deliver before 270 days relative to pregnant females that deliver on or after 280 days. In some embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a composition comprising a pair of isolated biomarkers consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, wherein said pair of biomarkers exhibits a change in reversal value between pregnant females that deliver before 270 days relative to pregnant females that deliver on or after 280 days. In some embodiments, the composition further comprises AACT_EIGELYLPK (SEQ ID NO:129).

In one embodiment, the present invention provides a composition comprising a pair of isolated biomarkers consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, wherein said pair of biomarkers exhibits a change between pregnant females that deliver before 270 days relative to pregnant females that deliver on or after 280 days. In some embodiments, the composition further comprises AACT_EIGELYLPK (SEQ ID NO:129).

In one embodiment, the present invention provides a method of determining the estimated due date (EDD) for a pregnant female, the method comprising measuring in a biological sample obtained from said pregnant female a reversal value for a pair of biomarkers consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, to determine the EDD for said pregnant female. In some embodiments, the pregnant female is nulliparous. In additional embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the estimated due date (EDD) for a pregnant female, the method comprising measuring in a biological sample obtained from said pregnant female a pair of biomarkers consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, to determine the EDD for said pregnant female. In some embodiments the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the time to birth (TTB) for a pregnant female, the method comprising measuring in a biological sample obtained from said pregnant female a reversal value for a pair of biomarkers consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, to determine the TTB for said pregnant female. In some embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the time to birth (TTB) for a pregnant female, the method comprising measuring in a biological sample obtained from said pregnant female a pair of biomarkers consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, to determine the TTB for said pregnant female. In some embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method for separating a pregnancy that delivers before 270 days from a pregnancy that delivers on or after 280 days comprising measuring a change in a reversal value of a biomarker pair consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, wherein said pair of biomarkers exhibits a change in a reversal value between pregnant females that deliver before 270 days relative to pregnant females that deliver on or after 280 days. In some embodiments, the pregnant female is nulliparous. In additional embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method for separating a pregnancy that delivers before 270 days from a pregnancy that delivers on or after 280 days comprising measuring a change in a biomarker pair consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, wherein said pair of biomarkers exhibits a change between pregnant females that deliver before 270 days relative to pregnant females that deliver on or after 280 days. In some embodiments, the pregnant female is nulliparous. In additional embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the estimated due date (EDD) for a pregnant female, the method comprising measuring in a biological sample obtained from said pregnant female a reversal value for a pair of biomarkers selected from the group consisting of ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), and CRIS3_YEDLYSNCK (SEQ ID NO:70) and TETN_LDT-LAQEVALLK (SEQ ID NO:106), to determine the EDD for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method of determining the estimated due date (EDD) for a pregnant female, the method comprising measuring in a biological sample obtained from said pregnant female a pair of biomarkers selected from the group consisting of ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), and CRIS3_YEDLYSNCK (SEQ ID NO:70) and TETN_LDT-LAQEVALLK (SEQ ID NO:106), to determine the EDD for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a reversal value for a pair of biomarkers selected from the group consisting of ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), and CRIS3_YEDLYSNCK (SEQ ID NO:70) and TETN_LDT-LAQEVALLK (SEQ ID NO:106), to determine the TTB for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a pair of biomarkers selected from the group consisting of ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), and CRIS3_YEDLYSNCK (SEQ ID NO:70) and TETN_LDT-LAQEVALLK (SEQ ID NO:106), to determine the TTB for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a reversal value of a biomarker pair selected from the group consisting of ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), and CRIS3_YEDLYSNCK (SEQ ID NO:70) and TETN_LDT-LAQEVALLK (SEQ ID NO:106), wherein said pair of biomarkers exhibits a change in a reversal value between pregnant females that deliver before 270 days relative to pregnant females that deliver on or after 280 days. In some embodiments, the biological sample is obtained at a gestational age at blood draw (GABD) from 23 0/7 weeks through 28 6/7 weeks. In some embodiments, the method further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a biomarker pair selected from the group consisting of ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), and CRIS3_YEDLYSNCK (SEQ ID NO:70) and TETN_LDT-LAQEVALLK (SEQ ID NO:106), wherein said pair of biomarkers exhibits a change between pregnant females that deliver before 270 days relative to pregnant females that deliver on or after 280 days. In some embodiments, the biological sample is obtained at a gestational age at blood draw (GABD) from 23 0/7 weeks through 28 6/7 weeks. In some embodiments, the method further comprises calculation of Inverse Parity as 1/(Parity−0.5).

In one embodiment, the present invention provides a composition comprising a pair of isolated biomarkers consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, wherein said pair of biomarkers exhibits a change in reversal value between pregnant females that deliver before 270 days relative to pregnant females that deliver on or after 280 days.

In one embodiment, the present invention provides a composition comprising a pair of isolated biomarkers consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, wherein said pair of biomarkers exhibits a change between pregnant females that deliver before 270 days relative to pregnant females that deliver on or after 280 days.

In one embodiment, the present invention provides a method of determining the estimated due date (EDD) for a pregnant female, the method comprising measuring in a biological sample obtained from said pregnant female a reversal value for a pair of biomarkers consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, to determine the EDD for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method of determining the estimated due date (EDD) for a pregnant female, the method comprising measuring in a biological sample obtained from said pregnant female a pair of biomarkers consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, to determine the EDD for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a reversal value for a pair of biomarkers consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, to determine the TTB for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a pair of biomarkers consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, to determine the TTB for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a reversal value of a biomarker pair consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, wherein said pair of biomarkers exhibits a change in a reversal value between pregnant females that deliver before 270 days relative to pregnant females that deliver on or after 280 days. In some embodiments, the biological sample is obtained at a gestational age at blood draw (GABD) from 23 0/7 weeks through 28 6/7 weeks. In some embodiments, the method further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a biomarker pair consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, wherein said pair of biomarkers exhibits a change between pregnant females that deliver before 270 days relative to pregnant females that deliver on or after 280 days. In additional embodiments, the biological sample is blood and the gestational age at blood draw (GABD) is from 23 0/7 weeks and 28 6/7 weeks. In some embodiments, the method further comprises calculation of Inverse Parity as 1/(Parity−0.5).

In one embodiment, the present invention provides a method of determining the estimated due date (EDD) for a pregnant female, the method comprising measuring in a biological sample obtained from said pregnant female a reversal value for a pair of biomarkers selected from the group consisting of B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), to determine the EDD for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method of determining the estimated due date (EDD) for a pregnant female, the method comprising measuring in a biological sample obtained from said pregnant female a pair of biomarkers selected from the group consisting of B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), to determine the EDD for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a reversal value for a pair of biomarkers selected from the group consisting of B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), to determine the TTB for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a pair of biomarkers selected from the group consisting of B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), to determine the TTB for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a reversal value of a biomarker pair selected from the group consisting of B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), wherein said pair of biomarkers exhibits a change in a reversal value between pregnant females that deliver before 270 days relative to pregnant females that deliver on or after 280 days. In some embodiments, the biological sample is obtained at a gestational age at blood draw (GABD) from 18 0/7 weeks through 22 6/7 weeks. In some embodiments, the method further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a biomarker pair selected from the group consisting of B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), wherein said pair of biomarkers exhibits a change between pregnant females that deliver before 270 days relative to pregnant females that deliver on or after 280 days. In some embodiments, the biological sample is obtained at a gestational age at blood draw (GABD) from 18 0/7 weeks through 22 6/7 weeks. In some embodiments, the method further comprises calculation of Inverse Parity as 1/(Parity−0.5).

In one embodiment, the present invention provides a composition comprising a pair of isolated biomarkers consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, wherein said pair of biomarkers exhibits a change in reversal value between pregnant females that deliver before 270 days relative to pregnant females that deliver on or after 280 days.

In one embodiment, the present invention provides a composition comprising a pair of isolated biomarkers consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, wherein said pair of biomarkers exhibits a change between pregnant females that deliver before 270 days relative to pregnant females that deliver on or after 280 days.

In one embodiment, the present invention provides a method of determining the estimated due date (EDD) for a pregnant female, the method comprising measuring in a biological sample obtained from said pregnant female a reversal value for a pair of biomarkers consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, to determine the EDD for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method of determining the estimated due date (EDD) for a pregnant female, the method comprising measuring in a biological sample obtained from said pregnant female a pair of biomarkers consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, to determine the EDD for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a reversal value for a pair of biomarkers consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, to determine the TTB for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a pair of biomarkers consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, to determine the TTB for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a reversal value of a biomarker pair consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, wherein said pair of biomarkers exhibits a change in a reversal value between pregnant females that deliver before 270 days relative to pregnant females that deliver on or after 280 days. In some embodiments, the biological sample is obtained at a gestational age at blood draw (GABD) from 18 0/7 weeks through 22 6/7 weeks. In some embodiments, the method further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a biomarker pair consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, wherein said pair of biomarkers exhibits a change between pregnant females that deliver before 270 days relative to pregnant females that deliver on or after 280 days. In some embodiments, the biological sample is obtained at a gestational age at blood draw (GABD) from 18 0/7 weeks through 22 6/7 weeks. In some embodiments, method further comprises calculation of Inverse Parity as 1/(Parity−0.5).

In one embodiment, the present invention provides a composition comprising a pair of isolated biomarkers selected from the group consisting of the biomarker pairs listed in Tables 1-27, wherein said pair of biomarkers exhibits a change in reversal value between pregnant females that deliver before 270 days relative to pregnant females that deliver on or after 280 days. In some embodiments, the composition comprises AACT_EIGELYLPK (SEQ ID NO:129).

In one embodiment, the present invention provides a composition comprising two or more pairs of isolated biomarkers selected from the group consisting of the biomarker pairs listed in Tables 1-27, wherein said pairs of biomarkers exhibit a change in reversal value between pregnant females that deliver before 270 days relative to pregnant females that deliver on or after 280 days. In some embodiments, the composition comprises AACT_EIGELYLPK (SEQ ID NO:129).

In one embodiment, the present invention provides a method of determining the estimated due date (EDD) for a pregnant female, the method comprising measuring in a biological sample obtained from said pregnant female a reversal value for a biomarker pair selected from the group consisting of the biomarker pairs listed in Tables 1-27 to determine the EDD for said pregnant female.

In one embodiment, the present invention provides a method of determining the estimated due date (EDD) for a pregnant female, the method comprising measuring in a biological sample obtained from said pregnant female a reversal value for two or more biomarker pairs selected from the group consisting of the biomarker pairs listed in Tables 1-27 to determine the EDD for said pregnant female.

In one embodiment, the present invention provides a method for separating a pregnancy that delivers before 270 days from a pregnancy that delivers on or after 280 days comprising measuring a change in reversal value of a biomarker pair selected from the group consisting of the biomarker pairs listed in Tables 1-27, wherein said pair of biomarkers exhibits a change in reversal value between pregnant females that deliver before 270 days relative to pregnant females that deliver on or after 280 days.

In one embodiment, the present invention provides a method for separating a pregnancy that delivers before 270 days from a pregnancy that delivers on or after 280 days comprising measuring a change in reversal value of two or more biomarker pairs selected from the group consisting of the biomarker pairs listed in Tables 1-27, wherein said pair of biomarkers exhibit a change in reversal value between pregnant females that deliver before 270 days relative to pregnant females that deliver on or after 280 days.

In one embodiment, the present invention further provides a method for prediction of gestational age at birth (GAB).

In a further embodiment, the present invention provides a method for estimating gestational age (GA).

In one embodiment, the present invention further provides a method for prediction of time to birth (TTB).

In some of the embodiments, the methods have an accuracy of 60% or more for predicting the EDD within plus or minus 5 days of the actual due date (DD).

In additional embodiments, the methods comprise measuring AACT_EIGELYLPK (SEQ ID NO:129).

In additional embodiments, the methods comprise calculation of Inverse Parity as 1/(Parity−0.5).

In some embodiments, the biological sample is obtained at a gestational age at blood draw (GABD) from 18 0/7 weeks through 22 6/7 weeks.

In some embodiments, the biological sample is obtained at a gestational age at blood draw (GABD) from 23 0/7 weeks through 28 6/7 weeks.

In some embodiments, the measuring comprises mass spectrometry (MS). In one embodiment, the measuring further comprises measuring surrogate peptides of said biomarkers in the biological sample obtained from said pregnant female. In one embodiment, the measuring of surrogate peptides of said biomarkers further comprises measuring stable isotope labeled standard peptides (SIS peptides) for each of the surrogate peptides.

In some embodiments, the biological sample is selected from the group consisting of whole blood, plasma, and serum. In one embodiment, the biological sample is serum.

In some embodiments, the measuring comprises an assay that utilizes a capture agent. In one embodiment, the measuring comprises an assay that utilizes a capture agent selected from the group consisting of and antibody, antibody fragment, nucleic acid-based protein binding reagent, small molecule or variant thereof. In one embodiment, the measuring comprises an assay selected from the group consisting of enzyme immunoassay (EIA), enzyme-linked immunosorbent assay (ELISA), and radioimmunoassay (MA).

Other features and advantages of the invention will be apparent from the detailed description, and from the claims.

BRIEF DESCRIPTION OF THE DRAWINGS

FIG. 2 discloses SEQ ID NO:49 (THBG_AVLHIGEK) and SEQ ID NO:111 (IBP4_Q.CHPALDGQR).

DETAILED DESCRIPTION

Figure 1:
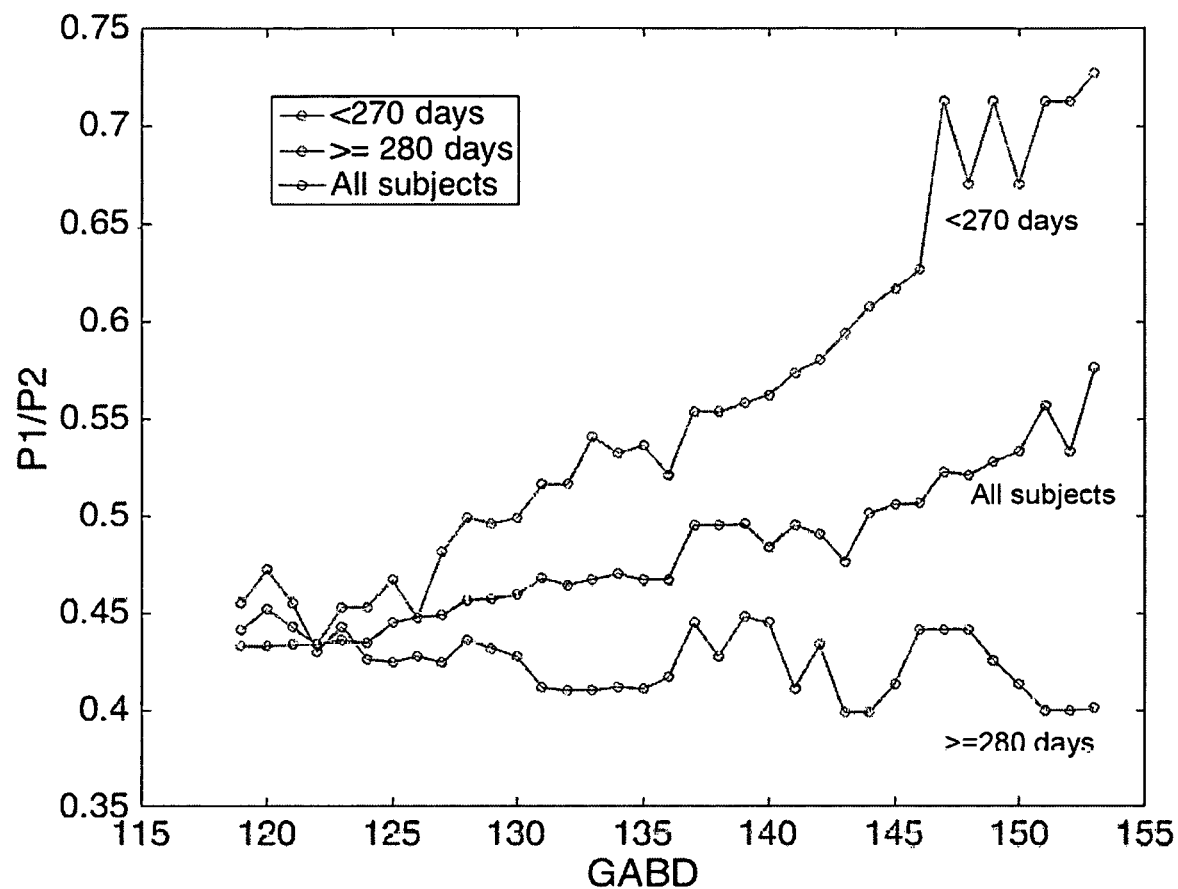
FIG. 1 Kinetic plot of the protein ratio of CATD/TENX over the a Gestational Age at Blood Draw (GABD) window of 140 to 153 shows an AUC of 82% in separating those subjects that gave birth significantly earlier (i.e. before 270 days) than the population average of 280 days.

The present disclosure is based, generally, on the discovery that certain proteins and peptides in biological samples obtained from a pregnant female are differentially expressed in pregnant females that deliver before 270 days relative to pregnant females that deliver on or after 280 days. The present disclosure is further based, generally, on the discovery that certain proteins and peptides in biological samples obtained from a pregnant female are differentially expressed in pregnant females that deliver before 270 days relative to pregnant females that deliver on or after 280 days.

The present disclosure is further specifically based, in part, on the unexpected discovery that pairs of biomarkers disclosed herein can be utilized in methods of estimating the due date of a pregnant female, subsequently referred to as the Estimated Due Date (EDD) and/or estimating time to birth (TTB). The present disclosure is further specifically based, in part, on the unexpected discovery that pairs of biomarkers disclosed herein can be utilized in methods of estimating the due date of a pregnant female, subsequently referred to as the EDD. Furthermore, each of the proteins, peptides and clinical variables disclosed herein as components of pairs, ratios and/or reversal pairs serve as biomarkers for determining the EDD, predicting gestational age at birth (GAB), predicting time to birth (TTB), estimating gestational age (GA) either individually, in ratios, reversal pairs or in panels of biomarkers/reversal pairs. Furthermore, the compositions and methods described herein comprise each of the proteins corresponding to the peptide biomarkers disclosed herein can serve as a component of pairs, ratios and/or reversal pairs for determining the EDD, predicting gestational age at birth (GAB), predicting time to birth (TTB), estimating gestational age (GA) either individually, in ratios, reversal pairs or in panels of biomarkers/reversal pairs. In addition, the compositions and methods described herein comprise surrogate peptides for each of the proteins corresponding to the peptide biomarkers disclosed herein can serve as a component of pairs, ratios and/or reversal pairs for determining the EDD, predicting gestational age at birth (GAB), predicting time to birth (TTB), estimating gestational age (GA) either individually, in ratios, reversal pairs or in panels of biomarkers/reversal pairs.

The present disclosure is further specifically based, in part, on the unexpected discovery that pairs of biomarkers disclosed herein can be utilized in methods of estimating the time to birth of a pregnant female, subsequently referred to as the Time To Birth (TTB). The present disclosure is further specifically based, in part, on the unexpected discovery that reversal values of pairs of biomarkers disclosed herein can be utilized in methods of estimating the due date of a pregnant female, subsequently referred to as TTB.

The present invention provides an improved process that applies the aforementioned discoveries to enable a new and useful process for estimating the due date of a pregnant female, subsequently referred to as the Estimated Due Date (EDD) and/or estimating time to birth (TTB) with much higher accuracy than currently practiced clinical methods.

The concepts of EDD and TTB are directly related and a skilled person can adjust the methods used to determine EDD to determine TTB and vice versa. Accordingly, the terms estimated due date (EDD) and time to birth (TTB) are used interchangeably in the context of predictors for DD. The EDD can be used to predict TTB and vice-versa. Explicitly, if the estimated gestational age of a pregnancy is X at the time of blood draw then TTB can be estimated from EDD as follows: TTB=EDD−X. And DD can be estimated from a TTB predictor as follows: EDD=X+TTB, where the units used are days.

The proteins and peptides disclosed herein as components of pairs, ratios and/or reversal pairs serve as biomarkers for determining the EDD, predicting gestational age at birth (GAB), predicting time to birth (TTB), either individually, in ratios, reversal pairs or in panels of biomarkers/reversal pairs.

A reversal value is the ratio of the relative peak area of an up regulated biomarker over the relative peak area of a down regulated biomarker and serves to both normalize variability and amplify diagnostic signal. The invention lies, in part, in the selection of particular biomarkers that, when paired together, can accurately determine the EDD and/or TTB based on pairs of biomarkers. Accordingly, it is human ingenuity in selecting the specific biomarkers that are informative upon being paired, for example, in novel reversals that underlies the present invention.

The disclosure provides biomarker reversal pairs and associated panels of reversal pairs, methods and kits for determining the EDD and/or TTB in a pregnant female.

In addition to the specific biomarkers identified in this disclosure, for example, by name, sequence, or reference, the invention also contemplates use of biomarker variants that are at least 90% or at least 95% or at least 97% identical to the exemplified sequences and that are now known or later discovered and that have utility for the methods of the invention. These variants may represent polymorphisms, splice variants, mutations, and the like. In this regard, the instant specification discloses multiple art-known proteins in the context of the invention and provides exemplary peptide sequences that can be used to identify these proteins. However, those skilled in the art appreciate that additional sequences or other information can easily be identified that can provide additional characteristics of the disclosed biomarkers and that the exemplified references are in no way limiting with regard to the disclosed biomarkers.

As described herein, various techniques and reagents find use in the methods of the present invention. Suitable samples in the context of the present invention include, for example, blood, plasma, serum, amniotic fluid, vaginal secretions, saliva, and urine. In some embodiments, the biological sample is selected from the group consisting of whole blood, plasma, and serum. In a particular embodiment, the biological sample is serum. As described herein, biomarkers can be detected through a variety of assays and techniques known in the art. As further described herein, such assays include, without limitation, mass spectrometry (MS)-based assays, antibody-based assays as well as assays that combine aspects of the two.

Protein biomarkers that are components of reversal pairs described herein include, for example, Cathepsin D (CATD) and Tenascin X (TENX).

In some embodiments, the invention provides a method of determining the EDD for a pregnant female, the method comprising measuring in a biological sample obtained from the pregnant female a reversal value for the biomarkers CATD and TENX.

In some embodiments, the invention provides a method of determining the EDD for a pregnant female, the method comprising measuring in a biological sample obtained from the pregnant female a reversal value for one pair of biomarkers consisting of CATD/TENX to determine the the EDD for said pregnant female.

The invention methods also contemplate measuring surrogate peptides of the biomarkers CATD and TENX. The biomarkers of the invention, their surrogate peptides and the corresponding stable isotope labeled standard peptides (SIS peptides) can be used in methods of determining the EDD for a pregnant female. In some embodiments, the SIS peptides correspond to surrogate peptides of the isolated biomarkers selected from the group consisting of CATD and TENX.

In some embodiments, the invention provides a pair of isolated biomarkers CATD/TENX, wherein the pair of biomarkers exhibits a higher ratio in pregnant females that deliver before 270 days relative to pregnant females that deliver on or after 280 days.

In one embodiment, the present invention provides a composition comprising a pair of isolated biomarkers selected from the group consisting of the biomarker pairs listed in Table 1, wherein said pair of biomarkers exhibits a change in reversal value between pregnant females that deliver before 270 days relative to pregnant females that deliver on or after 280 days.

In one embodiment, the present invention provides a pair of surrogate peptides of a pair of biomarkers selected from the group consisting of the biomarker pairs listed in Tables 1-27, wherein said pair of biomarkers exhibits a change in reversal value between pregnant females that deliver before 270 days relative to pregnant females that deliver on or after 280 days. In one embodiment, the present invention further provides stable isotope labeled standard peptides (SIS peptides) corresponding to each of the surrogate peptides.

In one embodiment, the present invention provides a method of determining the estimated due date (EDD) for a pregnant female, the method comprising measuring in a biological sample obtained from said pregnant female a reversal value for a pair of biomarkers selected from the group consisting of the biomarker pairs listed in Tables 1-27 to determine the EDD for said pregnant female.

In one embodiment, the present invention provides a method of determining the estimated due date (EDD) for a pregnant female, the method comprising measuring in a biological sample obtained from said pregnant female a reversal value for two or more biomarker pairs selected from the group consisting of the biomarker pairs listed in Tables 1-27 to determine the EDD for said pregnant female.

In one embodiment, the present invention provides a method for separating a pregnancy that delivers before 270 days from a pregnancy that delivers on or after 280 days comprising measuring a change in reversal value for a pair of biomarkers selected from the group consisting of the biomarker pairs listed in Tables 1-27, wherein said pair of biomarkers exhibits a change in reversal value between pregnant females that deliver before 270 days relative to pregnant females that deliver on or after 280 days.

In one embodiment, the present invention provides a method for separating a pregnancy that delivers before 270 days from a pregnancy that delivers on or after 280 days comprising measuring a change in reversal value of two or more biomarker pairs selected from the group consisting of biomarker pairs listed in Tables 1-27, wherein said pair of biomarkers exhibits a change in reversal value between pregnant females that deliver before 270 days relative to pregnant females that deliver on or after 280 days.

In some embodiments, the sample is obtained between 18 and 21 weeks of GABD. In further embodiments, the sample is obtained between 23 and 28 weeks of GABD. In some embodiments, the sample is obtained between 18 and 28 weeks of GABD. In some embodiments, the sample is obtained between 18 and 36 weeks of GABD. In further embodiments the sample is obtained between 19 and 21 weeks of GABD. In some embodiments, the sample is obtained between 20 and 22 weeks of GABD. In some embodiments, the sample is obtained between 21 and 23 weeks of GABD. In further embodiments, the sample is obtained between 22 and 24 weeks of GABD. In additional embodiments, the sample is obtained between 23 and 25 weeks of GABD. In some embodiments, the sample is obtained between 24 and 26 weeks of GABD. In further embodiments, the sample is obtained between 25 and 27 weeks of GABD. In additional embodiments, the sample is obtained between 26 and 28 weeks of GABD. In some embodiments, the sample is obtained between 27 and 29 weeks of GABD. In further embodiments, the sample is obtained between 28 and 30 weeks of GABD. In additional embodiments, the sample is obtained between 29 and 31 weeks of GABD. In some embodiments, the sample is obtained between 30 and 32 weeks of GABD. In further embodiments, the sample is obtained between 31 and 33 weeks of GABD. In additional embodiments, the sample is obtained between 32 and 34 weeks of GABD. In some embodiments, the sample is obtained between 33 and 35 weeks of GABD. In further embodiments, the sample is obtained between 34 and 36 weeks of GABD. In additional embodiments, the sample is obtained between 18 and 21 weeks of GABD.

In addition to the specific biomarkers, the disclosure further includes biomarker variants that are about 90%, about 95%, or about 97% identical to the exemplified sequences. Variants, as used herein, include polymorphisms, splice variants, mutations, and the like. Although described with reference to protein biomarkers, changes in reversal value can be identified in protein or gene expression levels for pairs of biomarkers.

The compositions and methods of the invention also can include clinical variables, including but not limited to, maternal characteristics, medical history, past pregnancy history, and obstetrical history. Such additional clinical variables can include, for example, previous low birth weight or preterm delivery, multiple 2nd trimester spontaneous abortions, prior first trimester induced abortion, familial and intergenerational factors, history of infertility, parity, nulliparity, placental abnormalities, cervical and uterine anomalies, short cervical length measurements, gestational bleeding, intrauterine growth restriction, in utero diethylstilbestrol exposure, multiple gestations, infant sex, short stature, low prepregnancy weight, low or high body mass index, diabetes, diabetes mellitus, chronic diabetes, chronic diabetes mellitus, chronic hypertension, urogenital infections (i.e. urinary tract infection), asthma, anxiety and depression, asthma, hypertension, hypothyroidism, high body mass index (BMI), low BMI, BMI. Demographic risk indicia for preterm birth can include, for example, maternal age, race/ethnicity, single marital status, low socioeconomic status, maternal age, employment-related physical activity, occupational exposures and environment exposures and stress. Further clinical variables can include, inadequate prenatal care, cigarette smoking, use of marijuana and other illicit drugs, cocaine use, alcohol consumption, caffeine intake, maternal weight gain, dietary intake, sexual activity during late pregnancy and leisure-time physical activities. (Preterm Birth: Causes, Consequences, and Prevention, Institute of Medicine (US) Committee on Understanding Premature Birth and Assuring Healthy Outcomes; Behrman R E, Butler A S, editors. Washington (DC): National Academies Press (US); 2007). Additional clinical variables useful for as markers can be identified using learning algorithms known in the art, such as linear discriminant analysis, support vector machine classification, recursive feature elimination, prediction analysis of microarray, logistic regression, CART, FlexTree, LART, random forest, MART, and/or survival analysis regression, which are known to those of skill in the art and are further described herein.

The present disclosure describes and exemplifies various models and corresponding biomarkers that perform at high levels of accuracy and precision in predicting the actual due date. It will be understood by those of skill in the art, that other models are known in the art that can be used to practice the claimed inventions and that the performance of a model can be evaluated in a variety of ways, including, but not limited to accuracy, precision, recall/sensitivity, weighted average of precision and recall. Models known in the art include, without limitation, linear discriminant analysis, support vector machine classification, recursive feature elimination, prediction analysis of microarray, logistic regression, CART, FlexTree, LART, random forest, MART, and/or survival analysis regression.

In some embodiments, performance of a model can be evaluated based on accuracy, which can be described as the difference between the EDD and the actual due date. For example, accuracy can be expressed as the percentage of time, for example, 50%, 51%, 52%, 53%, 54%, 55%, 56%, 57%, 58%, 59%, 60%, 61%, 62%, 63%, 64%, 65%, 70%, 71%, 72%, 73%, 74%, 75%, 76%, 77%, 80% or more that a model provides an EDD that falls within a certain range of days, for example, +/−10 days, +/−9 days, +/−8 days, +/−7 days, +/−6 days, +/−5 days, +/−4 days, +/−3 days +/−2 days, +/−1 day of the actual due date. In one embodiment, accuracy can be described by noting that the EDD or TTB predictor is accurate to within +/−5 days of the actual DD or TTB for a term pregnancy at least 60% of the time.

The present disclosure is based in part on the surprising discovery that the selection of certain biomarkers and/or clinical variables enables determining EDD and/or TTB at a significantly higher level of accuracy and precision compared to current clinical practice, which is accurate in making a due date prediction that falls within +/−5 days of the actual due date only about 35% of the time. In contrast, the present invention provides and exemplifies compositions and methods that enable a prediction time to birth or due date that falls within plus or minus five days of the actual time to birth or due date about 60% of the time.

It must be noted that, as used in this specification and the appended claims, the singular forms "a", "an" and "the" include plural referents unless the content clearly dictates otherwise. Thus, for example, reference to "a biomarker" includes a mixture of two or more biomarkers, and the like.

The term "about," particularly in reference to a given quantity, is meant to encompass deviations of plus or minus five percent.

As used in this application, including the appended claims, the singular forms "a," "an," and "the" include plural references, unless the content clearly dictates otherwise, and are used interchangeably with "at least one" and "one or more."

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

As used herein, the term "panel" refers to a composition, such as an array or a collection, comprising one or more biomarkers. The term can also refer to a profile or index of expression patterns of one or more biomarkers described herein. The number of biomarkers useful for a biomarker panel is based on the sensitivity and specificity value for the particular combination of biomarker values.

As used herein, and unless otherwise specified, the terms "isolated" and "purified" generally describes a composition of matter that has been removed from its native environment (e.g., the natural environment if it is naturally occurring), and thus is altered by the hand of man from its natural state so as to possess markedly different characteristics with regard to at least one of structure, function and properties. An isolated protein or nucleic acid is distinct from the way it exists in nature and includes synthetic peptides and proteins.

The term "biomarker" refers to a biological molecule, a fragment of a biological molecule, or a clinical variable the change and/or the detection of which can be correlated with a particular physical condition or state. The terms "marker" and "biomarker" are used interchangeably throughout the disclosure. For example, the biomarkers of the present invention are associated with a discrimination power between pregnant females that deliver before 270 days relative to pregnant females that deliver on or after 280 days. Such biomarkers include any suitable analyte, but are not limited to, biological molecules comprising nucleotides, nucleic acids, nucleosides, amino acids, sugars, fatty acids, steroids, metabolites, peptides, polypeptides, proteins, carbohydrates, lipids, hormones, antibodies, regions of interest that serve as surrogates for biological macromolecules and combinations thereof (e.g., glycoproteins, ribonucleoproteins, lipoproteins). The term also encompasses portions or fragments of a biological molecule, for example, peptide fragment of a protein or polypeptide that comprises at least 5 consecutive amino acid residues, at least 6 consecutive amino acid residues, at least 7 consecutive amino acid residues, at least 8 consecutive amino acid residues, at least 9 consecutive amino acid residues, at least 10 consecutive amino acid residues, at least 11 consecutive amino acid residues, at least 12 consecutive amino acid residues, at least 13 consecutive amino acid residues, at least 14 consecutive amino acid residues, at least 15 consecutive amino acid residues, at least 5 consecutive amino acid residues, at least 16 consecutive amino acid residues, at least 17 consecutive amino acid residues, at least 18 consecutive amino acid residues, at least 19 consecutive amino acid residues, at least 20 consecutive amino acid residues, at least 21 consecutive amino acid residues, at least 22 consecutive amino acid residues, at least 23 consecutive amino acid residues, at least 24 consecutive amino acid residues, at least 25 consecutive amino acid residues, or more consecutive amino acid residues.

As used herein, the term "surrogate peptide" refers to a peptide that is selected to serve as a surrogate for quantification of a biomarker of interest in an MRM assay configuration. Quantification of surrogate peptides is best achieved using stable isotope labeled standard surrogate peptides ("SIS surrogate peptides" or "SIS peptides") in conjunction with the MRM detection technique. A surrogate peptide can be synthetic. An SIS surrogate peptide can be synthesized with heavy labeled for example, with an Arginine or Lysine, or any other amino acid at the C-terminus of the peptide to serve as an internal standard in the MRM assay. An SIS surrogate peptide is not a naturally occurring peptide and has markedly different structure and properties compared to its naturally occurring counterpart. For any of the embodiments described herein, the biomarkers can be quantified by measuring surrogate peptides.

In some embodiments, the invention provides a method of separating a pregnancy that delivers before 270 days from a pregnancy that delivers on or after 280 days comprising measuring in a biological sample obtained from the pregnant female a ratio for at least a pair of biomarkers consisting of CATD/TENX to determine the EDD for said pregnant female, wherein a higher ratio indicates a greater likelihood of delivery before 270 days.

In some embodiments, the invention provides a method of separating a pregnancy that delivers before 270 days from a pregnancy that delivers on or after 280 days comprising measuring in a biological sample obtained from the pregnant female a ratio for at least a pair of biomarkers consisting of CATD/TENX to determine the EDD for said pregnant female, wherein a lower ratio indicates a greater likelihood of delivery on or after 280 days.

The term "clock protein" as used herein, refers to biomarkers that provide information on the due date of a pregnant subject, the state of development and/or age of a fetus or the progress through pregnancy. There are a number of important ways that these biomarkers can be advantageously used in assessing development including, for example, (1) for the prediction of gestational age at birth or time to birth (TTB) from the moment the blood is drawn to deliver and (2) for prediction of the gestational age at the time blood is drawn. In addition, clock proteins can serve to normalize component peptides in signatures to improve predictive performance or to select appropriate biomarkers and/or classifiers.

As used herein, the term "reversal" refers to the ratio of the measured value of an upregulated analyte over that of a down-regulated analyte. In some embodiments, the analyte value is itself a ratio of the peak area of the endogenous analyte over that of the peak area of the corresponding stable isotopic standard analyte, referred to herein as: response ratio or relative ratio.

As used herein, the term "reversal pair" refers to biomarkers in pairs that exhibit a change in value between the classes being compared. The detection of reversals in protein concentrations or gene expression levels eliminates the need for data normalization or the establishment of population-wide thresholds. Encompassed within the definition of any reversal pair is the corresponding reversal pair wherein individual biomarkers are switched between the numerator and denominator. One skilled in the art will appreciate that such a corresponding reversal pair is equally informative with regard to its predictive power.

The term "reversal value" refers to the ratio of the relative peak areas corresponding to the abundance of two analytes and serves to both normalize variability and amplify diagnostic signal. In some embodiments, a reversal value refers to the ratio of the relative peak area of an an up-regulated (interchangeably referred to as "over-abundant," up-regulation as used herein simply refers to an observation of relative abundance) analyte over the relative peak area of a down-regulated analyte (interchangeably referred to as "under-abundant,"down-regulation as used herein simply refers to an observation of relative abundance). In some embodiments, a reversal value refers to the ratio of the relative peak area of an up-regulated analyte over the relative peak area of a up-regulated analyte, where one analyte differs in the degree of up-regulation relative the other analyte. In some embodiments, a reversal value refers to the ratio of the relative peak area of a down-regulated analyte over the relative peak area of a down-regulated analyte, where one analyte differs in the degree of down-regulation relative the other analyte.

One advantageous aspect of a reversal is the presence of complementary information in the two analytes, so that the combination of the two is more diagnostic of the condition of interest than either one alone. Preferably the combination of the two analytes increases signal-to-noise ratio by compensating for biomedical conditions not of interest, pre-analytic variability and/or analytic variability. Out of all the possible reversals within a narrow window, a subset can be selected based on individual univariate performance. Additionally, a subset can be selected based on bivariate or multivariate performance in a training set, with testing on held-out data or on bootstrap iterations. For example, logistic or linear regression models can be trained, optionally with parameter shrinkage by L1 or L2 or other penalties, and tested in leave-one-out, leave-pair-out or leave-fold-out cross-validation, or in bootstrap sampling with replacement, or in a held-out data set. In some embodiments, the analyte value is itself a ratio of the peak area of the endogenous analyte over that of the peak area of the corresponding stable isotopic standard analyte, referred to herein as: response ratio or relative ratio. As disclosed herein, the ratio of the relative peak areas corresponding to the abundance of two analytes, for example, the ratio of the relative peak area of an up-regulated biomarker over the relative peak area of a down-regulated biomarker, referred herein as a reversal value, can be used to identify robust and accurate classifiers and predict EDD, GAB, and/or predicting time to birth (TTB). Use of a ratio of biomarkers in the methods disclosed herein corrects for variability that is the result of human manipulation after the removal of the biological sample from the pregnant female. Such variability can be introduced, for example, during sample collection, processing, depletion, digestion or any other step of the methods used to measure the biomarkers present in a sample and is independent of how the biomarkers behave in nature. Accordingly, the invention generally encompasses the use of a reversal pair in a method of diagnosis or prognosis to reduce variability and/or amplify, normalize or clarify diagnostic signal.

While the term reversal value refers to the ratio of the relative peak area of an up regulated analyte over the relative peak area of a down regulated analyte and serves to both normalize variability and amplify diagnostic signal, it is also contemplated that a pair of biomarkers of the invention could be measured by any other means, for example, by subtraction, addition or multiplication of relative peak areas. The methods disclosed herein encompass the measurement of biomarker pairs by such other means.

This method is advantageous because it provides the simplest possible classifier that is independent of data normalization, helps to avoid overfitting, and results in a very simple experimental test that is easy to implement in the clinic. The use of marker pairs based on changes in reversal values that are independent of data normalization enabled the development of the clinically relevant biomarkers disclosed herein. Because quantification of any single protein is subject to uncertainties caused by measurement variability, normal fluctuations, and individual related variation in baseline expression, identification of pairs of markers that may be under coordinated, systematic regulation enables robust methods for individualized diagnosis and prognosis.

While the specification discloses embodiments directed to measuring the particular pairs of biomarkers disclosed in Tables 1-27, the invention is not restricted to the particular pairs recited in Tables 1-27 and individual biomarkers disclosed herein as well as any pair or panel of the individual biomarkers is also encompassed by the present invention, as are methods comprising one or more pairs of biomarkers.

In one embodiment, the present invention provides a composition comprising a pair of isolated biomarkers consisting of cathepsin D (CATD) and tenascin X (TENX), wherein said pair of biomarkers exhibits a change in reversal value between pregnant females that deliver before 270 days relative to pregnant females that deliver on or after 280 days.

In one embodiment, the present invention provides a pair of surrogate peptides of a pair of biomarkers selected from the group consisting of CATD and TENX, wherein said pair of biomarkers exhibits a change in reversal value between pregnant females that deliver before 270 days relative to pregnant females that deliver on or after 280 days. In one embodiment, the present invention further provides stable isotope labeled standard peptides (SIS peptides) corresponding to each of the surrogate peptides.

In one embodiment, the present invention provides a method of determining the estimated due date (EDD) for a pregnant female, the method comprising measuring in a biological sample obtained from said pregnant female a reversal value for a pair of biomarkers consisting of CATD and TENX to determine the EDD for said pregnant female.

In one embodiment, the present invention provides a method for separating a pregnancy that delivers before 270 days from a pregnancy that delivers on or after 280 days comprising measuring a change in reversal value of a biomarker pair consisting of CATD and TENX, wherein said pair of biomarkers exhibits a change in reversal value between pregnant females that deliver before 270 days relative to pregnant females that deliver on or after 280 days.

In one embodiment, the present invention further provides a method for prediction of gestational age at birth (GAB).

In a further embodiment, the present invention further provides a method for prediction of time to birth (TTB).

The present invention further contemplates that the methods and compositions can encompass changes in reversal value between pregnant females that deliver before 270 days relative to pregnant females that deliver, for example, on or after 280 days; before 260 days relative to pregnant females that deliver on or after 270 days; before 250 days relative to pregnant females that deliver on or after 260 days; before 240 days relative to pregnant females that deliver on or after 250 days; before 230 days relative to pregnant females that deliver on or after 240 days. One skilled in the art will be able to select additional time windows, time windows with different cut-offs as well as time windows with different gaps, for example, 5 days, 15 days or 20 days. All of these variations are contemplated by the invention disclosed herein.

In one embodiment, the present invention provides a composition comprising a pair of isolated biomarkers selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), FETUA_FSVVYAK (SEQ ID NO:50) and IBP4_Q.CHPALDGQR (SEQ ID NO:111), ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), CRIS3_YEDLYSNCK (SEQ ID NO:70) and TETN_LDTLAQEVALLK (SEQ ID NO:106), B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), wherein said pair of biomarkers exhibits a change in reversal value between pregnant females that deliver before 270 days relative to pregnant females that deliver on or after 280 days. In some embodiments, the composition further comprises AACT_EIGELYLPK (SEQ ID NO:129).

In one embodiment, the present invention provides a composition comprising a pair of isolated biomarkers selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), FETUA_FSVVYAK (SEQ ID NO:50) and IBP4_Q.CHPALDGQR (SEQ ID NO:111), ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), CRIS3_YEDLYSNCK (SEQ ID NO:70) and TETN_LDTLAQEVALLK (SEQ ID NO:106), B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), wherein said pair of biomarkers exhibits a change between pregnant females that deliver before 270 days relative to pregnant females that deliver on or after 280 days. In some embodiments, the composition further comprises AACT_EIGELYLPK (SEQ ID NO:129).

In one embodiment, the present invention provides a method of determining the estimated due date (EDD) for a pregnant female, the method comprising measuring in a biological sample obtained from said pregnant female a reversal value for a pair of biomarkers selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), and FETUA_FSVVYAK (SEQ ID NO:50) and IBP4_Q.CHPALDGQR (SEQ ID NO:111), to determine the EDD for said pregnant female. In some embodiments, the pregnant female is nulliparous. In additional embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the estimated due date (EDD) for a pregnant female, the method comprising measuring in a biological sample obtained from said pregnant female a pair of biomarkers selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), and FETUA_FSVVYAK (SEQ ID NO:50) and IBP4_Q.CHPALDGQR (SEQ ID NO:111), to determine the EDD for said pregnant female. In some embodiments, the pregnant female is nulliparous. In additional embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the time to birth (TTB) for a pregnant female, the method comprising measuring in a biological sample obtained from said pregnant female a reversal value for a pair of biomarkers selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), and FETUA_FSVVYAK (SEQ ID NO:50) and IBP4_Q.CHPALDGQR (SEQ ID NO:111), to determine the TTB for said pregnant female. In some embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the time to birth (TTB) for a pregnant female, the method comprising measuring in a biological sample obtained from said pregnant female a pair of biomarkers selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), and FETUA_FSVVYAK (SEQ ID NO:50) and IBP4_Q.CHPALDGQR (SEQ ID NO:111), to determine the TTB for said pregnant female. In some embodiments, the pregnant female is nulliparous. In additional embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method for separating a pregnancy that delivers before 270 days from a pregnancy that delivers on or after 280 days comprising measuring a change in a reversal value of a biomarker pair selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), and FETUA_FSVVYAK (SEQ ID NO:50) and IBP4_Q.CHPALDGQR (SEQ ID NO:111), wherein said pair of biomarkers exhibits a change in a reversal value between pregnant females that deliver before 270 days relative to pregnant females that deliver on or after 280 days. In some embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method for separating a pregnancy that delivers before 270 days from a pregnancy that delivers on or after 280 days comprising measuring a change in a biomarker pair selected from the group consisting of ADA12_FGFGGSTDSGPIR (SEQ ID NO:84) and PAEP_HLWYLLDLK (SEQ ID NO:116), PAEP_HLWYLLDLK (SEQ ID NO:116) and PRG4_GLPNVVTSAISLPNIR (SEQ ID NO:168), IBP4_Q.CHPALDGQR (SEQ ID NO:111) and PAEP_HLWYLLDLK (SEQ ID NO:116), and FETUA_FSVVYAK (SEQ ID NO:50) and IBP4_Q.CHPALDGQR (SEQ ID NO:111), wherein said pair of biomarkers exhibits a change between pregnant females that deliver before 270 days relative to pregnant females that deliver on or after 280 days. In some embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a composition comprising a pair of isolated biomarkers consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, wherein said pair of biomarkers exhibits a change in reversal value between pregnant females that deliver before 270 days relative to pregnant females that deliver on or after 280 days. In some embodiments, the composition further comprises AACT_EIGELYLPK (SEQ ID NO:129).

In one embodiment, the present invention provides a composition comprising a pair of isolated biomarkers consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, wherein said pair of biomarkers exhibits a change between pregnant females that deliver before 270 days relative to pregnant females that deliver on or after 280 days. In some embodiments, the composition further comprises AACT_EIGELYLPK (SEQ ID NO:129).

In one embodiment, the present invention provides a method of determining the estimated due date (EDD) for a pregnant female, the method comprising measuring in a biological sample obtained from said pregnant female a reversal value for a pair of biomarkers consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, to determine the EDD for said pregnant female. In some embodiments, the pregnant female is nulliparous. In additional embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the estimated due date (EDD) for a pregnant female, the method comprising measuring in a biological sample obtained from said pregnant female a pair of biomarkers consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, to determine the EDD for said pregnant female. In some embodiments the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the time to birth (TTB) for a pregnant female, the method comprising measuring in a biological sample obtained from said pregnant female a reversal value for a pair of biomarkers consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, to determine the TTB for said pregnant female. In some embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the time to birth (TTB) for a pregnant female, the method comprising measuring in a biological sample obtained from said pregnant female a pair of biomarkers consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, to determine the TTB for said pregnant female. In some embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method for separating a pregnancy that delivers before 270 days from a pregnancy that delivers on or after 280 days comprising measuring a change in a reversal value of a biomarker pair consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, wherein said pair of biomarkers exhibits a change in a reversal value between pregnant females that deliver before 270 days relative to pregnant females that deliver on or after 280 days. In some embodiments, the pregnant female is nulliparous. In additional embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method for separating a pregnancy that delivers before 270 days from a pregnancy that delivers on or after 280 days comprising measuring a change in a biomarker pair consisting of FETUA_HTLNQIDEVK (SEQ ID NO:51), PRG4_GLPNVVTSAISLPNIR (SEQ ID NO:168) or KNG1_DIPTNSPELEETLTHTITK (SEQ ID NO:27) and one of the biomarkers listed in Tables 1-27, wherein said pair of biomarkers exhibits a change between pregnant females that deliver before 270 days relative to pregnant females that deliver on or after 280 days. In some embodiments, the pregnant female is nulliparous. In additional embodiments, the biological sample is obtained at a gestational age at blood draw (GABD) from 23 0/7 weeks through 28 6/7 weeks. In some embodiments, the method further comprises measuring AACT_EIGELYLPK (SEQ ID NO:129).

In one embodiment, the present invention provides a method of determining the estimated due date (EDD) for a pregnant female, the method comprising measuring in a biological sample obtained from said pregnant female a reversal value for a pair of biomarkers selected from the group consisting of ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), and CRIS3_YEDLYSNCK (SEQ ID NO:70) and TETN_LDTLAQEVALLK (SEQ ID NO:106), to determine the EDD for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method of determining the estimated due date (EDD) for a pregnant female, the method comprising measuring in a biological sample obtained from said pregnant female a pair of biomarkers selected from the group consisting of ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), and CRIS3_YEDLYSNCK (SEQ ID NO:70) and TETN_LDT- LAQEVALLK (SEQ ID NO:106), to determine the EDD for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a reversal value for a pair of biomarkers selected from the group consisting of ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), and CRIS3_YEDLYSNCK (SEQ ID NO:70) and TETN_LDTLAQEVALLK (SEQ ID NO:106), to determine the TTB for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a pair of biomarkers selected from the group consisting of ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), and CRIS3_YEDLYSNCK (SEQ ID NO:70) and TETN_LDTLAQEVALLK (SEQ ID NO:106), to determine the TTB for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a reversal value of a biomarker pair selected from the group consisting of ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), and CRIS3_YEDLYSNCK (SEQ ID NO:70) and TETN_LDTLAQEVALLK (SEQ ID NO:106), wherein said pair of biomarkers exhibits a change in a reversal value between pregnant females that deliver before 270 days relative to pregnant females that deliver on or after 280 days. In some embodiments, the biological sample is obtained at a gestational age at blood draw (GABD) from 23 0/7 weeks through 28 6/7 weeks. In some embodiments, the method further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a biomarker pair selected from the group consisting of ADA12_FGFGGSTDSGPIR (SEQ ID NO:84) and CRIS3_YEDLYSNCK (SEQ ID NO:70), CO5_TLLPVSKPEIR (SEQ ID NO:17) and ADA12_FGFGGSTDSGPIR (SEQ ID NO:84), AFAM_HFQNLGK (SEQ ID NO:39) and AACT_EIGELYLPK (SEQ ID NO:129), ALS_IRPHTFTGLSGLR (SEQ ID NO:67) and PCD12_AHDADLGINGK (SEQ ID NO:94), VTNC_GQYCYELDEK (SEQ ID NO:7) and PCD12_AHDADLGINGK (SEQ ID NO:94), and CRIS3_YEDLYSNCK (SEQ ID NO:70) and TETN_LDTLAQEVALLK (SEQ ID NO:106), wherein said pair of biomarkers exhibits a change between pregnant females that deliver before 270 days relative to pregnant females that deliver on or after 280 days. In some embodiments, the biological sample is obtained at a gestational age at blood draw (GABD) from 23 0/7 weeks through 28 6/7 weeks. In some embodiments, the method further comprises calculation of Inverse Parity as 1/(Parity−0.5).

In one embodiment, the present invention provides a composition comprising a pair of isolated biomarkers consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, wherein said pair of biomarkers exhibits a change in reversal value between pregnant females that deliver before 270 days relative to pregnant females that deliver on or after 280 days.

In one embodiment, the present invention provides a composition comprising a pair of isolated biomarkers consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, wherein said pair of biomarkers exhibits a change between pregnant females that deliver before 270 days relative to pregnant females that deliver on or after 280 days.

In one embodiment, the present invention provides a method of determining the estimated due date (EDD) for a pregnant female, the method comprising measuring in a biological sample obtained from said pregnant female a reversal value for a pair of biomarkers consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, to determine the EDD for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method of determining the estimated due date (EDD) for a pregnant female, the method comprising measuring in a biological sample obtained from said pregnant female a pair of biomarkers consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, to determine the EDD for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a reversal value for a pair of biomarkers consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, to determine the TTB for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a pair of biomarkers consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, to determine the TTB for said pregnant female. In some embodiments, the biological sample is obtained at a gestational age at blood draw (GABD) from 23 0/7 weeks through 28 6/7 weeks. In some embodiments, the determination further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a reversal value of a biomarker pair consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, wherein said pair of biomarkers exhibits a change in a reversal value between pregnant females that deliver before 270 days relative to pregnant females that deliver on or after 280 days. In some embodiments, the biological sample is obtained at a gestational age at blood draw (GABD) from 23 0/7 weeks through 28 6/7 weeks. In some embodiments, the method further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a biomarker pair consisting of ADA12_FGFGGSTDSGPIR (SEQ ID NO:84), PCD12_AHDADLGINGK (SEQ ID NO:94), CD14_LTVGAAQVPAQLLVGALR (SEQ ID NO:13) or CRIS3_YEDLYSNCK (SEQ ID NO:70) and one of the biomarkers listed in Tables 1-27, wherein said pair of biomarkers exhibits a change between pregnant females that deliver before 270 days relative to pregnant females that deliver on or after 280 days. In additional embodiments, the biological sample is blood and the gestational age at blood draw (GABD) is from 23 0/7 weeks and 28 6/7 weeks. In some embodiments, the method further comprises calculation of Inverse Parity as 1/(Parity−0.5).

In one embodiment, the present invention provides a method of determining the estimated due date (EDD) for a pregnant female, the method comprising measuring in a biological sample obtained from said pregnant female a reversal value for a pair of biomarkers selected from the group consisting of B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), to determine the EDD for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method of determining the estimated due date (EDD) for a pregnant female, the method comprising measuring in a biological sample obtained from said pregnant female a pair of biomarkers selected from the group consisting of B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), to determine the EDD for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a reversal value for a pair of biomarkers selected from the group consisting of B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), to determine the TTB for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a pair of biomarkers selected from the group consisting of B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), to determine the TTB for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a reversal value of a biomarker pair selected from the group consisting of B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), wherein said pair of biomarkers exhibits a change in a reversal value between pregnant females that deliver before 270 days relative to pregnant females that deliver on or after 280 days. In some embodiments, the biological sample is obtained at a gestational age at blood draw (GABD) from 18 0/7 weeks through 22 6/7 weeks. In some embodiments, the method further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a biomarker pair selected from the group consisting of B2MG_VEHSDLSFSK (SEQ ID NO:14) and FGFR1_IGPDNLPYVQILK (SEQ ID NO:154), GELS_TASDFITK (SEQ ID NO:102) and FGFR1_IGPDNLPYVQILK (SEQ ID NO:154), LIRB5_KPSLLIPQGSVVAR (SEQ ID NO:164) and FA9_SALVLQYLR (SEQ ID NO:113), B2MG_VEHSDLSFSK (SEQ ID NO:14) and CHL1_VIAVNEVGR (SEQ ID NO:66), and CHL1_VIAVNEVGR (SEQ ID NO:66) and IGF2_GIVEECCFR (SEQ ID NO:68), wherein said pair of biomarkers exhibits a change between pregnant females that deliver before 270 days relative to pregnant females that deliver on or after 280 days. In some embodiments, the biological sample is obtained at a gestational age at blood draw (GABD) from 18 0/7 weeks through 22 6/7 weeks. In some embodiments, the method further comprises calculation of Inverse Parity as 1/(Parity−0.5).

In one embodiment, the present invention provides a composition comprising a pair of isolated biomarkers consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, wherein said pair of biomarkers exhibits a change in reversal value between pregnant females that deliver before 270 days relative to pregnant females that deliver on or after 280 days.

In one embodiment, the present invention provides a composition comprising a pair of isolated biomarkers consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, wherein said pair of biomarkers exhibits a change between pregnant females that deliver before 270 days relative to pregnant females that deliver on or after 280 days.

In one embodiment, the present invention provides a method of determining the estimated due date (EDD) for a pregnant female, the method comprising measuring in a biological sample obtained from said pregnant female a reversal value for a pair of biomarkers consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, to determine the EDD for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method of determining the estimated due date (EDD) for a pregnant female, the method comprising measuring in a biological sample obtained from said pregnant female a pair of biomarkers consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, to determine the EDD for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a reversal value for a pair of biomarkers consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, to determine the TTB for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method of determining the time to birth (TTB) for a pregnant female, the method comprising measuring in a biological sample obtained from said pregnant female a pair of biomarkers consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, to determine the TTB for said pregnant female. In some embodiments, the biological sample is obtained at a gestational age at blood draw (GABD) from 18 0/7 weeks through 22 6/7 weeks. In some embodiments, the determination further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a reversal value of a biomarker pair consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, wherein said pair of biomarkers exhibits a change in a reversal value between pregnant females that deliver before 270 days relative to pregnant females that deliver on or after 280 days. In some embodiments, the biological sample is obtained at a gestational age at blood draw (GABD) from 18 0/7 weeks through 22 6/7 weeks. In some embodiments, the method further comprises calculation of Inverse Parity as 1/(Parity−0.5).

In one embodiment, the present invention provides a method for separating a pregnancy that delivers before 270 days from a pregnancy that delivers on or after 280 days comprising measuring a change in a biomarker pair consisting of CHL1_VIAVNEVGR (SEQ ID NO:66), FGFR1_IGPDNLPYVQILK (SEQ ID NO:154) or FA9_FGSGYVSGWGR (SEQ ID NO:112) and one of the biomarkers listed in Tables 1-27, wherein said pair of biomarkers exhibits a change between pregnant females that deliver before 270 days relative to pregnant females that deliver on or after 280 days. In some embodiments, the biological sample is obtained at a gestational age at blood draw (GABD) from 18 0/7 weeks through 22 6/7 weeks. In some embodiments, method further comprises calculation of Inverse Parity as 1/(Parity−0.5).

In one embodiment, the present invention provides a composition comprising a pair of isolated biomarkers selected from the group consisting of the biomarker pairs listed in Tables 1-27, wherein said pair of biomarkers exhibits a change in reversal value between pregnant females that deliver before 270 days relative to pregnant females that deliver on or after 280 days. In some embodiments, the composition comprises AACT_EIGELYLPK (SEQ ID NO:129).

In one embodiment, the present invention provides a composition comprising two or more pairs of isolated biomarkers selected from the group consisting of the biomarker pairs listed in Tables 1-27, wherein said pairs of biomarkers exhibit a change in reversal value between pregnant females that deliver before 270 days relative to pregnant females that deliver on or after 280 days. In some embodiments, the composition comprises AACT_EIGELYLPK (SEQ ID NO:129).

In one embodiment, the present invention provides a method of determining the estimated due date (EDD) for a pregnant female, the method comprising measuring in a biological sample obtained from said pregnant female a reversal value for a biomarker pair selected from the group consisting of the biomarker pairs listed in Tables 1-27 to determine the EDD for said pregnant female.

In one embodiment, the present invention provides a method of determining the estimated due date (EDD) for a pregnant female, the method comprising measuring in a biological sample obtained from said pregnant female a reversal value for two or more biomarker pairs selected from the group consisting of the biomarker pairs listed in Tables 1-27 to determine the EDD for said pregnant female.

In one embodiment, the present invention provides a method for separating a pregnancy that delivers before 270 days from a pregnancy that delivers on or after 280 days comprising measuring a change in reversal value of a biomarker pair selected from the group consisting of the biomarker pairs listed in Tables 1-27, wherein said pair of biomarkers exhibits a change in reversal value between pregnant females that deliver before 270 days relative to pregnant females that deliver on or after 280 days.

In one embodiment, the present invention provides a method for separating a pregnancy that delivers before 270 days from a pregnancy that delivers on or after 280 days comprising measuring a change in reversal value of two or more biomarker pairs selected from the group consisting of the biomarker pairs listed in Tables 1-27, wherein said pair of biomarkers exhibit a change in reversal value between pregnant females that deliver before 270 days relative to pregnant females that deliver on or after 280 days.

In one embodiment, the present invention further provides a method for prediction of gestational age at birth (GAB).

In a further embodiment, the present invention provides a method for estimating gestational age (GA) comprising measuring a change in reversal value of a biomarker pair selected from the group consisting of the biomarker pairs listed in Tables 1-27 and correlating said measurement to GA.

In one embodiment, the present invention further provides a method for prediction of time to birth (TTB).

In some of the embodiments, the methods have an accuracy of 60% or more for predicting the EDD within plus or minus 5 days of the actual due date (DD).

In additional embodiments, the methods comprise measuring AACT_EIGELYLPK (SEQ ID NO:129).

In additional embodiments, the methods comprise calculation of Inverse Parity as 1/(Parity−0.5).

In some embodiments, the biological sample is obtained at a gestational age at blood draw (GABD) from 18 0/7 weeks through 22 6/7 weeks.

In some embodiments, the biological sample is obtained at a gestational age at blood draw (GABD) from 23 0/7 weeks through 28 6/7 weeks.

In one embodiment, the measuring comprises mass spectrometry (MS). In one embodiment, the measuring further comprises measuring surrogate peptides of said biomarkers in the biological sample obtained from said pregnant female. In one embodiment, the measuring of surrogate peptides of said biomarkers further comprises measuring stable isotope labeled standard peptides (SIS peptides) for each of the surrogate peptides.

In one embodiment, the biological sample is selected from the group consisting of whole blood, plasma, and serum. In one embodiment, the biological sample is serum. In one embodiment, the sample is obtained between 18 and 21 weeks of gestational age. In an additional embodiment, the sample is obtained between 23 and 28 weeks of gestational age. In a further embodiment, the sample is obtained between 18 and 28 weeks of gestational age.

In one embodiment, the measuring comprises an assay that utilizes a capture agent. In one embodiment, the measuring comprises an assay that utilizes a capture agent selected from the group consisting of and antibody, antibody fragment, nucleic acid-based protein binding reagent, small molecule or variant thereof. In one embodiment, the measuring comprises an assay selected from the group consisting of enzyme immunoassay (EIA), enzyme-linked immunosorbent assay (ELISA), and radioimmunoassay (RIA)

Cathepsin D (NCBI GenBank: AAA51922.1) is a member of the A1 family of peptidases. The encoded preproprotein is proteolytically processed to generate multiple protein products. These products include the cathepsin D light and heavy chains, which heterodimerize to form the mature enzyme. This enzyme exhibits pepsin-like activity and plays a role in protein turnover and in the proteolytic activation of hormones and growth factors.

Tenascin X (NCBI GenBank: AAB47488.1) is a member of the tenascin family, a highly conserved group of four large extracellular glycoproteins denoted as tenascin-C, -X, -R, and -W. In most cells, the tenascin family interferes with the integrin-dependent spreading and affects cell motility and proliferation. Tenascin-X is the largest, over 400 kDa, member and is widely expressed during development. In adult tissue most of the expression of tenascin-X is seen in the connective tissue of the heart and skeletal muscle, as well as in the dermis. Tenascin-X is composed of a cysteine-rich segment at the N-terminus, epidermal growth factor- (EGF-) like repeats, fibronectin III-like repeats, and a fibrinogen-like domain at the C-terminus.

In one embodiment, the invention provides a composition comprising a pair of surrogate peptides corresponding to a pair of biomarkers selected from the group consisting of CATD/TENX, wherein the pair of biomarkers exhibits a change in reversal value between pregnant females at risk for pre-term birth and term controls.

For methods directed to predicating time to birth, it is understood that "birth" means birth following spontaneous onset of labor, with or without rupture of membranes.

Although described and exemplified with reference to methods of determining EDD in a pregnant female, the present disclosure is similarly applicable to related methods of predicting gestational age at birth (GAB), related methods for predicting term birth, methods for determining time to birth (TTB), methods of estimating gestational age (GA), methods of estimating gestational age at blood draw (GABD) in a pregnant female. Gestational age (GA), and gestational age at blood draw (GABD) are directly related in that estimation of GABD can be used to calculate GA post-blood draw. It will be apparent to one skilled in the art that each of the aforementioned methods has specific and substantial utilities and benefits with regard maternal-fetal health considerations.

In some embodiments, the present disclosure provides biomarkers, biomarker pairs and/or reversals, exemplified here by using CATD/TENX, that are strong predictors of time to birth (TTB). TTB is defined as the difference between the GABD and the gestational age at birth (GAB). This discovery enables prediction, either individually or in mathematical combination of such analytes of TTB or GAB. Analytes that lack a case versus control difference, but demonstrate changes in analyte intensity across pregnancy, are useful in a pregnancy clock according to the methods of the invention. Calibration of multiple analytes can be used to date pregnancy. Such a pregnancy clock is of value to confirm dating by another measure (e.g. date of last menstrual period and/or ultrasound dating), or useful alone to subsequently and more accurately predict GAB or TTB, for example. These analytes, also referred to herein as "clock proteins", can be used to date a pregnancy in the absence of or in conjunction with other dating methods. All of the embodiments described herein can therefore be used to accurately predict GA and GABD based on measurement of clock proteins.

In additional embodiments, the methods of determining the estimated due date (EDD) or time to birth (TTB) for a pregnant female further encompass detecting a measurable feature for one or more clinical variables. In additional embodiments, the clinical variables include without limitation previous low birth weight or preterm delivery, multiple 2nd trimester spontaneous abortions, prior first trimester induced abortion, familial and intergenerational factors, history of infertility, nulliparity, gravidity, primigravida, multigravida, placental abnormalities, cervical and uterine anomalies, gestational bleeding, intrauterine growth restriction, in utero diethylstilbestrol exposure, multiple gestations, infant sex, short stature, low prepregnancy weight, low or high body mass index, diabetes, diabetes mellitus, chronic hypertension, urogenital infections as well as any other clinical variable disclosed in the accompanying examples and tables.

A "measurable feature" is any property, characteristic or aspect that can be determined and correlated in connection with a prediction of EDD, a prediction of GAB, a prediction of term birth, or a prediction of TTB in a pregnant female. For a biomarker, such a measurable feature can include, for example, the presence, absence, or concentration of the biomarker, or a fragment thereof, in the biological sample, an altered structure, such as, for example, the presence or amount of a post-translational modification, such as oxidation at one or more positions on the amino acid sequence of the biomarker or, for example, the presence of an altered conformation in comparison to the conformation of the biomarker in term control subjects, and/or the presence, amount, or altered structure of the biomarker as a part of a profile of more than one biomarker.

In addition to biomarkers, measurable features can further include clinical variables including, for example, maternal characteristics, age, race, ethnicity, medical history, past pregnancy history, obstetrical history. For a risk indicium, a measurable feature can include, for example, previous low birth weight or preterm delivery, multiple 2nd trimester spontaneous abortions, prior first trimester induced abortion, familial and intergenerational factors, history of infertility, nulliparity, placental abnormalities, cervical and uterine anomalies, short cervical length measurements, gestational bleeding, intrauterine growth restriction, in utero diethylstilbestrol exposure, multiple gestations, infant sex, short stature, low prepregnancy weight/low body mass index, diabetes, hypertension, urogenital infections, hypothyroidism, asthma, low educational attainment, cigarette smoking, drug use and alcohol consumption.

In some embodiments, the methods of the invention comprise calculation of body mass index (BMI).

In some embodiments, the disclosed methods for determining the estimated due date (EDD) encompass detecting and/or quantifying one or more biomarkers using mass spectrometry, a capture agent or a combination thereof.

In additional embodiments, the disclosed methods methods for determining the estimated due date (EDD) encompass an initial step of providing a biological sample from the pregnant female.

In some embodiments, the disclosed methods of determining methods for determining the estimated due date (EDD) for a pregnant female encompass communicating the results to a health care provider. The disclosed methods of predicting GAB, the methods for predicting term birth, methods for determining the probability of term birth in a pregnant female as well methods of predicating time to birth in a pregnant female similarly encompass communicating the probability to a health care provider. As stated above, although described and exemplified with reference to determining methods for determining the estimated due date (EDD) for a pregnant female, all embodiments described throughout this disclosure are similarly applicable to methods of predicting GAB, methods for predicting term birth, methods for determining the probability of term birth in a pregnant female as well methods of predicating time to birth in a pregnant female. Specifically, the biomarkers and panels recited throughout this application with express reference to determining the estimated due date (EDD) can also be used in methods for predicting GAB, the methods for predicting term birth, methods for determining the probability of term birth in a pregnant female as well methods of predicating time to birth in a pregnant female. It will be apparent to one skilled in the art that each of the aforementioned methods has specific and substantial utilities and benefits with regard maternal-fetal health considerations.

In additional embodiments, the communication informs a subsequent treatment decision for the pregnant female. In some embodiments, the method of determining the estimated due date (EDD) for a pregnant female encompasses the initial or subsequent step of administering an additional test for predicting the probability of pre-term birth in said pregnant female, for example, the PreTRM™ test described in publication US2017/0022565A1, the entire contents of which are incorporated herein by reference.

In some embodiments, each of the proteins, peptides and clinical variables disclosed herein as components of pairs, ratios and/or reversal pairs can serve as clock proteins to normalize component peptides in signatures to improve predictive performance or to select appropriate biomarkers and/or classifiers. Accordingly, the present invention comprises methods for estimating gestational age (GABD) comprising measuring one or more clock proteins and correlating said measurement to GABD.

The utility of the biomarker pairs, ratios and/or reversal pairs as "clock proteins" to accurately date a pregnancy, i.e. accurately estimate gestational age (GA), is essential to the quality of obstetric care and maternal-fetal health. The utility of the clock proteins of the invention to date a pregnancy with significantly higher accuracy than can be achieved with current clinical extends to every prognostic, diagnostic or other clinical assessment of the pregnant female and fetus that relies on accurately estimating GA for its own accuracy. For example, acceptable ultrasonographic fetal measurements and algorithms for their use vary by gestational age at ultrasound. As a further example, the sensitivity of non-invasive prenatal testing (NIPT), which is increasingly used detection for aneuploidies and other conditions, relies on accurately estimating GA in defining an acceptable window for testing. Similarly, prenatal tests such as the Alpha-fetoprotein (AFP) test and the quadruple marker test (quad screen), which also measures human chorionic gonadotropin (HCG) estriol, and inhibin A in addition to AFP, interpret analyte abundances in view of estimated GA. When a pregnant female's EDD is changed based on new information, such as a new ultrasound, tests run earlier in pregnancy are re-assessed and may give medically different results, for example changing an AFP result from normal to abnormal, or vice versa. More generally, biomarkers associated with pregnancy are known to change continuously across pregnancy with individual kinetics. As a result, accurate GA estimation is crucial to the assessment of maternal and fetal health, and to obstetric care decisions. The biomarker pairs, ratios and/or reversal pairs can serve as "clock proteins" to improve the performance of every clinical assessment relating to maternal and fetal health that takes into account GA by enabling a new and useful process for estimating GA with much higher accuracy than currently practiced clinical methods.

Methods for assessment of GA with the clock proteins disclosed herein can serve to date prenatal tests for proper interpretation. As well, GA assessment can guide medical decisions related to fetal maturity. For example, a decision to induce labor or perform a C-section based on maternal health takes into account the estimated maturity of the fetus. Inaccurate assessment of GA can result in induction/C-sections that deliver: an early preterm baby when the fetus was thought to be at term; or a stillborn or ill baby and/or a mother with disseminated intravascular coagulation when the baby was thought to be full term. Further, the ARRIVE trial (Grobman, American Journal of Obstetrics & Gynecology, Volume 218, Issue 1, 5601) suggests that most nulliparous women will show benefit to fetal health without increasing risk of C-section if labor is induced in the 39th week of gestation. Reducing the trial findings to practice crucially requires differentiation between 38 and 39 weeks' GA, and between 39 and 40 weeks' GA. Further, current guidelines on proper management of late-term (41 0/7 weeks through 41 6/7 weeks) and postterm (42 0/7 weeks and beyond) require GA dating accurate to within a week. The critical importance for accurately dating a pregnancy to proper maternal and fetal health care is well documented in the literature and appreciated by those of skill in the art. (see, for example, Grobman et al., N Engl J Med 2018; 379, 6:513-23; Greene, N Engl J Med 2018; 379; 6:580-581; Ananth et al., JAMA Pediatr 2018; 172: 627-34; McDorman et al., Natl Vital Stat Rep 2015; 64: 1-24; Middleton et al., Cochrane Database Syst Rev 2018; 5: CD004945; Walker et al., N Engl J Med 2016; 374: 813-22; Martin et al., Natl Vital Stat Rep 2018; 67: 1-55).

The clock proteins and related methods provided by the invention address the crucial need for accurate, precise gestational age dating by estimating GABD and by predicting GAB, including specific prediction of preterm or late-term and postterm pregnancy with significantly higher accuracy than is achieved under current medical practice. Accordingly, in some embodiments of the invention, the clock protein compositions and corresponding methods can be used in tandem with an assessment of maternal and fetal health that depends on accurate GA estimation.

In some embodiments, the methods for determining the estimated due date (EDD) for a pregnant female encompasses the initial step of administering a test for predicting the probability of pre-term birth in said pregnant female, for example, the PreTRM™ test.

In the methods disclosed herein, determining the estimated due date (EDD) for a pregnant female encompasses an initial step that includes formation of a probability/risk index by measuring the ratio of isolated biomarkers selected from the group in a cohort of pregnancies that includes deliveries before 270 days and deliveries on or after 280 days. pregnancies with known gestational age at birth. For an individual pregnancy, determining the estimated due date (EDD) for a pregnant female encompasses measuring the ratio of the isolated biomarker using the same measurement method as used in the initial step of creating the probability/risk index, and comparing the measured ratio to the risk index to derive the personalized EDD for the individual pregnancy. In one embodiment, a probability/risk index is formed by measuring the ratio of CATD/TENX in a cohort of of pregnancies that includes deliveries before 270 days and deliveries on or after 280 days where the gestational age at birth is recorded. Then, in clinical practice the measured ratio of CATD/TENX in an individual pregnancy is compared in the index to derive the EDD using the same isolation and measurement technologies to derive CATD/TENX as in the index group.

As used herein, the term "risk score" refers to a score that can be assigned based on comparing the amount of one or more biomarkers or reversal values in a biological sample obtained from a pregnant female to a standard or reference score that represents an average amount of the one or more biomarkers calculated from biological samples obtained from a random pool of pregnant females. In some embodiments, the risk score is expressed as the log of the reversal value, i.e. the ratio of the relative intensities of the individual biomarkers. One skilled in the art will appreciate that a risk score can be expressed based on a various data transformations as well as being expressed as the ratio itself. Furthermore, with particular regard to reversal pairs, one skilled in the art will appreciate the any ratio is equally informative if the biomarkers in the numerator and denominator are switched or that related data transformations (e.g. subtraction) are applied. Because the level of a biomarker may not be static throughout pregnancy, a standard or reference score has to have been obtained for the gestational time point that corresponds to that of the pregnant female at the time the sample was taken. The standard or reference score can be predetermined and built into a predictor model such that the comparison is indirect rather than actually performed every time the probability is determined for a subject. A risk score can be a standard (e.g., a number) or a threshold (e.g., a line on a graph). The value of the risk score correlates to the deviation, upwards or downwards, from the average amount of the one or more biomarkers calculated from biological samples obtained from a random pool of pregnant females.

As exemplified herein, the predictive performance of the claimed methods can be improved with a BMI stratification of greater than 22 and equal or less than 37 kg/m$^2$. Accordingly, in some embodiments, the methods of the invention can be practiced with samples obtained from pregnant females with a specified BMI. Briefly, BMI is an individual's weight in kilograms divided by the square of height in meters. BMI does not measure body fat directly, but research has shown that BMI is correlated with more direct measures of body fat obtained from skinfold thickness measurements, bioelectrical impedance, densitometry (underwater weighing), dual energy x-ray absorptiometry (DXA) and other methods. Furthermore, BMI appears to be as strongly correlated with various metabolic and disease outcome as are these more direct measures of body fatness. Generally, an individual with a BMI below 18.5 is considered underweight, an individual with a BMI of equal or greater than 18.5 to 24.9 normal weight, while an individual with a BMI of equal or greater than 25.0 to 29.9 is considered overweight and an individual with a BMI of equal or greater than 30.0 is considered obese. In some embodiments, the predictive performance of the claimed methods can be improved with a BMI stratification of equal or greater than 18, equal or greater than 19, equal or greater than 20, equal or greater than 21, equal or greater than 22, equal or greater than 23, equal or greater than 24, equal or greater than 25, equal or greater than 26, equal or greater than 27, equal or greater than 28, equal or greater than 29 or equal or greater than 30. In other embodiments, the predictive performance of the claimed methods can be improved with a BMI stratification of equal or less than 18, equal or less than 19, equal or less than 20, equal or less than 21, equal or less than 22, equal or less than 23, equal or less than 24, equal or less than 25, equal or less than 26, equal or less than 27, equal or less than 28, equal or less than 29 or equal or less than 30.

In the context of the present invention, the term "biological sample," encompasses any sample that is taken from pregnant female and contains one or more of the biomarkers disclosed herein. Suitable samples in the context of the present invention include, for example, blood, plasma, serum, amniotic fluid, vaginal secretions, saliva, and urine. In some embodiments, the biological sample is selected from the group consisting of whole blood, plasma, and serum. In a particular embodiment, the biological sample is serum. As will be appreciated by those skilled in the art, a biological sample can include any fraction or component of blood, without limitation, T cells, monocytes, neutrophils, erythrocytes, platelets and microvesicles such as exosomes and exosome-like vesicles. In a particular embodiment, the biological sample is serum.

Gestational age is a proxy for the extent of fetal development and the fetus's readiness for birth. Gestational age has typically been defined as the length of time from the date of the last normal menses to the date of birth. However, obstetric measures and ultrasound estimates also can aid in estimating gestational age. In some embodiments, the methods disclosed herein are directed to predicting gestational age at birth.

As used herein, the term "estimated gestational age" or "estimated GA" refers to the GA determined based on the date of the last normal menses and additional obstetric measures, ultrasound estimates or other clinical parameters including, without limitation, those described in the preceding paragraph. In contrast the term "predicted gestational age at birth" or "predicted GAB" refers to the GAB determined based on the methods of the invention as disclosed herein. As used herein, "term birth" refers to birth at a gestational age equal or more than 37 completed weeks.

In some embodiments, the pregnant female is between 17 and 28 weeks of gestation at the time the biological sample is collected, also referred to as GABD (Gestational Age at Blood Draw). In other embodiments, the pregnant female is between 16 and 29 weeks, between 17 and 28 weeks, between 18 and 27 weeks, between 19 and 26 weeks, between 20 and 25 weeks, between 21 and 24 weeks, or between 22 and 23 weeks of gestation at the time the biological sample is collected. In further embodiments, the pregnant female is between about 17 and 22 weeks, between about 16 and 22 weeks between about 22 and 25 weeks, between about 13 and 25 weeks, between about 26 and 28, or between about 26 and 29 weeks of gestation at the time the biological sample is collected. Accordingly, the gestational age of a pregnant female at the time the biological sample is collected can be 15, 16, 17, 18, 19, 20, 21, 22, 23, 24, 25, 26, 27, 28, 29, 30, 31, 32, 33, 34, 35 weeks or older. In particular embodiments, the sample is obtained between 18 and 21 weeks of GABD. In further embodiments, the sample is obtained between 23 and 28 weeks of GABD. In some embodiments, the sample is obtained between 18 and 28 weeks of GABD. In some embodiments, the sample is obtained between 18 and 36 weeks of GABD. In further embodiments the sample is obtained between 19 and 21 weeks of GABD. In some embodiments, the sample is obtained between 20 and 22 weeks of GABD. In some embodiments, the sample is obtained between 21 and 23 weeks of GABD. In further embodiments, the sample is obtained between 22 and 24 weeks of GABD. In additional embodiments, the sample is obtained between 23 and 25 weeks of GABD. In some embodiments, the sample is obtained between 24 and 26 weeks of GABD. In further embodiments, the sample is obtained between 25 and 27 weeks of GABD. In additional embodiments, the sample is obtained between 26 and 28 weeks of GABD. In some embodiments, the sample is obtained between 27 and 29 weeks of GABD. In further embodiments, the sample is obtained between 28 and 30 weeks of GABD. In additional embodiments, the sample is obtained between 29 and 31 weeks of GABD. In some embodiments, the sample is obtained between 30 and 32 weeks of GABD. In further embodiments, the sample is obtained between 31 and 33 weeks of GABD. In additional embodiments, the sample is obtained between 32 and 34 weeks of GABD. In some embodiments, the sample is obtained between 33 and 35 weeks of GABD. In furthe embodiments, the sample is obtained between 34 and 36 weeks of GABD. In additional embodiments, the sample is obtained between 18 and 21 weeks of GABD.

The term "amount" or "level" as used herein refers to a quantity of a biomarker that is detectable or measurable in a biological sample and/or control. The quantity of a biomarker can be, for example, a quantity of polypeptide, the quantity of nucleic acid, or the quantity of a fragment or surrogate. The term can alternatively include combinations thereof. The term "amount" or "level" of a biomarker is a measurable feature of that biomarker.

The invention also provides a method of detecting a pair of isolated biomarkers consisting of CATD and TENX, said method comprising the steps of a. obtaining a biological sample from the pregnant female; b. detecting whether the pair of isolated biomarkers is present in the biological sample by contacting the biological sample with a first capture agent that specifically binds a first member of said pair and a second capture agent that specifically binds a second member of said pair; and detecting binding between the first biomarker of said pair and the first capture agent and between the second member of said pair and the second capture agent.

The invention also provides a method of detecting a pair of isolated biomarkers consisting of CATD/TENX in a pregnant female, said method comprising the steps of a. obtaining a biological sample from the pregnant female; b. detecting whether the pair of isolated biomarkers is present in the biological sample by contacting the biological sample with a first capture agent that specifically binds a first member of said pair and a second capture agent that specifically binds a second member of said pair; and detecting binding between the first biomarker of said pair and the first capture agent and between the second member of said pair and the second capture agent. In one embodiment the invention provides a method of detecting CATD and TENX in a pregnant female, said method comprising the steps of a. obtaining a biological sample from the pregnant female; b. detecting whether CATD and TENX are present in the biological sample by contacting the biological sample with a capture agent that specifically binds CATD and a capture agent that specifically binds TENX; and c. detecting binding between CATD and the capture agent and between TENX and the capture agent. In a further embodiment, the capture agent is selected from the group consisting of and antibody, antibody fragment, nucleic acid-based protein binding reagent, small molecule or variant thereof. In an additional embodiment, the method is performed by an assay selected from the group consisting of enzyme immunoassay (EIA), enzyme-linked immunosorbent assay (ELISA), and radioimmunoassay (MA).

The invention also provides a method of detecting a pair of isolated biomarkers consisting of CATD/TENX in a pregnant female, said method comprising the steps of a. obtaining a biological sample from the pregnant female; and b. detecting whether the pair of isolated biomarkers is present in the biological sample comprising subjecting the sample to a proteomics work-flow comprised of mass spectrometry quantification.

In one embodiment the invention provides a method of detecting CATD and TENX in a pregnant female, said method comprising the steps of a. obtaining a biological sample from the pregnant female; and b. detecting whether the pair of isolated biomarkers is present in the biological sample comprising subjecting the sample to a proteomics work-flow comprised of mass spectrometry quantification.

A "proteomics work-flow" generally encompasses one or more of the following steps: Serum samples are thawed and depleted of the 14 highest abundance proteins by immune-affinity chromatography. Depleted serum is digested with a protease, for example, trypsin, to yield peptides. The digest is subsequently fortified with a mixture of SIS peptides and then desalted and subjected to LC-MS/MS with a triple quadrupole instrument operated in MRM mode. Response ratios are formed from the area ratios of endogenous peptide peaks and the corresponding SIS peptide counterpart peaks. Those skilled in the art appreciate that other types of MS such as, for example, MALDI-TOF, or ESI-TOF, can be used in the methods of the invention. In addition, one skilled in the art can modify a proteomics work-flow, for example, by selecting particular reagents (such as proteases) or omitting or changing the order of certain steps, for example, it may not be necessary to immunodeplete, the SIS peptide could be added earlier or later and stable isotope labeled proteins could be used as standards instead of peptides.

Any existing, available or conventional separation, detection and quantification methods can be used herein to measure the presence or absence (e.g., readout being present vs. absent; or detectable amount vs. undetectable amount) and/or quantity (e.g., readout being an absolute or relative quantity, such as, for example, absolute or relative concentration) of biomarkers, peptides, polypeptides, proteins and/or fragments thereof and optionally of the one or more other biomarkers or fragments thereof in samples. In some embodiments, detection and/or quantification of one or more biomarkers comprises an assay that utilizes a capture agent. In further embodiments, the capture agent is an antibody, antibody fragment, nucleic acid-based protein binding reagent, small molecule or variant thereof. In additional embodiments, the assay is an enzyme immunoassay (EIA), enzyme-linked immunosorbent assay (ELISA), and radioimmunoassay (MA). In some embodiments, detection and/or quantification of one or more biomarkers further comprises mass spectrometry (MS). In yet further embodiments, the mass spectrometry is co-immunoprecipitation-mass spectrometry (co-IP MS), where coimmunoprecipitation, a technique suitable for the isolation of whole protein complexes is followed by mass spectrometric analysis.

As used herein, the term "mass spectrometer" refers to a device able to volatilize/ionize analytes to form gas-phase ions and determine their absolute or relative molecular masses. Suitable methods of volatilization/ionization are matrix-assisted laser desorption ionization (MALDI), electrospray, laser/light, thermal, electrical, atomized/sprayed and the like, or combinations thereof. Suitable forms of mass spectrometry include, but are not limited to, ion trap instruments, quadrupole instruments, electrostatic and magnetic sector instruments, time of flight instruments, time of flight tandem mass spectrometer (TOF MS/MS), Fourier-transform mass spectrometers, Orbitraps and hybrid instruments composed of various combinations of these types of mass analyzers. These instruments can, in turn, be interfaced with a variety of other instruments that fractionate the samples (for example, liquid chromatography or solid-phase adsorption techniques based on chemical, or biological properties) and that ionize the samples for introduction into the mass spectrometer, including matrix-assisted laser desorption (MALDI), electrospray, or nanospray ionization (ESI) or combinations thereof.

Generally, any mass spectrometric (MS) technique that can provide precise information on the mass of peptides, and preferably also on fragmentation and/or (partial) amino acid sequence of selected peptides (e.g., in tandem mass spectrometry, MS/MS; or in post source decay, TOF MS), can be used in the methods disclosed herein. Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000; Biemann 1990. Methods Enzymol 193: 455-79; or Methods in Enzymology, vol. 402: "Biological Mass Spectrometry", by Burlingame, ed., Academic Press 2005) and can be used in practicing the methods disclosed herein. Accordingly, in some embodiments, the disclosed methods comprise performing quantitative MS to measure one or more biomarkers. Such quantitative methods can be performed in an automated (Villanueva, et al., Nature Protocols (2006) 1(2):880-891) or semi-automated format. In particular embodiments, MS can be operably linked to a liquid chromatography device (LC-MS/MS or LC-MS) or gas chromatography device (GC-MS or GC-MS/MS). Other methods useful in this context include isotope-coded affinity tag (ICAT), tandem mass tags (TMT), or stable isotope labeling by amino acids in cell culture (SILAC), followed by chromatography and MS/MS.

As used herein, the terms "multiple reaction monitoring (MRM)" or "selected reaction monitoring (SRM)" refer to an MS-based quantification method that is particularly useful for quantifying analytes that are in low abundance. In an SRM experiment, a predefined precursor ion and one or more of its fragments are selected by the two mass filters of a triple quadrupole instrument and monitored over time for precise quantification. Multiple SRM precursor and fragment ion pairs can be measured within the same experiment on the chromatographic time scale by rapidly toggling between the different precursor/fragment pairs to perform an MRM experiment. A series of transitions (precursor/fragment ion pairs) in combination with the retention time of the targeted analyte (e.g., peptide or small molecule such as chemical entity, steroid, hormone) can constitute a definitive assay. A large number of analytes can be quantified during a single LC-MS experiment. The term "scheduled," or "dynamic" in reference to MRM or SRM, refers to a variation of the assay wherein the transitions for a particular analyte are only acquired in a time window around the expected retention time, significantly increasing the number of analytes that can be detected and quantified in a single LC-MS experiment and contributing to the selectivity of the test, as retention time is a property dependent on the physical nature of the analyte. A single analyte can also be monitored with more than one transition. Finally, included in the assay can be standards that correspond to the analytes of interest (e.g., same amino acid sequence), but differ by the inclusion of stable isotopes. Stable isotopic standards (SIS) can be incorporated into the assay at precise levels and used to quantify the corresponding unknown analyte. An additional level of specificity is contributed by the co-elution of the unknown analyte and its corresponding SIS and properties of their transitions (e.g., the similarity in the ratio of the level of two transitions of the unknown and the ratio of the two transitions of its corresponding SIS).

Mass spectrometry assays, instruments and systems suitable for biomarker peptide analysis can include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/$(MS)_n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-$(MS)_n$; ion mobility spectrometry (IMS); inductively coupled plasma mass spectrometry (ICP-MS) atmospheric pressure photoionization mass spectrometry (APPI-MS); APPI-MS/MS; and APPI-$(MS)_n$. Peptide ion fragmentation in tandem MS (MS/MS) arrangements can be achieved using manners established in the art, such as, e.g., collision induced dissociation (CID). As described herein, detection and quantification of biomarkers by mass spectrometry can involve multiple reaction monitoring (MRM), such as described among others by Kuhn et al. *Proteomics* 4: 1175-86 (2004). Scheduled multiple-reaction-monitoring (Scheduled MRM) mode acquisition during LC-MS/MS analysis enhances the sensitivity and accuracy of peptide quantitation. Anderson and Hunter, *Molecular and Cellular Proteomics* 5(4):573 (2006). As described herein, mass spectrometry-based assays can be advantageously combined with upstream peptide or protein separation or fractionation methods, such as for example with the chromatographic and other methods described herein below. As further described herein, shotgun quantitative proteomics can be combined with SRM/MRM-based assays for high-throughput identification and verification of biomarkers useful for separating a pregnancy that delivers before 270 days from a pregnancy that delivers on or after 280 days.

A person skilled in the art will appreciate that a number of methods can be used to determine the amount of a biomarker, including mass spectrometry approaches, such as MS/MS, LC-MS/MS, multiple reaction monitoring (MRM) or SRM and product-ion monitoring (PIM) and also including antibody based methods such as immunoassays such as Western blots, enzyme-linked immunosorbant assay (ELISA), immunoprecipitation, immunohistochemistry, immunofluorescence, radioimmunoassay, dot blotting, and FACS. Accordingly, in some embodiments, determining the level of the at least one biomarker comprises using an immunoassay and/or mass spectrometric methods. In additional embodiments, the mass spectrometric methods are selected from MS, MS/MS, LC-MS/MS, SRM, PIM, and other such methods that are known in the art. In other embodiments, LC-MS/MS further comprises 1D LC-MS/MS, 2D LC-MS/MS or 3D LC-MS/MS. Immunoassay techniques and protocols are generally known to those skilled in the art (Price and Newman, *Principles and Practice of Immunoassay*, 2nd Edition, Grove's Dictionaries, 1997; and Gosling, *Immunoassays: A Practical Approach*, Oxford University Press, 2000.) A variety of immunoassay techniques, including competitive and non-competitive immunoassays, can be used (Self et al., *Curr. Opin. Biotechnol.*, 7:60-65 (1996).

In further embodiments, the immunoassay is selected from Western blot, ELISA, immunoprecipitation, immunohistochemistry, immunofluorescence, radioimmunoassay (MA), dot blotting, and FACS. In certain embodiments, the immunoassay is an ELISA. In yet a further embodiment, the ELISA is direct ELISA (enzyme-linked immunosorbent assay), indirect ELISA, sandwich ELISA, competitive ELISA, multiplex ELISA, ELISPOT technologies, and other similar techniques known in the art. Principles of these immunoassay methods are known in the art, for example John R. Crowther, *The ELISA Guidebook*, 1st ed., Humana Press 2000, ISBN 0896037282. Typically ELISAs are performed with antibodies but they can be performed with any capture agents that bind specifically to one or more biomarkers of the invention and that can be detected. Multiplex ELISA allows simultaneous detection of two or more analytes within a single compartment (e.g., microplate well) usually at a plurality of array addresses (Nielsen and Geierstanger 2004. *J Immunol Methods* 290: 107-20 (2004) and Ling et al. 2007. *Expert Rev Mol Diagn* 7: 87-98 (2007)).

In some embodiments, Radioimmunoassay (RIA) can be used to detect one or more biomarkers in the methods of the invention. MA is a competition-based assay that is well known in the art and involves mixing known quantities of radioactively-labelled (e.g., $^{125}$I or $^{131}$I-labelled) target analyte with antibody specific for the analyte, then adding non-labeled analyte from a sample and measuring the amount of labeled analyte that is displaced (see, e.g., *An Introduction to Radioimmunoassay and Related Techniques*, by Chard T, ed., Elsevier Science 1995, ISBN 0444821198 for guidance).

A detectable label can be used in the assays described herein for direct or indirect detection of the biomarkers in the methods of the invention. A wide variety of detectable labels can be used, with the choice of label depending on the sensitivity required, ease of conjugation with the antibody, stability requirements, and available instrumentation and disposal provisions. Those skilled in the art are familiar with selection of a suitable detectable label based on the assay detection of the biomarkers in the methods of the invention. Suitable detectable labels include, but are not limited to, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), enzymes (e.g., luciferase, horseradish peroxidase, alkaline phosphatase, etc.), nanoparticles, biotin, digoxigenin, metals, and the like.

For mass-spectrometry based analysis, differential tagging with isotopic reagents, e.g., isotope-coded affinity tags (ICAT) or the more recent variation that uses isobaric tagging reagents, iTRAQ (Applied Biosystems, Foster City, Calif.), or tandem mass tags, TMT, (Thermo Scientific, Rockford, Ill.), followed by multidimensional liquid chromatography (LC) and tandem mass spectrometry (MS/MS) analysis can provide a further methodology in practicing the methods of the invention.

A chemiluminescence assay using a chemiluminescent antibody can be used for sensitive, non-radioactive detection of protein levels. An antibody labeled with fluorochrome also can be suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), beta-galactosidase, urease, and the like. Detection systems using suitable substrates for horseradish-peroxidase, alkaline phosphatase, and beta-galactosidase are well known in the art.

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, assays used to practice the invention can be automated or performed robotically, and the signal from multiple samples can be detected simultaneously.

In some embodiments, the methods described herein encompass quantification of the biomarkers using mass spectrometry (MS). In further embodiments, the mass spectrometry can be liquid chromatography-mass spectrometry (LC-MS), multiple reaction monitoring (MRM) or selected reaction monitoring (SRM). In additional embodiments, the MRM or SRM can further encompass scheduled MRM or scheduled SRM.

As described above, chromatography can also be used in practicing the methods of the invention. Chromatography encompasses methods for separating chemical substances and generally involves a process in which a mixture of analytes is carried by a moving stream of liquid or gas ("mobile phase") and separated into components as a result of differential distribution of the analytes as they flow around or over a stationary liquid or solid phase ("stationary phase"), between the mobile phase and said stationary phase. The stationary phase can be usually a finely divided solid, a sheet of filter material, or a thin film of a liquid on the surface of a solid, or the like. Chromatography is well understood by those skilled in the art as a technique applicable for the separation of chemical compounds of biological origin, such as, e.g., amino acids, proteins, fragments of proteins or peptides, etc.

Chromatography can be columnar (i.e., wherein the stationary phase is deposited or packed in a column), preferably liquid chromatography, and yet more preferably high-performance liquid chromatography (HPLC), or ultra high performance/pressure liquid chromatography (UHPLC). Particulars of chromatography are well known in the art (Bidlingmeyer, *Practical HPLC Methodology and Applications*, John Wiley & Sons Inc., 1993). Exemplary types of chromatography include, without limitation, high-performance liquid chromatography (HPLC), UHPLC, normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immuno-affinity, immobilized metal affinity chromatography, and the like. Chromatography, including single-, two- or more-dimensional chromatography, can be used as a peptide fractionation method in conjunction with a further peptide analysis method, such as for example, with a downstream mass spectrometry analysis as described elsewhere in this specification.

Further peptide or polypeptide separation, identification or quantification methods can be used, optionally in conjunction with any of the above described analysis methods, for measuring biomarkers in the present disclosure. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In the context of the invention, the term "capture agent" refers to a compound that can specifically bind to a target, in particular a biomarker. The term includes antibodies, antibody fragments, nucleic acid-based protein binding reagents (e.g. aptamers, Slow Off-rate Modified Aptamers (SOMAmer™)), protein-capture agents, natural ligands (i.e. a hormone for its receptor or vice versa), small molecules or variants thereof.

Capture agents can be configured to specifically bind to a target, in particular a biomarker. Capture agents can include but are not limited to organic molecules, such as polypeptides, polynucleotides and other non polymeric molecules that are identifiable to a skilled person. In the embodiments disclosed herein, capture agents include any agent that can be used to detect, purify, isolate, or enrich a target, in particular a biomarker. Any art-known affinity capture technologies can be used to selectively isolate and enrich/concentrate biomarkers that are components of complex mixtures of biological media for use in the disclosed methods.

Antibody capture agents that specifically bind to a biomarker can be prepared using any suitable methods known in the art. See, e.g., Coligan, *Current Protocols in Immunology* (1991); Harlow & Lane, *Antibodies: A Laboratory Manual* (1988); Goding, *Monoclonal Antibodies: Principles and Practice* (2d ed. 1986). Antibody capture agents can be any immunoglobulin or derivative thereof, whether natural or wholly or partially synthetically produced. All derivatives thereof which maintain specific binding ability are also included in the term. Antibody capture agents have a binding domain that is homologous or largely homologous to an immunoglobulin binding domain and can be derived from natural sources, or partly or wholly synthetically produced. Antibody capture agents can be monoclonal or polyclonal antibodies. In some embodiments, an antibody is a single chain antibody. Those of ordinary skill in the art will appreciate that antibodies can be provided in any of a variety of forms including, for example, humanized, partially humanized, chimeric, chimeric humanized, etc. Antibody capture agents can be antibody fragments including, but not limited to, Fab, Fab', F(ab')2, scFv, Fv, dsFv diabody, and Fd fragments. An antibody capture agent can be produced by any means. For example, an antibody capture agent can be enzymatically or chemically produced by fragmentation of an intact antibody and/or it can be recombinantly produced from a gene encoding the partial antibody sequence. An antibody capture agent can comprise a single chain antibody fragment. Alternatively or additionally, antibody capture agent can comprise multiple chains which are linked together, for example, by disulfide linkages; and, any functional fragments obtained from such molecules, wherein such fragments retain specific-binding properties of the parent antibody molecule. Because of their smaller size as functional components of the whole molecule, antibody fragments can offer advantages over intact antibodies for use in certain immunochemical techniques and experimental applications.

Suitable capture agents useful for practicing the invention also include aptamers. Aptamers are oligonucleotide sequences that can bind to their targets specifically via unique three dimensional (3-D) structures. An aptamer can include any suitable number of nucleotides and different aptamers can have either the same or different numbers of nucleotides. Aptamers can be DNA or RNA or chemically modified nucleic acids and can be single stranded, double stranded, or contain double stranded regions, and can include higher ordered structures. An aptamer can also be a photoaptamer, where a photoreactive or chemically reactive functional group is included in the aptamer to allow it to be covalently linked to its corresponding target. Use of an aptamer capture agent can include the use of two or more aptamers that specifically bind the same biomarker. An aptamer can include a tag. An aptamer can be identified using any known method, including the SELEX (systematic evolution of ligands by exponential enrichment), process. Once identified, an aptamer can be prepared or synthesized in accordance with any known method, including chemical synthetic methods and enzymatic synthetic methods and used in a variety of applications for biomarker detection. Liu et al., *Curr Med Chem.* 18(27):4117-25 (2011). Capture agents useful in practicing the methods of the invention also include SOMAmers (Slow Off-Rate Modified Aptamers) known in the art to have improved off-rate characteristics. Brody et al., *J Mol Biol.* 422(5):595-606 (2012). SOMAmers can be generated using any known method, including the SELEX method.

It is understood by those skilled in the art that biomarkers can be modified prior to analysis to improve their resolution or to determine their identity. For example, the biomarkers can be subject to proteolytic digestion before analysis. Any protease can be used. Proteases, such as trypsin, that are likely to cleave the biomarkers into a discrete number of fragments are particularly useful. The fragments that result from digestion function as a fingerprint for the biomarkers, thereby enabling their detection indirectly. This is particularly useful where there are biomarkers with similar molecular masses that might be confused for the biomarker in question. Also, proteolytic fragmentation is useful for high molecular weight biomarkers because smaller biomarkers are more easily resolved by mass spectrometry. In another example, biomarkers can be modified to improve detection resolution. For instance, neuraminidase can be used to remove terminal sialic acid residues from glycoproteins to improve binding to an anionic adsorbent and to improve detection resolution. In another example, the biomarkers can be modified by the attachment of a tag of particular molecular weight that specifically binds to molecular biomarkers, further distinguishing them. Optionally, after detecting such modified biomarkers, the identity of the biomarkers can be further determined by matching the physical and chemical characteristics of the modified biomarkers in a protein database (e.g., SwissProt).

It is further appreciated in the art that biomarkers in a sample can be captured on a substrate for detection. Traditional substrates include antibody-coated 96-well plates or nitrocellulose membranes that are subsequently probed for the presence of the proteins. Alternatively, protein-binding molecules attached to microspheres, microparticles, microbeads, beads, or other particles can be used for capture and detection of biomarkers. The protein-binding molecules can be antibodies, peptides, peptoids, aptamers, small molecule ligands or other protein-binding capture agents attached to the surface of particles. Each protein-binding molecule can include unique detectable label that is coded such that it can be distinguished from other detectable labels attached to other protein-binding molecules to allow detection of biomarkers in multiplex assays. Examples include, but are not limited to, color-coded microspheres with known fluorescent light intensities (see e.g., microspheres with xMAP technology produced by Luminex (Austin, Tex.); microspheres containing quantum dot nanocrystals, for example, having different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), glass microparticles with digital holographic code images (see e.g., CyVera microbeads produced by Illumina (San Diego, Calif.); chemiluminescent dyes, combinations of dye compounds; and beads of detectably different sizes.

In another aspect, biochips can be used for capture and detection of the biomarkers of the invention. Many protein biochips are known in the art. These include, for example, protein biochips produced by Packard BioScience Company (Meriden Conn.), Zyomyx (Hayward, Calif.) and Phylos (Lexington, Mass.). In general, protein biochips comprise a substrate having a surface. A capture reagent or adsorbent is attached to the surface of the substrate. Frequently, the surface comprises a plurality of addressable locations, each of which location has the capture agent bound there. The capture agent can be a biological molecule, such as a polypeptide or a nucleic acid, which captures other biomarkers in a specific manner. Alternatively, the capture agent can be a chromatographic material, such as an anion exchange material or a hydrophilic material. Examples of protein biochips are well known in the art.

The present disclosure also provides methods for separating pregnancies that deliver before 270 days and deliveries from pregancnies that deliver on or after 280 days comprising measuring a change in reversal value of a biomarker pair. In one embodiment, the present invention provides a method for separating a pregnancy that delivers before 270 days from a pregnancy that delivers on or after 280 days comprising measuring a change in reversal value of a biomarker pair consisting of CATD and TENX, wherein said pair of biomarkers exhibits a change in reversal value between pregnant females that deliver before 270 days relative to pregnant females that deliver on or after 280 days. For example, a biological sample can be contacted with a panel comprising one or more polynucleotide binding agents. The expression of one or more of the biomarkers detected can then be evaluated according to the methods disclosed below, e.g., with or without the use of nucleic acid amplification methods. Skilled practitioners appreciate that in the methods described herein, a measurement of gene expression can be automated. For example, a system that can carry out multiplexed measurement of gene expression can be used, e.g., providing digital readouts of the relative abundance of hundreds of mRNA species simultaneously.

In some embodiments, nucleic acid amplification methods can be used to detect a polynucleotide biomarker. For example, the oligonucleotide primers and probes of the present invention can be used in amplification and detection methods that use nucleic acid substrates isolated by any of a variety of well-known and established methodologies (e.g., Sambrook et al., Molecular Cloning, A laboratory Manual, pp. 7.37-7.57 (2nd ed., 1989); Lin et al., in Diagnostic Molecular Microbiology, Principles and Applications, pp. 605-16 (Persing et al., eds. (1993); Ausubel et al., Current Protocols in Molecular Biology (2001 and subsequent updates)). Methods for amplifying nucleic acids include, but are not limited to, for example the polymerase chain reaction (PCR) and reverse transcription PCR (RT-PCR) (see e.g., U.S. Pat. Nos. 4,683,195; 4,683,202; 4,800,159; 4,965,188), ligase chain reaction (LCR) (see, e.g., Weiss, Science 254:1292-93 (1991)), strand displacement amplification (SDA) (see e.g., Walker et al., Proc. Natl. Acad. Sci. USA 89:392-396 (1992); U.S. Pat. Nos. 5,270,184 and 5,455,166), Thermophilic SDA (tSDA) (see e.g., European Pat. No. 0 684 315) and methods described in U.S. Pat. No. 5,130,238; Lizardi et al., BioTechnol. 6:1197-1202 (1988); Kwoh et al., Proc. Natl. Acad. Sci. USA 86:1173-77 (1989); Guatelli et al., Proc. Natl. Acad. Sci. USA 87:1874-78 (1990); U.S. Pat. Nos. 5,480,784; 5,399,491; US Publication No. 2006/46265.

In some embodiments, measuring mRNA in a biological sample can be used as a surrogate for detection of the level of the corresponding protein biomarker in a biological sample. Thus, any of the biomarkers, biomarker pairs or biomarker reversal panels described herein can also be detected by detecting the appropriate RNA. Levels of mRNA can be measured by reverse transcription quantitative polymerase chain reaction (RT-PCR followed with qPCR). RT-PCR is used to create a cDNA from the mRNA. The cDNA can be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See *Gene Expression Profiling: Methods and Protocols*, Richard A. Shimkets, editor, Humana Press, 2004.

Some embodiments disclosed herein relate to methods of determining the method of determining the estimated due date (EDD) for a pregnant female. The detection of the level of expression of one or more biomarkers and/or the determination of a ratio of biomarkers can be used to determine the estimated due date (EDD) for a pregnant female. Such detection methods can be used, for example, for early diagnosis of a pregnancy-related condition, to determine whether a subject is predisposed to preterm birth, to monitor the progress of preterm birth or the progress of treatment protocols, to assess the severity of preterm birth, to forecast the outcome of preterm birth and/or prospects of recovery or birth at full term, or to aid in the determination of a suitable treatment for preterm birth.

The quantitation of biomarkers in a biological sample can be determined, without limitation, by the methods described above as well as any other method known in the art. The quantitative data thus obtained is then subjected to an analytic classification process. In such a process, the raw data is manipulated according to an algorithm, where the algorithm has been pre-defined by a training set of data, for example as described in the examples provided herein. An algorithm can utilize the training set of data provided herein, or can utilize the guidelines provided herein to generate an algorithm with a different set of data.

In some embodiments, analyzing a measurable feature to determine the estimated due date (EDD) for a pregnant female encompasses the use of a predictive model. In further embodiments, analyzing a measurable feature to determine the estimated due date (EDD) for a pregnant female encompasses comparing said measurable feature with a reference feature. As those skilled in the art can appreciate, such comparison can be a direct comparison to the reference feature or an indirect comparison where the reference feature has been incorporated into the predictive model. In further embodiments, analyzing a measurable feature to determine the estimated due date (EDD) for a pregnant female encompasses one or more of a linear discriminant analysis model, a support vector machine classification algorithm, a recursive feature elimination model, a prediction analysis of microarray model, a logistic regression model, a CART algorithm, a flex tree algorithm, a LART algorithm, a random forest algorithm, a MART algorithm, a machine learning algorithm, a penalized regression method, or a combination thereof. In particular embodiments, the analysis comprises logistic regression.

An analytic classification process can use any one of a variety of statistical analytic methods to manipulate the quantitative data and provide for classification of the sample. Examples of useful methods include linear discriminant analysis, recursive feature elimination, a prediction analysis of microarray, a logistic regression, a CART algorithm, a FlexTree algorithm, a LART algorithm, a random forest algorithm, a MART algorithm, machine learning algorithms; etc.

For creation of a random forest for prediction of GAB one skilled in the art can consider a set of k subjects (pregnant women) for whom the gestational age at birth (GAB) is known, and for whom N analytes (transitions) have been measured in a blood specimen taken several weeks prior to birth. A regression tree begins with a root node that contains all the subjects. The average GAB for all subjects can be calculated in the root node. The variance of the GAB within the root node will be high, because there is a mixture of women with different GAB's. The root node is then divided (partitioned) into two branches, so that each branch contains women with a similar GAB. The average GAB for subjects in each branch is again calculated. The variance of the GAB within each branch will be lower than in the root node, because the subset of women within each branch has relatively more similar GAB's than those in the root node. The two branches are created by selecting an analyte and a threshold value for the analyte that creates branches with similar GAB. The analyte and threshold value are chosen from among the set of all analytes and threshold values, usually with a random subset of the analytes at each node. The procedure continues recursively producing branches to create leaves (terminal nodes) in which the subjects have very similar GAB's. The predicted GAB in each terminal node is the average GAB for subjects in that terminal node. This procedure creates a single regression tree. A random forest can consist of several hundred or several thousand such trees.

Classification can be made according to predictive modeling methods that set a threshold for determining the probability that a sample belongs to a given class. The probability preferably is at least 50%, or at least 60%, or at least 70%, or at least 80% or higher. Classifications also can be made by determining whether a comparison between an obtained dataset and a reference dataset yields a statistically significant difference. If so, then the sample from which the dataset was obtained is classified as not belonging to the reference dataset class. Conversely, if such a comparison is not statistically significantly different from the reference dataset, then the sample from which the dataset was obtained is classified as belonging to the reference dataset class.

The predictive ability of a model can be evaluated according to its ability to provide a quality metric, e.g. AUROC (area under the ROC curve) or accuracy, of a particular value, or range of values. Area under the curve measures are useful for comparing the accuracy of a classifier across the complete data range. Classifiers with a greater AUC have a greater capacity to classify unknowns correctly between two groups of interest. In some embodiments, a desired quality threshold is a predictive model that will classify a sample with an accuracy of at least about 0.5, at least about 0.55, at least about 0.6, at least about 0.7, at least about 0.75, at least about 0.8, at least about 0.85, at least about 0.9, at least about 0.95, or higher. As an alternative measure, a desired quality threshold can refer to a predictive model that will classify a sample with an AUC of at least about 0.7, at least about 0.75, at least about 0.8, at least about 0.85, at least about 0.9, or higher.

As is known in the art, the relative sensitivity and specificity of a predictive model can be adjusted to favor either the selectivity metric or the sensitivity metric, where the two metrics have an inverse relationship. The limits in a model as described above can be adjusted to provide a selected sensitivity or specificity level, depending on the particular requirements of the test being performed. One or both of sensitivity and specificity can be at least about 0.7, at least about 0.75, at least about 0.8, at least about 0.85, at least about 0.9, or higher.

The raw data can be initially analyzed by measuring the values for each biomarker, usually in triplicate or in multiple triplicates. The data can be manipulated, for example, raw data can be transformed using standard curves, and the average of triplicate measurements used to calculate the average and standard deviation for each patient. These values can be transformed before being used in the models, e.g. log-transformed, Box-Cox transformed (Box and Cox, *Royal Stat. Soc.*, Series B, 26:211-246(1964). The data are then input into a predictive model, which will classify the sample according to the state. The resulting information can be communicated to a patient or health care provider.

To generate a predictive model for separating a pregnancy that delivers before 270 days from a pregnancy that delivers on or after 280 days, a robust data set, comprising known control samples and samples corresponding to the birth classification of interest is used in a training set. A sample size can be selected using generally accepted criteria. As discussed above, different statistical methods can be used to obtain a highly accurate predictive model.

In one embodiment, hierarchical clustering is performed in the derivation of a predictive model, where the Pearson correlation is employed as the clustering metric. One approach is to consider a given birth dataset as a "learning sample" in a problem of "supervised learning." CART is a standard in applications to medicine (Singer, Recursive Partitioning in the Health Sciences, Springer (1999)) and can be modified by transforming any qualitative features to quantitative features; sorting them by attained significance levels, evaluated by sample reuse methods for Hotelling's $T^2$ statistic; and suitable application of the lasso method. Problems in prediction are turned into problems in regression without losing sight of prediction, indeed by making suitable use of the Gini criterion for classification in evaluating the quality of regressions.

This approach led to what is termed FlexTree (Huang, *Proc. Nat. Acad. Sci. U.S.A* 101:10529-10534(2004)). FlexTree performs very well in simulations and when applied to multiple forms of data and is useful for practicing the claimed methods. Software automating FlexTree has been developed. Alternatively, LARTree or LART can be used (Turnbull (2005) *Classification Trees with Subset Analysis Selection by the Lasso*, Stanford University). The name reflects binary trees, as in CART and FlexTree; the lasso, as has been noted; and the implementation of the lasso through what is termed LARS by Efron et al. (2004) *Annals of Statistics* 32:407-451 (2004). See, also, Huang et al., *Proc. Natl. Acad. Sci. USA.* 101(29):10529-34 (2004). Other methods of analysis that can be used include logic regression. One method of logic regression Ruczinski, *Journal of Computational and Graphical Statistics* 12:475-512 (2003). Logic regression resembles CART in that its classifier can be displayed as a binary tree. It is different in that each node has Boolean statements about features that are more general than the simple "and" statements produced by CART.

Another approach is that of nearest shrunken centroids (Tibshirani, *Proc. Natl. Acad. Sci. U.S.A* 99:6567-72(2002)). The technology is k-means-like, but has the advantage that by shrinking cluster centers, one automatically selects features, as is the case in the lasso, to focus attention on small numbers of those that are informative. The approach is available as PAM software and is widely used. Two further sets of algorithms that can be used are random forests (Breiman, *Machine Learning* 45:5-32 (2001)) and MART (Hastie, *The Elements of Statistical Learning*, Springer (2001)). These two methods are known in the art as "committee methods," that involve predictors that "vote" on outcome.

To provide significance ordering, the false discovery rate (FDR) can be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (Tusher et al., *Proc. Natl. Acad. Sci. U.S.A* 98, 5116-21 (2001)). The set of null distribution is obtained by: permuting the values of each profile for all available profiles; calculating the pair-wise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value can be applied to the correlations between experimental profiles. Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pair wise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

In an alternative analytical approach, variables chosen in the cross-sectional analysis are separately employed as predictors in a time-to-event analysis (survival analysis), where the event is the occurrence of preterm birth, and subjects with no event are considered censored at the time of giving birth. Given the specific pregnancy outcome (preterm birth event or no event), the random lengths of time each patient will be observed, and selection of proteomic and other features, a parametric approach to analyzing survival can be better than the widely applied semi-parametric Cox model. A Weibull parametric fit of survival permits the hazard rate to be monotonically increasing, decreasing, or constant, and also has a proportional hazards representation (as does the Cox model) and an accelerated failure-time representation. All the standard tools available in obtaining approximate maximum likelihood estimators of regression coefficients and corresponding functions are available with this model.

In addition the Cox models can be used, especially since reductions of numbers of covariates to manageable size with the lasso will significantly simplify the analysis, allowing the possibility of a nonparametric or semi-parametric approach to prediction of time to preterm birth. These statistical tools are known in the art and applicable to all manner of proteomic data. A set of biomarker, clinical and genetic data that can be easily determined, and that is highly informative regarding the probability for preterm birth and predicted time to a preterm birth event in said pregnant female is provided. Also, algorithms provide information regarding the probability for preterm birth in the pregnant female.

Survival analyses are commonly used to understand time to occurrence of an event of interest such as birth or death. Commonly, the Kaplan-Meier estimator is used to estimate the survival function, while Cox proportional hazards models are used to estimate the effects of covariates on the hazard of event occurrence. These models conventionally assume that survival time is based on risk of exactly one type of event. However a competing risk for a different event may be present that either hinders the observation of an event of interest or modifies the chance that this event occurs. Conventional methods may be inappropriate in the presence of competing risks. Alternative methods appropriate for analysis of competing risks either asses competing hazards in subdistribution hazards models or cause-specific modified Cox proportional hazards models; or estimate cumulative incidence over competing events (Jason P. Fine & Robert J. Gray. Journal of the American Statistical Association Vol. 94, Issue 446, 1999. A Proportional Hazards Model for the Subdistribution of a Competing Risk).

In the development of a predictive model, it can be desirable to select a subset of markers, i.e. at least 3, at least 4, at least 5, at least 6, up to the complete set of markers. Usually a subset of markers will be chosen that provides for the needs of the quantitative sample analysis, e.g. availability of reagents, convenience of quantitation, etc., while maintaining a highly accurate predictive model. The selection of a number of informative markers for building classification models requires the definition of a performance metric and a user-defined threshold for producing a model with useful predictive ability based on this metric. For example, the performance metric can be the AUC, the sensitivity and/or specificity of the prediction as well as the overall accuracy of the prediction model.

As will be understood by those skilled in the art, an analytic classification process can use any one of a variety of statistical analytic methods to manipulate the quantitative data and provide for classification of the sample. Examples of useful methods include, without limitation, linear discriminant analysis, recursive feature elimination, a prediction analysis of microarray, a logistic regression, a CART algorithm, a FlexTree algorithm, a LART algorithm, a random forest algorithm, a MART algorithm, and machine learning algorithms. Various methods are used in a training model. The selection of a subset of markers can be for a forward selection or a backward selection of a marker subset. The number of markers can be selected that will optimize the performance of a model without the use of all the markers. One way to define the optimum number of terms is to choose the number of terms that produce a model with desired predictive ability (e.g. an AUC>0.75, or equivalent measures of sensitivity/specificity) that lies no more than one standard error from the maximum value obtained for this metric using any combination and number of terms used for the given algorithm.

In yet another aspect, the invention provides kits for determining the EDD for a pregnant female. The kit can include one or more agents for detection of biomarkers, a container for holding a biological sample isolated from a pregnant female; and printed instructions for reacting agents with the biological sample or a portion of the biological sample to detect the presence or amount of the isolated biomarkers in the biological sample. The agents can be packaged in separate containers. The kit can further comprise one or more control reference samples and reagents for performing an immunoassay.

The kit can comprise one or more containers for compositions or reagents contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods for separating a pregnancy that delivers before 270 days from a pregnancy that delivers on or after 280 days.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference. 5

TABLE 1

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| CATD_VGFAEAAR | 1 | TENX_LSQLSVTDVTTSSLR | 60 | 2.4E-06 | 0.839 |
| CATD_VGFAEAAR | 1 | TENX_LNWEAPPGAFDSFLLR | 61 | 1.7E-05 | 0.838 |
| CATD_VSTLPAITLK | 2 | TENX_LNWEAPPGAFDSFLLR | 61 | 7.5E-06 | 0.821 |
| CATD_VSTLPAITLK | 2 | TENX_LSQLSVTDVTTSSLR | 60 | 1.7E-06 | 0.813 |
| CATD_VGFAEAAR | 1 | SPRL1_VLTHSELAPLR | 62 | 3.0E-04 | 0.800 |
| APOC3_GWVTDGFSSLK | 3 | TENX_LSQLSVTDVTTSSLR | 60 | 1.9E-05 | 0.797 |
| APOC3_GWVTDGFSSLK | 3 | TENX_LNWEAPPGAFDSFLLR | 61 | 1.4E-05 | 0.792 |
| APOC3_GWVTDGFSSLK | 3 | IBP3_FLNVLSPR | 63 | 3.0E-05 | 0.790 |
| APOC3_GWVTDGFSSLK | 3 | IBP3_YGQPLPGYTTK | 64 | 4.6E-05 | 0.789 |
| APOC3_GWVTDGFSSLK | 3 | LYAM1_SYYWIGIR | 65 | 6.1E-05 | 0.788 |
| APOC3_GWVTDGFSSLK | 3 | SPRL1_VLTHSELAPLR | 62 | 1.6E-05 | 0.782 |
| CATD_VGFAEAAR | 1 | IBP3_YGQPLPGYTTK | 64 | 9.0E-04 | 0.782 |
| CATD_VGFAEAAR | 1 | CHL1_VIAVNEVGR | 66 | 4.1E-04 | 0.781 |
| APOC3_GWVTDGFSSLK | 3 | ALS_IRPHTFTGLSGLR | 67 | 4.7E-05 | 0.777 |
| CATD_VSTLPAITLK | 2 | IBP3_YGQPLPGYTTK | 64 | 4.9E-04 | 0.777 |
| APOC3_GWVTDGFSSLK | 3 | IGF2_GIVEECCFR | 68 | 7.1E-05 | 0.773 |
| IBP4_QCHPALDGQR | 4 | TENX_LNWEAPPGAFDSFLLR | 61 | 4.0E-06 | 0.773 |
| APOC3_GWVTDGFSSLK | 3 | PGRP2_AGLLRPDYALLGHR | 69 | 1.8E-04 | 0.773 |
| CATD_VGFAEAAR | 1 | IGF2_GIVEECCFR | 68 | 1.8E-03 | 0.773 |
| VTNC_VDTVDPPYPR | 5 | TENX_LNWEAPPGAFDSFLLR | 61 | 4.8E-06 | 0.773 |
| APOC3_GWVTDGFSSLK | 3 | CRIS3_YEDLYSNCK | 70 | 7.4E-05 | 0.771 |
| APOC3_GWVTDGFSSLK | 3 | TIE1_VSWSLPLVPGPLVGDGFLLR | 71 | 2.2E-05 | 0.770 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| CATD_VGFAEAAR | 1 | LYAM1_SYYWIGIR | 65 | 8.4E-04 | 0.770 |
| IBP4_QCHPALDGQR | 4 | TENX_LSQLSVTDVTTSSLR | 60 | 7.1E-06 | 0.770 |
| CATD_VGFAEAAR | 1 | TIE1_VSWSLPLVPGPLVGDGFLLR | 71 | 4.7E-04 | 0.769 |
| APOC3_GWVTDGFSSLK | 3 | CRIS3_AVSPPAR | 72 | 1.0E-04 | 0.767 |
| CATD_VSTLPAITLK | 2 | SPRL1_VLTHSELAPLR | 62 | 3.0E-04 | 0.766 |
| APOC3_GWVTDGFSSLK | 3 | VTDB_ELPEHTVK | 36 | 2.2E-05 | 0.766 |
| CATD_VGFAEAAR | 1 | PGRP2_AGLLRPDYALLGHR | 69 | 2.7E-03 | 0.764 |
| B2MG_VNHVTLSQPK | 6 | TENX_LSQLSVTDVTTSSLR | 60 | 1.5E-05 | 0.763 |
| CATD_VGFAEAAR | 1 | IBP3_FLNVLSPR | 63 | 1.2E-03 | 0.763 |
| VTNC_GQYCYELDEK | 7 | TENX_LNWEAPPGAFDSFLLR | 61 | 1.8E-05 | 0.762 |
| APOC3_GWVTDGFSSLK | 3 | HEMO_NFPSPVDAAFR | 26 | 3.0E-05 | 0.761 |
| CATD_VSTLPAITLK | 2 | CHL1_VIAVNEVGR | 66 | 3.6E-04 | 0.761 |
| VTNC_VDTVDPPYPR | 5 | TENX_LSQLSVTDVTTSSLR | 60 | 2.1E-05 | 0.761 |
| APOC3_GWVTDGFSSLK | 3 | HABP2_FLNWIK | 48 | 1.4E-01 | 0.760 |
| CD14_SWLAELQQWLKPGLK | 8 | TENX_LNWEAPPGAFDSFLLR | 61 | 1.5E-05 | 0.760 |
| INHBC_LDFHFSSDR | 9 | TENX_LNWEAPPGAFDSFLLR | 61 | 8.6E-06 | 0.760 |
| APOC3_GWVTDGFSSLK | 3 | FETUA_FSVVYAK | 50 | 3.6E-05 | 0.759 |
| APOC3_GWVTDGFSSLK | 3 | PEDF_TVQAVLTVPK | 44 | 6.5E-05 | 0.759 |
| CO5_VFQFLEK | 10 | TENX_LNWEAPPGAFDSFLLR | 61 | 1.1E-05 | 0.758 |
| APOC3_GWVTDGFSSLK | 3 | FETUA_HTLNQIDEVK | 51 | 2.3E-05 | 0.758 |
| INHBC_LDFHFSSDR | 9 | TENX_LSQLSVTDVTTSSLR | 60 | 2.0E-05 | 0.757 |
| APOC3_GWVTDGFSSLK | 3 | CHL1_VIAVNEVGR | 66 | 6.8E-05 | 0.756 |
| B2MG_VNHVTLSQPK | 6 | TENX_LNWEAPPGAFDSFLLR | 61 | 8.4E-06 | 0.756 |
| CATD_VGFAEAAR | 1 | CRIS3_YEDLYSNCK | 70 | 2.1E-03 | 0.756 |
| CATD_VSTLPAITLK | 2 | IGF2_GIVEECCFR | 68 | 1.2E-03 | 0.755 |
| APOC3_GWVTDGFSSLK | 3 | CO6_ALNHLPLEYNSALYSR | 37 | 2.4E-05 | 0.755 |
| CATD_VSTLPAITLK | 2 | IBP3_FLNVLSPR | 63 | 7.0E-04 | 0.753 |
| CATD_VGFAEAAR | 1 | CRIS3_AVSPPAR | 72 | 7.7E-03 | 0.752 |
| IBP4_QCHPALDGQR | 4 | SPRL1_VLTHSELAPLR | 62 | 1.3E-04 | 0.752 |
| APOC3_GWVTDGFSSLK | 3 | CBPN_EALIQFLEQVHQGIK | 55 | 2.0E-04 | 0.751 |
| KNG1_QVVAGLNFR | 11 | TENX_LNWEAPPGAFDSFLLR | 61 | 2.4E-05 | 0.751 |
| CD14_SWLAELQQWLKPGLK | 8 | TENX_LSQLSVTDVTTSSLR | 60 | 8.0E-05 | 0.750 |
| APOC3_GWVTDGFSSLK | 3 | KNG1_DIPTNSPELEETLTHTITK | 27 | 2.4E-05 | 0.749 |
| CATD_VGFAEAAR | 1 | ALS_IRPHTFTGLSGLR | 67 | 2.9E-03 | 0.747 |
| KNG1_QVVAGLNFR | 11 | TENX_LSQLSVTDVTTSSLR | 60 | 4.1E-05 | 0.747 |
| APOC3_GWVTDGFSSLK | 3 | ANGT_DPTFIPAPIQAK | 20 | 6.4E-05 | 0.746 |
| CATD_VGFAEAAR | 1 | FETUA_HTLNQIDEVK | 51 | 2.3E-02 | 0.746 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| APOC3_GWVTDGFSSLK | 3 | NCAM1_GLGEISAASEFK | 54 | 1.6E-04 | 0.745 |
| B2MG_VNHVTLSQPK | 6 | LYAM1_SYYWIGIR | 65 | 9.1E-05 | 0.745 |
| VTNC_VDTVDPPYPR | 5 | IBP3_YGQPLPGYTTK | 64 | 1.2E-04 | 0.745 |
| APOC3_GWVTDGFSSLK | 3 | BGH3_LTLLAPLNSVFK | 73 | 4.5E-05 | 0.744 |
| APOC3_GWVTDGFSSLK | 3 | PTGDS_GPGEDFR | 53 | 2.4E-03 | 0.744 |
| APOC3_GWVTDGFSSLK | 3 | AFAM_DADPDTFFAK | 41 | 1.0E-04 | 0.744 |
| B2MG_VNHVTLSQPK | 6 | CRIS3_AVSPPAR | 72 | 5.3E-04 | 0.743 |
| APOC3_GWVTDGFSSLK | 3 | APOH_ATVVYQGER | 22 | 7.0E-04 | 0.742 |
| CATD_VSTLPAITLK | 2 | TIE1_VSWSLPLVPGPLVGDGFLLR | 71 | 5.3E-04 | 0.742 |
| B2MG_VNHVTLSQPK | 6 | SPRL1_VLTHSELAPLR | 62 | 2.1E-04 | 0.741 |
| LBP_ITGFLKPGK | 12 | TENX_LNWEAPPGAFDSFLLR | 61 | 9.1E-05 | 0.741 |
| B2MG_VNHVTLSQPK | 6 | IBP3_YGQPLPGYTTK | 64 | 1.8E-04 | 0.741 |
| CATD_VGFAEAAR | 1 | NCAM1_GLGEISAASEFK | 54 | 6.8E-04 | 0.741 |
| CO5_VFQFLEK | 10 | TENX_LSQLSVTDVTTSSLR | 60 | 4.6E-05 | 0.741 |
| CD14_LTVGAAQVPAQLLVGALR | 13 | TENX_LNWEAPPGAFDSFLLR | 61 | 4.1E-05 | 0.740 |
| APOC3_GWVTDGFSSLK | 3 | AFAM_HFQNLGK | 39 | 1.6E-04 | 0.740 |
| APOC3_GWVTDGFSSLK | 3 | SOM2.CSH_NYGLLYCFR | 38 | 3.6E-04 | 0.740 |
| B2MG_VNHVTLSQPK | 6 | CHL1_VIAVNEVGR | 66 | 1.3E-03 | 0.739 |
| CATD_VSTLPAITLK | 2 | LYAM1_SYYWIGIR | 65 | 8.1E-04 | 0.739 |
| APOC3_GWVTDGFSSLK | 3 | CO8A_SLLQPNK | 31 | 1.4E-04 | 0.739 |
| APOC3_GWVTDGFSSLK | 3 | SHBG_IALGGLLFPASNLR | 74 | 5.1E-04 | 0.739 |
| CATD_VGFAEAAR | 1 | PEDF_TVQAVLTVPK | 44 | 5.9E-03 | 0.739 |
| CO5_VFQFLEK | 10 | SPRL1_VLTHSELAPLR | 62 | 3.7E-04 | 0.739 |
| APOC3_GWVTDGFSSLK | 3 | CSH_AHQLAIDTYQEFEETYIPK | 33 | 3.9E-04 | 0.738 |
| APOC3_GWVTDGFSSLK | 3 | KNG1_QVVAGLNFR | 11 | 1.7E-04 | 0.738 |
| B2MG_VEHSDLSFSK | 14 | TENX_LSQLSVTDVTTSSLR | 60 | 6.1E-05 | 0.738 |
| CO5_VFQFLEK | 10 | IBP3_YGQPLPGYTTK | 64 | 4.0E-04 | 0.738 |
| CO5_VFQFLEK | 10 | LYAM1_SYYWIGIR | 65 | 1.2E-04 | 0.737 |
| IBP6_HLDSVLQQLQTEVYR | 15 | TENX_LNWEAPPGAFDSFLLR | 61 | 6.4E-05 | 0.737 |
| ITIH3_ALDLSLK | 16 | LYAM1_SYYWIGIR | 65 | 9.4E-04 | 0.737 |
| APOC3_GWVTDGFSSLK | 3 | C163A_INPASLDK | 75 | 1.0E-04 | 0.737 |
| B2MG_VEHSDLSFSK | 14 | TENX_LNWEAPPGAFDSFLLR | 61 | 4.6E-05 | 0.737 |
| CATD_VGFAEAAR | 1 | PTGDS_GPGEDFR | 53 | 1.1E-03 | 0.736 |
| VTNC_GQYCYELDEK | 7 | TENX_LSQLSVTDVTTSSLR | 60 | 7.7E-05 | 0.736 |
| CATD_VGFAEAAR | 1 | FETUA_FSVVYAK | 50 | 3.2E-02 | 0.736 |
| CATD_VSTLPAITLK | 2 | PGRP2_AGLLRPDYALLGHR | 69 | 2.3E-03 | 0.736 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| APOC3_GWVTDGFSSLK | 3 | F13B_GDTYPAELYITGSILR | 46 | 2.0E-04 | 0.735 |
| CATD_VGFAEAAR | 1 | AFAM_DADPDTFFAK | 41 | 1.1E-02 | 0.735 |
| APOC3_GWVTDGFSSLK | 3 | PEDF_LQSLFDSPDFSK | 24 | 4.9E-04 | 0.735 |
| B2MG_VNHVTLSQPK | 6 | IGF2_GIVEECCFR | 68 | 4.7E-04 | 0.735 |
| APOC3_GWVTDGFSSLK | 3 | CBPN_NNANGVDLNR | 42 | 4.8E-04 | 0.734 |
| APOC3_GWVTDGFSSLK | 3 | THBG_AVLHIGEK | 49 | 7.8E-05 | 0.734 |
| CATD_VSTLPAITLK | 2 | CRIS3_YEDLYSNCK | 70 | 1.8E-03 | 0.734 |
| CO5_TLLPVSKPEIR | 17 | TENX_LNWEAPPGAFDSFLLR | 61 | 6.0E-05 | 0.734 |
| APOC3_GWVTDGFSSLK | 3 | PSG3_VSAPSGTGHLPGLNPL | 76 | 4.1E-04 | 0.734 |
| ENPP2_TYLHTYESEI | 18 | TENX_LNWEAPPGAFDSFLLR | 61 | 8.7E-04 | 0.734 |
| LBP_ITGFLKPGK | 12 | LYAM1_SYYWIGIR | 65 | 1.7E-03 | 0.733 |
| CATD_VGFAEAAR | 1 | AFAM_HFQNLGK | 39 | 8.4E-03 | 0.733 |
| CATD_VGFAEAAR | 1 | CBPN_EALIQFLEQVHQGIK | 55 | 5.6E-03 | 0.733 |
| SOM2.CSH_SVEGSCGF | 19 | TENX_LNWEAPPGAFDSFLLR | 61 | 3.8E-04 | 0.733 |
| ANGT_DPTFIPAPIQAK | 20 | TENX_LNWEAPPGAFDSFLLR | 61 | 1.6E-04 | 0.732 |
| B2MG_VNHVTLSQPK | 6 | CRIS3_YEDLYSNCK | 70 | 2.5E-04 | 0.732 |
| CATD_VGFAEAAR | 1 | HEMO_NFPSPVDAAFR | 26 | 4.5E-03 | 0.732 |
| CD14_LTVGAAQVPAQLLVGALR | 13 | TENX_LSQLSVTDVTTSSLR | 60 | 2.1E-04 | 0.732 |
| LBP_ITLPDFTGDLR | 21 | LYAM1_SYYWIGIR | 65 | 1.1E-03 | 0.732 |
| LBP_ITLPDFTGDLR | 21 | TENX_LNWEAPPGAFDSFLLR | 61 | 8.9E-05 | 0.732 |
| APOC3_GWVTDGFSSLK | 3 | CLUS_LFDSDPITVTVPVEVSR | 56 | 1.6E-04 | 0.732 |
| APOC3_GWVTDGFSSLK | 3 | CO8B_QALEEFQK | 28 | 3.5E-04 | 0.731 |
| CATD_VGFAEAAR | 1 | CO6_ALNHLPLEYNSALYSR | 37 | 3.7E-03 | 0.731 |
| CATD_VGFAEAAR | 1 | F13B_GDTYPAELYITGSILR | 46 | 2.6E-03 | 0.731 |
| IBP6_HLDSVLQQLQTEVYR | 15 | TENX_LSQLSVTDVTTSSLR | 60 | 8.9E-05 | 0.731 |
| APOH_ATVVYQGER | 22 | TENX_LNWEAPPGAFDSFLLR | 61 | 1.9E-04 | 0.730 |
| ENPP2_TYLHTYESEI | 18 | TENX_LSQLSVTDVTTSSLR | 60 | 9.9E-04 | 0.730 |
| VTNC_GQYCYELDEK | 7 | IBP3_YGQPLPGYTTK | 64 | 6.7E-04 | 0.730 |
| APOC3_GWVTDGFSSLK | 3 | CLUS_ASSIIDELFQDR | 34 | 2.6E-04 | 0.730 |
| APOC3_GWVTDGFSSLK | 3 | IBP6_GAQTLYVPNCDHR | 40 | 3.9E-04 | 0.730 |
| APOC3_GWVTDGFSSLK | 3 | ITIH4_ILDDLSPR | 30 | 3.2E-04 | 0.730 |
| CATD_VSTLPAITLK | 2 | ALS_IRPHTFTGLSGLR | 67 | 2.1E-03 | 0.730 |
| CFAB_YGLVTYATYPK | 23 | TENX_LNWEAPPGAFDSFLLR | 61 | 1.2E-04 | 0.730 |
| PEDF_LQSLFDSPDFSK | 24 | TENX_LNWEAPPGAFDSFLLR | 61 | 2.8E-04 | 0.730 |
| ENPP2_TEFLSNYLTNVDDITLVPGTLGR | 25 | TENX_LSQLSVTDVTTSSLR | 60 | 1.2E-03 | 0.729 |
| APOC3_GWVTDGFSSLK | 3 | CO5_TLLPVSKPEIR | 17 | 4.3E-04 | 0.728 |
| ENPP2_TEFLSNYLTNVDDITLVPGTLGR | 25 | TENX_LNWEAPPGAFDSFLLR | 61 | 9.2E-04 | 0.728 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| HEMO_NFPSPVDAAFR | 26 | TENX_LNWEAPPGAFDSFLLR | 61 | 1.5E-04 | 0.727 |
| IBP4_QCHPALDGQR | 4 | CRIS3_YEDLYSNCK | 70 | 1.6E-04 | 0.727 |
| KNG1_DIPTNSPELEETLTHTITK | 27 | TENX_LNWEAPPGAFDSFLLR | 61 | 9.0E-05 | 0.727 |
| LBP_ITGFLKPGK | 12 | TENX_LSQLSVTDVTTSSLR | 60 | 1.4E-04 | 0.727 |
| IBP4_QCHPALDGQR | 4 | CRIS3_AVSPPAR | 72 | 2.3E-04 | 0.727 |
| CATD_VGFAEAAR | 1 | VTDB_ELPEHTVK | 36 | 5.4E-03 | 0.727 |
| CO8B_QALEEFQK | 28 | TENX_LNWEAPPGAFDSFLLR | 61 | 7.6E-05 | 0.727 |
| LBP_ITGFLKPGK | 12 | CHL1_VIAVNEVGR | 66 | 2.2E-03 | 0.727 |
| VTNC_VDTVDPPYPR | 5 | IBP3_FLNVLSPR | 63 | 3.2E-04 | 0.726 |
| CATD_VGFAEAAR | 1 | SHBG_IALGGLLFPASNLR | 74 | 7.7E-03 | 0.726 |
| APOC3_GWVTDGFSSLK | 3 | CD14_LTVGAAQVPAQLLVGALR | 13 | 3.5E-04 | 0.726 |
| CATD_VGFAEAAR | 1 | THBG_AVLHIGEK | 49 | 1.0E-02 | 0.726 |
| CO5_TLLPVSKPEIR | 17 | TENX_LSQLSVTDVTTSSLR | 60 | 1.5E-04 | 0.725 |
| IBP4_QCHPALDGQR | 4 | IBP3_YGQPLPGYTTK | 64 | 2.4E-04 | 0.725 |
| B2MG_VNHVTLSQPK | 6 | IBP3_FLNVLSPR | 63 | 2.9E-04 | 0.724 |
| CO5_VFQFLEK | 10 | IBP3_FLNVLSPR | 63 | 9.6E-04 | 0.724 |
| APOC3_GWVTDGFSSLK | 3 | CD14_SWLAELQQWLKPGLK | 8 | 8.2E-04 | 0.724 |
| IBP4_QCHPALDGQR | 4 | CHL1_VIAVNEVGR | 66 | 5.6E-04 | 0.723 |
| ITIH3_ALDLSLK | 16 | TENX_LNWEAPPGAFDSFLLR | 61 | 1.1E-04 | 0.723 |
| LBP_ITLPDFTGDLR | 21 | CRIS3_YEDLYSNCK | 70 | 2.4E-04 | 0.723 |
| IBP4_QCHPALDGQR | 4 | LYAM1_SYYWIGIR | 65 | 2.6E-04 | 0.722 |
| PEDF_LQSLFDSPDFSK | 24 | TENX_LSQLSVTDVTTSSLR | 60 | 3.8E-04 | 0.722 |
| LBP_ITGFLKPGK | 12 | CRIS3_YEDLYSNCK | 70 | 2.2E-04 | 0.722 |
| APOC3_GWVTDGFSSLK | 3 | CSH_ISLLLIESWLEPVR | 43 | 1.4E-03 | 0.722 |
| CATD_VGFAEAAR | 1 | HABP2_FLNWIK | 48 | 4.0E-01 | 0.722 |
| ENPP2_TYLHTYESEI | 18 | CRIS3_YEDLYSNCK | 70 | 1.0E-02 | 0.722 |
| ENPP2_TYLHTYESEI | 18 | LYAM1_SYYWIGIR | 65 | 1.1E-02 | 0.722 |
| A2GL_DLLLPQPDLR | 29 | TENX_LSQLSVTDVTTSSLR | 60 | 8.5E-04 | 0.721 |
| KNG1_QVVAGLNFR | 11 | CHL1_VIAVNEVGR | 66 | 1.1E-03 | 0.721 |
| LBP_ITGFLKPGK | 12 | IBP3_YGQPLPGYTTK | 64 | 9.0E-04 | 0.721 |
| CATD_VSTLPAITLK | 2 | CRIS3_AVSPPAR | 72 | 5.6E-03 | 0.721 |
| KNG1_QVVAGLNFR | 11 | SPRL1_VLTHSELAPLR | 62 | 9.0E-04 | 0.721 |
| LBP_ITLPDFTGDLR | 21 | CHL1_VIAVNEVGR | 66 | 1.8E-03 | 0.721 |
| A2GL_DLLLPQPDLR | 29 | TENX_LNWEAPPGAFDSFLLR | 61 | 2.1E-04 | 0.720 |
| LBP_ITLPDFTGDLR | 21 | TENX_LSQLSVTDVTTSSLR | 60 | 1.4E-04 | 0.720 |
| APOC3_GWVTDGFSSLK | 3 | IBP6_HLDSVLQQLQTEVYR | 15 | 4.1E-04 | 0.720 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| APOC3_GWVTDGFSSLK | 3 | PAPP1_DIPHWLNPTR | 77 | 1.1E-03 | 0.720 |
| ITIH3_ALDLSLK | 16 | TENX_LSQLSVTDVTTSSLR | 60 | 1.8E-04 | 0.720 |
| KNG1_DIPTNSPELEETLTHTITK | 27 | TENX_LSQLSVTDVTTSSLR | 60 | 1.8E-04 | 0.720 |
| APOC3_GWVTDGFSSLK | 3 | PRG2_WNFAYWAAHQPWSR | 78 | 1.2E-03 | 0.719 |
| CO5_VFQFLEK | 10 | CHL1_VIAVNEVGR | 66 | 4.6E-04 | 0.719 |
| INHBC_LDFHFSSDR | 9 | IBP3_YGQPLPGYTTK | 64 | 7.5E-04 | 0.719 |
| ITIH4_ILDDLSPR | 30 | TENX_LNWEAPPGAFDSFLLR | 61 | 1.3E-04 | 0.719 |
| LBP_ITLPDFTGDLR | 21 | IBP3_YGQPLPGYTTK | 64 | 1.3E-03 | 0.719 |
| CATD_VSTLPAITLK | 2 | FETUA_HTLNQIDEVK | 51 | 1.6E-02 | 0.718 |
| CATD_VSTLPAITLK | 2 | PTGDS_GPGEDFR | 53 | 1.6E-03 | 0.718 |
| CO8B_QALEEFQK | 28 | TENX_LSQLSVTDVTTSSLR | 60 | 2.7E-04 | 0.718 |
| VTNC_VDTVDPPYPR | 5 | ALS_IRPHTFTGLSGLR | 67 | 1.3E-03 | 0.718 |
| KNG1_QVVAGLNFR | 11 | IBP3_YGQPLPGYTTK | 64 | 1.0E-03 | 0.717 |
| VTNC_VDTVDPPYPR | 5 | CRIS3_YEDLYSNCK | 70 | 4.6E-04 | 0.717 |
| CATD_VGFAEAAR | 1 | PAPP1_DIPHWLNPTR | 77 | 3.5E-03 | 0.717 |
| APOC3_GWVTDGFSSLK | 3 | VTNC_GQYCYELDEK | 7 | 3.6E-04 | 0.716 |
| VTNC_GQYCYELDEK | 7 | IBP3_FLNVLSPR | 63 | 1.6E-03 | 0.716 |
| CO8A_SLLQPNK | 31 | TENX_LNWEAPPGAFDSFLLR | 61 | 4.1E-04 | 0.716 |
| ENPP2_TEFLSNYLTNVDDITLVPGTLGR | 25 | CRIS3_YEDLYSNCK | 70 | 7.9E-03 | 0.716 |
| LBP_ITLPDFTGDLR | 21 | CRIS3_AVSPPAR | 72 | 4.1E-04 | 0.716 |
| APOC3_GWVTDGFSSLK | 3 | CO5_VFQFLEK | 10 | 1.0E-03 | 0.716 |
| LBP_ITGFLKPGK | 12 | CRIS3_AVSPPAR | 72 | 6.2E-04 | 0.716 |
| VTNC_GQYCYELDEK | 7 | LYAM1_SYYWIGIR | 65 | 8.7E-04 | 0.716 |
| CATD_VGFAEAAR | 1 | IBP6_GAQTLYVPNCDHR | 40 | 3.8E-03 | 0.715 |
| APOH_ATVVYQGER | 22 | TENX_LSQLSVTDVTTSSLR | 60 | 3.4E-04 | 0.715 |
| VTNC_VDTVDPPYPR | 5 | SPRL1_VLTHSELAPLR | 62 | 6.0E-04 | 0.715 |
| ENPP2_TYLHTYESEI | 18 | CRIS3_AVSPPAR | 72 | 1.5E-02 | 0.714 |
| CATD_VGFAEAAR | 1 | CBPN_NNANGVDLNR | 42 | 1.5E-02 | 0.714 |
| ENPP2_TEFLSNYLTNVDDITLVPGTLGR | 25 | LYAM1_SYYWIGIR | 65 | 1.1E-02 | 0.714 |
| APOC3_GWVTDGFSSLK | 3 | ITIH4_NPLVWVHASPEHVVVTR | 45 |  | 0.713 |
| B2MG_VEHSDLSFSK | 14 | LYAM1_SYYWIGIR | 65 | 6.3E-04 | 0.713 |
| VTNC_VDTVDPPYPR | 5 | LYAM1_SYYWIGIR | 65 | 1.3E-03 | 0.713 |
| CATD_VGFAEAAR | 1 | PRG2_WNFAYWAAHQPWSR | 78 | 2.4E-03 | 0.713 |
| CD14_SWLAELQQWLKPGLK | 8 | IBP3_YGQPLPGYTTK | 64 | 5.4E-04 | 0.713 |
| ENPP2_TEFLSNYLTNVDDITLVPGTLGR | 25 | CRIS3_AVSPPAR | 72 | 1.2E-02 | 0.713 |
| IBP4_QCHPALDGQR | 4 | IBP3_FLNVLSPR | 63 | 3.7E-04 | 0.712 |
| ITIH4_ILDDLSPR | 30 | TENX_LSQLSVTDVTTSSLR | 60 | 3.0E-04 | 0.712 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| CATD_VGFAEAAR | 1 | ITIH4_ILDDLSPR | 30 | 1.0E-02 | 0.711 |
| VTNC_VDTVDPPYPR | 5 | CHL1_VIAVNEVGR | 66 | 6.2E-04 | 0.711 |
| B2MG_VEHSDLSFSK | 14 | CHL1_VIAVNEVGR | 66 | 3.5E-03 | 0.711 |
| B2MG_VEHSDLSFSK | 14 | SPRL1_VLTHSELAPLR | 62 | 1.4E-03 | 0.711 |
| CFAB_YGLVTYATYPK | 23 | TENX_LSQLSVTDVTTSSLR | 60 | 5.4E-04 | 0.711 |
| HEMO_NFPSPVDAAFR | 26 | TENX_LSQLSVTDVTTSSLR | 60 | 6.7E-04 | 0.711 |
| C1QB_VPGLYYFTYHASSR | 32 | TENX_LNWEAPPGAFDSFLLR | 61 | 2.7E-03 | 0.710 |
| CSH_AHQLAIDTYQEFEETYIPK | 33 | TENX_LNWEAPPGAFDSFLLR | 61 | 9.6E-04 | 0.710 |
| CATD_VGFAEAAR | 1 | KNG1_DIPTNSPELEETLTHTITK | 27 | 1.3E-02 | 0.710 |
| ITIH3_ALDLSLK | 16 | CHL1_VIAVNEVGR | 66 | 3.8E-03 | 0.710 |
| VTNC_VDTVDPPYPR | 5 | IGF2_GIVEECCFR | 68 | 8.6E-04 | 0.710 |
| APOC3_GWVTDGFSSLK | 3 | VTNC_VDTVDPPYPR | 5 | 5.6E-04 | 0.709 |
| VTNC_GQYCYELDEK | 7 | IGF2_GIVEECCFR | 68 | 3.7E-03 | 0.709 |
| INHBC_LDFHFSSDR | 9 | IBP3_FLNVLSPR | 63 | 8.8E-04 | 0.709 |
| ITIH3_ALDLSLK | 16 | CRIS3_AVSPPAR | 72 | 1.7E-03 | 0.708 |
| KNG1_QVVAGLNFR | 11 | LYAM1_SYYWIGIR | 65 | 9.7E-04 | 0.708 |
| ITIH3_ALDLSLK | 16 | CRIS3_YEDLYSNCK | 70 | 1.5E-03 | 0.707 |
| SOM2.CSH_SVEGSCGF | 19 | TENX_LSQLSVTDVTTSSLR | 60 | 7.0E-04 | 0.707 |
| CLUS_ASSIIDELFQDR | 34 | TENX_LSQLSVTDVTTSSLR | 60 | 5.1E-04 | 0.706 |
| CATD_VGFAEAAR | 1 | C163A_INPASLDK | 75 | 1.3E-02 | 0.705 |
| ITIH4_ILDDLSPR | 30 | CHL1_VIAVNEVGR | 66 | 2.6E-03 | 0.705 |
| VTNC_VDTVDPPYPR | 5 | CRIS3_AVSPPAR | 72 | 7.1E-04 | 0.705 |
| CLUS_ASSIIDELFQDR | 34 | TENX_LNWEAPPGAFDSFLLR | 61 | 2.2E-04 | 0.705 |
| CO5_VFQFLEK | 10 | CRIS3_YEDLYSNCK | 70 | 6.7E-04 | 0.705 |
| ITIH3_ALDLSLK | 16 | SPRL1_VLTHSELAPLR | 62 | 3.5E-03 | 0.705 |
| INHBC_LDFHFSSDR | 9 | SPRL1_VLTHSELAPLR | 62 | 1.5E-03 | 0.705 |
| B2MG_VNHVTLSQPK | 6 | TIE1_VSWSLPLVPGPLVGDGFLLR | 71 | 3.8E-03 | 0.703 |
| CATD_VGFAEAAR | 1 | IBP6_HLDSVLQQLQTEVYR | 15 | 5.5E-03 | 0.703 |
| VTNC_GQYCYELDEK | 7 | ALS_IRPHTFTGLSGLR | 67 | 3.5E-03 | 0.703 |
| VTNC_GQYCYELDEK | 7 | CHL1_VIAVNEVGR | 66 | 1.7E-03 | 0.703 |
| LBP_ITLPDFTGDLR | 21 | SPRL1_VLTHSELAPLR | 62 | 6.9E-04 | 0.703 |
| B2MG_VEHSDLSFSK | 14 | CRIS3_YEDLYSNCK | 70 | 8.6E-04 | 0.702 |
| CO5_VFQFLEK | 10 | CRIS3_AVSPPAR | 72 | 6.2E-04 | 0.702 |
| CO5_VFQFLEK | 10 | IGF2_GIVEECCFR | 68 | 1.3E-03 | 0.702 |
| ANGT_DPTFIPAPIQAK | 20 | TENX_LSQLSVTDVTTSSLR | 60 | 3.6E-04 | 0.702 |
| B2MG_VNHVTLSQPK | 6 | ALS_IRPHTFTGLSGLR | 67 | 1.4E-03 | 0.702 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| CATD_VGFAEAAR | 1 | ANGT_DPTFIPAPIQAK | 20 | 1.2E-02 | 0.702 |
| CATD_VGFAEAAR | 1 | SOM2.CSH_NYGLLYCFR | 38 | 2.5E-03 | 0.702 |
| IBP2_LIQGAPTIR | 35 | TENX_LNWEAPPGAFDSFLLR | 61 | 5.3E-03 | 0.702 |
| VTDB_ELPEHTVK | 36 | TENX_LNWEAPPGAFDSFLLR | 61 | 3.8E-04 | 0.702 |
| CATD_VGFAEAAR | 1 | PEDF_LQSLFDSPDFSK | 24 | 8.2E-03 | 0.701 |
| APOC3_GWVTDGFSSLK | 3 | IBP4_QCHPALDGQR | 4 | 1.3E-03 | 0.701 |
| C1QB_VPGLYYFTYHASSR | 32 | TENX_LSQLSVTDVTTSSLR | 60 | 2.8E-03 | 0.701 |
| CATD_VGFAEAAR | 1 | APOH_ATVVYQGER | 22 | 1.4E-02 | 0.701 |
| CD14_SWLAELQQWLKPGLK | 8 | IBP3_FLNVLSPR | 63 | 1.2E-03 | 0.701 |
| CO5_TLLPVSKPEIR | 17 | IBP3_YGQPLPGYTTK | 64 | 1.3E-03 | 0.701 |
| CO5_VFQFLEK | 10 | ALS_IRPHTFTGLSGLR | 67 | 3.7E-03 | 0.701 |
| INHBC_LDFHFSSDR | 9 | CHL1_VIAVNEVGR | 66 | 9.3E-04 | 0.701 |
| ITIH4_ILDDLSPR | 30 | LYAM1_SYYWIGIR | 65 | 3.7E-03 | 0.700 |
| B2MG_VEHSDLSFSK | 14 | CRIS3_AVSPPAR | 72 | 2.1E-03 | 0.700 |
| B2MG_VEHSDLSFSK | 14 | IBP3_YGQPLPGYTTK | 64 | 7.1E-04 | 0.700 |
| INHBC_LDFHFSSDR | 9 | IGF2_GIVEECCFR | 68 | 1.3E-03 | 0.700 |
| LBP_ITGFLKPGK | 12 | IBP3_FLNVLSPR | 63 | 1.2E-03 | 0.700 |
| APOC3_GWVTDGFSSLK | 3 | FBLN1_TGYYFDGISR | 79 | 2.3E-02 | 0.699 |
| CO5_VFQFLEK | 10 | TIE1_VSWSLPLVPGPLVGDGFLLR | 71 | 3.3E-03 | 0.699 |
| INHBC_LDFHFSSDR | 9 | LYAM1_SYYWIGIR | 65 | 1.1E-03 | 0.699 |
| CFAB_YGLVTYATYPK | 23 | IBP3_FLNVLSPR | 63 | 5.3E-03 | 0.699 |
| CO5_TLLPVSKPEIR | 17 | SPRL1_VLTHSELAPLR | 62 | 6.5E-03 | 0.699 |
| CO6_ALNHLPLEYNSALYSR | 37 | TENX_LNWEAPPGAFDSFLLR | 61 | 1.1E-03 | 0.699 |
| IBP4_QCHPALDGQR | 4 | PGRP2_AGLLRPDYALLGHR | 69 | 2.4E-03 | 0.699 |
| KNG1_QVVAGLNFR | 11 | CRIS3_YEDLYSNCK | 70 | 8.5E-04 | 0.699 |
| LBP_ITGFLKPGK | 12 | SPRL1_VLTHSELAPLR | 62 | 9.0E-04 | 0.699 |
| CATD_VSTLPAITLK | 2 | CO6_ALNHLPLEYNSALYSR | 37 | 3.3E-03 | 0.698 |
| LBP_ITGFLKPGK | 12 | PGRP2_AGLLRPDYALLGHR | 69 | 2.5E-03 | 0.698 |
| VTNC_GQYCYELDEK | 7 | CRIS3_AVSPPAR | 72 | 1.2E-03 | 0.698 |
| B2MG_VEHSDLSFSK | 14 | IGF2_GIVEECCFR | 68 | 1.4E-03 | 0.698 |
| CATD_VSTLPAITLK | 2 | HEMO_NFPSPVDAAFR | 26 | 4.9E-03 | 0.698 |
| CATD_VSTLPAITLK | 2 | PEDF_TVQAVLTVPK | 44 | 5.6E-03 | 0.698 |
| CFAB_YGLVTYATYPK | 23 | IBP3_YGQPLPGYTTK | 64 | 2.6E-03 | 0.698 |
| CO8B_QALEEFQK | 28 | IBP3_YGQPLPGYTTK | 64 | 1.2E-03 | 0.698 |
| IBP4_QCHPALDGQR | 4 | IGF2_GIVEECCFR | 68 | 7.1E-04 | 0.698 |
| INHBC_LDFHFSSDR | 9 | TIE1_VSWSLPLVPGPLVGDGFLLR | 71 | 3.3E-03 | 0.698 |
| LBP_ITLPDFTGDLR | 21 | IBP3_FLNVLSPR | 63 | 1.3E-03 | 0.698 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| SOM2.CSH_NYGLLYCFR | 38 | TENX_LNWEAPPGAFDSFLLR | 61 | 1.4E-03 | 0.698 |
| A2GL_DLLLPQPDLR | 29 | LYAM1_SYYWIGIR | 65 | 2.8E-03 | 0.697 |
| AFAM_HFQNLGK | 39 | TENX_LNWEAPPGAFDSFLLR | 61 | 9.2E-04 | 0.697 |
| CATD_VGFAEAAR | 1 | PSG3_VSAPSGTGHLPGLNPL | 76 | 1.2E-02 | 0.697 |
| CFAB_YGLVTYATYPK | 23 | LYAM1_SYYWIGIR | 65 | 1.1E-03 | 0.697 |
| IBP6_GAQTLYVPNCDHR | 40 | TENX_LNWEAPPGAFDSFLLR | 61 | 9.3E-04 | 0.697 |
| A2GL_DLLLPQPDLR | 29 | SPRL1_VLTHSELAPLR | 62 | 9.2E-03 | 0.697 |
| INHBC_LDFHFSSDR | 9 | CRIS3_AVSPPAR | 72 | 1.5E-03 | 0.697 |
| VTNC_GQYCYELDEK | 7 | SPRL1_VLTHSELAPLR | 62 | 2.9E-03 | 0.697 |
| CATD_VGFAEAAR | 1 | BGH3_LTLLAPLNSVFK | 73 | 1.5E-02 | 0.696 |
| CSH_AHQLAIDTYQEFEETYIPK | 33 | TENX_LSQLSVTDVTTSSLR | 60 | 2.2E-03 | 0.696 |
| ENPP2_TYLHTYESEI | 18 | IBP3_YGQPLPGYTTK | 64 | 4.4E-03 | 0.696 |
| AFAM_DADPDTFFAK | 41 | TENX_LNWEAPPGAFDSFLLR | 61 | 7.6E-04 | 0.695 |
| CATD_VSTLPAITLK | 2 | NCAM1_GLGEISAASEFK | 54 | 1.4E-03 | 0.695 |
| CATD_VSTLPAITLK | 2 | FETUA_FSVVYAK | 50 | 2.3E-02 | 0.695 |
| ENPP2_TEFLSNYLTNVDDITLVPGTLGR | 25 | CHL1_VIAVNEVGR | 66 | 3.4E-03 | 0.695 |
| B2MG_VEHSDLSFSK | 14 | IBP3_FLNVLSPR | 63 | 1.1E-03 | 0.694 |
| CO5_TLLPVSKPEIR | 17 | LYAM1_SYYWIGIR | 65 | 1.2E-03 | 0.694 |
| LBP_ITGFLKPGK | 12 | IGF2_GIVEECCFR | 68 | 1.7E-03 | 0.694 |
| APOC3_GWVTDGFSSLK | 3 | B2MG_VNHVTLSQPK | 6 | 3.3E-03 | 0.694 |
| CO8B_QALEEFQK | 28 | IBP3_FLNVLSPR | 63 | 2.1E-03 | 0.694 |
| ENPP2_TYLHTYESEI | 18 | CHL1_VIAVNEVGR | 66 | 3.3E-03 | 0.694 |
| CATD_VSTLPAITLK | 2 | PAPP1_DIPHWLNPTR | 77 | 3.2E-03 | 0.693 |
| CATD_VSTLPAITLK | 2 | PRG2_WNFAYWAAHQPWSR | 78 | 2.5E-03 | 0.693 |
| CD14_SWLAELQQWLKPGLK | 8 | ALS_IRPHTFTGLSGLR | 67 | 1.9E-03 | 0.693 |
| CFAB_YGLVTYATYPK | 23 | CHL1_VIAVNEVGR | 66 | 5.6E-03 | 0.693 |
| VTNC_VDTVDPPYPR | 5 | VTDB_ELPEHTVK | 36 | 2.5E-03 | 0.693 |
| CATD_VSTLPAITLK | 2 | VTDB_ELPEHTVK | 36 | 4.9E-03 | 0.693 |
| CBPN_NNANGVDLNR | 42 | TENX_LNWEAPPGAFDSFLLR | 61 | 1.9E-03 | 0.693 |
| CD14_SWLAELQQWLKPGLK | 8 | LYAM1_SYYWIGIR | 65 | 1.8E-03 | 0.693 |
| CSH_ISLLLIESWLEPVR | 43 | TENX_LNWEAPPGAFDSFLLR | 61 | 1.4E-03 | 0.693 |
| LBP_ITGFLKPGK | 12 | ALS_IRPHTFTGLSGLR | 67 | 5.5E-03 | 0.693 |
| ENPP2_TYLHTYESEI | 18 | IGF2_GIVEECCFR | 68 | 1.4E-02 | 0.693 |
| LBP_ITGFLKPGK | 12 | TIE1_VSWSLPLVPGPLVGDGFLLR | 71 | 2.0E-03 | 0.693 |
| LBP_ITLPDFTGDLR | 21 | PGRP2_AGLLRPDYALLGHR | 69 | 2.3E-03 | 0.693 |
| A2GL_DLLLPQPDLR | 29 | IBP3_YGQPLPGYTTK | 64 | 1.6E-03 | 0.692 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| CATD_VGFAEAAR | 1 | CO5_TLLPVSKPEIR | 17 | 1.4E-02 | 0.692 |
| VTNC_GQYCYELDEK | 7 | CRIS3_YEDLYSNCK | 70 | 1.3E-03 | 0.692 |
| AFAM_HFQNLGK | 39 | TENX_LSQLSVTDVTTSSLR | 60 | 1.6E-03 | 0.692 |
| ENPP2_TYLHTYESEI | 18 | IBP3_FLNVLSPR | 63 | 5.5E-03 | 0.692 |
| INHBC_LDFHFSSDR | 9 | CRIS3_YEDLYSNCK | 70 | 1.2E-03 | 0.692 |
| LBP_ITLPDFTGDLR | 21 | ALS_IRPHTFTGLSGLR | 67 | 4.4E-03 | 0.692 |
| CATD_VSTLPAITLK | 2 | F13B_GDTYPAELYITGSILR | 46 | 3.6E-03 | 0.691 |
| CO5_TLLPVSKPEIR | 17 | IBP3_FLNVLSPR | 63 | 2.9E-03 | 0.691 |
| INHBC_LDFHFSSDR | 9 | PEDF_TVQAVLTVPK | 44 | 1.2E-03 | 0.691 |
| KNG1_QVVAGLNFR | 11 | IBP3_FLNVLSPR | 63 | 1.4E-03 | 0.691 |
| PEDF_TVQAVLTVPK | 44 | TENX_LNWEAPPGAFDSFLLR | 61 | 1.1E-03 | 0.691 |
| PEDF_TVQAVLTVPK | 44 | TENX_LSQLSVTDVTTSSLR | 60 | 2.0E-03 | 0.691 |
| CATD_VSTLPAITLK | 2 | AFAM_DADPDTFFAK | 41 | 1.0E-02 | 0.691 |
| AFAM_DADPDTFFAK | 41 | TENX_LSQLSVTDVTTSSLR | 60 | 1.1E-03 | 0.690 |
| CFAB_YGLVTYATYPK | 23 | ALS_IRPHTFTGLSGLR | 67 | 1.2E-02 | 0.690 |
| ITIH4_ILDDLSPR | 30 | SPRL1_VLTHSELAPLR | 62 | 1.2E-02 | 0.690 |
| CATD_VSTLPAITLK | 2 | AFAM_HFQNLGK | 39 | 7.4E-03 | 0.690 |
| CATD_VSTLPAITLK | 2 | HABP2_FLNWIK | 48 | 3.9E-01 | 0.690 |
| APOC3_GWVTDGFSSLK | 3 | A2GL_DLLLPQPDLR | 29 | 5.4E-03 | 0.689 |
| ITIH3_ALDLSLK | 16 | IBP3_YGQPLPGYTTK | 64 | 2.0E-03 | 0.689 |
| VTNC_VDTVDPPYPR | 5 | TIE1_VSWSLPLVPGPLVGDGFLLR | 71 | 1.1E-03 | 0.689 |
| A2GL_DLLLPQPDLR | 29 | CRIS3_YEDLYSNCK | 70 | 1.4E-03 | 0.689 |
| C1QB_VPGLYYFTYHASSR | 32 | IBP3_YGQPLPGYTTK | 64 | 3.5E-03 | 0.689 |
| CATD_VGFAEAAR | 1 | CLUS_ASSIIDELFQDR | 34 | 1.7E-02 | 0.689 |
| ENPP2_TYLHTYESEI | 18 | ALS_IRPHTFTGLSGLR | 67 | 1.9E-02 | 0.689 |
| ENPP2_TYLHTYESEI | 18 | SPRL1_VLTHSELAPLR | 62 | 6.8E-03 | 0.689 |
| IBP4_QCHPALDGQR | 4 | ALS_IRPHTFTGLSGLR | 67 | 3.8E-03 | 0.689 |
| INHBC_LDFHFSSDR | 9 | ALS_IRPHTFTGLSGLR | 67 | 2.3E-03 | 0.689 |
| CATD_VSTLPAITLK | 2 | SHBG_IALGGLLFPASNLR | 74 | 8.6E-03 | 0.688 |
| CD14_SWLAELQQWLKPGLK | 8 | SPRL1_VLTHSELAPLR | 62 | 1.5E-03 | 0.688 |
| C1QB_VPGLYYFTYHASSR | 32 | LYAM1_SYYWIGIR | 65 | 5.8E-03 | 0.688 |
| CATD_VGFAEAAR | 1 | CLUS_LFDSDPITVTVPVEVSR | 56 | 1.6E-02 | 0.688 |
| CO8A_SLLQPNK | 31 | TENX_LSQLSVTDVTTSSLR | 60 | 1.5E-03 | 0.688 |
| IBP6_GAQTLYVPNCDHR | 40 | TENX_LSQLSVTDVTTSSLR | 60 | 7.5E-04 | 0.688 |
| ITIH3_ALDLSLK | 16 | PGRP2_AGLLRPDYALLGHR | 69 | 1.8E-03 | 0.688 |
| CLUS_ASSIIDELFQDR | 34 | IBP3_YGQPLPGYTTK | 64 | 3.0E-03 | 0.688 |
| ENPP2_TEFLSNYLTNVDDITLVPGTLGR | 25 | IBP3_YGQPLPGYTTK | 64 | 3.3E-03 | 0.688 |

TABLE 1-continued

Reversals with AUC >=0.65, comprising blood draw windows starting from day 137 to 150 of gestation.

| P1 | SEQ ID NO:P2 | | SEQ ID NO: | p.value | AUC |
|---|---|---|---|---|---|
| LBP_ITGFLKPGK | 12 | CO6_ALNHLPLEYNSALYSR | 37 | 5.2E-03 | 0.688 |
| LBP_ITGFLKPGK | 12 | FETUA_HTLNQIDEVK | 51 | 2.0E-03 | 0.688 |
| LBP_ITLPDFTGDLR | 21 | TIE1_VSWSLPLVPGPLVGDGFLLR | 71 | 2.4E-03 | 0.688 |
| CBPN_NNANGVDLNR | 42 | TENX_LSQLSVTDVTTSSLR | 60 | 4.2E-03 | 0.687 |
| IBP2_LIQGAPTIR | 35 | TENX_LSQLSVTDVTTSSLR | 60 | 3.0E-03 | 0.687 |
| SOM2.CSH_NYGLLYCFR | 38 | TENX_LSQLSVTDVTTSSLR | 60 | 3.4E-03 | 0.687 |
| ENPP2_TYLHTYESEI | 18 | BGH3_LTLLAPLNSVFK | 73 | 1.1E-02 | 0.687 |
| ITIH4_NPLVWVHASPEHVVVTR | 45 | TENX_LNWEAPPGAFDSFLLR | 61 | 1.5E-03 | 0.687 |
| LBP_ITGFLKPGK | 12 | PEDF_TVQAVLTVPK | 44 | 3.6E-03 | 0.687 |
| VTDB_ELPEHTVK | 36 | TENX_LSQLSVTDVTTSSLR | 60 | 1.5E-03 | 0.687 |
| ENPP2_TEFLSNYLTNVDDITLVPGTLGR | 25 | SPRL1_VLTHSELAPLR | 62 | 6.4E-03 | 0.686 |
| APOC3_GWVTDGFSSLK | 3 | B2MG_VEHSDLSFSK | 14 | 3.1E-03 | 0.686 |
| CATD_VGFAEAAR | 1 | KNG1_QVVAGLNFR | 11 | 1.4E-02 | 0.686 |
| ITIH4_NPLVWVHASPEHVVVTR | 45 | TENX_LSQLSVTDVTTSSLR | 60 | 2.2E-03 | 0.685 |
| LBP_ITGFLKPGK | 12 | CO8A_SLLQPNK | 31 | 9.9E-03 | 0.685 |
| LBP_ITLPDFTGDLR | 21 | IGF2_GIVEECCFR | 68 | 1.8E-03 | 0.685 |
| F13B_GDTYPAELYITGSILR | 46 | TENX_LNWEAPPGAFDSFLLR | 61 | 8.1E-04 | 0.685 |
| FBLN3_IPSNPSHR | 47 | TENX_LNWEAPPGAFDSFLLR | 61 | 4.7E-03 | 0.685 |
| LBP_ITLPDFTGDLR | 21 | FETUA_HTLNQIDEVK | 51 | 1.7E-03 | 0.685 |
| ENPP2_TYLHTYESEI | 18 | PGRP2_AGLLRPDYALLGHR | 69 | 3.4E-02 | 0.684 |
| F13B_GDTYPAELYITGSILR | 46 | TENX_LSQLSVTDVTTSSLR | 60 | 1.7E-03 | 0.684 |
| LBP_ITLPDFTGDLR | 21 | BGH3_LTLLAPLNSVFK | 73 | 3.0E-03 | 0.684 |
| IBP4_QCHPALDGQR | 4 | TIE1_VSWSLPLVPGPLVGDGFLLR | 71 | 5.3E-03 | 0.684 |
| A2GL_DLLLPQPDLR | 29 | CRIS3_AVSPPAR | 72 | 3.3E-03 | 0.684 |
| CATD_VSTLPAITLK | 2 | CBPN_EALIQFLEQVHQGIK | 55 | 9.6E-03 | 0.684 |
| CFAB_YGLVTYATYPK | 23 | CRIS3_AVSPPAR | 72 | 3.3E-03 | 0.684 |
| ITIH4_NPLVWVHASPEHVVVTR | 45 | CHL1_VIAVNEVGR | 66 | 6.5E-03 | 0.684 |
| LBP_ITGFLKPGK | 12 | BGH3_LTLLAPLNSVFK | 73 | 3.6E-03 | 0.684 |
| CATD_VGFAEAAR | 1 | CO8A_SLLQPNK | 31 | 1.0E-02 | 0.683 |
| KNG1_QVVAGLNFR | 11 | CRIS3_AVSPPAR | 72 | 2.7E-03 | 0.683 |
| HABP2_FLNWIK | 48 | TENX_LSQLSVTDVTTSSLR | 60 | 4.0E-03 | 0.683 |
| THBG_AVLHIGEK | 49 | TENX_LNWEAPPGAFDSFLLR | 61 | 7.7E-04 | 0.683 |
| INHBC_LDFHFSSDR | 9 | FETUA_HTLNQIDEVK | 51 | 1.6E-03 | 0.683 |
| CATD_VGFAEAAR | 1 | CSH_AHQLAIDTYQEFEETYIPK | 33 | 5.1E-03 | 0.682 |
| CO5_TLLPVSKPEIR | 17 | CRIS3_AVSPPAR | 72 | 3.5E-03 | 0.682 |
| APOC3_GWVTDGFSSLK | 3 | SOM2.CSH_SVEGSCGF | 19 | | 0.682 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| CATD_VSTLPAITLK | 2 | IBP6_GAQTLYVPNCDHR | 40 | 4.4E-03 | 0.682 |
| FETUA_FSVVYAK | 50 | TENX_LNWEAPPGAFDSFLLR | 61 | 2.4E-03 | 0.682 |
| IBP4_QCHPALDGQR | 4 | FETUA_HTLNQIDEVK | 51 | 6.1E-03 | 0.682 |
| B2MG_VNHVTLSQPK | 6 | PEDF_TVQAVLTVPK | 44 | 8.3E-03 | 0.682 |
| CFAB_YGLVTYATYPK | 23 | SPRL1_VLTHSELAPLR | 62 | 3.8E-03 | 0.682 |
| ENPP2_TYLHTYESEI | 18 | TIE1_VSWSLPLVPGPLVGDGFLLR | 71 | 2.4E-02 | 0.682 |
| HABP2_FLNWIK | 48 | TENX_LNWEAPPGAFDSFLLR | 61 | 3.2E-03 | 0.682 |
| FETUA_FSVVYAK | 50 | TENX_LSQLSVTDVTTSSLR | 60 | 3.7E-03 | 0.681 |
| CATD_VSTLPAITLK | 2 | CBPN_NNANGVDLNR | 42 | 2.5E-02 | 0.680 |
| CO5_TLLPVSKPEIR | 17 | CHL1_VIAVNEVGR | 66 | 4.3E-03 | 0.680 |
| KNG1_QVVAGLNFR | 11 | IGF2_GIVEECCFR | 68 | 3.2E-03 | 0.680 |
| LBP_ITLPDFTGDLR | 21 | SHBG_IALGGLLFPASNLR | 74 | 7.7E-03 | 0.680 |
| CD14_SWLAELQQWLKPGLK | 8 | CRIS3_YEDLYSNCK | 70 | 1.1E-03 | 0.680 |
| CLUS_ASSIIDELFQDR | 34 | CHL1_VIAVNEVGR | 66 | 9.8E-03 | 0.680 |
| B2MG_VNHVTLSQPK | 6 | FETUA_HTLNQIDEVK | 51 | 1.2E-02 | 0.679 |
| C1QB_VPGLYYFTYHASSR | 32 | CRIS3_YEDLYSNCK | 70 | 7.5E-03 | 0.679 |
| CD14_LTVGAAQVPAQLLVGALR | 13 | IBP3_YGQPLPGYTTK | 64 | 1.7E-03 | 0.679 |
| ENPP2_TEFLSNYLTNVDDITLVPGTLGR | 25 | TIE1_VSWSLPLVPGPLVGDGFLLR | 71 | 1.6E-02 | 0.679 |
| FETUA_HTLNQIDEVK | 51 | TENX_LNWEAPPGAFDSFLLR | 61 | 1.0E-02 | 0.679 |
| VTNC_VDTVDPPYPR | 5 | HEMO_NFPSPVDAAFR | 26 | 3.2E-03 | 0.679 |
| APOC3_GWVTDGFSSLK | 3 | CFAB_YGLVTYATYPK | 23 | 1.6E-03 | 0.679 |
| CD14_SWLAELQQWLKPGLK | 8 | CRIS3_AVSPPAR | 72 | 2.6E-03 | 0.679 |
| CD14_SWLAELQQWLKPGLK | 8 | IGF2_GIVEECCFR | 68 | 3.7E-03 | 0.679 |
| KNG1_DIPTNSPELEETLTHTITK | 27 | LYAM1_SYYWIGIR | 65 | 5.1E-03 | 0.679 |
| B2MG_VNHVTLSQPK | 6 | PTGDS_GPGEDFR | 53 | 6.8E-03 | 0.678 |
| ENPP2_TEFLSNYLTNVDDITLVPGTLGR | 25 | CBPN_EALIQFLEQVHQGIK | 55 | 2.2E-02 | 0.678 |
| LBP_ITGFLKPGK | 12 | SHBG_IALGGLLFPASNLR | 74 | 9.1E-03 | 0.678 |
| VTDB_ELPEHTVK | 36 | CHL1_VIAVNEVGR | 66 | 1.5E-02 | 0.678 |
| CATD_VGFAEAAR | 1 | FBLN1_TGYYFDGISR | 79 | 1.3E-02 | 0.678 |
| APOH_ATVVYQGER | 22 | IBP3_YGQPLPGYTTK | 64 | 3.7E-03 | 0.677 |
| CATD_VSTLPAITLK | 2 | PSG3_VSAPSGTGHLPGLNPL | 76 | 1.3E-02 | 0.677 |
| ENPP2_TEFLSNYLTNVDDITLVPGTLGR | 25 | PGRP2_AGLLRPDYALLGHR | 69 | 3.9E-02 | 0.677 |
| LBP_ITLPDFTGDLR | 21 | CO8A_SLLQPNK | 31 | 6.5E-03 | 0.677 |
| ANGT_DPTFIPAPIQAK | 20 | IBP3_YGQPLPGYTTK | 64 | 2.2E-03 | 0.677 |
| C1QB_VPGLYYFTYHASSR | 32 | CRIS3_AVSPPAR | 72 | 9.1E-03 | 0.677 |
| CD14_SWLAELQQWLKPGLK | 8 | CHL1_VIAVNEVGR | 66 | 4.1E-03 | 0.677 |
| CFAB_YGLVTYATYPK | 23 | IGF2_GIVEECCFR | 68 | 4.8E-03 | 0.677 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| CSH_ISLLLIESWLEPVR | 43 | TENX_LSQLSVTDVTTSSLR | 60 | 2.7E-03 | 0.677 |
| ENPP2_TYLHTYESEI | 18 | FETUA_HTLNQIDEVK | 51 | 2.4E-02 | 0.677 |
| KNG1_DIPTNSPELEETLTHTITK | 27 | CRIS3_YEDLYSNCK | 70 | 4.5E-03 | 0.677 |
| LBP_ITGFLKPGK | 12 | C163A_INPASLDK | 75 | 4.3E-03 | 0.677 |
| CFAB_YGLVTYATYPK | 23 | CRIS3_YEDLYSNCK | 70 | 3.5E-03 | 0.676 |
| ITIH4_ILDDLSPR | 30 | IBP3_YGQPLPGYTTK | 64 | 3.0E-03 | 0.676 |
| CO8B_QALEEFQK | 28 | LYAM1_SYYWIGIR | 65 | 3.2E-03 | 0.676 |
| A2GL_DLLLPQPDLR | 29 | CHL1_VIAVNEVGR | 66 | 4.4E-03 | 0.676 |
| ENPP2_TEFLSNYLTNVDDITLVPGTLGR | 25 | IGF2_GIVEECCFR | 68 | 6.6E-03 | 0.676 |
| KNG1_QVVAGLNFR | 11 | ALS_IRPHTFTGLSGLR | 67 | 4.1E-03 | 0.676 |
| CD14_LTVGAAQVPAQLLVGALR | 13 | SPRL1_VLTHSELAPLR | 62 | 4.8E-03 | 0.675 |
| CO5_VFQFLEK | 10 | CO6_ALNHLPLEYNSALYSR | 37 | 2.9E-02 | 0.675 |
| FBLN3_IPSNPSHR | 47 | TENX_LSQLSVTDVTTSSLR | 60 | 3.6E-03 | 0.675 |
| KNG1_DIPTNSPELEETLTHTITK | 27 | SPRL1_VLTHSELAPLR | 62 | 1.4E-02 | 0.675 |
| LBP_ITGFLKPGK | 12 | FETUA_FSVVYAK | 50 | 4.0E-03 | 0.675 |
| LBP_ITGFLKPGK | 12 | THBG_AVLHIGEK | 49 | 1.3E-02 | 0.675 |
| LBP_ITLPDFTGDLR | 21 | CO6_ALNHLPLEYNSALYSR | 37 | 4.0E-03 | 0.675 |
| LBP_ITLPDFTGDLR | 21 | PEDF_TVQAVLTVPK | 44 | 3.0E-03 | 0.675 |
| THBG_AVLHIGEK | 49 | TENX_LSQLSVTDVTTSSLR | 60 | 1.5E-03 | 0.675 |
| VTNC_VDTVDPPYPR | 5 | FETUA_HTLNQIDEVK | 51 | 2.1E-03 | 0.675 |
| ENPP2_TEFLSNYLTNVDDITLVPGTLGR | 25 | BGH3_LTLLAPLNSVFK | 73 | 1.1E-02 | 0.675 |
| ITIH3_ALDLSLK | 16 | SHBG_IALGGLLFPASNLR | 74 | 6.8E-03 | 0.675 |
| LBP_ITLPDFTGDLR | 21 | VTDB_ELPEHTVK | 36 | 5.3E-03 | 0.675 |
| C1QB_VPGLYYFTYHASSR | 32 | SPRL1_VLTHSELAPLR | 62 | 2.3E-02 | 0.674 |
| ENPP2_TYLHTYESEI | 18 | PEDF_TVQAVLTVPK | 44 | 3.8E-02 | 0.674 |
| INHBC_LDFHFSSDR | 9 | HEMO_NFPSPVDAAFR | 26 | 1.3E-02 | 0.674 |
| KNG1_DIPTNSPELEETLTHTITK | 27 | CHL1_VIAVNEVGR | 66 | 6.3E-03 | 0.674 |
| B2MG_VEHSDLSFSK | 14 | TIE1_VSWSLPLVPGPLVGDGFLLR | 71 | 1.3E-02 | 0.674 |
| CATD_VGFAEAAR | 1 | CSH_ISLLLIESWLEPVR | 43 | 4.3E-03 | 0.674 |
| CATD_VSTLPAITLK | 2 | C163A_INPASLDK | 75 | 1.2E-02 | 0.674 |
| CO6_ALNHLPLEYNSALYSR | 37 | TENX_LSQLSVTDVTTSSLR | 60 | 3.0E-03 | 0.674 |
| CO8B_QALEEFQK | 28 | SPRL1_VLTHSELAPLR | 62 | 2.7E-03 | 0.674 |
| ENPP2_TYLHTYESEI | 18 | FETUA_FSVVYAK | 50 | 3.0E-02 | 0.674 |
| LBP_ITGFLKPGK | 12 | VTDB_ELPEHTVK | 36 | 4.2E-03 | 0.674 |
| PSG2_IHPSYTNYR | 52 | TENX_LNWEAPPGAFDSFLLR | 61 | 2.1E-02 | 0.674 |
| PTGDS_GPGEDFR | 53 | TENX_LSQLSVTDVTTSSLR | 60 | 5.5E-03 | 0.674 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| THBG_AVLHIGEK | 49 | CHL1_VIAVNEVGR | 66 | 2.1E-02 | 0.674 |
| CATD_VSTLPAITLK | 2 | IBP6_HLDSVLQQLQTEVYR | 15 | 6.8E-03 | 0.673 |
| KNG1_DIPTNSPELEETLTHTITK | 27 | IBP3_YGQPLPGYTTK | 64 | 4.0E-03 | 0.673 |
| VTNC_VDTVDPPYPR | 5 | PGRP2_AGLLRPDYALLGHR | 69 | 5.3E-03 | 0.673 |
| C1QB_VPGLYYFTYHASSR | 32 | IBP3_FLNVLSPR | 63 | 7.3E-03 | 0.673 |
| CATD_VSTLPAITLK | 2 | APOH_ATVVYQGER | 22 | 1.8E-02 | 0.673 |
| CD14_LTVGAAQVPAQLLVGALR | 13 | CRIS3_YEDLYSNCK | 70 | 2.3E-03 | 0.673 |
| IBP2_LIQGAPTIR | 35 | CRIS3_YEDLYSNCK | 70 | 1.2E-02 | 0.673 |
| IBP6_HLDSVLQQLQTEVYR | 15 | IBP3_YGQPLPGYTTK | 64 | 3.0E-03 | 0.673 |
| ITIH3_ALDLSLK | 16 | IBP3_FLNVLSPR | 63 | 4.1E-03 | 0.673 |
| KNG1_DIPTNSPELEETLTHTITK | 27 | IBP3_FLNVLSPR | 63 | 4.2E-03 | 0.673 |
| LBP_ITGFLKPGK | 12 | HEMO_NFPSPVDAAFR | 26 | 4.1E-03 | 0.673 |
| LBP_ITLPDFTGDLR | 21 | FETUA_FSVVYAK | 50 | 3.2E-03 | 0.673 |
| APOC3_GWVTDGFSSLK | 3 | PSG1_FQLPGQK | 80 | 4.3E-01 | 0.672 |
| C1QB_VPGLYYFTYHASSR | 32 | IGF2_GIVEECCFR | 68 | 7.0E-03 | 0.672 |
| CATD_VGFAEAAR | 1 | CO5_VFQFLEK | 10 | 1.7E-02 | 0.672 |
| CO8B_QALEEFQK | 28 | IGF2_GIVEECCFR | 68 | 5.0E-03 | 0.672 |
| ENPP2_TEFLSNYLTNVDDITLVPGTLGR | 25 | ALS_IRPHTFTGLSGLR | 67 | 9.1E-03 | 0.672 |
| B2MG_VNHVTLSQPK | 6 | PGRP2_AGLLRPDYALLGHR | 69 | 3.0E-03 | 0.672 |
| INHBC_LDFHFSSDR | 9 | PGRP2_AGLLRPDYALLGHR | 69 | 3.5E-03 | 0.672 |
| INHBC_LDFHFSSDR | 9 | PTGDS_GPGEDFR | 53 | 4.3E-03 | 0.672 |
| ITIH3_ALDLSLK | 16 | TIE1_VSWSLPLVPGPLVGDGFLLR | 71 | 2.2E-02 | 0.672 |
| LBP_ITLPDFTGDLR | 21 | C163A_INPASLDK | 75 | 5.5E-03 | 0.672 |
| VTNC_VDTVDPPYPR | 5 | NCAM1_GLGEISAASEFK | 54 | 7.4E-03 | 0.672 |
| AFAM_HFQNLGK | 39 | IBP3_YGQPLPGYTTK | 64 | 6.0E-03 | 0.671 |
| CATD_VGFAEAAR | 1 | CD14_LTVGAAQVPAQLLVGALR | 13 | 6.9E-03 | 0.671 |
| ENPP2_TEFLSNYLTNVDDITLVPGTLGR | 25 | IBP3_FLNVLSPR | 63 | 3.7E-03 | 0.671 |
| INHBC_LDFHFSSDR | 9 | FETUA_FSVVYAK | 50 | 3.3E-03 | 0.671 |
| CO5_TLLPVSKPEIR | 17 | CRIS3_YEDLYSNCK | 70 | 3.3E-03 | 0.671 |
| KNG1_QVVAGLNFR | 11 | TIE1_VSWSLPLVPGPLVGDGFLLR | 71 | 3.7E-03 | 0.671 |
| IBP2_LIQGAPTIR | 35 | LYAM1_SYYWIGIR | 65 | 2.1E-02 | 0.670 |
| APOH_ATVVYQGER | 22 | IBP3_FLNVLSPR | 63 | 6.6E-03 | 0.670 |
| ENPP2_TYLHTYESEI | 18 | HABP2_FLNWIK | 48 | 2.2E-01 | 0.670 |
| IBP6_HLDSVLQQLQTEVYR | 15 | CHL1_VIAVNEVGR | 66 | 1.6E-02 | 0.670 |
| IBP6_HLDSVLQQLQTEVYR | 15 | SPRL1_VLTHSELAPLR | 62 | 9.2E-03 | 0.670 |
| PSG2_IHPSYTNYR | 52 | TENX_LSQLSVTDVTTSSLR | 60 | 2.5E-02 | 0.670 |
| CO8B_QALEEFQK | 28 | ALS_IRPHTFTGLSGLR | 67 | 1.5E-02 | 0.670 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| ENPP2_TEFLSNYLTNVDDITLVPGTLGR | 25 | PAPP1_DIPHWLNPTR | 77 | 1.7E-02 | 0.670 |
| ITIH3_ALDLSLK | 16 | IGF2_GIVEECCFR | 68 | 3.3E-03 | 0.670 |
| A2GL_DLLLPQPDLR | 29 | IBP3_FLNVLSPR | 63 | 4.0E-03 | 0.669 |
| APOC3_GWVTDGFSSLK | 3 | IBP2_LIQGAPTIR | 35 | 8.2E-03 | 0.669 |
| C1QB_VPGLYYFTYHASSR | 32 | CHL1_VIAVNEVGR | 66 | 2.1E-02 | 0.669 |
| CATD_VGFAEAAR | 1 | CO8B_QALEEFQK | 28 | 1.6E-02 | 0.669 |
| CATD_VSTLPAITLK | 2 | THBG_AVLHIGEK | 49 | 1.2E-02 | 0.669 |
| CD14_LTVGAAQVPAQLLVGALR | 13 | IBP3_FLNVLSPR | 63 | 3.4E-03 | 0.669 |
| PTGDS_GPGEDFR | 53 | TENX_LNWEAPPGAFDSFLLR | 61 | 3.0E-03 | 0.669 |
| VTDB_ELPEHTVK | 36 | LYAM1_SYYWIGIR | 65 | 8.7E-03 | 0.669 |
| B2MG_VNHVTLSQPK | 6 | FETUA_FSVVYAK | 50 | 2.2E-02 | 0.669 |
| ENPP2_TYLHTYESEI | 18 | CBPN_EALIQFLEQVHQGIK | 55 | 3.9E-02 | 0.669 |
| KNG1_DIPTNSPELEETLTHTITK | 27 | CRIS3_AVSPPAR | 72 | 7.9E-03 | 0.669 |
| VTNC_VDTVDPPYPR | 5 | CBPN_EALIQFLEQVHQGIK | 55 | 1.0E-02 | 0.669 |
| PEDF_LQSLFDSPDFSK | 24 | CHL1_VIAVNEVGR | 66 | 7.2E-03 | 0.668 |
| SOM2.CSH_SVEGSCGF | 19 | LYAM1_SYYWIGIR | 65 | 1.5E-02 | 0.668 |
| CATD_VGFAEAAR | 1 | VTNC_GQYCYELDEK | 7 | 2.8E-02 | 0.668 |
| ENPP2_TEFLSNYLTNVDDITLVPGTLGR | 25 | FETUA_HTLNQIDEVK | 51 | 1.7E-02 | 0.668 |
| INHBC_LDFHFSSDR | 9 | CO6_ALNHLPLEYNSALYSR | 37 | 1.1E-02 | 0.668 |
| ITIH4_NPLVWVHASPEHVVVTR | 45 | LYAM1_SYYWIGIR | 65 | 6.9E-03 | 0.668 |
| CATD_VSTLPAITLK | 2 | ITIH4_ILDDLSPR | 30 | 1.3E-02 | 0.667 |
| CFAB_YGLVTYATYPK | 23 | TIE1_VSWSLPLVPGPLVGDGFLLR | 71 | 3.0E-02 | 0.667 |
| CLUS_ASSIIDELFQDR | 34 | IBP3_FLNVLSPR | 63 | 5.3E-03 | 0.667 |
| CO5_VFQFLEK | 10 | PGRP2_AGLLRPDYALLGHR | 69 | 5.4E-03 | 0.667 |
| LBP_ITLPDFTGDLR | 21 | HEMO_NFPSPVDAAFR | 26 | 3.3E-03 | 0.667 |
| CATD_VSTLPAITLK | 2 | BGH3_LTLLAPLNSVFK | 73 | 1.1E-02 | 0.667 |
| ENPP2_TYLHTYESEI | 18 | HEMO_NFPSPVDAAFR | 26 | 4.4E-02 | 0.667 |
| IBP6_HLDSVLQQLQTEVYR | 15 | CRIS3_YEDLYSNCK | 70 | 4.8E-03 | 0.667 |
| INHBC_LDFHFSSDR | 9 | AFAM_DADPDTFFAK | 41 | 8.9E-03 | 0.667 |
| THBG_AVLHIGEK | 49 | LYAM1_SYYWIGIR | 65 | 4.3E-03 | 0.667 |
| VTNC_GQYCYELDEK | 7 | TIE1_VSWSLPLVPGPLVGDGFLLR | 71 | 5.4E-03 | 0.667 |
| A2GL_DLLLPQPDLR | 29 | IGF2_GIVEECCFR | 68 | 6.2E-03 | 0.666 |
| ENPP2_TYLHTYESEI | 18 | CO6_ALNHLPLEYNSALYSR | 37 | 2.6E-02 | 0.666 |
| IBP2_LIQGAPTIR | 35 | CHL1_VIAVNEVGR | 66 | 3.4E-02 | 0.666 |
| IBP2_LIQGAPTIR | 35 | CRIS3_AVSPPAR | 72 | 2.8E-02 | 0.666 |
| INHBC_LDFHFSSDR | 9 | CBPN_EALIQFLEQVHQGIK | 55 | 4.4E-03 | 0.666 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| SOM2.CSH_SVEGSCGF | 19 | CHL1_VIAVNEVGR | 66 | 1.1E-02 | 0.666 |
| A2GL_DLLLPQPDLR | 29 | TIE1_VSWSLPLVPGPLVGDGFLLR | 71 | 9.9E-03 | 0.666 |
| ANGT_DPTFIPAPIQAK | 20 | CRIS3_YEDLYSNCK | 70 | 3.3E-03 | 0.666 |
| ANGT_DPTFIPAPIQAK | 20 | LYAM1_SYYWIGIR | 65 | 7.6E-03 | 0.666 |
| ANGT_DPTFIPAPIQAK | 20 | SPRL1_VLTHSELAPLR | 62 | 4.7E-03 | 0.666 |
| B2MG_VNHVTLSQPK | 6 | SHBG_IALGGLLFPASNLR | 74 | 1.7E-02 | 0.666 |
| CATD_VSTLPAITLK | 2 | KNG1_DIPTNSPELEETLTHTITK | 27 | 1.4E-02 | 0.666 |
| CD14_LTVGAAQVPAQLLVGALR | 13 | LYAM1_SYYWIGIR | 65 | 3.9E-03 | 0.666 |
| ENPP2_TEFLSNYLTNVDDITLVPGTLGR | 25 | SHBG_IALGGLLFPASNLR | 74 | 4.4E-02 | 0.665 |
| FETUA_HTLNQIDEVK | 51 | TENX_LSQLSVTDVTTSSLR | 60 | 1.5E-02 | 0.665 |
| AFAM_DADPDTFFAK | 41 | IBP3_YGQPLPGYTTK | 64 | 7.5E-03 | 0.665 |
| LBP_ITLPDFTGDLR | 21 | THBG_AVLHIGEK | 49 | 1.3E-02 | 0.665 |
| PEDF_LQSLFDSPDFSK | 24 | IBP3_YGQPLPGYTTK | 64 | 6.1E-03 | 0.665 |
| VTNC_VDTVDPPYPR | 5 | F13B_GDTYPAELYITGSILR | 46 | 7.2E-02 | 0.665 |
| CO8B_QALEEFQK | 28 | CHL1_VIAVNEVGR | 66 | 8.9E-03 | 0.665 |
| ENPP2_TEFLSNYLTNVDDITLVPGTLGR | 25 | FETUA_FSVVYAK | 50 | 2.5E-02 | 0.665 |
| CLUS_ASSIIDELFQDR | 34 | CRIS3_YEDLYSNCK | 70 | 2.7E-03 | 0.664 |
| HEMO_NFPSPVDAAFR | 26 | IBP3_YGQPLPGYTTK | 64 | 4.1E-03 | 0.664 |
| LBP_ITGFLKPGK | 12 | NCAM1_GLGEISAASEFK | 54 | 1.1E-02 | 0.664 |
| NCAM1_GLGEISAASEFK | 54 | TENX_LNWEAPPGAFDSFLLR | 61 | 4.5E-03 | 0.664 |
| C1QB_VPGLYYFTYHASSR | 32 | SHBG_IALGGLLFPASNLR | 74 | 4.3E-02 | 0.664 |
| ENPP2_TEFLSNYLTNVDDITLVPGTLGR | 25 | HABP2_FLNWIK | 48 | 1.7E-01 | 0.664 |
| SOM2.CSH_SVEGSCGF | 19 | CRIS3_YEDLYSNCK | 70 | 9.3E-03 | 0.664 |
| VTDB_ELPEHTVK | 36 | IBP3_YGQPLPGYTTK | 64 | 4.7E-03 | 0.664 |
| ANGT_DPTFIPAPIQAK | 20 | CHL1_VIAVNEVGR | 66 | 1.1E-02 | 0.663 |
| B2MG_VEHSDLSFSK | 14 | ALS_IRPHTFTGLSGLR | 67 | 3.6E-03 | 0.663 |
| CATD_VSTLPAITLK | 2 | SOM2.CSH_NYGLLYCFR | 38 | 3.6E-03 | 0.663 |
| CBPN_EALIQFLEQVHQGIK | 55 | TENX_LSQLSVTDVTTSSLR | 60 | 2.1E-02 | 0.663 |
| CLUS_ASSIIDELFQDR | 34 | ALS_IRPHTFTGLSGLR | 67 | 1.7E-02 | 0.663 |
| IBP6_HLDSVLQQLQTEVYR | 15 | LYAM1_SYYWIGIR | 65 | 1.9E-02 | 0.663 |
| LBP_ITLPDFTGDLR | 21 | PRG2_WNFAYWAAHQPWSR | 78 | 1.3E-02 | 0.663 |
| SOM2.CSH_SVEGSCGF | 19 | IGF2_GIVEECCFR | 68 | 1.3E-02 | 0.663 |
| HEMO_NFPSPVDAAFR | 26 | SPRL1_VLTHSELAPLR | 62 | 1.5E-02 | 0.663 |
| IBP6_GAQTLYVPNCDHR | 40 | IBP3_YGQPLPGYTTK | 64 | 6.7E-03 | 0.663 |
| KNG1_DIPTNSPELEETLTHTITK | 27 | IGF2_GIVEECCFR | 68 | 1.1E-02 | 0.663 |
| CD14_LTVGAAQVPAQLLVGALR | 13 | CHL1_VIAVNEVGR | 66 | 1.1E-02 | 0.662 |
| CO5_TLLPVSKPEIR | 17 | IGF2_GIVEECCFR | 68 | 4.9E-03 | 0.662 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| ENPP2_TEFLSNYLTNVDDITLVPGTLGR | 25 | PRG2_WNFAYWAAHQPWSR | 78 | 1.9E-02 | 0.662 |
| ITIH4_ILDDLSPR | 30 | CRIS3_YEDLYSNCK | 70 | 5.7E-03 | 0.662 |
| VTNC_VDTVDPPYPR | 5 | HABP2_FLNWIK | 48 | 3.6E-01 | 0.662 |
| ANGT_DPTFIPAPIQAK | 20 | CRIS3_AVSPPAR | 72 | 4.2E-03 | 0.662 |
| CD14_SWLAELQQWLKPGLK | 8 | TIE1_VSWSLPLVPGPLVGDGFLLR | 71 | 5.5E-03 | 0.662 |
| CLUS_LFDSDPITVTVPVEVSR | 56 | TENX_LNWEAPPGAFDSFLLR | 61 | 6.7E-03 | 0.662 |
| CO8B_QALEEFQK | 28 | CRIS3_AVSPPAR | 72 | 6.0E-03 | 0.662 |
| FBLN3_IPSNPSHR | 47 | CHL1_VIAVNEVGR | 66 | 6.0E-02 | 0.662 |
| B2MG_VNHVTLSQPK | 6 | NCAM1_GLGEISAASEFK | 54 | 2.0E-02 | 0.661 |
| CLUS_ASSIIDELFQDR | 34 | LYAM1_SYYWIGIR | 65 | 5.9E-03 | 0.661 |
| ENPP2_TEFLSNYLTNVDDITLVPGTLGR | 25 | CLUS_LFDSDPITVTVPVEVSR | 56 | 2.4E-02 | 0.661 |
| SOM2.CSH_SVEGSCGF | 19 | IBP3_YGQPLPGYTTK | 64 | 6.9E-03 | 0.661 |
| SOM2.CSH_SVEGSCGF | 19 | SPRL1_VLTHSELAPLR | 62 | 1.2E-02 | 0.661 |
| APOC3_GWVTDGFSSLK | 3 | IBP1_VVESLAK | 81 | 1.7E-02 | 0.660 |
| CATD_VGFAEAAR | 1 | PSG1_FQLPGQK | 80 | 2.8E-01 | 0.660 |
| CO5_TLLPVSKPEIR | 17 | TIE1_VSWSLPLVPGPLVGDGFLLR | 71 | 2.2E-02 | 0.660 |
| CO8B_QALEEFQK | 28 | CRIS3_YEDLYSNCK | 70 | 6.1E-03 | 0.660 |
| ENPP2_TEFLSNYLTNVDDITLVPGTLGR | 25 | VTDB_ELPEHTVK | 36 | 3.0E-02 | 0.660 |
| ENPP2_TYLHTYESEI | 18 | PAPP1_DIPHWLNPTR | 77 | 3.2E-02 | 0.660 |
| ENPP2_TYLHTYESEI | 18 | SHBG_IALGGLLFPASNLR | 74 | 3.4E-02 | 0.660 |
| ENPP2_TYLHTYESEI | 18 | VTDB_ELPEHTVK | 36 | 4.7E-02 | 0.660 |
| IBP4_QCHPALDGQR | 4 | SHBG_IALGGLLFPASNLR | 74 | 1.8E-02 | 0.660 |
| LBP_ITGFLKPGK | 12 | CO8B_QALEEFQK | 28 | 2.3E-02 | 0.660 |
| PSG11_LFIPQITPK | 57 | TENX_LNWEAPPGAFDSFLLR | 61 | 4.5E-03 | 0.660 |
| B2MG_VNHVTLSQPK | 6 | CO6_ALNHLPLEYNSALYSR | 37 | 2.9E-02 | 0.660 |
| B2MG_VNHVTLSQPK | 6 | HEMO_NFPSPVDAAFR | 26 | 1.3E-02 | 0.660 |
| ENPP2_TEFLSNYLTNVDDITLVPGTLGR | 25 | C163A_INPASLDK | 75 | 7.7E-03 | 0.660 |
| IBP6_HLDSVLQQLQTEVYR | 15 | IBP3_FLNVLSPR | 63 | 5.3E-03 | 0.660 |
| IBP6_HLDSVLQQLQTEVYR | 15 | IGF2_GIVEECCFR | 68 | 8.7E-03 | 0.660 |
| ITIH3_ALDLSLK | 16 | PAPP1_DIPHWLNPTR | 77 | 6.3E-03 | 0.660 |
| ITIH4_ILDDLSPR | 30 | IBP3_FLNVLSPR | 63 | 5.7E-03 | 0.660 |
| KNG1_QVVAGLNFR | 11 | NCAM1_GLGEISAASEFK | 54 | 1.2E-02 | 0.660 |
| LBP_ITGFLKPGK | 12 | PRG2_WNFAYWAAHQPWSR | 78 | 1.2E-02 | 0.660 |
| VTNC_VDTVDPPYPR | 5 | CO6_ALNHLPLEYNSALYSR | 37 | 1.0E-02 | 0.660 |
| ANGT_DPTFIPAPIQAK | 20 | IBP3_FLNVLSPR | 63 | 3.9E-03 | 0.659 |
| APOC3_GWVTDGFSSLK | 3 | ITIH4_QLGLPGPPDVPDHAAYHPF | 82 | | 0.659 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| CO8A_SLLQPNK | 31 | IBP3_YGQPLPGYTTK | 64 | 6.9E-03 | 0.659 |
| PSG9_LFIPQITR | 58 | TENX_LNWEAPPGAFDSFLLR | 61 | 1.5E-02 | 0.659 |
| CATD_VSTLPAITLK | 2 | PEDF_LQSLFDSPDFSK | 24 | 1.0E-02 | 0.659 |
| CFAB_YGLVTYATYPK | 23 | PGRP2_AGLLRPDYALLGHR | 69 | 2.0E-02 | 0.659 |
| HEMO_NFPSPVDAAFR | 26 | CHL1_VIAVNEVGR | 66 | 1.6E-02 | 0.659 |
| INHBC_LDFHFSSDR | 9 | HABP2_FLNWIK | 48 | 3.0E-01 | 0.659 |
| ENPP2_TEFLSNYLTNVDDITLVPGTLGR | 25 | CO6_ALNHLPLEYNSALYSR | 37 | 1.6E-02 | 0.659 |
| INHBC_LDFHFSSDR | 9 | BGH3_LTLLAPLNSVFK | 73 | 1.0E-02 | 0.659 |
| VTDB_ELPEHTVK | 36 | SPRL1_VLTHSELAPLR | 62 | 1.8E-02 | 0.659 |
| CLUS_ASSIIDELFQDR | 34 | CRIS3_AVSPPAR | 72 | 4.8E-03 | 0.658 |
| SOM2.CSH_SVEGSCGF | 19 | CRIS3_AVSPPAR | 72 | 5.9E-03 | 0.658 |
| ENPP2_TYLHTYESEI | 18 | THBG_AVLHIGEK | 49 | 6.2E-02 | 0.658 |
| ITIH3_ALDLSLK | 16 | PRG2_WNFAYWAAHQPWSR | 78 | 6.2E-03 | 0.658 |
| LBP_ITGFLKPGK | 12 | IBP6_GAQTLYVPNCDHR | 40 | 1.3E-02 | 0.658 |
| ENPP2_TEFLSNYLTNVDDITLVPGTLGR | 25 | PEDF_TVQAVLTVPK | 44 | 2.7E-02 | 0.657 |
| APOC3_GWVTDGFSSLK | 3 | ITIH3_ALDLSLK | 16 | 3.3E-02 | 0.657 |
| CATD_VSTLPAITLK | 2 | FBLN1_TGYYFDGISR | 79 | 1.8E-02 | 0.657 |
| PEDF_LQSLFDSPDFSK | 24 | LYAM1_SYYWIGIR | 65 | 8.4E-03 | 0.657 |
| SOM2.CSH_SVEGSCGF | 19 | IBP3_FLNVLSPR | 63 | 9.6E-03 | 0.657 |
| VTNC_VDTVDPPYPR | 5 | PAPP1_DIPHWLNPTR | 77 | 7.8E-03 | 0.657 |
| INHBC_LDFHFSSDR | 9 | APOH_ATVVYQGER | 22 | 5.0E-02 | 0.657 |
| CATD_VGFAEAAR | 1 | CD14_SWLAELQQWLKPGLK | 8 | 1.0E-02 | 0.656 |
| CBPN_EALIQFLEQVHQGIK | 55 | TENX_LNWEAPPGAFDSFLLR | 61 | 1.1E-02 | 0.656 |
| VTNC_VDTVDPPYPR | 5 | FETUA_FSVVYAK | 50 | 9.4E-03 | 0.656 |
| CATD_VSTLPAITLK | 2 | CLUS_LFDSDPITVTVPVEVSR | 56 | 1.5E-02 | 0.656 |
| ITIH4_ILDDLSPR | 30 | CRIS3_AVSPPAR | 72 | 8.2E-03 | 0.656 |
| ITIH4_NPLVWVHASPEHVVVTR | 45 | IBP3_YGQPLPGYTTK | 64 | 7.9E-03 | 0.656 |
| LBP_ITGFLKPGK | 12 | CO5_TLLPVSKPEIR | 17 | 2.1E-02 | 0.656 |
| THBG_AVLHIGEK | 49 | SPRL1_VLTHSELAPLR | 62 | 2.6E-02 | 0.656 |
| CD14_LTVGAAQVPAQLLVGALR | 13 | ALS_IRPHTFTGLSGLR | 67 | 6.1E-03 | 0.655 |
| CFAB_YGLVTYATYPK | 23 | FETUA_FSVVYAK | 50 | 5.5E-02 | 0.655 |
| ENPP2_TYLHTYESEI | 18 | KNG1_DIPTNSPELEETLTHTITK | 27 | 6.5E-02 | 0.655 |
| PEDF_LQSLFDSPDFSK | 24 | SPRL1_VLTHSELAPLR | 62 | 1.7E-02 | 0.655 |
| PSG9_LFIPQITR | 58 | TENX_LSQLSVTDVTTSSLR | 60 | 2.1E-02 | 0.655 |
| APOH_ATVVYQGER | 22 | CHL1_VIAVNEVGR | 66 | 1.7E-02 | 0.655 |
| KNG1_QVVAGLNFR | 11 | FETUA_HTLNQIDEVK | 51 | 1.6E-02 | 0.655 |
| AFAM_HFQNLGK | 39 | IBP3_FLNVLSPR | 63 | 1.4E-02 | 0.654 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| LBP_ITLPDFTGDLR | 21 | HABP2_FLNWIK | 48 | 2.6E-01 | 0.654 |
| CATD_VGFAEAAR | 1 | B2MG_VEHSDLSFSK | 14 | 1.9E-02 | 0.654 |
| ENPP2_TYLHTYESEI | 18 | PRG2_WNFAYWAAHQPWSR | 78 | 3.2E-02 | 0.654 |
| INHBC_LDFHFSSDR | 9 | F13B_GDTYPAELYITGSILR | 46 | 1.2E-02 | 0.654 |
| LBP_ITLPDFTGDLR | 21 | F13B_GDTYPAELYITGSILR | 46 | 9.9E-03 | 0.654 |
| PSG11_LFIPQITPK | 57 | TENX_LSQLSVTDVTTSSLR | 60 | 8.1E-03 | 0.654 |
| VTNC_GQYCYELDEK | 7 | PGRP2_AGLLRPDYALLGHR | 69 | 6.5E-03 | 0.654 |
| VTNC_VDTVDPPYPR | 5 | AFAM_DADPDTFFAK | 41 | 1.0E-02 | 0.654 |
| ENPP2_TYLHTYESEI | 18 | CO8A_SLLQPNK | 31 | 6.0E-02 | 0.653 |
| IBP6_HLDSVLQQLQTEVYR | 15 | CRIS3_AVSPPAR | 72 | 8.4E-03 | 0.653 |
| LBP_ITGFLKPGK | 12 | HABP2_FLNWIK | 48 | 2.3E-01 | 0.653 |
| PEDF_LQSLFDSPDFSK | 24 | CRIS3_AVSPPAR | 72 | 3.8E-03 | 0.653 |
| PSG9_DVLLLVHNLPQNLPGYFWYK | 59 | TENX_LNWEAPPGAFDSFLLR | 61 | 9.9E-03 | 0.653 |
| AFAM_DADPDTFFAK | 41 | IBP3_FLNVLSPR | 63 | 1.5E-02 | 0.653 |
| CATD_VSTLPAITLK | 2 | CSH_AHQLAIDTYQEFEETYIPK | 33 | 6.2E-03 | 0.653 |
| ENPP2_TEFLSNYLTNVDDITLVPGTLGR | 25 | HEMO_NFPSPVDAAFR | 26 | 2.9E-02 | 0.653 |
| ENPP2_TEFLSNYLTNVDDITLVPGTLGR | 25 | THBG_AVLHIGEK | 49 | 3.7E-02 | 0.653 |
| ENPP2_TYLHTYESEI | 18 | AFAM_HFQNLGK | 39 | 6.4E-02 | 0.653 |
| IBP2_LIQGAPTIR | 35 | SPRL1_VLTHSELAPLR | 62 | 6.2E-02 | 0.653 |
| KNG1_QVVAGLNFR | 11 | PGRP2_AGLLRPDYALLGHR | 69 | 1.1E-02 | 0.653 |
| LBP_ITLPDFTGDLR | 21 | CBPN_EALIQFLEQVHQGIK | 55 | 6.5E-03 | 0.653 |
| LBP_ITLPDFTGDLR | 21 | CO5_TLLPVSKPEIR | 17 | 2.0E-02 | 0.653 |
| VTNC_GQYCYELDEK | 7 | VTDB_ELPEHTVK | 36 | 1.4E-02 | 0.653 |
| APOC3_GWVTDGFSSLK | 3 | HLACI_WAAVVVPSGEEQR | 83 | 3.2E-02 | 0.653 |
| B2MG_VNHVTLSQPK | 6 | PRG2_WNFAYWAAHQPWSR | 78 | 2.0E-02 | 0.653 |
| CBPN_NNANGVDLNR | 42 | IBP3_YGQPLPGYTTK | 64 | 1.8E-02 | 0.653 |
| CD14_LTVGAAQVPAQLLVGALR | 13 | CRIS3_AVSPPAR | 72 | 5.3E-03 | 0.653 |
| CD14_LTVGAAQVPAQLLVGALR | 13 | IGF2_GIVEECCFR | 68 | 1.1E-02 | 0.653 |
| CO8A_SLLQPNK | 31 | IBP3_FLNVLSPR | 63 | 1.2E-02 | 0.653 |
| ENPP2_TYLHTYESEI | 18 | PTGDS_GPGEDFR | 53 | 5.1E-02 | 0.653 |
| ENPP2_TYLHTYESEI | 18 | SOM2.CSH_NYGLLYCFR | 38 | 4.3E-02 | 0.653 |
| IBP6_GAQTLYVPNCDHR | 40 | IBP3_FLNVLSPR | 63 | 1.0E-02 | 0.653 |
| LBP_ITLPDFTGDLR | 21 | NCAM1_GLGEISAASEFK | 54 | 1.2E-02 | 0.653 |
| VTNC_GQYCYELDEK | 7 | FETUA_FSVVYAK | 50 | 1.4E-02 | 0.653 |
| APOH_ATVVYQGER | 22 | LYAM1_SYYWIGIR | 65 | 1.1E-02 | 0.652 |
| CO5_VFQFLEK | 10 | NCAM1_GLGEISAASEFK | 54 | 2.2E-02 | 0.652 |

TABLE 1-continued

Reversals with AUC >=0.65, comprising blood draw windows starting from day 137 to 150 of gestation.

| P1 | SEQ ID NO: | P2 | SEQ ID NO: | p.value | AUC |
|---|---|---|---|---|---|
| LBP_ITGFLKPGK | 12 | CFAB_YGLVTYATYPK | 23 | 5.7E-02 | 0.652 |
| LBP_ITGFLKPGK | 12 | PSG3_VSAPSGTGHLPGLNPL | 76 | 6.4E-02 | 0.652 |
| PSG9_DVLLLVHNLPQNLPGYFWYK | 59 | TENX_LSQLSVTDVTTSSLR | 60 | 1.0E-02 | 0.652 |
| APOC3_GWVTDGFSSLK | 3 | INHBC_LDFHFSSDR | 9 | 9.4E-03 | 0.652 |
| CBPN_NNANGVDLNR | 42 | CHL1_VIAVNEVGR | 66 | 4.2E-02 | 0.652 |
| HEMO_NFPSPVDAAFR | 26 | CRIS3_YEDLYSNCK | 70 | 6.8E-03 | 0.652 |
| INHBC_LDFHFSSDR | 9 | AFAM_HFQNLGK | 39 | 1.1E-02 | 0.652 |
| VTNC_GQYCYELDEK | 7 | FETUA_HTLNQIDEVK | 51 | 8.6E-03 | 0.652 |
| VTNC_VDTVDPPYPR | 5 | AFAM_HFQNLGK | 39 | 1.1E-02 | 0.652 |
| A2GL_DLLLPQPDLR | 29 | ALS_IRPHTFTGLSGLR | 67 | 1.6E-02 | 0.651 |
| CO5_VFQFLEK | 10 | VTDB_ELPEHTVK | 36 | 1.1E-02 | 0.651 |
| LBP_ITGFLKPGK | 12 | PTGDS_GPGEDFR | 53 | 1.5E-02 | 0.651 |
| PEDF_LQSLFDSPDFSK | 24 | IBP3_FLNVLSPR | 63 | 9.4E-03 | 0.651 |
| VTNC_VDTVDPPYPR | 5 | SHBG_IALGGLLFPASNLR | 74 | 3.2E-02 | 0.651 |
| CATD_VGFAEAAR | 1 | CATD_VSTLPAITLK | 2 | 2.3E-02 | 0.651 |
| CLUS_ASSIIDELFQDR | 34 | SPRL1_VLTHSELAPLR | 62 | 1.1E-02 | 0.651 |
| ENPP2_TYLHTYESEI | 18 | AFAM_DADPDTFFAK | 41 | 5.6E-02 | 0.651 |
| ENPP2_TYLHTYESEI | 18 | C163A_INPASLDK | 75 | 1.5E-02 | 0.651 |
| LBP_ITGFLKPGK | 12 | CBPN_EALIQFLEQVHQGIK | 55 | 7.2E-03 | 0.651 |
| LBP_ITGFLKPGK | 12 | PAPP1_DIPHWLNPTR | 77 | 1.6E-02 | 0.651 |
| LBP_ITLPDFTGDLR | 21 | IBP6_GAQTLYVPNCDHR | 40 | 1.1E-02 | 0.651 |
| APOH_ATVVYQGER | 22 | CRIS3_AVSPPAR | 72 | 9.3E-03 | 0.650 |
| INHBC_LDFHFSSDR | 9 | CLUS_LFDSDPITVTVPVEVSR | 56 | 3.2E-02 | 0.650 |
| INHBC_LDFHFSSDR | 9 | PEDF_LQSLFDSPDFSK | 24 | 1.4E-02 | 0.650 |
| VTDB_ELPEHTVK | 36 | CRIS3_AVSPPAR | 72 | 9.7E-03 | 0.650 |
| VTDB_ELPEHTVK | 36 | IBP3_FLNVLSPR | 63 | 1.1E-02 | 0.650 |
| CO5_TLLPVSKPEIR | 17 | PGRP2_AGLLRPDYALLGHR | 69 | 1.9E-02 | 0.650 |
| HEMO_NFPSPVDAAFR | 26 | LYAM1_SYYWIGIR | 65 | 8.7E-03 | 0.650 |
| IBP4_QCHPALDGQR | 4 | FETUA_FSVVYAK | 50 | 7.6E-03 | 0.650 |
| NCAM1_GLGEISAASEFK | 54 | TENX_LSQLSVTDVTTSSLR | 60 | 7.9E-03 | 0.650 |
| PEDF_LQSLFDSPDFSK | 24 | CRIS3_YEDLYSNCK | 70 | 3.0E-03 | 0.650 |

The following examples are provided by way of illustration, not limitation.

EXAMPLES

Example 1. Development of an Estimated Due Date (EDD) Predictor (EDDp)

This example provides a new due date and time to birth prediction for a pregnancy. It identifies those pregnancies, with high accuracy, that will deliver earlier than the official EDD and/or TTB as derived from LMP and/or US dating.

Blood was drawn in blood draw window 140 to 153 days. Blood was subsequently processed including depletion, digestion into peptides, inclusion of synthetic peptides, analyzed my MRM-MS with protein transitions (fragments) of CATD and TENX measured relative to the synthetic peptide analogues of CATD and TENX. If CATD/TENX was larger than threshold T=0.50 then new_EDD was set to the official EDD. If CATD/TENX was equal to or less than threshold T=0.50 then new_EDD was set to the official_EDD—16 days. The 16 day decrement was derived from studies of actual pregnancies. Other decrements may be selected depending on the optimization criteria. Additionally, the threshold T=0.50 can be adjusted depending on the optimization criteria and/or subpopulation.

Performance of the EDDmp can be measured in multiple ways. Presented below are some key metrics of performance. Performance of the test has been assessed on a dataset of 357 subjects with known outcomes and official EDDs.

The protein ratio CATD/TENX measured within blood draw window 140 to 153 days had an AUC of 82% in separating those subjects that gave birth significantly earlier (i.e. before 270 days) than the population average of 280 days. The kinetic plot of this ratio over the blood draw day (GABD) is shown in FIG. 1.

From FIG. 1, a threshold of T=0.5 for separating group A (<270 days) and group B (>=280 days) is a reasonable choice. This could be optimized by making T a function of GABD. With these parameters, performance of this molecular test (CATD, TENX, T) was evaluated and a Due Date Prediction (DDP) was developed where 10 days are added to those subjects the test identifies as being early (group A). Additional observations about the sensitivity and specificity are as follows:

Sensitivity 280|280: 63%. The majority of pregnancies delivering earlier than expected are detected by the test.

Sensitivity 270|280: 86%. The large majority of pregnancies delivering much earlier than expected are detected by the test.

Specificity 280|280: 68%. The majority of pregnancies delivering as expected are not identified as early by the test.

PPV 280|280: 84%. When the test is positive, it is very likely the pregnancy will be earlier than predicted.

Average error of official EDD estimate: 12.1 days.

Average error of EDDmp estimate: 9.6 days (This is a 21% improvement).

Here, error is calculated as follows:

$$error = \frac{\sum_{i}^{n} Actual\ Delivery_i - 280}{n}$$

Example 2. Further Models for Development of an Estimated Due Date (EDD) Molecular Predictor (EDDmp)

This example illustrates three additional methods for due date prediction for a pregnancy (TTB or EDD).

Prediction

The terms estimated due date (EDD) and time to birth (TTB) are used interchangeably in the context of predictors for DD. The EDD can be used to predict TTB and vice-versa. Explicitly, if the estimated gestational age of a pregnancy is X at the time of blood draw then TTB can be estimated from EDD as follows: TTB=EDD−X. And DD can be estimated from a TTB predictor as follows: EDD=X+TTB, where the units used are days.

Furthermore, the time of blood draw can be estimated using standard clinical practice such as Last Menstrual Period (LMP), Ultrasound Dating (US) and/or a combination LMP and US. Formulae for these estimates are readily available in the literature and practice guidelines acog.org/Clinical-Guidance-and-Publications/Committee-Opinions/Committee-on-Obstetric-Practice/Methods-for-Estimating-the-Due-Date and references therein.

Performance of Prediction

The performance of a TTB (or EDD) predictor can be measured in numerous ways. One approach is accuracy and precision. Accuracy being how far from the actual TTB (or EDD) the estimated TTB (or EDD) actually is. Precision is the variability around this estimate. Standard metrics for precision are the standard deviation or variation. Alternatively, performance statements can indicate accuracy as the percentage of time the TTB predictor is correct within a specified number of days before or after the actual TTB (or EDD). Such statements provide insight into both the accuracy and precision of the estimation.

Performance in Clinical Practice

In the Proteomic Assessment of Preterm_Risk (PAPR) study (Saade et al. Development and validation of a spontaneous preterm delivery predictor in asymptomatic women. Am J Obstet Gynecol 2016; 214:633.e1-24.), the TTB estimates, based on standard clinical dating, were accurate to within +/−5 days of the actual TTB about 35% of the time for deliveries that were term (i.e. delivered 37 weeks or later in gestation). This establishes a baseline to compare models for predicting TTB (or EDD).

Model 1: Linear Regression Model

Generalized linear regression models were built using the estimated due date from clinical practice (i.e. based on LMP and/or US dating) and the ratio of two peptide measurements. To illustrate, using the following two peptide measurement ratio:

CRIS3_YEDLYSNCK (SEQ ID NO:70)/ ADA12_FGFGGSTDSGPIR (SEQ ID NO:84)

The model details are as follows:

| Generalized Linear regression model $y \sim 1 + x1 + x2$ Distribution = Normal | | | | |
|---|---|---|---|---|
| | Estimate | SE | tStat | pValue |
| (Intercept) | 3.5404 | 6.8273 | 0.51856 | 0.60526 |
| x1 | 0.92355 | 0.069505 | 13.288 | 1.7723e−23 |
| x2 | 6.2221 | 1.4261 | 4.3629 | 3.2316e−05 |

For term deliveries without complications (such as preeclampsia) and for multiparous pregnancies, this model correctly predicted the TTB within +/−5 days, 61% of the time whereas standard clinical practice was correct about 38% of the time. All pairs of such peptides with performance above 60% appear in Table 2. Similarly, for all term deliveries for nulliparous pregnancies, all pairs of such peptides with performance above 60% appear in Table 3.

TABLE 2

Best Reversals, Term, Multiparous

| Numerator | SEQ ID NO: | Denominator | SEQ ID NO: | Percentage within 5 days |
|---|---|---|---|---|
| 'ALS_IRPHTFTGLSGLR' | 67 | 'CO8B_QALEEFQK' | 28 | 0.61 |
| 'APOH_ATVVYQGER' | 22 | 'ITIH3_ALDLSLK' | 16 | 0.62 |
| 'APOH_ATVVYQGER' | 22 | 'C1QA_SLGFCDTTNK' | 87 | 0.64 |
| 'APOH_ATVVYQGER' | 22 | 'C1QC_TNQVNSGGVLLR' | 90 | 0.61 |
| 'APOH_ATVVYQGER' | 22 | 'PCD12_AHDADLGINGK' | 94 | 0.61 |
| 'CBPN_NNANGVDLNR' | 42 | 'DPEP2_LTLEQIDLIR' | 95 | 0.62 |
| 'CO8A_SLLQPNK' | 31 | 'PCD12_AHDADLGINGK' | 94 | 0.62 |
| 'CO8B_QALEEFQK' | 28 | 'ANT3_TSDQIHFFFAK' | 96 | 0.61 |
| 'CO8B_QALEEFQK' | 28 | 'C1QB_LEQGENVFLQATDK' | 88 | 0.61 |
| 'CO8B_QALEEFQK' | 28 | 'C1QC_FNAVLTNPOGDYDTSTGK' | 89 | 0.61 |
| 'CO8B_QALEEFQK' | 28 | 'CADH5_YEIVVEAR' | 97 | 0.61 |
| 'CO8B_QALEEFQK' | 28 | 'CADH5_YTFVVPEDTR' | 98 | 0.61 |
| 'CO8B_QALEEFQK' | 28 | 'CNTN1_FIPLIPIPER' | 99 | 0.61 |
| 'CRIS3_YEDLYSNCK' | 70 | 'SHBG_IALGGLLFPASNLR' | 74 | 0.61 |
| 'CRIS3_YEDLYSNCK' | 70 | 'SHBG_IALGGLLFPASNLR.2' | 100 | 0.61 |
| 'CRIS3_YEDLYSNCK' | 70 | 'ADA12_FGFGGSTDSGPIR' | 84 | 0.61 |
| 'CRIS3_YEDLYSNCK' | 70 | 'SHBG_IALGGLLFPASNLR' | 74 | 0.61 |
| 'CRIS3_YEDLYSNCK' | 70 | 'PCD12_AHDADLGINGK' | 94 | 0.61 |
| 'ITIH4_ILDDLSPR' | 30 | 'DPEP2_ALEVSQAPVIFSHSAAR' | 101 | 0.61 |
| 'ITIH4_NPLVWVHASPEHVVVTR' | 45 | 'GELS_TASDFITK' | 102 | 0.61 |
| 'ITIH4_NPLVWVHASPEHVVVTR' | 45 | 'CNTN1_FIPLIPIPER' | 99 | 0.61 |
| 'KNG1_QVVAGLNFR' | 11 | 'C1QA_DQPRPAFSAIR' | 86 | 0.61 |
| 'PTGDS_GPGEDFR' | 53 | 'ECM1_LLPAQLPAEK' | 103 | 0.61 |
| 'IBP4_QCHPALDGQR.2' | 85 | 'CNTN1_FIPLIPIPER' | 99 | 0.61 |
| 'C1QA_DQPRPAFSAIR' | 86 | 'PROS_FSAEFDFR' | 104 | 0.61 |
| 'C1QA_SLGFCDTTNK' | 87 | 'PROS_FSAEFDFR' | 104 | 0.62 |
| 'C1QB_LEQGENVFLQATDK' | 88 | 'PROS_FSAEFDFR' | 104 | 0.61 |
| 'C1QC_FNAVLTNPOGDYDTSTGK' | 89 | 'PROS_FSAEFDFR' | 104 | 0.61 |
| 'C1QC_TNQVNSGGVLLR' | 90 | 'PROS_FSAEFDFR' | 104 | 0.62 |
| 'LEP_DLLHVLAFSK' | 91 | 'DPEP2_ALEVSQAPVIFSHSAAR' | 101 | 0.61 |
| 'PTGDS_AQGFTEDTIVFLPQTDK' | 92 | 'CNTN1_FIPLIPIPER' | 99 | 0.61 |
| 'CAMP_AIDGINQR' | 93 | 'SVEP1_LLSDFPVVPTATR' | 105 | 0.61 |

TABLE 3

Best Reversals, Term, Nulliparous

| Numerator | SEQ ID NO: | Denominator | SEQ ID NO: | Percentage within 5 days |
|---|---|---|---|---|
| 'IBP4_QCHPALDGQR' | 4 | 'TETN_LDTLAQEVALLK' | 106 | 0.62962963 |
| 'IBP4_QCHPALDGQR.2' | 85 | 'TETN_LDTLAQEVALLK' | 106 | 0.611111111 |
| 'ADA12_FGFGGSTDSGPIR' | 84 | 'GELS_AQPVQVAEGSEPDGFWEALGGK' | 107 | 0.611111111 |
| 'ADA12_FGFGGSTDSGPIR' | 84 | 'PROS_FSAEFDFR' | 104 | 0.611111111 |

Consequently, depending on the parity of the pregnancy, the corresponding predictive model for TTB (or EDD) can be used.

Model 2: Tree Models

This section describes a conditional inference tree and its development. Conditional inference trees embed tree-structured regression models into a well-defined theory of conditional inference procedures. This non-parametric class of regression trees is applicable to categorical and numeric regression analyses, including multivariate models and arbitrary measurement scales of the covariates.

Step 1) Boosted ElasticNet to Select Predictive Variables.

523 Term subjects and clinical numeric variables were repeatedly sampled to generate partial data sets, then used to train ElasticNet models predicting GAB or TTB. The penalty mixture parameter was varied between 0 (full lasso) and 1 (full ridge). Analytes and clinical numeric variables were ranked by the number of times they were present in models. The intersection of high-ranking variables for GAB and TTB prediction resulted in the selection of the following 75 of 197 available variables:

1. APOH_ATVVYQGER (SEQ ID NO: 22)
2. CD14_LTVGAAQVPAQLLVGALR (SEQ ID NO: 13)
3. CD14_SWLAELQQWLKPGLK (SEQ ID NO: 8)
4. CHL1_VIAVNEVGR (SEQ ID NO: 66)
5. CLUS_ASSIIDELFQDR (SEQ ID NO: 34)
6. CLUS_LFDSDPITVTVPVEVSR (SEQ ID NO: 56)
7. CO6_ALNHLPLEYNSALYSR (SEQ ID NO: 37)
8. CO8B_QALEEFQK (SEQ ID NO: 28)
9. CRIS3_AVSPPAR (SEQ ID NO: 72)
10. CRIS3_YEDLYSNCK (SEQ ID NO: 70)
11. CSH_AHQLAIDTYQEFEETYIPK (SEQ ID NO: 33)
12. CSH_ISLLLIESWLEPVR (SEQ ID NO: 43)
13. ENPP2_TEFLSNYLTNVDDITLVPGTLGR (SEQ ID NO: 25)
14. ENPP2_TYLHTYESEI (SEQ ID NO: 18)
15. F13B_GDTYPAELYITGSILR (SEQ ID NO: 46)
16. FBLN1_TGYYFDGISR (SEQ ID NO: 79)
17. HABP2_FLNWIK (SEQ ID NO: 48)
18. HEMO_NFPSPVDAAFR (SEQ ID NO: 26)
19. IBP1_VVESLAK (SEQ ID NO: 81)
20. KNG1_DIPTNSPELEETLTHTITK (SEQ ID NO: 27)
21. KNG1_QVVAGLNFR (SEQ ID NO: 11)
22. LYAM1_SYYWIGIR (SEQ ID NO: 65)
23. PAPP1_DIPHWLNPTR (SEQ ID NO: 77)
24. PGRP2_AGLLRPDYALLGHR (SEQ ID NO: 69)
25. PRG2_WNFAYWAAHQPWSR (SEQ ID NO: 78)
26. PSG1_FQLPGQK (SEQ ID NO: 80)
27. PSG2_IHPSYTNYR (SEQ ID NO: 52)
28. PSG9_LFIPQITR (SEQ ID NO: 58)
29. PTGDS_GPGEDFR (SEQ ID NO: 53)
30. SOM2_CSH_NYGLLYCFR (SEQ ID NO: 108)
31. SOM2_CSH_SVEGSCGF (SEQ ID NO: 109)
32. SPRL1_VLTHSELAPLR (SEQ ID NO: 62)
33. TENX_LNWEAPPGAFDSFLLR (SEQ ID NO: 61)
34. TENX_LSQLSVTDVTTSSLR (SEQ ID NO: 60)
35. GPX3_QEPGENSEILPTLK (SEQ ID NO: 110)
36. IBP4_Q.CHPALDGQR (SEQ ID NO: 111)
37. ADA12_FGFGGSTDSGPIR (SEQ ID NO: 84)
38. FA9_FGSGYVSGWGR (SEQ ID NO: 112)
39. FA9_SALVLQYLR (SEQ ID NO: 113)
40. ANT3_TSDQIHFFFAK (SEQ ID NO: 96)
41. TIMP1_HLACLPR (SEQ ID NO: 114)
42. IGF1_GFYFNKPTGYGSSSR (SEQ ID NO: 115)
43. GELS_AQPVQVAEGSEPDGFWEALGGK (SEQ ID NO: 107)
44. GELS_TASDFITK (SEQ ID NO: 102)
45. PAEP_HLWYLLDLK (SEQ ID NO: 116)
46. PAEP_VHITSLLPTPEDNLEIVLHR (SEQ ID NO: 117)
47. EGLN_GPITSAAELNDPQSILLR (SEQ ID NO: 118)

-continued

48. VGFR1_YLAVPTSK (SEQ ID NO: 119)
49. AOC1_AVHSFLWSK (SEQ ID NO: 120)
50. AOC1_DNGPNYVQR (SEQ ID NO: 121)
51. MUC18_EVTVPVFYPTEK (SEQ ID NO: 122)
52. SEPP1_LVYHLGLPFSFLTFPYVEEAIK (SEQ ID NO: 123)
53. CNTN1_FIPLIPIPER (SEQ ID NO: 99)
54. MFAP5_LYSVHRPVK (SEQ ID NO: 124)
55. SVEP1_LLSDFPVVPTATR (SEQ ID NO: 105)
56. ISM2_TRPCGYGCTATETR (SEQ ID NO: 125)
57. NOTUM_GLADSGWFLDNK (SEQ ID NO: 126)
58. PAPP2_LLLRPEVLAEIPR (SEQ ID NO: 127)
59. PCD12_AHDADLGINGK (SEQ ID NO: 94)
60. PCD12_YQVSEEVPSGTVIGK (SEQ ID NO: 128)
61. MDHTC
62. LABPGAW
63. LABGAD
64. GABD
65. IPMLOS
66. GABD.
67. NpregComp
68. NdelComp
69. PriorPTBvTerm
70. cDM (chronic diabetes mellitus)
71. cHTN (chronic hypertension)
72. Bleeding
73. Cervix
74. PriorSPTB
75. InvParity Step 2) Build Whole-Data-Set ElasticNet Models Predicting TTB Difference from the Median TTB to Further Down-Select Predictive Variables.

Beginning with the 75 variables selected by boosting in step 1 and adding subsets of non-selected variables, ElasticNet was repeatedly used to select models predicting the difference between 532 Term subjects' TTB and the median TTB across all Term subjects. Cross-validation was used to select the degree of shrinkage of each ElasticNet model, with the penalty mixture fixed at 50:50 ridge & lasso regression. Models were selected wherein cross-validation selected a significant model with SD of TTB difference from the median TTB<=7 days. A significant model is defined as one that retains features (is not the null model) and shows performance within 1 SD (in cross validation) of the maximum performance observed. Models were ranked by the SD of the TTB difference from the median TTB. 42 of the previously selected variables remained in the top performing model, which showed an SD of 6.56 days (Table 2). 28 of these 42 variables were also selected in step 1.

TABLE 4

42 variables and their coefficients in best-performing ElasticNet model reducing SD of predicted TTB - median TTB, selected by Step 2.

| Variable | SEQ ID NO: | Coefficient |
|---|---|---|
| AFAM_HFQNLGK | 39 | 0.837750667 |
| APOC3_GWVTDGFSSLK | 3 | 0.321658826 |
| CATD_VSTLPAITLK | 2 | -0.168168895 |
| CHL1_VIAVNEVGR | 66 | -0.275132675 |
| CRIS3_AVSPPAR | 72 | -0.322009195 |
| CRIS3_YEDLYSNCK | 70 | -1.461737374 |
| ENPP2_TEFLSNYLTNVDDITLVPGTLGR | 25 | 0.359267642 |
| ENPP2_TYLHTYESEI | 18 | 0.992405023 |
| KNG1_DIPTNSPELEETLTHTITK | 27 | 0.348982569 |
| PSG1_FQLPGQK | 80 | 0.175481153 |
| PTGDS_GPGEDFR | 53 | -1.428859538 |
| SPRL1_VLTHSELAPLR | 62 | -0.269526267 |
| TENX_LNWEAPPGAFDSFLLR | 61 | -1.619671074 |
| THBG_AVLHIGEK | 49 | 3.115902267 |
| AACT_EIGELYLPK | 134 | 0.059616842 |
| IBP4_Q.CHPALDGQR | 111 | 0.574729040 |
| ADA12_FGFGGSTDSGPIR | 84 | 3.016398873 |
| FA9_SALVLQYLR | 113 | 0.413311773 |
| AMBP_ETLLQDFR | 130 | 0.841283058 |
| TETN_CFLAFTQTK | 131 | -0.324854826 |
| GELS_AQPVQVAEGSEPDGFWEALGGK | 107 | -0.018002056 |
| PAEP_HLWYLLDLK | 116 | -0.012537300 |
| EGLN_GPITSAAELNDPQSILLR | 118 | 0.035853781 |
| VGFR1_YLAVPTSK | 119 | -0.252293075 |
| CADH5_YTFVVPEDTR | 98 | -0.071423172 |
| PTGDS_AQGFTEDTIVFLPQTDK | 92 | -0.377531783 |
| MUC18_EVTVPVFYPTEK | 122 | -0.241983821 |
| SEPP1_VSLATVDK | 132 | 0.262838312 |
| SVEP1_LLSDFPVVPTATR | 105 | 0.558871111 |
| PRG4_ITEVWGIPSPIDTVFTR | 133 | 0.481197951 |
| MDHT | | 0.005398994 |
| LABPGAW | | 1.314846931 |

TABLE 4-continued 42 variables and their coefficients in best-performing ElasticNet model reducing SD of predicted TTB - median TTB, selected by Step 2.

| Variable | SEQ ID NO: | Coefficient |
|---|---|---|
| GABD | | 0.346278498 |
| IPMLOS | | -0.279300039 |
| GABD. | | 0.343634891 |
| NpregComp | | 0.838803565 |
| InvParity. | | -0.557343349 |
| InvCSecParity | | -0.432671923 |
| cDM | | 0.338073730 |
| cHTN | | 0.595655360 |
| PriorSPTB | | 1.897198024 |
| PEspec | | 0.977028773 |

Step 3) Build Conditional Inference Trees

Figure 2:
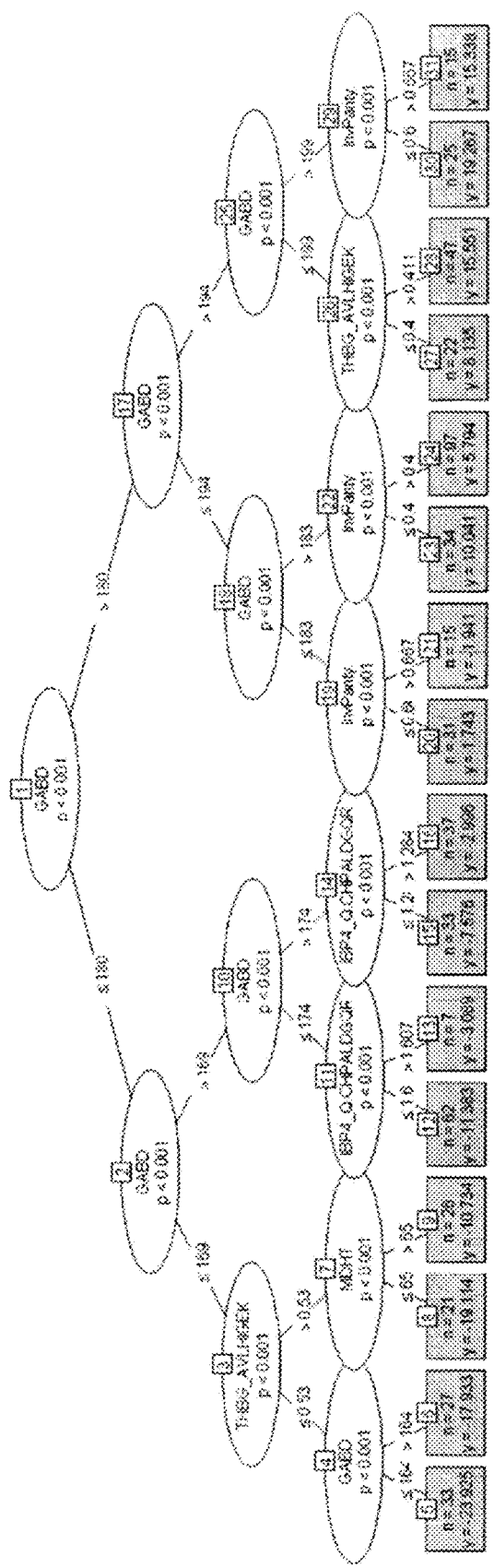
FIG. 2 depicts a conditional inference tree for the prediction of a subject TTB's difference from the median TTB.

Conditional inference trees were built using the party package in R, on all 532 Term subjects, restricting the analysis to variables selected in step 2. Trees predicted the difference between a subject's TTB and the median TTB. Trees were restricted to 4 levels of branching and were grown by selecting new variables at each node via the best single-test significance of improved prediction. These trees use variables more efficiently than ElasticNet—there are fewer than a dozen variables per model used in decisions. Trees were observed to split the subjects by GABD week, then use 2-6 analytes+clinical variables to predict TTB-median TTB. An example inference tree appears in FIG. 2.

Model 3: Rolling Window Models

The regression results in Model 1 and tree results in Model 2 suggest that a model can also use distinct analytes and clinical variables to predict TTB in different GABD windows.

These models demonstrate that a combination of GABD, parity and analytes aligned with GABD and parity provides robust accuracy in estimating TTB. This analysis confirms and extends the findings of Model 1 linear regression analysis and Model 2 conditional inference tree analysis, and provides motivation to survey models that split subjects by GABD, parity or both, to identify the best analytes and analyte pairs for each subset of the population.

TABLE 5

Performance of models containing 2 analytes and/or clinical variables plus GABD in subjects of all parities and without regard to pregnancy complications, with GABD between 23(0/7) and 28(6/7).

| Variable 1 | SEQ ID NO: | Variable 2 | SEQ ID NO: | % in 5 days | 95% CI |
|---|---|---|---|---|---|
| ADA12_FGFGGSTDSGPIR | 84 | CRIS3_AVSPPAR | 72 | 0.5363 | 0.4450:0.6275 |
| ADA12_FGFGGSTDSGPIR | 84 | CRIS3_YEDLYSNCK | 70 | 0.5308 | 0.4475:0.6140 |
| AMBP_ETLLQDFR | 168 | ENPP2_TEFLSNYLTNVDDITLVPGTLGR | 25 | 0.5317 | 0.4511:0.6122 |
| AMBP_ETLLQDFR | 168 | GELS_AQPVQVAEGSEPDGFWEALGGK | 107 | 0.5354 | 0.4392:0.6317 |
| InvParity. | | TENX_LNWEAPPGAFDSFLLR | 61 | 0.5312 | 0.4512:0.6112 |
| InvParity. | | FA9_SALVLQYLR | 113 | 0.532 | 0.4501:0.6140 |
| InvParity. | | SVEP1_LLSDFPVVPTATR | 105 | 0.5307 | 0.4396:0.6218 |
| InvParity. | | ADA12_FGFGGSTDSGPIR | 84 | 0.543 | 0.4582:0.6279 |
| NpregComp | | ADA12_FGFGGSTDSGPIR | 84 | 0.5301 | 0.4357:0.6244 |

Example 3. Further Models for Development of an Estimated Due Date (EDD) Molecular Predictor (EDDmp)

This example shows the utility of discovering optimal analyte pairs for subjects with limited, prespecified ranges of GABD and Parity. It is an aspect of this invention to discover that 1) predictors of TTB vary with GABD; 2) predictors of TTB vary with Parity; and 3) prediction of TTB for nulliparous women, but not for multiparous women, improves with increasing GABD. To reduce these discoveries to practice, we surveyed all possible predictor pairs within the contexts of 3 model types described below, and discovered highly accurate predictors for each model type.

Performance of predictor pairs was evaluated by comparing models containing predictor pairs to null models containing prespecified covariates (GABD, InvParity, and/or AACT) but no predictor pairs. Null model accuracies were estimated by bootstrapping, using subjects in GA weeks 23-28. Table 6 shows null model performance for the various subject splits and model types described in Example 3. As specified below, Example 3 models explored all possible analyte, but a subset with highest performance is reported in Tables 2-27. The 2-analyte model thresholds correspond to null models for Example 3 Model 1 and Example 3 Model 2. A 3-analyte threshold corresponds to the null model for Example 3 Model 3. Example 3 model 3 was explored only for Parity 0; this is the subset of subjects with most apparent effect of inclusion of AACT. In building Tables 2-27, For cases where the null model threshold returned more than 10% of all possible analyte pairs, the accuracy threshold was incremented by 0.25% iteratively until 10% or fewer of the pairs were returned. Therefore, all reported analyte combinations exceeded the accuracy reported by the corresponding null model.

For each subject subset and model type described in this Example, 2 columns representing analyte pairs are reported in the tables below. Each table comprises 2 columns: (1) Analyte1 (abbreviated) and, for each analyte in column 1, (2) column 2 provides abbreviated names for all other analytes participating in models with Analyte1 whose accuracy exceeded a specified threshold as a comma-separated list. Table 28 below lists the full names corresponding to each of the abbreviated analytes. In the models described in this example, accuracy is defined as the percentage of subjects whose absolute value (actual TTB—predicted TTB) is less than or equal to (<=) 5 days.

Time to birth (TTB), in days, was calculated from date and time of blood draw, and date and time of delivery. Estimated time to birth (ETTB)=280–GA at blood draw. Here 280 as a constant was not required but was left for clarity, based on the US method of TTB estimation: 280 days–gestational age (GA) at assessment. Parity is defined by ACOG as the number of pregnancies progressing to $20^{0/7}$ weeks' GA or beyond. It was estimated here as the maximum of the number of living children or the total of previous full-term births, spontaneous preterm births and stillbirths, not counting the current pregnancy. InvParity: Inverse Parity as used herein is calculated as 1/(Parity−0.5). This transform emphasizes Parity differences at low Parities. Analyte1 as used in this example is the log Response Ratio of the first analyte. Analyte2 as used in this example is the log Response Ratio of the second analyte.

Model 1: Two Analyte Models for Different Parity Subsets

Model 1 (TTB ETB+Analyte1+Analyte2) was run for 171 analytes in all possible pairs, in 3 subsets of subjects by estimated Parity. All TERM samples were used (975 subjects were TERM). Analytes were included not as a ratio (i.e. a reversal) to allow for different coefficients for each. The model was applied to subjects with all GAs at blood draw split by Parity: 0, 1 or 2+. The performance metric was accuracy.

TABLE 6

Accuracy thresholds specified for reporting of analyte pairs.

| Parity restriction on subjects | 2-analyte models (Include GABD; and InvParity if Parity is not restricted) | 3-analyte models (include AACT, GABD; and InvParity if Parity is not restricted) |
| --- | --- | --- |
| All | 0.5157 | 0.5188 |
| 0 | 0.4322 | 0.4784 |
| 1 | 0.5568 | 0.5579 |
| 2+ | 0.5769 | 0.6019 |

TABLE 7

Parity subsets, the number of samples in each and the minimum, median and maximum accuracy in each window.

| Parity | nTERM | min | med | max |
| --- | --- | --- | --- | --- |
| 0 | 365 | 39.2 | 43.0 | 48.2 |
| 1 | 282 | 49.6 | 54.3 | 59.6 |
| 2+ | 328 | 52.7 | 55.8 | 60.4 |

TABLE 8

Two analyte models for Parity 0

| Analyte1 | Analyte2 |
| --- | --- |
| A2GL_1 | FETUA_2, SVEP1_1, TENX_1 |
| AACT_1 | ADA12_1, C1QC_1, C1QC_2, CAMP_1, CAMP_2, CNTN1_1, CRAC1_1, CRAC1_2, CRAC1_3, DPEP2_1, DPEP2_2, FGFR1_1, GELS_2, IBP4_1, IBP4_3, KIT_1, KIT_2, MUC18_1, MUC18_2, NOTUM_2, PRG4_1, PRG4_2, PRL_2, SHBG_2, SHBG_3, TETN_1, TETN_2 |
| ADA12_1 | TETN_1 |
| AFAM_1 | FETUA_2, GELS_2 |
| AFAM_2 | GELS_2, TENX_2, TETN_1 |
| ALS_1 | AACT_1, GELS_2 |
| AMBP_1 | GELS_2, PRG4_1 |
| ANGT_1 | AACT_1, GELS_2 |
| APOC3_1 | AACT_1, ITIH3_1 |
| APOH_1 | FETUA_2 |
| B2MG_1 | AACT_1, FETUA_2, GELS_2, TENX_1 |

TABLE 8-continued

| Two analyte models for Parity 0 | |
|---|---|
| Analyte1 | Analyte2 |
| B2MG__2 | AACT__1, FETUA__2, GELS__2 |
| C163A__1 | GELS__2 |
| C1QA__2 | PRG4__1 |
| C1QB__1 | PRG4__1 |
| C1QB__2 | GELS__2 |
| C1QB__3 | FBLN1__1, FETUA__2 |
| C1QC__1 | TETN__1 |
| C1QC__2 | PRG4__1 |
| CAH1__1 | AACT__1, FETUA__2, GELS__2 |
| CAMP__1 | PRG4__1 |
| CBPN__1 | AACT__1 |
| CD14__1 | AACT__1, FETUA__1, FETUA__2, GELS__2, IBP2__1, ITIH3__1, PRG4__2, PSG11__1 |
| CFAB__1 | FETUA__2 |
| CGB1__2 | GELS__2 |
| CHL1__1 | FETUA__2, GELS__2, PSG1__1, TENX__1 |
| CLUS__1 | AACT__1, FA9__2, TETN__2 |
| CLUS__2 | TETN__1, TETN__2 |
| CNTN1__2 | SVEP1__1 |
| CO5__1 | FETUA__1, FETUA__2, PRG4__1 |
| CO5__2 | AACT__1 |
| CO6__1 | PSG11__1 |
| CO8A__1 | FA9__2, FETUA__2, PSG1__1, TENX__1, TETN__1 |
| CO8B__1 | FA9__2, FETUA__2, KNG1__2, TENX__1, TETN__1 |
| CRIS3__1 | FETUA__2, GELS__2 |
| CRIS3__2 | AACT__1, FETUA__1, FETUA__2, GELS__2 |
| CSH__1 | CNTN1__2, GELS__2, PRG4__1, TENX__2, TETN__1, TETN__2 |
| CSH__2 | FETUA__2 |
| ENPP2__1 | AACT__1, FA9__2, FETUA__2 |
| ENPP2__2 | AACT__1, FA9__1, TETN__1 |
| F13B__1 | FETUA__2 |
| FA11__1 | GELS__2 |
| FA11__2 | GELS__2 |
| FA9__1 | DPEP2__2, PROS__2 |
| FA9__2 | CRAC1__2, CRAC1__3, ISM2__2, KIT__2, MUC18__1, TETN__1, TETN__2 |
| FBLN1__1 | AACT__1, FETUA__1, PRG4__2, TENX__1, TETN__2, THBG__1 |
| FBLN3__1 | AACT__1, FA9__2, FETUA__2, GELS__2, TETN__1 |
| FETUA__1 | AACT__1, C1QA__2, CNTN1__2, FA9__1, FA9__2, GELS__2, IBP4__2, IBP4__3, ISM2__1, ISM2__2, LEP__1, MUC18__1, NOTUM__1, PRG4__1, PRG4__2, PSG11__1, TENX__1, TENX__2, TETN__2, THRB__1, VTNC__1, VTNC__2 |
| FETUA__2 | AACT__1, AMBP__1, AOC1__1, AOC1__2, ATL4__1, ATS13__1, ATS13__2, C1QA__1, C1QA__2, C1QB__1, C1QC__1, C1QC__2, CNTN1__2, CRAC1__2, DEF1__1, ECM1__1, ECM1__2, EGLN__1, EGLN__2, FA11__1, FA11__2, FA5__2, FA9__1, FA9__2, FGFR1__1, FGFR1__2, GELS__1, GPX3__1, HABP2__1, HLACI__1, IBP1__1, IBP3__1, IBP6__1, IGF1__1, INHBC__1, IPSP__1, LEP__1, LIRB5__1, LYAM1__1, MUC18__2, PAEP__1, PAEP__2, PAPP1__1, PRDX2__1, PRG2__1, PRG4__1, PROS__2, PSG3__1, PSG9__2, SEPP1__2, SHBG__1, SHBG__2, SHBG__3, SPRL1__1, TENX__1, TETN__2, THRB__1, TIE1__1, TIMP1__1, VGFR1__1, VTDB__1, VTNC__2 |
| FGFR1__1 | PRG4__2 |
| GELS__2 | ATS13__1, CADH5__1, CNTN1__1, CNTN1__2, CRAC1__2, DEF1__1, DEF1__2, DPEP2__2, FGFR1__1, IL1R1__1, ISM2__1, KIT__1, MFAP5__1, MUC18__1, MUC18__2, PAEP__1, PCD12__1, PROS__1, PROS__2, PTGDS__1 |
| HABP2__1 | AACT__1 |
| HLACI__1 | GELS__2 |
| IBP1__1 | TENX__1 |
| IBP2__1 | GELS__2 |
| IBP3__1 | GELS__2, TENX__1 |
| IBP4__2 | FGFR1__1, PROS__1, TETN__1 |
| IBP4__3 | C1QC__1, DPEP2__1, DPEP2__2, PRG4__2, SVEP1__1 |
| IBP6__2 | AACT__1 |
| IGF2__1 | FA9__2 |
| IL1R1__1 | PRG4__1, PRG4__2 |
| ITIH3__1 | AACT__1, PSG1__1, PSG11__1, TENX__1, TENX__2 |
| ITIH4__1 | PRG4__1 |
| ITIH4__2 | GELS__2, TETN__2 |
| ITIH4__3 | GELS__2 |
| KNG1__1 | AACT__1, KIT__1, PAPP2__1, PRG4__1, PSG1__1 |
| KNG1__2 | AACT__1, DEF1__2, IL1R1__1, ISM2__2, PRG4__1, PRL__1, PSG11__1, TETN__2 |
| LBP__2 | TETN__2 |
| LYAM1__1 | FGFR1__1, PRG4__1 |
| PEDF__2 | AACT__1 |
| PGRP2__1 | AACT__1 |
| PRG2__1 | GELS__2 |
| PRG4__1 | CRAC1__1, CRAC1__2, CRAC1__3, DPEP2__1 |
| PRL__1 | GELS__2, PRG4__1, PRG4__2, TETN__1 |
| PRL__2 | TETN__1 |
| PROS__2 | PRG4__1 |

TABLE 8-continued

Two analyte models for Parity 0

| Analyte1 | Analyte2 |
|---|---|
| PSG1_1 | AACT_1, FA9_1, PRG4_1, PRG4_2, THBG_1, VTNC_2 |
| PSG11_1 | AACT_1, PRG4_1, PRG4_2, TETN_1, THBG_1, VTNC_1, VTNC_2 |
| PSG2_1 | AACT_1, PRG4_1, TETN_1, VTNC_2 |
| PSG3_1 | AACT_1, GELS_2 |
| PSG9_1 | SVEP1_1 |
| PSG9_2 | GELS_2 |
| RET4_1 | GELS_2, PRG4_1 |
| SHBG_1 | AACT_1, GELS_2, TENX_1 |
| SHBG_2 | GELS_2 |
| SHBG_3 | GELS_2 |
| SOM2_1 | TETN_2 |
| SPRL1_1 | GELS_2, TENX_1 |
| SVEP1_1 | PRG4_1 |
| TENX_1 | AACT_1, ADA12_1, ATS13_1, C1QB_1, C1QB_2, C1QC_2, CNTN1_2, EGLN_1, EGLN_2, FGFR1_1, GELS_1, GELS_2, GPX3_1, ISM2_2, KIT_2, MFAP5_1, NOTUM_1, NOTUM_2, PAEP_1, SEPP1_2, TETN_1, VTNC_1 |
| TENX_2 | AACT_1, ADA12_1, FGFR1_1, LEP_1, PRL_1 |
| TETN_1 | ATS13_1, CNTN1_1, CRAC1_3, FA5_2, FGFR1_1, GELS_2, IL1R1_1, KIT_2, LEP_1, MFAP5_1, PRG4_1, PRG4_2, PROS_1, SEPP1_2 |
| TETN_2 | FGFR1_1, GELS_2, LEP_2, PRG4_1, PRG4_2 |
| THBG_1 | AACT_1, ADA12_1, DPEP2_2 |
| TIE1_1 | GELS_2 |
| TIMP1_1 | GELS_2 |
| VTNC_1 | FA9_2, GELS_2, TETN_1 |
| VTNC_2 | CRAC1_1, FGFR1_1, GELS_2, KIT_1, PRG4_1, TETN_1 |

TABLE 9

Two analyte models for Parity 1

| Analyte1 | Analyte2 |
|---|---|
| A2GL_1 | FA9_1, FA9_2, HEMO_1, PCD12_1 |
| AACT_1 | FA9_1, FA9_2, PCD12_1 |
| ADA12_1 | FA9_1, FA9_2, PCD12_1, PRG4_2 |
| AFAM_1 | C1QA_1 |
| AFAM_2 | FA9_2 |
| ALS_1 | FA9_1, FA9_2, PCD12_1 |
| ANGT_1 | BGH3_1, CLUS_1, CLUS_2, FA9_1, FA9_2, ITIH4_1, NOTUM_1, PCD12_1, SEPP1_2, TETN_2 |
| ANT3_1 | PCD12_1, TETN_2 |
| AOC1_1 | PCD12_1 |
| AOC1_2 | PCD12_1 |
| APOC3_1 | CHL1_1, FA9_1, FA9_2, PCD12_1 |
| APOH_1 | FA9_1, FA9_2, PCD12_1 |
| ATL4_1 | PCD12_1 |
| ATS13_2 | PCD12_1 |
| B2MG_1 | CLUS_1, EGLN_1, FA9_1, FA9_2, FGFR1_1, ITIH4_1, LIRB5_1, NOTUM_1, PCD12_1, PGRP2_1, PRG2_1, SEPP1_1 |
| B2MG_2 | EGLN_1, FA9_1, FGFR1_1, FGFR1_2, HEMO_1, ITIH4_1, KIT_2, PCD12_1, SEPP1_1 |
| BGH3_1 | FA9_1, FA9_2, PCD12_1, PCD12_2 |
| C163A_1 | CHL1_1, CLUS_1, FA9_1, FA9_2, FGFR1_2 |
| C1QA_1 | PCD12_1, PRG4_1 |
| C1QA_2 | PCD12_1 |
| C1QB_1 | PCD12_1 |
| C1QB_2 | PCD12_1 |
| C1QB_3 | CLUS_2, EGLN_1, FA9_1, FA9_2, HEMO_1, ITIH4_1, PCD12_1, PTGDS_1, SVEP1_1 |
| C1QC_1 | AMBP_1, ISM2_2, MUC18_1, PCD12_1 |
| C1QC_2 | PCD12_1 |
| CADH5_1 | CAMP_1, CAMP_2, PCD12_1 |
| CADH5_2 | PCD12_1, SVEP1_1 |
| CAH1_1 | CHL1_1, CNTN1_2, FA9_1, FA9_2, HEMO_1, PCD12_1 |
| CAMP_1 | PCD12_1 |
| CAMP_2 | PCD12_1 |
| CATD_1 | FA9_1, FA9_2, PCD12_1 |
| CATD_2 | FA9_1, FA9_2, PCD12_1 |
| CBPN_1 | FA9_2, PCD12_1 |
| CBPN_2 | FA9_1, FA9_2, INHBC_1, PCD12_1 |
| CD14_1 | FA9_1, FA9_2, HEMO_1, ITIH4_1, PCD12_1 |
| CD14_2 | FA9_1, FA9_2, PCD12_1 |
| CFAB_1 | PCD12_1 |

TABLE 9-continued

| Two analyte models for Parity 1 | |
|---|---|
| Analyte1 | Analyte2 |
| CHL1_1 | ADA12_1, ANT3_1, AOC1_1, CLUS_1, CO6_1, CO8B_1, DPEP2_2, EGLN_1, FA5_1, FA5_2, FA9_1, FA9_2, HEMO_1, IBP3_2, IBP6_2, IGF2_1, IPSP_1, IPSP_2, ITIH4_1, ITIH4_3, LYAM1_1, PAPP2_1, PCD12_1, PRL_2, PTGDS_1, SEPP1_2, SVEP1_1, TENX_1, TETN_2, VGFR1_1 |
| CLUS_1 | AOC1_1, AOC1_2, ATL4_1, CADH5_1, CADH5_2, CAMP_1, CAMP_2, CO8B_1, CRIS3_1, DEF1_1, EGLN_1, F13B_1, FA5_1, FA9_1, FA9_2, FGFR1_1, FGFR1_2, HEMO_1, IL1R1_1, IPSP_1, KNG1_1, NOTUM_1, PCD12_1, PGRP2_1, PROS_2, PSG9_2, PTGDS_2, SVEP1_1, TIE1_1 |
| CLUS_2 | CRIS3_2, FA9_1, FA9_2, FGFR1_1, PCD12_1 |
| CNTN1_1 | PCD12_1 |
| CO5_1 | FA9_2, NOTUM_1, PCD12_1 |
| CO5_2 | FA9_1, FA9_2, ITIH4_1, PCD12_1 |
| CO6_1 | FA9_1, FA9_2, PCD12_1 |
| CO8A_1 | FA9_1, FA9_2, PCD12_1, TETN_2 |
| CO8B_1 | FA9_1, FA9_2, PCD12_1, PRG4_1, PTGDS_1 |
| CRIS3_1 | ATS13_2, EGLN_1, FA9_1, FA9_2, FETUA_2, IBP3_1, IGF2_1, SEPP1_2 |
| CRIS3_2 | ATS13_2, C1QC_1, CADH5_1, DPEP2_2, FA5_1, FA9_1, FA9_2, FETUA_2, FGFR1_2, HABP2_1, IGF2_1, PCD12_1, SEPP1_2, SVEP1_1, THBG_1 |
| CSH_1 | FA9_1, PCD12_1 |
| DEF1_1 | PCD12_1 |
| DEF1_2 | PCD12_1 |
| DPEP2_1 | PCD12_1 |
| DPEP2_2 | PCD12_1 |
| ECM1_1 | PCD12_1 |
| ECM1_2 | PCD12_1 |
| EGLN_1 | EGLN_2, LEP_1, PCD12_1, PRG4_2 |
| EGLN_2 | PCD12_1 |
| ENPP2_1 | PCD12_1 |
| F13B_1 | FA9_1, FA9_2, PCD12_1 |
| FA11_1 | PCD12_1 |
| FA11_2 | PCD12_1 |
| FA5_1 | PCD12_1, SVEP1_1 |
| FA5_2 | PCD12_1 |
| FA9_1 | ANT3_1, AOC1_1, AOC1_2, ATL4_1, ATS13_1, ATS13_2, C1QB_1, C1QC_1, C1QC_2, CADH5_1, CADH5_2, CAMP_1, CAMP_2, CNTN1_1, CNTN1_2, CRAC1_1, CRAC1_2, CRAC1_3, DEF1_1, DEF1_2, DPEP2_1, DPEP2_2, ECM1_1, EGLN_1, EGLN_2, FA11_1, FA11_2, FA5_1, FA5_2, FA9_2, FGFR1_1, FGFR1_2, GELS_1, GELS_2, IGF1_1, IL1R1_1, IPSP_1, IPSP_2, ISM2_1, ISM2_2, KIT_1, KIT_2, LEP_1, LEP_2, MFAP5_1, MUC18_1, MUC18_2, NOTUM_1, NOTUM_2, PAEP_1, PAEP_2, PAPP2_1, PCD12_1, PRL_1, PRL_2, PROS_1, PROS_2, PTGDS_1, RET4_1, SEPP1_1, SEPP1_2, SHBG_2, SVEP1_1, TETN_1, TETN_2, THRB_1, TIMP1_1, VGFR1_1 |
| FA9_2 | ANT3_1, AOC1_1, AOC1_2, ATL4_1, ATS13_1, ATS13_2, C1QC_1, C1QC_2, CADH5_1, CADH5_2, CRAC1_1, CRAC1_3, DEF1_1, DEF1_2, DPEP2_1, DPEP2_2, ECM1_1, EGLN_1, FA11_1, FA11_2, FA5_1, FA5_2, FGFR1_1, FGFR1_2, GELS_2, IGF1_1, IL1R1_1, IPSP_1, IPSP_2, ISM2_1, ISM2_2, KIT_1, LEP_2, MFAP5_1, MUC18_2, NOTUM_1, NOTUM_2, PAEP_1, PAEP_2, PAPP2_1, PCD12_1, PRL_1, PRL_2, PROS_1, PROS_2, PTGDS_1, RET4_1, SEPP1_1, SEPP1_2, SHBG_2, SVEP1_1, TETN_1, TETN_2, THRB_1, TIMP1_1, VGFR1_1 |
| FBLN1_1 | FA9_1, FA9_2, PCD12_1 |
| FBLN3_1 | FA9_1, FA9_2, IBP4_1, PCD12_1 |
| FETUA_1 | FA9_1, PCD12_1, PTGDS_1 |
| FETUA_2 | PCD12_1, PRG4_1 |
| FGFR1_1 | PCD12_1 |
| FGFR1_2 | CNTN1_2, PCD12_1 |
| GELS_2 | PCD12_1 |
| GPX3_1 | FA9_1, FA9_2, PCD12_1 |
| GPX3_2 | FA9_1, FA9_2, PCD12_1 |
| HABP2_1 | FA9_1, PSG11_1 |
| HEMO_1 | AOC1_1, AOC1_2, DPEP2_1, FA5_1, FA9_1, FA9_2, FGFR1_2, IBP4_2, ISM2_1, KIT_1, LBP_2, LYAM1_1, NOTUM_1, NOTUM_2, PAEP_2, PCD12_1, PGRP2_1, PSG9_2, SEPP1_1, TETN_2, VTDB_1, VTNC_2 |
| HLACL_1 | FA9_1, FA9_2, PCD12_1, PCD12_2 |
| IBP1_1 | FA9_1, PCD12_1 |
| IBP2_1 | PCD12_1 |
| IBP3_1 | FA9_1, FA9_2, PCD12_1, PCD12_2 |
| IBP3_2 | FA9_1, FA9_2, PCD12_1 |
| IBP4_1 | FA9_1, FA9_2, PCD12_1, SEPP1_1 |
| IBP4_2 | FA9_1, FA9_2, PCD12_1 |
| IBP4_3 | FA9_1, FA9_2, PCD12_1 |
| IBP6_1 | PCD12_1 |
| IBP6_2 | FA9_1, FA9_2, PCD12_1 |
| IGF1_1 | IPSP_1, PCD12_1, SEPP1_2 |
| IGF2_1 | FA9_1, FA9_2, PCD12_1 |
| IL1R1_1 | PCD12_1 |

TABLE 9-continued

Two analyte models for Parity 1

| Analyte1 | Analyte2 |
|---|---|
| INHBC_1 | DPEP2_2, ITIH4_1, KIT_1, LBP_1, PTGDS_2, SVEP1_1, TENX_1 |
| IPSP_1 | CADH5_1, NOTUM_1, PCD12_1, SVEP1_1 |
| IPSP_2 | ATL4_1, PCD12_1 |
| ISM2_1 | PCD12_1 |
| ISM2_2 | PCD12_1 |
| ITIH3_1 | FA9_1, FA9_2, LBP_2, PCD12_1, THBG_1 |
| ITIH4_1 | FA9_1, FGFR1_2, IBP4_1, KNG1_1, KNG1_2, LIRB5_1, PAPP1_1, PCD12_1, PGRP2_1, SVEP1_1, TENX_2 |
| ITIH4_2 | FA9_1, FA9_2, PCD12_1 |
| ITIH4_3 | FA9_1, PCD12_1, PCD12_2 |
| KIT_1 | PCD12_1 |
| KIT_2 | PCD12_1 |
| KNG1_1 | FA9_1, FA9_2, PCD12_1, PCD12_2, PTGDS_1 |
| KNG1_2 | FA9_1, FA9_2, PCD12_1 |
| LBP_1 | FA9_1, FA9_2, PCD12_1, PTGDS_1, TETN_2 |
| LBP_2 | ADA12_1, CRAC1_1, DPEP2_2, EGLN_1, FGFR1_1, IGF1_1, PTGDS_1 |
| LEP_1 | PCD12_1, PCD12_2 |
| LEP_2 | PCD12_1 |
| LIRB5_1 | CNTN1_2, FA9_1, FA9_2, PCD12_1 |
| LYAM1_1 | FA9_1, FA9_2, PCD12_1 |
| MFAP5_1 | PCD12_1 |
| MUC18_1 | PCD12_1 |
| MUC18_2 | SVEP1_1 |
| NOTUM_1 | PCD12_1 |
| NOTUM_2 | PCD12_1 |
| PAEP_1 | PCD12_1 |
| PAEP_2 | PCD12_1 |
| PAPP1_1 | FA9_1, FA9_2, PCD12_1 |
| PAPP2_1 | PCD12_1 |
| PCD12_1 | CRAC1_1, CRAC1_2, THRB_1 |
| PEDF_2 | FA9_1 |
| PGRP2_1 | C1QC_1, FA9_1, FA9_2, IPSP_2, PAEP_2, PCD12_1, PCD12_2, PTGDS_2, SEPP1_2, THBG_1 |
| PRDX2_1 | FA9_1, FA9_2, PCD12_1 |
| PRG2_1 | ATL4_1, CADH5_2, FA9_1, FA9_2, IPSP_1, PCD12_1 |
| PRG4_1 | PCD12_1 |
| PRL_1 | PCD12_1 |
| PRL_2 | PCD12_1 |
| PROS_1 | PCD12_1 |
| PROS_2 | PCD12_1 |
| PSG1_1 | FA9_1, FA9_2, PCD12_1, TETN_2 |
| PSG11_1 | FA9_1, PCD12_1 |
| PSG2_1 | FA9_1, PCD12_1, SEPP1_2 |
| PSG3_1 | FA9_1, FA9_2, PCD12_1 |
| PSG9_1 | FA9_1, FA9_2, LIRB5_1, PCD12_1 |
| PSG9_2 | FA9_1, FA9_2, PCD12_1, TENX_2, TETN_2 |
| PTGDS_1 | PCD12_1, SVEP1_1 |
| PTGDS_2 | FA9_1, FA9_2, FGFR1_2, PCD12_1 |
| RET4_1 | IPSP_1, PCD12_1 |
| SEPP1_1 | NOTUM_2, PCD12_1 |
| SEPP1_2 | NOTUM_1, PCD12_1 |
| SHBG_1 | FA9_1, FA9_2, PCD12_1, PCD12_2 |
| SHBG_2 | PCD12_1 |
| SHBG_3 | FA9_1, FA9_2, PCD12_1 |
| SOM2_1 | PCD12_1, SVEP1_1 |
| SOM2_2 | FA9_1, PCD12_1 |
| SPRL1_1 | FA9_1, FA9_2, PCD12_1, PCD12_2 |
| SVEP1_1 | NOTUM_2, PCD12_1, PCD12_2, PRG4_1, PRG4_2 |
| TENX_1 | FA9_1, FA9_2, PCD12_1, TETN_2 |
| TENX_2 | FA9_1, FA9_2, IPSP_1, PCD12_1 |
| TETN_1 | PCD12_1, PTGDS_1 |
| TETN_2 | FGFR1_2, GELS_2, NOTUM_1, PCD12_1 |
| THBG_1 | KIT_1, PCD12_1, PTGDS_1 |
| TIE1_1 | FA9_1, FA9_2, PCD12_1, PCD12_2 |
| TIMP1_1 | IPSP_1, PCD12_1 |
| VGFR1_1 | PCD12_1 |
| VTDB_1 | FA9_1, FA9_2, PCD12_1 |
| VTNC_1 | FA9_2 |
| VTNC_2 | FA9_1, PCD12_1, PTGDS_1, SVEP1_1 |

TABLE 10

| | Two analyte models for Parity 2+ |
|---|---|
| Analyte1 | Analyte2 |
| A2GL_1 | ADA12_1, AFAM_2, CD14_1, CD14_2, CNTN1_1, CRAC1_1, FBLN3_1, TETN_1 |
| AACT_1 | CNTN1_1, GELS_2, PRL_1 |
| ADA12_1 | ATL4_1, ATS13_1, C1QA_2, C1QB_1, CNTN1_1, CNTN1_2, CRAC1_1, CRAC1_3, DPEP2_1, DPEP2_2, FA9_2, FGFR1_2, GELS_1, GELS_2, KIT_1, KIT_2, LEP_1, MFAP5_1, PAEP_1, PAEP_2, PCD12_1, PRL_1, SHBG_2, TETN_1 |
| AFAM_1 | CD14_1, CRAC1_3, IBP4_1, TETN_1 |
| AFAM_2 | ATL4_1, CRAC1_2, CSH_1, PRL_1, TETN_1 |
| ALS_1 | CD14_1, CD14_2, CNTN1_1, TETN_1 |
| AMBP_1 | ATL4_1, CNTN1_1, GELS_1, MUC18_1, TETN_1 |
| ANGT_1 | CD14_1, CD14_2, CNTN1_1, TETN_1 |
| ANT3_1 | ATL4_1, CRAC1_3, KIT_1, PAEP_1, TETN_1, TETN_2 |
| AOC1_1 | CNTN1_1, CRAC1_3 |
| AOC1_2 | CNTN1_1 |
| APOC3_1 | ADA12_1 |
| APOH_1 | CD14_1, CD14_2, CNTN1_1 |
| B2MG_1 | ADA12_1, CD14_1, CD14_2, CNTN1_1, CRAC1_1, FA9_1, PEDF_1, TETN_1, TETN_2 |
| B2MG_2 | CD14_2 |
| BGH3_1 | CD14_1, CD14_2, CNTN1_1, TETN_1 |
| C163A_1 | ADA12_1, CD14_1, CD14_2, CNTN1_1, CSH_1, TETN_1 |
| C1QA_1 | CNTN1_1, TETN_1 |
| C1QA_2 | CNTN1_1, TETN_1 |
| C1QB_1 | TETN_1 |
| C1QB_2 | AMBP_1, TETN_1 |
| C1QB_3 | CD14_1, CD14_2, CNTN1_1, TETN_1, TETN_2 |
| C1QC_1 | CNTN1_1 |
| C1QC_2 | CNTN1_1, TETN_1 |
| CADH5_1 | CNTN1_1 |
| CADH5_2 | CNTN1_1 |
| CAH1_1 | CD14_1, CD14_2, CNTN1_1, TETN_1 |
| CAMP_1 | CNTN1_1 |
| CAMP_2 | CNTN1_1 |
| CATD_1 | CD14_1, CNTN1_1, TETN_1 |
| CATD_2 | ADA12_1, CD14_1, CD14_2, CNTN1_1, CRAC1_1, CRAC1_3, CSH_1, FBLN3_1, TETN_1 |
| CBPN_1 | CD14_2, CNTN1_1, TETN_1 |
| CBPN_2 | CD14_1, CD14_2 |
| CD14_1 | AACT_1, ADA12_1, AMBP_1, ANT3_1, AOC1_1, AOC1_2, ATL4_1, ATS13_1, ATS13_2, C1QA_1, C1QA_2, C1QB_1, C1QB_2, C1QC_1, C1QC_2, CADH5_1, CADH5_2, CAMP_1, CAMP_2, CD14_2, CGB1_1, CGB1_2, CHL1_1, CLUS_1, CLUS_2, CNTN1_1, CNTN1_2, CO5_1, CO5_2, CO8A_1, CO8B_1, CRAC1_1, CRIS3_1, CRIS3_2, CSH_1, CSH_2, ECM1_1, ECM1_2, EGLN_1, EGLN_2, ENPP1_1, ENPP2_2, F13B_1, FA11_2, FA5_1, FA5_2, FA9_1, FA9_2, FBLN1_1, FBLN3_1, FETUA_2, FGFR1_1, FGFR1_2, GELS_1, GELS_2, GPX3_1, HABP2_1, HEMO_1, HLACI_1, IBP1_1, IBP2_1, IBP3_1, IBP4_1, IBP4_2, IBP6_1, IBP6_2, IGF1_1, IGF2_1, IL1R1_1, INHBC_1, IPSP_1, ISM2_1, ITIH3_1, ITIH4_1, ITIH4_2, ITIH4_3, KIT_1, KIT_2, KNG1_2, LBP_1, LBP_2, LEP_1, LEP_2, LIRB5_1, LYAM1_1, MFAP5_1, MUC18_1, MUC18_2, NOTUM_1, NOTUM_2, PAEP_1, PAEP_2, PCD12_1, PCD12_2, PEDF_1, PGRP2_1, PRDX2_1, PRG4_1, PRG4_2, PROS_1, PROS_2, PSG11_1, PSG2_1, PSG3_1, PSG9_1, PSG9_2, PTGDS_1, PTGDS_2, RET4_1, SEPP1_1, SHBG_1, SHBG_2, SHBG_3, SOM2_1, SOM2_2, SPRL1_1, SVEP1_1, TENX_1, TENX_2, TETN_1, TETN_2, THBG_1, THRB_1, TIE1_1, TIMP1_1, VTDB_1, VTNC_1 |
| CD14_2 | AACT_1, ADA12_1, AMBP_1, ANT3_1, ATL4_1, ATS13_1, ATS13_2, C1QA_2, C1QB_1, C1QB_2, C1QC_1, C1QC_2, CADH5_1, CADH5_2, CAMP_1, CAMP_2, CFAB_1, CGB1_1, CGB1_2, CHL1_1, CLUS_2, CNTN1_1, CNTN1_2, CO5_1, CO5_2, CO6_1, CO8A_1, CO8B_1, CRAC1_1, CRAC1_3, CRIS3_1, CRIS3_2, CSH_1, CSH_2, DEF1_1, DEF1_2, DPEP2_1, DPEP2_2, ECM1_1, ECM1_2, EGLN_1, EGEN_2, ENPP2_1, FT3B_1, FA11_1, FA11_2, FA5_1, FA9_1, FBLN1_1, FBLN3_1, FETUA_1, FETUA_2, FGR1_1, F6FR1_2, GELS_1, GELS_2, GPX3_1, GPX3_2, HABP2_1, HEMO_1, IBP1_1, IBP2_1, IBP3_1, IBP3_2, IBP4_1, IBP4_2, IBP4_3, IBP6_1, IBP6_2, IGF1_1, IGF2_1, IL1R1_1, IPSP_1, IPSP_2, ISM2_1, ITIH3_1, ITIH4_1, ITIH4_2, ITIH4_3, KIT_1, KIT_2, KNG1_1, KNG1_2, LBP_1, LBP_2, LEP_1, LEP_2, LIRB5_1, MFAP5_1, MUC18_2, NOTUM_1, PAEP_1, PAEP_2, PAPP2_1, PCD12_1, PCD12_2, PEDF_1, PEDF_2, PGRP2_1, PRDX2_1, PRG2_1, PRG4_1, PRG4_2, PRL_1, PROS_1, PROS_2, PSG1_1, PSG11_1, PSG2_1, PSG3_1, PSG9_1, PSG9_2, PTGDS_1, PTG5S_2, RET4_1, SEPP1_1, SHBG_1, SHBG_2, SHBG_3, SOM2_1, SPRL1_1, SVEP1_1, TENX_1, TENX_2, TETN_1, TETN_2, THRB_1, TIMP1_1, VTDB_1, VTNC_1, VTNC_2 |
| CFAB_1 | ADA12_1, CNTN1_1, TETN_1 |
| CGB1_1 | CNTN1_1, CRAC1_1, TETN_1 |
| CGB1_2 | ATL4_1, CNTN1_1, CRAC1_1, TETN_1 |

TABLE 10-continued

| Two analyte models for Parity 2+ | |
|---|---|
| Analyte1 | Analyte2 |
| CHL1_1 | ADA12_1, CNTN1_1, CO5_1, CO5_2, CO8A_1, CSH_1, FA5_1, IBP4_2, PSG11_1, PSG2_1, TETN_1, TETN_2, THBG_1, VTNC_2 |
| CLUS_1 | CNTN1_1 |
| CLUS_2 | ADA12_1, CRAC1_3, CSH_1, FBLN3_1 |
| CNTN1_1 | ATS13_1, ATS13_2, CRAC1_1, CRAC1_2, DPEP2_1, DPEP2_2, MFAP5_1, NOTUM_1, PCD12_1, PCD12_2, PRG4_1, SVEP1_1 |
| CNTN1_2 | CRAC1_1 |
| CO5_1 | ATL4_1, CNTN1_1, CRAC1_1, CRAC1_3, FBLN1_1, FBLN3_1, GELS_2, KIT_2, SHBG_1, SHBG_2, TETN_1 |
| CO5_2 | ADA12_1, CRAC1_1, FBLN3_1, TETN_1 |
| CO8A_1 | ADA12_1, CNTN1_1, CRAC1_3, CSH_1, FBLN1_1, PRL_1, TETN_1, TETN_2 |
| CO8B_1 | ADA12_1, ATL4_1, CNTN1_1, FBLN1_1, TETN_1, TETN_2 |
| CRIS3_1 | CNTN1_1 |
| CRIS3_2 | CNTN1_1, CSH_1 |
| CSH_1 | AACT_1, ADA12_1, AMBP_1, ANT3_1, ATL4_1, ATS13_1, CNTN1_1, CNTN1_2, CRAC1_1, CRAC1_2, CRAC1_3, DPEP2_1, DPEP2_2, ENPP2_2, FA11_2, FA5_2, FA9_1, FBLN3_1, FETUA_1, FETUA_2, FGFR1_2, IBP1_1, IBP4_2, ITIH3_1, KIT_1, LIRB5_1, PEDF_1, PRG2_1, PRL_1, PSG1_1, SHBG_1, SHBG_2, SHBG_3, SPRL1_1, TENX_1, TETN_1, TETN_2, THBG_1, TIE1_1, TIMP1_1, VTDB_1, VTNC_2 |
| CSH_2 | CNTN1_1, TETN_1 |
| EGLN_2 | CNTN1_1 |
| ENPP2_1 | CRAC1_3 |
| F13B_1 | CNTN1_1, TETN_1 |
| FA11_1 | CNTN1_1, TETN_1 |
| FA11_2 | CNTN1_1, TETN_1 |
| FA5_1 | ATL4_1, CNTN1_1 |
| FA5_2 | ATL4_1, CNTN1_1, CNTN1_2 |
| FA9_1 | CNTN1_1, FGFR1_2, GELS_2, MUC18_1, TETN_1 |
| FA9_2 | ATL4_1, CNTN1_1, CNTN1_2, CRAC1_3, FGFR1_2, GELS_1, TETN_1, TETN_2 |
| FBLN1_1 | ADA12_1, AMBP_1, GELS_2, TETN_1 |
| FBLN3_1 | AACT_1, CNTN1_1, CRAC1_1, FA5_2, IBP4_2, PRL_1, PSG11_1, TETN_1 |
| FETUA_1 | CNTN1_1, TETN_1 |
| FETUA_2 | CNTN1_1, TETN_1 |
| FGFR1_1 | CNTN1_1 |
| FGFR1_2 | CNTN1_1 |
| GELS_1 | CNTN1_1, EGLN_1, PROS_1 |
| GELS_2 | EGLN_1, PROS_1 |
| GPX3_1 | ADA12_1, TETN_1 |
| GPX3_2 | CNTN1_1 |
| HEMO_1 | CNTN1_1 |
| HLACl_1 | CNTN1_1 |
| IBP2_1 | TETN_1 |
| IBP3_1 | CNTN1_1, TETN_2 |
| IBP3_2 | CNTN1_1, TETN_1 |
| IBP4_1 | CNTN1_1, PAEP_1, TETN_1 |
| IBP4_2 | CNTN1_1, CNTN1_2, SHBG_2, TETN_1 |
| IBP4_3 | CNTN1_1, TETN_1 |
| IBP6_1 | CNTN1_1, TETN_1 |
| IBP6_2 | ADA12_1, CNTN1_1, TETN_2 |
| IGF1_1 | CNTN1_1 |
| IGF2_1 | CNTN1_1, TETN_1 |
| INHBC_1 | CRAC1_3, TETN_1 |
| IPSP_1 | CNTN1_1, TETN_1 |
| IPSP_2 | CNTN1_1 |
| ITIH3_1 | CNTN1_1, TETN_1 |
| ITIH4_1 | ADA12_1, CNTN1_1, TETN_1 |
| ITIH4_2 | CNTN1_1 |
| ITIH4_3 | TETN_1 |
| KIT_1 | CNTN1_1 |
| KIT_2 | CNTN1_1 |
| KNG1_1 | ATL4_1, CNTN1_1 |
| KNG1_2 | CNTN1_1 |
| LBP_1 | CNTN1_1, TETN_1 |
| LBP_2 | CNTN1_1, TETN_1 |
| LEP_1 | CNTN1_1 |
| LEP_2 | CNTN1_1 |
| LIRB5_1 | CNTN1_1, TETN_1 |
| LYAM1_1 | TETN_1 |
| PAEP_1 | CRAC1_3, FA5_2 |
| PAPP1_1 | CNTN1_1, TETN_1 |
| PEDF_1 | AACT_1, ADA12_1, CNTN1_1, CNTN1_2, CRAC1_1, CRAC1_3, GELS_1, TETN_1, TETN_2 |
| PEDF_2 | TETN_1 |
| PGRP2_1 | TETN_1 |
| PRDX2_1 | CNTN1_1, TETN_1 |

TABLE 10-continued

Two analyte models for Parity 2+

| Analyte1 | Analyte2 |
| --- | --- |
| PRG2__1 | ADA12__1, CNTN1__1, TETN__1 |
| PRL__1 | ATL4__1, CNTN1__1, CNTN1__2, GELS__1, GELS 2, PROS__1, TETN__1 |
| PRL__2 | ATL4__1, CNTN1__1, CRAC1__1, GELS__2, TETN__1 |
| PROS__1 | CNTN1__1, CNTN1__2, CRAC1__3 |
| PSG11__1 | AACT__1, ADA12__1, ATL4__1, CNTN1__1, KIT__1, PSG2__1, TETN__1, VTNC__2 |
| PSG2__1 | AACT__1, ADA12__1, AMBP__1, ATL4__1, CNTN1__1, CNTN1__2, CRAC1__1, GELS__1, GELS__2, KIT__1, PAEP__1, PSG9__1, TETN__1 |
| PSG3__1 | TETN__1 |
| PSG9__1 | CNTN1__1, TETN__1 |
| PSG9__2 | TETN__1 |
| PTGDS__1 | CNTN1__1 |
| PTGDS__2 | CNTN1__1, TETN__1 |
| RET4__1 | CNTN1__1, TETN__1, TETN__2 |
| SEPP1__2 | CNTN1__1 |
| SHBG__1 | ADA12__1, CNTN1__1, CRAC1__3, TENX__2, TETN__1, TETN__2 |
| SHBG__2 | CNTN1__1, TETN__1, TETN__2 |
| SHBG__3 | CNTN1__1, CRAC1__3, TETN__1, TETN__2 |
| SOM2__1 | ADA12__1, CNTN1__1, TETN__1 |
| SOM2__2 | ADA12__1, CRAC1__1, FA9__2, KIT__1, TETN__1 |
| SPRL1__1 | CNTN1__1, TETN__1 |
| SVEP1__1 | CRAC1__3 |
| TENX__1 | TETN__1 |
| TENX__2 | ADA12__1, CNTN1__1, TETN__1 |
| TETN__1 | ATL4__1, ATS13__1, ATS13__2, CADH5__1, CADH5__2, CNTN1__1, CRAC1__3, DPEP2__1, DPEP2__2, ECM1__2, EGLN__1, EGLN__2, FA5__1, FA5__2, FGFR1__1, FGFR1__2, GELS__1, KIT__2, LEP__1, LEP__2, MFAP5__1, NOTUM__1, PAEP__1, PCD12__1, PCD12__2, PRG4__1, PROS__2, PTGDS__1, SEPP1__1, SEPP1__2, TETN__2, THRB__1 |
| TETN__2 | ATL4__1, CNTN1__1, KIT__1, PCD12__1, PROS__1 |
| THBG__1 | CNTN1__1, CRAC1__1, TETN__1 |
| TIE1__1 | ADA12__1, ATL4__1, CNTN1__1, CNTN1__2, CRAC1__3, TETN__1, TETN__2 |
| TIMP1__1 | CNTN1__1, TETN__1 |
| VTDB__1 | CNTN1__1 |
| VTNC__1 | CNTN1__1, CRAC1__3, KIT__1 |
| VTNC__2 | ADA12__1, CNTN1__1 |

Model 2: Two Analyte Models Containing InvParity as a Variable for Overlapping GABD Windows Model 2 (TTB~ETB+InvParity+Analyte1+Analyte2) was run for 171 analytes in all possible pairs, in overlapping three-week windows with an overlap of one week. All TERM samples were used (975 subjects were TERM). Analytes were included not as a ratio (i.e. a reversal) to allow for different coefficients for each. This model was applied to subjects of all Parities for GA windows: $-18^{0/7}$ to $28^{6/7}$—and in 3-week GA windows from $18^{0/7}$ to $20^{6/7}$, $19^{0/7}$ to $21^{6/7}$, etc. to $26^{0/7}$ to $28^{6/7}$. The performance metric was accuracy.

TABLE 11

Overlapping windows of GA at blood draw, the number of samples in each and the minimum, median and maximum accuracy in each window. Nomenclature: for example [126-147) means GA day $126 \leq$ GA at blood draw day $<$ GA day 147.

| Windows | nTERM | min | med | max |
| --- | --- | --- | --- | --- |
| [126-147) | 262 | 46.9 | 50.4 | 54.2 |
| [133-154) | 267 | 44.9 | 48.7 | 53.2 |
| [140-161) | 265 | 45.7 | 48.7 | 54.0 |
| [147-168) | 265 | 45.3 | 48.7 | 53.2 |
| [154-175) | 266 | 47.4 | 52.3 | 56.4 |
| [161-182) | 264 | 45.5 | 50.4 | 54.9 |
| [168-189) | 271 | 48.3 | 51.3 | 56.8 |
| [175-196) | 261 | 44.8 | 49.0 | 54.0 |
| [182-203) | 269 | 47.2 | 51.3 | 56.1 |
| [126-203) | 975 | 48.5 | 50.2 | 52.6 |

TABLE 12

Analyte pairs in models containing InvParity for GABD 126-147

| Analyte1 | Analyte2 |
| --- | --- |
| A2GL__1 | AFAM__2, CD14__1, CFAB__1, CHL1__1, FA9__1, FA9__2, FGFR1__1, IBP1__1, ITIH3__1, ITIH4__2, LIRB5__1, PRG4__1, PRG4__2, VTNC__2 |
| AACT__1 | CNTN1__2, CRAC1__1, FA9__1, FA9__2, GELS__2, KIT__1, SHBG__3 |

TABLE 12-continued

Analyte pairs in models containing InvParity for GABD 126-147

| Analyte1 | Analyte2 |
|---|---|
| AFAM_1 | AACT_1, AOC1_2, APOH_1, ATL4_1, B2MG_1, C1QA_1, C1Q2B_3, CAMP_1, CBPN_1, CBPN_2, CD14_1, CFAB_1, CGB1_1, CHL1_1, CNTNT_1, CNTNT1_2, CO5_1, CO5_2, CO8A_1, CRIS3_1, CRIS3_2, DPEP2_2, EGLN_2, FA9_1, FA9_2, FGFR1_1, GELS_2, IBP4_1, IBP4_2, IBP4_3, IBP6_2, IGF2_1, IL1R1_1, INHBC_1, ITIH3_1, KIT_2, KNG1_2, LBP_1, LBP_2, LIRB5_1, MUC18_1, PAEP_2, PEDF_-1, PRG4_1, PSG1_1, PSG11_1, PSG3_1, PSG9_2, PTGDS_2, SHBG_2, SHBG_3, SOM2_1, SPRLT1_1, THBG_1, TIMP1_1, VGFR1_1, VTNC_2 |
| AFAM_2 | AACT_1, ADA12_1, ANT3_1, ATL4_1, C1QA_1, C1QB_3, CADH5_1, CFAB_1, CHL1_1, CLUS_1, CNTN1_2, CO8A_1, CRAE1_1, CRIS3_1, DPEP2_2, EGTN_1, EGLN_2, ENPP2_2, FGFR1_1, IBP1_1, IGF2_1, ITIH3_1, KIT_1, LIRB5_1, LYAM1_1, PAPP1_1, PEDF_1, PRG4_1, PRG4_2, PSG2_1, PSG9_1, RET4_1, SEPP1_1, SHBG_1, SHBG_2, SHBG_3, TETN_1, THBG_1, VTNC_2 |
| AMBP_1 | CNTN1_2, LEP_1, PRG4_1, PRG4_2, SHBG_2 |
| ANT3_1 | LEP_1, PRG4_2, SHBG_2, TETN_1 |
| AOC1_1 | PRG4_1, PRG4_2 |
| AOC1_2 | PRG4_2 |
| APOC3_1 | CHL1_1, ENPP2_2, FA9_1, FGFR1_1, ITIH3_1, LEP_1, SOM2_2 |
| APOH_1 | CHL1_1, FA9_1, PRG4_2, SHBG_2, SHBG_3, VTNC_2 |
| ATL4_1 | CRAC1_1, PRG4_2 |
| ATS13_2 | PRG4_1, PRG4_2 |
| B2MG_1 | B2MG_2, CRIS3_1, FA9_1, IBP4_1, KIT_2, LEP_2 |
| B2MG_2 | PRG4_2, THBG_1, VTNC_2 |
| BGH3_1 | C1QC_1, CFAB_1, FA9_2, KIT_1, LBP_2, PEDF_1 |
| C163A_1 | CFAB_1, CHL1_1, GELS_2 |
| C1QA_1 | CRAC1_1, DPEP2_1, ECM1_2, PRG4_1, PRG4_2, SHBG_2, TETN_1 |
| C1QA_2 | C1QC_1, PRG4_1, PRG4_2 |
| C1QB_1 | C1QC_1, PRG4_1, PRG4_2, SHBG_2 |
| C1QB_2 | GELS_2, PRG4_2, SHBG_2, TETN_1 |
| C1QB_3 | CATD_1, CFAB_1, CHL1_1, CO8A_1, CRAC1_1, ECM1_2, ENPP2_1, FA9_1, FBLN3_1, IBP1_1, IBP6_2, IGF1_1, IGF2_1, ISM2_1, ITIH3_1, MUC18_1, NOTUM_2, PRG4_1, PRG4_2, PTGDS_1, THBG_1, TIE1_1 |
| C1QC_1 | AOC1_2, C1QC_2, CAMP_1, CAMP_2, CNTN1_2, CRAC1_2, CRAC1_3, DEF1_1, DPEP2_1, DPEP2_2, ECM1_1, ECM1_2, FGFR1_1, FGFR1_2, IGF1_1, IL1R1_1, IPSP_1, KIT_2, LEP_2, NOTUM_1, PAEP_2, PAPP2_1, PCD12_1, PTGDS_1, SEPP1_1, VGFR1_1 |
| C1QC_2 | PRG4_1, PRG4_2, SHBG_2 |
| CADH5_1 | CNTN1_2, PRG4_1, PRG4_2, PTGDS_1 |
| CADH5_2 | PRG4_1, PRG4_2 |
| CAH1_1 | C1QC_1, CHL1_1, KIT_1, PRDX2_1, PRG4_1, PRG4_2, TETN_1, THBG_1, VTNC_2 |
| CAMP_1 | PRG4_1, PRG4_2 |
| CAMP_2 | PRG4_2 |
| CATD_1 | CAMP_1, CAMP_2, CHL1_1, CNTN1_2, CRAC1_1, CRAC1_3, CRIS3_1, EGLN_2, ENPP2_1, HLACI_1, IGF2_1, ITIH3_1, KIT_1, KNG1_1, MUC18_1, PAPP1_1, PRG2_1, SOM2_2, TETN_1, TETN_2, THBG_1 |
| CATD_2 | KIT_1 |
| CBPN_1 | CHL1_1, FA9_1, KIT_1, SHBG_2, SHBG_3, VTNC_2 |
| CBPN_2 | C1QC_1, CHL1_1 |
| CD14_1 | AACT_1, C1QA_1, C1QA_2, CFAB_1, CHL1_1, CLUS_2, CNTN1_2, CO5_2, CO8A_1, CRIS3_2, ECM1_2, FA9_2, GELS_2, IBP1_1, ITIH3_1, ITIH4_2, KIT_2, LIRB5_1, PRG4_2, PROS_1, PROS_2, SHBG_2, SHBG_3, TENX_1, THRB_1, VTNC_2 |
| CD14_2 | CNTN1_2, FGFR1_1, GELS_2, THRB_1 |
| CFAB_1 | AACT_1, AT513_2, CHL1_1, CLUS_1, CNTN1_2, CO6_1, CRIS3_1, DPEP2_1, DPEP2_2, EGLN_1, ENPP2_2, FA11_2, FA9_2, FGFR1_1, FGFR1_2, IBP4_1, IGF1_1, ISM2_1,SM2_2, ITIH3_1, ITIH4_3, KIT_1, KIT_2, LEP_1, DRB5_1, LYAM1_1, MUC18_1, NOTUM_1, PRG4_2, PSG2_1, PTGDS_2, SEPP1_2, TETN_1, THBG_1, THRB_1 |
| CGB1_1 | C1QC_1, CRAC1_1, FA9_1, LIRB5_1, PRG4_1, TETN_1 |
| CGB1_2 | CRAC1_1, LIRB5_1, PRG4_1 |
| CHL1_1 | AACT_1, AMBP_1, ANT3_1, AOC1_1, AOC1_2, ATL4_1, C1QA_1, C1QA_2, C1QB_1, C1QB_2, C1QC_1, C1QC_2, CADH5_1, CADH5_2, CAMP_1, CAMP_2, CGB1_1, CGB1_2, CLUS_1, CLUS_2, CNTN1_1, CNTN1_2, CO5_1, CO5_2, CO8A_1, CRAC1_1, DEF1_1, DEF1_2, DPEP2_2, ECM1_1, ECM1_2, EGLN_2, ENPP2_1, ENPP2_2, FA11_1, FA11_2, FA9_1, FBLN1_1, FBLN3_1, FETUA_2, FGFR1_1, FGFR1_2, GELS_1, GPX3_1, GPX3_2, HABP2_1, HLACI_1, IBP1_1, IBP3_2, IBP6_1, IBP6_2, IGF1_1, IGF2_1, IL1R1_1, INHBC_1, IPSP_1, IPSP_2, ISM2_1, ITIH3_1, ITIH4_1, ITIH4_3, KIT_1, KNG1_1, KNG1_2, LEP_1, LEP_2, LIRB5_1, LYAM1_1, MUC18_1, MUC18_2, NOTUM_1, NOTUM_2, PAEP_2, PAPP1_1, PEDF_1, PEDF_2, PRDX2_1, PRG2_1, PRG4_1, PRG4_2, PROS_1, PROS_2, PSG1_1, PSG11_1, PSG3_1, PSG9_1, PSG9_2, PTGDS_1, PTGDS_2, SEPP1_1, SEPP1_2, SHBG_2, SHBG_3, SPRL1_1, TENX_1, TETN_1, THBG_1, THRB_1, TIE1_1, VGFR1_1, VTNC_2 |
| CLUS_1 | EGLN_2, FA9_2, INHBC_1, KIT_1, LEP_1, PRG4_1, PRG4_2, TETN_1, VTNC_2 |
| CLUS_2 | FA9_1, ITIH3_1, PEDF_1, PRG4_1, PRG4_2, SHBG_1, VTNC_2 |
| CNTN1_1 | PRG4_1, PRG4_2 |

TABLE 12-continued

Analyte pairs in models containing InvParity for GABD 126-147

| Analyte1 | Analyte2 |
|---|---|
| CNTN1_2 | ATL4_1, DPEP2_2, NOTUM_1, PRG4_1, THRB_1 |
| CO5_1 | C1QC_1, CNTN1_2, CRIS3_1, IBP1_1, PRG4_1, PRG4_2 |
| CO5_2 | AACT_1, C1QC_1, CNTN1_2, FA9_1, FGFR1_1, HEMO_1, IGF2_1, ITIH4_2, KIT_1, KIT_2, LEP_1, PEDF_1, PRG4_2, SEPP1_1, THBG_1, VTNC_2 |
| CO6_1 | GELS_2 |
| CO8A_1 | AACT_1, ATL4_1, C1QA_1, C1QA_2, C1QC_1, CADH5_1, CNTN1_1, CNTN1_2, CRAC1_1, DPEP2_2, EGLN_2, ENPP2_1, ENPP2_2, FA9_1, HLACI_1, IBP1_1, IGF2_1, ILIR1_1, ITIH3_1, LIRB5_1, LYAM1_1, MFAP5_1, MUC18_1, MUC18_2, PAPP1_1, PCD12_1, PRG4_1, PRG4_2, PSG2_1, PSG3_1, PSG9_1, PSG9_2, SHBG_2, SHBG_3, SPRL1_1, TETN_1, THBG_1, VTNC_2 |
| CRIS3_1 | AACT_1, CRIS3_2, FA9_2, FBLN1_1, FGFR1_1, LIRB5_1, PRG4_1, PTGDS_1, |
| CRIS3_1 | THBG-_1, VTNC_-2 |
| CRIS3_2 | AACT_1, DPEP2_2, ENPP2_2, FGFR1_1, IGF2_1, ITIH4_2, ITIH4_3, KIT_1, LEP_1, PEDF_1, PRG4_1, PRG4_2, PSG2_1, TETN_1, TIMP1_1 |
| CSH_1 | ENPP2_2, FA9_1, GELS_2, ITIH3_1, TETN_1, THBG_1 |
| CSH_2 | C1QC_1, ENPP2_2, FA9_1, ITIH3_1, TETN_1, VTNC_1, VTNC_2 |
| DEF1_1 | PRG4_2 |
| DEF1_2 | PRG4_2 |
| ECM1_1 | PRG4_1, PRG4_2 |
| ECM1_2 | CRAC1_1, PRG4_1, PRG4_2 |
| EGLN_2 | CNTN1_2, CRAC1_1, MUC18_2 |
| ENPP2_1 | C1QC_1, ITIH3_1, KIT_1, PRG4_1, PRG4_2, SHBG_2, SHBG_3, TETN_1 |
| ENPP2_2 | AACT_1, ATS13_1, C1QA_1, CADH5_1, ECM1_1, ECM1_2, EGLN_2, FA9_1, FA9_2, FGFR1_1, GELS_1, ITIH3_1, KIT_1, KIT_2, LBP_2, LIRB5_1, LYAM1_1, PCD12_1, PRG4_2, SHBG_3, TENX_1, TETN_1, THBG_1 |
| F13B_1 | FA9_1, PRG4_2 |
| FA11_1 | FA11_2, SHBG_2, TETN_1 |
| FA5_2 | CNTN1_2, CRAC1_3, PRG4_2 |
| FA9_1 | AMBP_1, ANT3_1, ATL4_1, C1QB_1, C1QB_2, C1QC_1, C1QC_2, CNTN1_2, CRAC1_2, CRAC1_3, DPEP2_1, DPEP2_2, ECM1_2, FA11_2, FA9_2, FGFR1_1, FGFR1_2, GELS_1, GELS_2, ILIR1_1, KIT_1, LEP_2, MFAP5_1, MUC18_1, MUC18_2, PCD12_2, PRG4_1, PRL_1, PRL_2, PROS_1, PROS_2, SEPP1_1, SHBG_2, TETN_1, THRB_1, TIMP1_1 |
| FA9_2 | ANT3_1, C1QA_1, C1QA_2, C1QC_1, CRAC1_1, FGFR1_1, FGFR1_2, MUC18_1, PRG4_2, PROS_1, PROS_2, RET4_1, TETN_1, TETN_2, THRB_1 |
| FBLN1_1 | C1QC_1, PRG4_2 |
| FBLN3_1 | CNTN1_2, IGF2_1, KIT_1, PRG4_2, SHBG_2, THBG_1, VTNC_2 |
| FETUA_1 | C1QC_1 |
| FETUA_2 | AACT_1, C1QC_1, ITIH3_1, PRG4_1, PRG4_2, VTNC_2 |
| FGFR1_1 | CNTN1_2, CRAC1_2, LEP_1, MFAP5_1, MUC18_2 |
| FGFR1_2 | LEP_1, PRG4_1, PRG4_2 |
| GELS_1 | CRAC1_1, FGFR1_1, KIT_1, LEP_1, PRG4_1 |
| GELS_2 | DPEP2_2, ECM1_1, FGFR1_1, LEP_2, MUC18_2, PRG4_1, PRG4_2, PTGDS_1 |
| GPX3_1 | C1QC_1, ECM1_2, FA9_1 |
| GPX3_2 | C1QA_1, CRAC1_1, FA9_1, SHBG_2, TETN_1 |
| HABP2_1 | C1QC_1, ITIH3_1, LIRB5_1, PRG4_1, PRG4_2, SHBG_2, SHBG_3, VTNC_2 |
| HEMO_1 | ATL4_1, CRAC1_2, IL1R1_1, TETN_1 |
| HLACI_1 | CNTN1_2, PRG4_1, PRG4_2, SHBG_3, TETN_1, VTNC_2 |
| IBP1_1 | C1QA_1, C1QA_2, C1QC_1, CADH5_1, CRAC1_1, IBP4_1, IGF2_1, KIT_1, PRG4_1, PRG4_2, SHBG_2, VTNC_2 |
| IBP2_1 | C1QC_1 |
| IBP3_1 | C1QC_1, IGF2_1, SHBG_2, VTNC_2 |
| IBP3_2 | |
| IBP4_1 | FA9_1, GELS_2, LEP_1 |
| IBP4_2 | AACT_1, DPEP2_2, FA9_1, FGFR1_1, KIT_1, PRG4_1, PRG4_2, THBG_1 |
| IBP4_3 | FA9_1, FGFR1_1, KIT_1 |
| IBP6_1 | LEP_1 |
| IBP6_2 | C1QC_1, CRAC1_1, KIT_1, LIRB5_1, PRG4_2 |
| IGF1_1 | PRG4_1, PRG4_2, TETN_1 |
| IGF2_1 | AACT_1, AOC1_1, ATL4_1, CNTN1_1, CNTN1_2, DEF1_1, EGLN_2, GELS_2, LBP_1, LIRB5_1, LYAM1_1, MUC18_2, PAPP1_1, PRG4_1, PRG4_2, PSG9_1, PSG9_2, SEPP1_1, SHBG_1, SHBG_2, SHBG_3, SPRL1_1, TETN_1, THBG_1, VTNC_2 |
| IL1R1_1 | CNTN1_2, CRAC1_1, DEF1_2, LEP_1, PRG4_1 |
| INHBC_1 | C1QC_1, CNTN1_2, CRAC1_1, FGFR1_1, LIRB5_1, MFAP5_1, PRG4_1, PRG4_2, SHBG_2, SHBG_3, THBG_1, VTNC_2 |
| IPSP_1 | GELS_2, PRG4_1, PRG4_2, TETN_1 |
| IPSP_2 | GELS_2, LEP_1, PRG4_2 |
| ITIH3_1 | AACT_1, ADA12_1, C1QA_2, CAMP_1, CAMP_2, CRAC1_3, ECM1_1, ECM1_2, FA9_1, FA9_2, FGFR1_1, GELS_2, IBP4_3, IGF1_1, IPSP_2, KIT_1, KIT_2, LBP_1, LBP_2, LYAM1_1, MUC18_1, PEDF_1, PRDX2_1, PRG4_1, PSG11_1, PSG2_1, PTGDS_1, SOM2_1, SOM2_2, THBG_1, TIE1_1, VTNC_1, VTNC_2 |
| ITIH4_1 | C1QC_1, PRG4_1, PRG4_2, SHBG_2, SHBG_3, TETN_1, THBG_1 |
| ITIH4_2 | ATL4_1, C1QC_1, CNTN1_2, FA9_1, GELS_2, LYAM1_1, MUC18_1, PRG2_1, SHBG_1, SHBG_2, TETN_1, THBO_1 |

TABLE 12-continued

Analyte pairs in models containing InvParity for GABD 126-147

| Analyte1 | Analyte2 |
|---|---|
| ITIH4_3 | AACT_1, C1QC_1, CNTN1_2, CRAC1_1, DEF1_2, FA9_1, GELS_2, KIT_1, LEP_1, SHBG_1, THBG_1, VTNC_2 |
| KIT_1 | AOC1_2, ATL4_1, CADH5_1, CNTN1_2, DPEP2_2, FGFR1_1, LEP_1, MUC18_1, NOTUM_1, SEPP1_1, SEPP1_2, VGFR1_1 |
| KIT_2 | FGFR1_1, ISM2_2, LEP_1 |
| KNG1_1 | C1QC_1, CNTN1_2, LIRB5_1, PRG4_1, PRG4_2, THBG_1, VTNC_2 |
| KNG1_2 | C1QC_1, CNTN1_2, PRG4_2, VTNC_2 |
| LBP_1 | ATL4_1, CRAC1_1, CRAC1_3, FGFR1_1, KIT_1, LIRB5_1, PSG1_1, PSG11_1, PTGDS_1, VTNC_2 |
| LBP_2 | CNTN1_2, CRAC1_1, FA9_1, FGFR1_1, IL1R1_1, PSG1_1, VTNC_2 |
| LEP_1 | ATS13_2, CRAC1_1, PCD12_1, PTGDS_1, SEPP1_1, THRB_1 |
| LIRB5_1 | C1QA_2, C1QC_1, CRAC1_1, FA9_1, FA9_2, KIT_1, KIT_2, MUC18_1, MUC18_2, PRG4_1, PRG4_2, TETN_1 |
| LYAM1_1 | EGLN_2, FA9_2, KIT_1, LIRB5_1, PCD12_1, PRG2_1, PRG4_2, PTGDS_1, TETN_1, THB_1, TIE1_1 |
| MFAP5_1 | PRG4_2 |
| MUC18_2 | DPEP2_2, PRG4_1, PRG4_2 |
| PAEP_1 | ECM1_2, PRG4_1 |
| PAPP1_1 | FA9_1, FGFR1_1, GELS_2 |
| PEDF_1 | AACT_1, CADH5_1, CNTN1_2, CRAC1_1, EGLN_2, FA9_1, GELS_1, KIT_2, LEP_1, PSG2_1, TETN_1, THBG_1, TIE1_1, VTNC_2 |
| PEDF_2 | C1QC_1, PRG4_2, SHBG_2, SHBG_3 |
| PGRP2_1 | GELS_2 |
| PRDX2_1 | PRG4_1, PRG4_2, TETN_1, THBG_1 |
| PRG2_1 | GELS_2, TETN_1 |
| PRG4_1 | DPEP2_2, PCD12_1, PRG4_2 |
| PRG4_2 | DPEP2_1, DPEP2_2, PCD12_1 |
| PROS_2 | EGLN_2 |
| PSG1_1 | FA9_2, TETN_1, THBG_1 |
| PSG11_1 | C1QC_1, FA9_1, THBG_1 |
| PSG2_1 | C1QC_1, FA9_1, FA9_2, GELS_2, IL1R1_1, VTNC_2 |
| PSG3_1 | PRG4_1, PRG4_2, SHBG_2, SHBG_3, VTNC_2 |
| PSG9_1 | CADH5_1, CNTN1_2, PRG4_1, PRG4_2, SHBG_2, SHBG_3, TETN_1, THBG_1, VTNC_2 |
| PSG9_2 | C1QC_1, KIT_1, PRG4_1, PRG4_2, SHBG_2, SHBG_3 |
| PTGDS_1 | CRAC1_2, MUC18_2 |
| PTGDS_2 | AACT_1, C1QC_1, FA9_2, LIRB5_1, PRG4_2, TETN_1 |
| RET4_1 | GELS_2, KIT_1, PRG4_1, PRG4_2, TETN_1 |
| SEPP1_1 | CRAC1_1, PRG4_1, PRG4_2 |
| SEPP1_2 | PCD12_1 |
| SHBG_1 | ATL4_1, CADH5_1, CNTN1_2, CRAC1_1, DPEP2_2, ECM1_2, FA9_1, FGFR1_1, FGFR1_2, GPX3_1, GPX3_2, KIT_1, LIRB5_1, NOTUM_1, PRG4_1, PRG4_2, RET4_1, SHBG_2, SHBG_3, THBG_1, VTNC_2 |
| SHBG_2 | AOC1_2, ATL4_1, CADH5_1, CADH5_2, CAMP_1, CAMP_2, CNTN1_1, CNTN1_2, CRAC1_1, DPEP2_2, EGLN_2, FGFR1_1, FGFR1_2, IGF1_1, PRG4_1, PRG4_2, PROS_1, SEPP1_1, VGFR1_1 |
| SHBG_3 | AMBP_1, ANT3_1, ATL4_1, C1QA_1, C1QB_2, C1QC_2, CADH5_1, CNTN1_1, CNTN1_2, CRAC1_1, DPEP2_2, EGLN_2, FGFR1_1, FGFR1_2, IPSP_1, LIRB5_1, PCD12_1, PRG4_1, PRG4_2, PROS_1, SEPP1_1, VGFR1_1 |
| SOM2_1 | FA9_1, SHBG_2, TETN_1, THBG_1 |
| SOM2_2 | FA9_1, GELS_2, PRG4_2 |
| SPRL1_1 | PRG4_1, PRG4_2, SHBG_2, SHBG_3, VTNC_2 |
| SVEP1_1 | CRAC1_3 |
| TENX_1 | CRAC1_1, FA9_1, PRG4_1, PRG4_2 |
| TENX_2 | FGFR1_1, KIT_2 |
| TETN_1 | AOC1_1, CAMP_1, CNTN1_1, DEF1_1, DEF1_2, ECM1_1, ECM1_2, EGLN_1, FGFR1_1, ISM2_2, LEP_1, LEP_2, MFAP5_1, PROS_2, PTGDS_1, SEPP1_1, SEPP1_2, THRB_1, VGFR1_1 |
| TETN_2 | KIT_1 |
| THBG_1 | AACT_1, ANT3_1, ATL4_1, ATS13_2, C1QB_1, C1QC_1, CADH5_2, CAMP_1, CNTN1_1, CNTN1_2, CRAC1_1, DEF1_1, DEF1_2, DPEP2_1, DPEP2_2, ECM1_2, EGLN_1, FA9_1, FA9_2, FGFR1_1, FGFR1_2, GPX3_2, IBP4_1, IGF1_1, IL1R1_1, KIT_1, KIT_2, LEP_1, LIRB5_1, MUC18_1, PAEP_1, PAEP_2, PRG4_2, PTGDS_1, SEPP1_1, SHBG_2, SHBG_3, TETN_1, THRB_1, VTNC_1, VTNC_2 |
| TIE1_1 | C1QC_1, CNTN1_2, FA9_1, KIT_2, VTNC_2 |
| TIMP1_1 | ATL4_1, CRAC1_1, GELS_2 |
| VGFR1_1 | PRG4_1, PRG4_2 |
| VTDB_1 | C1QC_1, VTNC_2 |
| VTNC_1 | CRAC1_1, FA9_1, FGFR1_1, LIRB5_1, THRB_1, VTNC_2 |
| VTNC_2 | AACT_1, AMBP_1, ANT3_1, AOC1_1, C1QB_1, C1QC_2, CADH5_1, CAMP_2, CNTN1_1, CNTN1_2, CRAC1_1, DEF1_1, DEF1_2, DPEP2_1, DPEP2_2, ECM1_2, EGLN_1, EGLN_2, FA11_2, FA5_2, FA9_1, FA9_2, FGFR1_1, FGFR1_2, GPX3_1, GPX3_2, IPSP_1, KIT_1, KIT_2, LIRB5_1, MFAP5_1, MUC18_1, PAEP_1, PRG4_1, PRG4_2, PROS_1, PTGDS_1, RET4_1, SEPP1_1, SEPP1_2, SHBG_2, SHBG_3, TETN_1, THRB_1, TIMP1_1, VGFR1_1 |

TABLE 13

Analyte pairs in models containing InvParity for GABD 126-203

| Analyte1 | Analyte2 |
|---|---|
| A2GL_1 | FA9_2 |
| AACT_1 | ANT3_1, CRAC1_1, CRAC1_3, FA9_1, FA9_2, GELS_2, SVEP1_1 |
| ADA12_1 | FA9_1, FA9_2 |
| AFAM_2 | AACT_1, FGFR1_1 |
| ALS_1 | CD14_1, FA9_1, FA9_2 |
| AMBP_1 | SVEP1_1, TETN_1 |
| ANGT_1 | AACT_1, FA9_1, FA9_2 |
| ANT3_1 | TETN_1 |
| APOC3_1 | FA9_2 |
| APOH_1 | FA9_1, FA9_2 |
| B2MG_1 | FA9_1, FA9_2, SVEP1_1 |
| B2MG_2 | FA9_2 |
| C163A_1 | FA9_1 |
| C1QA_1 | CRAC1_3 |
| C1QB_3 | CD14_1, FA9_1, FA9_2 |
| C1QC_1 | CRAC1_3, TETN_1 |
| CAH1_1 | FA9_1, FA9_2 |
| CATD_1 | SVEP1_1 |
| CATD_2 | FA9_1 |
| CBPN_1 | FA9_1, FA9_2 |
| CBPN_2 | FA9_1, FA9_2 |
| CD14_1 | ADA12_1, ANT3_1, AOC1_1, C1QA_1, CD14_2, CHL1_1, CNTN1_1, CO5_2, CRIS3_2, ECM1_2, FA5_2, FA9_1, FA9_2, FBLN1_1, FETUA_1, GELS_2, HABP2_1, HLACI_1, IBP4_1, IBP6_2, ISM2_1, ITIH3_1, ITIH4_2, LIRB5_1, NOTUM_1, PAEP_1, PCD12_2, PROS_2, PSG1_1, PSG11_1, PSG2_1, PSG9_1, SVEP1_1, TENX_2, TETN_1, TIMP1_1, VTDB_1 |
| CD14_2 | FA9_2 |
| CGB1_1 | FA9_1 |
| CGB1_2 | FA9_1 |
| CHL1_1 | FA9_1, FA9_2 |
| CLUS_1 | FA9_1, FA9_2 |
| CLUS_2 | FA9_1, FA9_2 |
| CO5_1 | FA9_1, FA9_2 |
| CO5_2 | FA9_1, FA9_2, SVEP1_1 |
| CO6_1 | FA9_2 |
| CO8A_1 | FA9_1, FA9_2 |
| CO8B_1 | FA9_1, FA9_2 |
| CRIS3_1 | AACT_1 |
| CRIS3_2 | FA9_1, FA9_2, IBP4_1 |
| CSH_1 | FA9_1, FA9_2 |
| CSH_2 | FA9_2 |
| ENPP2_2 | FA9_1 |
| F13B_1 | FA9_2 |
| FA5_1 | CNTN1_1 |
| FA5_2 | CNTN1_1, SVEP1_1 |
| FA9_1 | ANT3_1, ATL4_1, ATS13_1, ATS13_2, C1QA_1, C1QB_1, C1QB_2, C1QC_1, C1QC_2, CADH5_2, CAMP_1, CAMP_2, CNTN1_1, CNTN1_2, CRAC1_2, CRAC1_3, DEF1_1, DPEP2_2, ECM1_1, ECM1_2, EGLN_2, FA9_2, FGFR1_2, GELS_2, IL1R1_1, IPSP_1, ISM2_2, KIT_1, KIT_2, LEP_1, MUC18_1, NOTUM_1, PAEP_1, PAEP_2, PCD12_2, PROS_1, PROS_2, PTGDS_1, SEPP1_1, SEPP1_2, SVEP1_1, THRB_1, TIMP1_1 |
| FA9_2 | AMBP_1, ANT3_1, AOC1_1, ATS13_1, ATS13_2, C1QA_1, C1QA_2, C1QB_1, C1QB_2, C1QC_1, C1QC_2, CADH5_1, CAMP_1, CAMP_2, CNTN1_1, CNTN1_2, CRAC1_1, CRAC1_2, CRAC1_3, DEF1_1, DEF1_2, DPEP2_1, DPEP2_2, ECM1_1, ECM1_2, EGLN_1, EGLN_2, FA11_1, FA11_2, FA5_1, FGFR1_2, GELS_1, GELS_2, IGF1_1, IL1R1_1, IPSP_1, IPSP_2, ISM2_1, ISM2_2, KIT_1, KIT_2, MUC18_1, MUC18_2, NOTUM_1, NOTUM_2, PAEP_1, PAEP_2, PCD12_1, PCD12_2, PRG4_1, PROS_1, PROS_2, SEPP1_1, SEPP1_2, SHBG_2, SVEP1_1, TETN_1, TETN_2, TIMP1_1, VGFR1_1 |
| FBLN1_1 | FA9_1, FA9_2 |
| FETUA_1 | FA9_1, FA9_2 |
| FETUA_2 | FA9_1, FA9_2 |
| GELS_1 | FGFR1_1 |
| GELS_2 | FGFR1_1, PCD12_2 |
| GPX3_1 | FA9_2 |
| GPX3_2 | FA9_2 |
| HABP2_1 | C1QC_1 |
| HLACI_1 | FA9_1, FA9_2 |
| IBP1_1 | FA9_2 |
| IBP2_1 | FA9_2 |
| IBP3_1 | FA9_1, FA9_2 |
| IBP3_2 | FA9_2 |
| IBP4_1 | FA9_1, FA9_2, SVEP1_1, TETN_1 |
| IBP4_2 | AACT_1, FA9_1, FA9_2, SVEP1_1 |
| IBP4_3 | FA9_1, FA9_2 |
| IBP6_1 | FA9_1, FA9_2 |

TABLE 13-continued

Analyte pairs in models containing InvParity for GABD 126-203

| Analyte1 | Analyte2 |
|---|---|
| IBP6_2 | FA9_1, FA9_2 |
| IGF2_1 | FA9_2 |
| IPSP_1 | TETN_1 |
| ITIH3_1 | SVEP1_1 |
| ITIH4_1 | FA9_1, FA9_2 |
| ITIH4_3 | FA9_1, FA9_2 |
| KNG1_1 | FA9_1, PCD12_1 |
| KNG1_2 | AACT_1, FA9_1, FA9_2 |
| LIRB5_1 | FA9_1, FA9_2 |
| LYAM1_1 | THBG_1 |
| PAPP1_1 | FA9_2 |
| PEDF_1 | GELS_2, SVEP1_1 |
| PEDF_2 | FA9_1, FA9_2 |
| PGRP2_1 | FA9_2 |
| PRDX2_1 | FA9_1, FA9_2 |
| PRG2_1 | FA9_1, FA9_2 |
| PRL_1 | TETN_1 |
| PRL_2 | TETN_1 |
| PSG1_1 | AACT_1, FA9_1, FA9_2 |
| PSG11_1 | AACT_1, FA9_1, FA9_2 |
| PSG2_1 | FA9_2, TETN_1 |
| PSG3_1 | FA9_1, FA9_2 |
| PSG9_1 | FA9_2 |
| PSG9_2 | FA9_1, FA9_2 |
| PTGDS_2 | FA9_1 |
| SHBG_3 | FA9_2 |
| SOM2_1 | FA9_1, FA9_2 |
| SOM2_2 | FA9_2 |
| SPRL1_1 | FA9_2 |
| SVEP1_1 | CRAC1_3, PRG4_1 |
| TENX_1 | FA9_1, FA9_2 |
| TENX_2 | FA9_1, FA9_2, TETN_1 |
| TETN_1 | FA5_1, FA5_2, FGFR1_1, LEP_1 |
| THBG_1 | ADA12_1, SVEP1_1, TETN_1 |
| TIE1_1 | FA9_2 |
| VTDB_1 | FA9_1, FA9_2 |
| VTNC_1 | FA9_2 |
| VTNC_2 | ADA12_1, EGLN_1, SVEP1_1 |

TABLE 14

Analyte pairs in models containing InvParity for GABD 133-154

| Analyte1 | Analyte2 |
|---|---|
| APOH_1 | CD14_1 |
| B2MG_1 | CHL1_1, CO5_2, FGFR1_1, HEMO_1, KIT_2, RET4_1, THBG_1 |
| B2MG_2 | CHL1_1, SEPP1_1 |
| C163A_1 | CO5_2 |
| C1QB_3 | CHL1_1 |
| C1QC_1 | CRAC1_1 |
| CAH1_1 | ADA12_1, CHL1_1, FETUA_1, ITIH4_3, KNG1_1, LEP_2, NOTUM_2, PTGDS_1, TIE1_1 |
| CBPN_2 | C1QC_1 |
| CD14_1 | CNTN1_1, CO5_2, RET4_1, SEPP1_1 |
| CD14_2 | CNTN1_1, CO5_2, RET4_1 |
| CFAB_1 | CHL1_1, CNTN1_1, CNTN1_2, CO5_2, FGFR1_1, IL1R1_1, THRB_1 |
| CHL1_1 | ATL4_1, C1QA_2, C1QB_2, C1QC_1, CLUS_2, CNTN1_2, CO5_2, CSH_2, ECM1_1, ECM1_2, ENPP2_1, ENPP2_2, IBP1_1, IBP4_1, IBP6_2, IL1R1_1, INHBC_1, LEP_1, PRDX2_1, PSG9_2, PTGDS_2, SEPP1_2, SHBG_1, SHBG_2, SHBG_3, THBG_1, VTNC_2 |
| CLUS_2 | PRDX2_1 |
| CNTN1_1 | ECM1_2 |
| CO5_2 | ANT3_1, ENPP2_1, FGFR1_1, HEMO_1, IPSP_2, MUC18_1, PEDF_1, PRG2_1, PTGDS_1, SEPP1_1, THBG_1, THRB_1 |
| CO6_1 | PRDX2_1 |
| CO8A_1 | MUC18_2 |
| ECM1_2 | ATL4_1 |
| ENPP2_2 | LIRB5_1, RET4_1 |
| FA5_1 | CNTN1_1 |
| FA9_1 | CNTN1_2 |
| FA9_2 | CNTN1_1 |
| FGFR1_1 | MUC18_1 |

TABLE 14-continued

Analyte pairs in models containing InvParity for GABD 133-154

| Analyte1 | Analyte2 |
| --- | --- |
| HEMO_1 | KIT_2, PRDX2_1 |
| IBP6_2 | CNTN1_2 |
| IL1R1_1 | SEPP1_1 |
| INHBC_1 | CNTN1_1, CNTN1_2 |
| ITIH4_2 | PRDX2_1 |
| ITIH4_3 | CNTN1_2 |
| PEDF_1 | CNTN1_1, CNTN1_2, SEPP1_1 |
| PRDX2_1 | C1QC_1, FA9_1, IPSP_2, THBG_1 |
| PTGDS_1 | CNTN1_2 |
| RET4_1 | MUC18_1 |
| SHBG_1 | IL1R1_1, LIRB5_1, RET4_1, SEPP1_1 |
| THBG_1 | CNTN1_1, GELS_2, KIT_1, KIT_2, MFAP5_1, RET4_1 |

TABLE 15

Analyte pairs in models containing InvParity for GABD 140-161

| Analyte1 | Analyte2 |
| --- | --- |
| ADA12_1 | FGFR1_1 |
| AFAM_1 | FBLN1_1 |
| ANGT_1 | FGFR1_1 |
| B2MG_1 | C1QB_1, FBLN1_1, FGFR1_1, FGFR1_2 |
| B2MG_2 | AMBP_1, C1QB_1, FGFR1_1, LIRB5_1, PEDF_1, PROS_2, TIE1_1, VTDB_1 |
| C1QB_1 | FGFR1_1, TETN_1 |
| C1QB_3 | PEDF_1 |
| CATD_1 | FBLN1_1 |
| CATD_2 | C1QB_1, FA11_2, FA5_2, FBLN1_1, FGFR1_1, THRB_1 |
| CBPN_2 | FGFR1_1 |
| CD14_1 | C1QB_1, FBLN1_1, FGFR1_1, HEMO_1, TETN_1, TIE1_1, VTDB_1 |
| CD14_2 | FGFR1_2 |
| CO5_2 | ANT3_1, TETN_1, VTDB_1 |
| CO6_1 | FGFR1_1 |
| ENPP2_1 | FGFR1_1 |
| ENPP2_2 | FGFR1_1 |
| FA9_2 | FGFR1_2 |
| FBLN1_1 | CADH5_1, CGB1_1, FGFR1_1, GELS_2, HABP2_1, KIT_2, PEDF_1, TETN_1 |
| FGFR1_1 | FA5_2, FGFR1_2, MUC18_1, PAPP2_1, PCD12_2, PTGDS_1, SVEP1_1 |
| FGFR1_2 | FA5_2, THRB_1 |
| GELS_2 | FGFR1_1 |
| GPX3_1 | FGFR1_1 |
| GPX3_2 | FGFR1_1 |
| HABP2_1 | AMBP_1, C1QB_1, FA9_1, FGFR1_2, IBP2_1, PEDF_1, RET4_1, THRB_1, VTDB_1 |
| HEMO_1 | IBP4_3 |
| IBP1_1 | FGFR1_1 |
| IBP2_1 | FGFR1_1, PEDF_1 |
| IBP3_1 | FGFR1_1 |
| IBP3_2 | FGFR1_1 |
| ITIH4_2 | FGFR1_2 |
| LBP_1 | FGFR1_1 |
| LIRB5_1 | FGFR1_1 |
| LYAM1_1 | FGFR1_2 |
| PEDF_1 | ANT3_1, C1QB_1, FGFR1_1, FGFR1_2, IL1R1_1, PSG11_1, SPRL1_1, TETN_1 |
| PEDF_2 | FGFR1_1 |
| PSG1_1 | FGFR1_1 |
| PTGDS_2 | FGFR1_1 |
| SPRL1_1 | FGFR1_1 |
| TENX_2 | FGFR1_1 |
| TETN_1 | FA5_1, FGFR1_1 |
| THBG_1 | FGFR1_1, VTDB_1 |
| TIMP1_1 | FGFR1_1 |
| VTDB_1 | IBP4_3, LEP_1 |
| VTNC_2 | FGFR1_1 |

TABLE 16

Analyte pairs in models containing InvParity for GABD 147-168

| Analyte1 | Analyte2 |
| --- | --- |
| ADA12_1 | PAEP_1, TETN_1 |
| ALS_1 | HABP2_1 |
| ANT3_1 | CAMP_2, ECM1_1, SEPP1_2, SVEP1_1, TETN_1 |
| APOC3_1 | TETN_1 |
| APOH_1 | ANT3_1 |
| B2MG_1 | FBLN1_1, PSG1_1 |
| B2MG_2 | FBLN1_1, PSG1_1, TETN_1 |
| C163A_1 | ANT3_1 |
| C1QB_3 | TETN_1 |
| CATD_2 | TETN_1 |
| CBPN_1 | TETN_1 |
| CBPN_2 | TETN_1 |
| CD14_1 | TETN_1 |
| CD14_2 | ANT3_1, TETN_1 |
| CGB1_1 | ANT3_1 |
| CLUS_2 | ANT3_1 |
| CO5_2 | ANT3_1 |
| CO6_1 | TETN_1 |
| CO8A_1 | TETN_1 |
| CO8B_1 | TETN_1 |
| CSH_1 | ANT3_1, TETN_1 |
| FA11_2 | TETN_1 |
| FA9_1 | PAEP_1 |
| FA9_2 | ANT3_1, TETN_1 |
| FBLN1_1 | ANT3_1, ISM2_1, PCD12_2, TENX_2, TETN_1, TETN_2 |
| HABP2_1 | PEDF_1, PRL_2, TETN_1 |
| HEMO_1 | TETN_1 |
| HLACI_1 | ANT3_1 |
| IBP1_1 | TETN_1 |
| IBP2_1 | ANT3_1 |
| IBP3_2 | TETN_1 |
| IBP4_1 | TETN_1 |
| IBP4_3 | ANT3_1, TETN_1 |
| IBP6_1 | ANT3_1, TETN_1 |
| IBP6_2 | ANT3_1, TETN_1 |
| IGF2_1 | TETN_1 |
| ITIH4_1 | TETN_1 |
| ITIH4_2 | ANT3_1 |
| ITIH4_3 | TETN_1 |
| LIRB5_1 | TETN_1 |
| PEDF_1 | TETN_1 |
| PRL_1 | TETN_1 |
| PRL_2 | TETN_1 |
| PSG1_1 | TETN_1 |
| PSG11_1 | ANT3_1, TETN_1 |
| PSG3_1 | TETN_1 |
| PSG9_2 | TETN_1 |
| SOM2_2 | ANT3_1, TETN_1 |
| SPRL1_1 | ANT3_1, TETN_1 |
| TENX_1 | TETN_1 |
| TENX_2 | PAEP_2, TETN_1 |
| TETN_1 | ATL4_1, ATS13_1, CADH5_2, CNTN1_2, DEF1_1, DEF1_2, DPEP2_1, ECM1_1, EGLN_1, EGLN_2, FGFR1_2, GELS_2, KIT_1, KIT_2, MFAP5_1, PAEP_1, PCD12_1, PCD12_2, PROS_2, PTGDS_1, SEPP1_2, SVEP1_1, TETN_2 |
| TIE1_1 | TETN_1 |

TABLE 17

Analyte pairs in models containing InvParity for GABD 154-175

| Analyte1 | Analyte2 |
| --- | --- |
| A2GL_1 | ADA12_1, APOH_1, B2MG_1, B2MG_2, CO5_2, IBP4_3, LYAM1_1, PRDX2_1, PSG11_1, TETN_1, TETN_2 |
| AACT_1 | ADA12_1, IBP4_3, SVEP1_1, TETN_1 |
| ADA12_1 | AMBP_1, ANT3_1, ATS13_1, ATS13_2, C1QA_1, C1QB_1, C1QB_2, CAMP_1, CNTN1_1, CRAC1_1, CRAC1_2, EGLN_1, FA11_1, FA11_2, FA5_2, FA9_1, FA9_2, FGFR1_2, LIRB5_1, NOTUM_2, PAEP_1, PAEP_2, PRL_1, PRL_2, PROS_1, PROS_2, RET4_1, TETN_2, THRB_1, TIMP1_1 |
| AFAM_2 | B2MG_1, CRIS3_2 |
| ALS_1 | APOH_1, B2MG_2, IBP4_3 |
| AMBP_1 | SVEP1_1, TETN_1, TETN_2 |

TABLE 17-continued

Analyte pairs in models containing InvParity for GABD 154-175

| Analyte1 | Analyte2 |
| --- | --- |
| ANGT_1 | ADA12_1, B2MG_1, B2MG_2, CNTN1_2, CRAC1_1, CRAC1_3, CRIS3_2, CSH_1, EGLN_2, FA9_1, IBP4_3, PAEP_1, PRL_2, PSG1_1, SOM2_1, SVEP1_1, TENX_2 |
| ANT3_1 | EGLN_1 |
| APOC3_1 | APOH_1, B2MG_1, B2MG_2, CO5_2, IBP4_3, LYAM1_1, SVEP1_1, TETN_2 |
| APOH_1 | AACT_1, AMBP_1, ATL4_1, ATS13_2, B2MG_1, B2MG_2, C1QB_3, CAMP_1, CAMP_2, CATD_2, CD14_2, CFAB_1, CLUS_2, CNTN1_2, CO5_1, CO5_2, CO6_1, CO8B_1, CSH_1, CSH_2, DPEP2_1, DPEP2_2, ECM1_2, EGLN_2, ENPP2_1, FA11_1, FA11_2, FA9_1, FA9_2, FETUA_1, FETUA_2, FGFR1_1, FGFR1_2, GELS_1, GELS_2, GPX3_2, HLACI_1, IBP1_1, IBP3_2, IBP4_1, IBP4_2, IBP4_3, IBP6_1, IBP6_2, IGF1_1, IPSP_1, IPSP_2, ITIH3_1, ITIH4_1, ITIH4_2, KIT_2, KNG1_2, LBP_1, LBP_2, MFAP5_1, PAEP_1, PAEP_2, PCD12_1, PEDF_1, PEDF_2, PGRP2_1, PRL_1, PRL_2, PROS_2, PSG11_1, PSG2_1, PSG3_1, PSG9_1, PSG9_2, PTGDS_1, RET4_1, SHBG_1, SHBG_2, SHBG_3, SOM2_1, SPRL1_1, SVEP1_1, TENX_1, TENX_2, TETN_1, TETN_2, TIMP1_1 |
| B2MG_1 | AACT_1, ADA12_1, AMBP_1, ATL4_1, ATS13_1, ATS13_2, B2MG_2, BGH3_1, C1QB_1, C1QB_3, CADH5_1, CAH1_1, CAMP_1, CAMP_2, CATD_1, CBPN_1, CBPN_2, CFAB_1, CGB1_1, CGB1_2, CHL1_1, CLUS_2, CNTN1_2, CO5_1, CO5_2, CO6_1, CO8A_1, CO8B_1, CRAC1_1, CRAC1_2, CRAC1_3, CRIS3_1, CSH_1, CSH_2, DEF1_1, DEF1_2, DPEP2_1, DPEP2_2, EGLN_1, ENPP2_1, FA11_1, FA11_2, FA9_1, FA9_2, FBLN3_1, FETUA_1, FETUA_2, FGFR1_1, GELS_1, GELS_2, GPX3_1, GPX3_2, HABP2_1, HEMO_1, HLACI_1, IBP1_1, IBP2_1, IBP3_1, IBP3_2, IBP4_2, IBP4_3, IBP6_1, IGF2_1, ISM2_1, ITIH3_1, ITIH4_2, KIT_1, KIT_2, KNG1_2, LBP_1, LEP_1, LIRB5_1, LYAM1_1, MFAP5_1, NOTUM_1, NOTUM_2, PAEP_1, PAPP2_1, PCD12_1, PCD12_2, PEDF_2, PGRP2_1, PRDX2_1, PROS_2, PSG1_1, PSG11_1, PSG2_1, PSG3_1, PSG9_1, PSG9_2, PTGDS_1, RET4_1, SHBG_1, SHBG_2, SHBG_3, SOM2_1, SOM2_2, SVEP1_1, TENX_1, TENX_2, TETN_1, TETN_2, TIMP1_1, VTNC_1 |
| B2MG_2 | AACT_1, ADA12_1, AMBP_1, ATL4_1, ATS13_1, ATS13_2, BGH3_1, C1QB_2, C1QB_3, C1QC_1, C1QC_2, CADH5_1, CAH1_1, CAMP_1, CAMP_2, CATD_2, CBPN_1, CBPN_2, CFAB_1, CGB1_1, CGB1_2, CHL1_1, CLUS_2, CNTN1_1, CNTN1_2, CO5_1, CO5_2, CO6_1, CO8A_1, CO8B_1, CRAC1_1, CRAC1_2, CRAC1_3, CSH_1, CSH_2, DPEP2_1, DPEP2_2, EGLN_1, ENPP2_1, FA11_1, FA11_2, FA9_1, FA9_2, FBLN3_1, FETUA_1, FETUA_2, FGFR1_1, GELS_1, GELS_2, GPX3_1, GPX3_2, HEMO_1, HLACI_1, IBP1_1, IBP2_1, IBP3_1, IBP3_2, IBP4_2, IBP4_3, IBP6_1, IGF2_1, INHBC_1, IPSP_1, ISM2_1, ISM2_2, ITIH3_1, ITIH4_1, ITIH4_2, KIT_1, KIT_2, KNG1_2, LBP_1, LBP_2, LIRB5_1, MFAP5_1, NOTUM_2, PAEP_1, PAEP_2, PCD12_1, PCD12_2, PEDF_1, PEDF_2, PGRP2_1, PRDX2_1, PROS_2, PSG1_1, PSG11_1, PSG2_1, PSG3_1, PSG9_2, PTGDS_1, RET4_1, SEPP1_2, SHBG_2, SHBG_3, SOM2_1, SOM2_2, SPRL1_1, SVEP1_1, TENX_1, TENX_2, TETN_1, TETN_2, TIE1_1, TIMP1_1 |
| BGH3_1 | IBP4_2, IBP4_3, LEP_1, LYAM1_1 |
| C163A_1 | ADA12_1, CRIS3_2, IBP4_1 |
| C1QB_1 | SVEP1_1 |
| C1QB_2 | LEP_1 |
| C1QB_3 | ADA12_1, CSH_1, IBP4_2, IBP4_3, LYAM1_1, PAPP1_1, PSG1_1, SVEP1_1, TETN_1, TETN_2 |
| C1QC_1 | SVEP1_1 |
| CAH1_1 | C1QC_1, FA11_1, FA9_1, IBP4_1, PEDF_2, PRDX2_1, PSG1_1, SVEP1_1 |
| CAMP_2 | SVEP1_1 |
| CATD_1 | IBP4_3, PEDF_2 |
| CATD_2 | ADA12_1, CNTN1_2, FA9_1, IBP4_2, IBP4_3, LYAM1_1 |
| CBPN_1 | CRIS3_2, FA9_1, IBP4_2, IBP4_3, LEP_1, PRDX2_1, TETN_1 |
| CBPN_2 | ADA12_1, CAMP_2, IBP4_3 |
| CD14_1 | FA9_1, FA9_2, IBP4_1, IBP4_2, IBP4_3, LYAM1_1 |
| CD14_2 | IBP4_3 |
| CFAB_1 | ADA12_1, IBP4_2, IBP4_3, LYAM1_1, PAPP1_1, TETN_1 |
| CGB1_1 | TETN_1, TETN_2 |
| CGB1_2 | TETN_1, TETN_2 |
| CHL1_1 | CRIS3_2, LYAM1_1, PAEP_1, PAEP_2, PRDX2_1, PROS_2, SEPP1_2, SVEP1_1 |
| CLUS_1 | TETN_1 |
| CLUS_2 | CO5_2, IBP4_3, LYAM1_1, TETN_1 |
| CO5_1 | ADA12_1, IBP4_3 |
| CO5_2 | AACT_1, ATL4_1, CAMP_1, CAMP_2, CSH_1, FETUA_1, FGFR1_1, GELS_1, HLACI_1, IBP4_1, IBP4_2, IBP4_3, IBP6_2, ISM2_1, KIT_2, KNG1_2, LBP_2, PCD12_1, PGRP2_1, PSG11_1, PSG9_1, PSG9_2, SHBG_1, SHBG_2, SHBG_3, SOM2_1 |
| CO6_1 | EGLN_1, IBP2_1, PRDX2_1, PSG1_1, SVEP1_1 |
| CO8A_1 | ADA12_1, FA9_1, IBP4_3, TETN_1 |
| CO8B_1 | IBP4_3, LYAM1_1, TETN_1, TETN_2 |
| CRIS3_1 | FA9_1, IBP4_2 |
| CRIS3_2 | ADA12_1, FA9_1, IBP4_2, IBP4_3, PEDF_2, PROS_2, SOM2_2, TETN_1 |

TABLE 17-continued

Analyte pairs in models containing InvParity for GABD 154-175

| Analyte1 | Analyte2 |
| --- | --- |
| CSH_1 | AACT_1, ADA12_1, C1QB_1, C1QB_2, C1QC_2, CAMP_1, CNTN1_2, CRAC1_2, FA5_2, FA9_1, FA9_2, GPX3_1, IBP4_1, IBP4_2, IBP4_3, ITIH4_1, KIT_1, LEP_1, MUC18_2, PAEP_1, PAEP_2, PAPP1_1, PRDX2_1, PROS_2, PSG1_1, PSG11_1, RET4_1, SEPP1_2, SVEP1_1, TENX_2, TETN_1, TETN_2 |
| CSH_2 | CRAC1_2, IBP4_2, IBP4_3, LYAM1_1, TETN_1 |
| EGLN_1 | CAMP_1, LEP_1, SVEP1_1 |
| EGLN_2 | CNTN1_2, CRAC1_3, SVEP1_1 |
| ENPP2_1 | FA5_2, IBP4_3 |
| ENPP2_2 | FA5_2, IBP4_3, PEDF_2, PRDX2_1 |
| F13B_1 | IBP4_3, TETN_1 |
| FA11_1 | CAMP_2, DEF1_1, TETN_1, TETN_2 |
| FA11_2 | TETN_1, TETN_2 |
| FA5_2 | CAMP_2, CRAC1_1, DPEP2_1, SVEP1_1 |
| FA9_1 | AMBP_1, ANT3_1, C1QA_1, CAMP_1, CRAC1_1, CRAC1_3, DEF1_2, EGLN_1, EGLN_2, FA11_1, FA11_2, GELS_2, IL1R1_1, ISM2_1, NOTUM_1, PAEP_1, PAEP_2, PRL_1, PRL_2, PROS_1, SEPP1_2, SVEP1_1, TETN_2 |
| FA9_2 | FA11_2, GELS_2, PAEP_1, PAEP_2, PRL_1, SVEP1_1, TETN_1, TETN_2 |
| FBLN1_1 | ADA12_1, FA9_1, IBP4_3, PRDX2_1, TETN_1 |
| FBLN3_1 | FA9_1, IBP4_3, LYAM1_1, PSG1_1 |
| FETUA_1 | ADA12_1, FA9_1, FA9_2, IBP4_1, IBP4_3, PRDX2_1, PSG11_1, TETN_1 |
| FETUA_2 | IBP4_2, IBP4_3, LYAM1_1, PAPP1_1, TETN_1, TETN_2 |
| GELS_2 | FA5_2, SEPP1_2, SVEP1_1 |
| GPX3_1 | ADA12_1, FA9_1, FA9_2, IBP4_1, IBP4_3, PRL_1, PRL_2, SVEP1_1 |
| GPX3_2 | IBP4_3, SVEP1_1, TETN_1, TETN_2 |
| HABP2_1 | SVEP1_1 |
| HEMO_1 | FA9_1, IBP4_1, IBP4_2, IBP4_3 |
| HLACI_1 | IBP4_3, LYAM1_1, TETN_1, TETN_2 |
| IBP1_1 | ADA12_1, CAMP_1, CNTN1_2, DEF1_2, FA9_1, FA9_2, GPX3_1, IBP4_2, IBP4_3, PAEP_2, PAPP1_1, TETN_1, TETN_2 |
| IBP2_1 | ADA12_1, CRAC1_1, CRAC1_2, CRAC1_3, IBP4_2, IBP4_3, PRDX2_1, SHBG_1, SHBG_2, TETN_1, TETN_2 |
| IBP3_1 | IBP4_3, PRDX2_1 |
| IBP3_2 | IBP4_3, TETN_1 |
| IBP4_1 | ADA12_1, AMBP_1, ANT3_1, ATS13_1, CRAC1_1, DEF1_1, EGLN_1, EGLN_2, FA11_1, FA11_2, IBP4_3, PAPP2_1, PRL_2, SVEP1_1 |
| IBP4_2 | AACT_1, ADA12_1, ATS13_1, ATS13_2, C1QB_2, C1QC_2, CADH5_1, CAMP_1, CGB1_2, CNTN1_1, CNTN1_2, CRAC1_1, CRAC1_2, DPEP2_1, EGLN_1, FA11_1, FA11_2, FA9_1, GPX3_2, IBP4_3, ITIH3_1, ITIH4_1, ITIH4_2, KIT_1, KIT_2, KNG1_2, LBP_2, LIRB5_1, LYAM1_1, PAEP_1, PAEP_2, PRDX2_1, PRL_2, PROS_1, PROS_2, PSG11_1, PSG9_1, PSG9_2, SHBG_1, SHBG_2, SHBG_3, SVEP1_1, TENX_1, TETN_1 |
| IBP4_3 | ADA12_1, AMBP_1, ANT3_1, ATL4_1, ATS13_1, ATS13_2, C1QA_1, C1QB_1, C1QB_2, C1QC_1, CADH5_1, CADH5_2, CGB1_1, CGB1_2, CNTN1_1, CNTN1_2, CRAC1_1, CRAC1_2, CRAC1_3, DEF1_1, DPEP2_1, DPEP2_2, ECM1_1, EGLN_1, EGLN_2, FA11_1, FA11_2, FA9_1, FA9_2, FGFR1_1, FGFR1_2, GELS_1, GELS_2, IGF1_1, IL1R1_1, KIT_1, KIT_2, LEP_1, LIRB5_1, MFAP5_1, PAEP_1, PAEP_2, PAPP2_1, PCD12_1, PCD12_2, PRL_1, PRL_2, PROS_1, PROS_2, PTGDS_1, SEPP1_1, SEPP1_2, SHBG_2, SHBG_3, SVEP1_1, TETN_1, TETN_2, TIMP1_1 |
| IBP6_1 | IBP4_3, LYAM1_1, PRDX2_1 |
| IBP6_2 | IBP4_3, LYAM1_1 |
| IGF2_1 | IBP4_1, PSG1_1 |
| INHBC_1 | ADA12_1, LYAM1_1 |
| ITIH3_1 | IBP4_3, LYAM1_1 |
| ITIH4_1 | FA9_1, FA9_2, IBP4_3, SOM2_1, TETN_2 |
| ITIH4_2 | ADA12_1, CAMP_2, FA9_1, FA9_2, IBP4_3, PEDF_2, PRL_2, SOM2_2, TETN_1, TETN_2, VTNC_2 |
| ITIH4_3 | IBP4_3, PRDX2_1 |
| KIT_1 | EGLN_2, SVEP1_1 |
| KIT_2 | SVEP1_1 |
| KNG1_2 | IBP4_3, LYAM1_1, TETN_1, TETN_2 |
| LBP_1 | ADA12_1, IBP4_3, LYAM1_1, TETN_2 |
| LBP_2 | ADA12_1, IBP4_3, LYAM1_1, PRDX2_1, PRL_2, PSG11_1, SVEP1_1, TETN_1 |
| LIRB5_1 | TETN_1, TETN_2 |
| LYAM1_1 | AACT_1, ADA12_1, ATS13_2, CADH5_1, CAMP_1, CGB1_1, CGB1_2, CNTN1_1, CRAC1_2, DPEP2_1, DPEP2_2, ECM1_1, ECM1_2, FA11_2, FA9_1, GELS_1, GPX3_2, IBP4_1, IPSP_1, KIT_1, MFAP5_1, MUC18_1, MUC18_2, PAEP_1, PCD12_1, PGRP2_1, PROS_1, PROS_2, PSG2_1, PSG9_2, SHBG_1, SHBG_2, SHBG_3, TETN_2, TIMP1_1, VTNC_1 |
| PAEP_1 | CAMP_2, KIT_1, SVEP1_1 |
| PAEP_2 | KIT_1, KIT_2 |
| PAPP1_1 | CGB1_1, CGB1_2, PCD12_1, PEDF_1, PTGDS_1, SHBG_2, SVEP1_1, TENX_1 |
| PEDF_1 | IBP4_3 |
| PEDF_2 | ADA12_1, CGB1_1, FA9_1, GPX3_1, IBP4_3, PRDX2_1, PRL_1, PRL_2, PSG11_1, PTGDS_2, SOM2_1, SOM2_2, SVEP1_1, TENX_1, TENX_2, TETN_1, TETN_2 |

TABLE 17-continued

Analyte pairs in models containing InvParity for GABD 154-175

| Analyte1 | Analyte2 |
|---|---|
| PGRP2_1 | IBP4_3 |
| PRDX2_1 | ADA12_1, AMBP_1, CADH5_1, CAMP_1, CAMP_2, CRAC1_2, EGLN_1, FA11_1, FA11_2, IBP4_1, NOTUM_2, PRG2_1, PTGDS_1, RET4_1, SOM2_2, SVEP1_1, TENX_1, TENX_2, TIMP1_1 |
| PRG2_1 | FA9_1 |
| PRL_1 | C1QB_1, TETN_1 |
| PRL_2 | AMBP_1, RET4_1, TETN_1 |
| PSG1_1 | ADA12_1, C1QB_2, CNTN1_2, EGLN_2, FA9_1, FA9_2, GELS_2, GPX3_1, IBP4_1, NOTUM_2, SHBG_1, SHBG_3, SOM2_2, SVEP1_1 |
| PSG11_1 | ADA12_1, ATS13_1, CAMP_2, CNTN1_2, FA9_1, IBP4_3, TETN_1 |
| PSG2_1 | IBP4_3, TETN_1, TETN_2 |
| PSG3_1 | IBP4_3, LEP_1 |
| PSG9_1 | IBP4_1, IBP4_3, TETN_1 |
| PSG9_2 | IBP4_1, IBP4_3, TETN_1 |
| PTGDS_2 | FA9_1, IBP4_3 |
| RET4_1 | CAMP_2, CNTN1_2, TETN_1 |
| SEPP1_2 | CAMP_2 |
| SHBG_1 | IBP4_3, PAEP_1, PAEP_2, SVEP1_1, TETN_1 |
| SHBG_2 | CAMP_2, SVEP1_1 |
| SHBG_3 | PAEP_2, TETN_1 |
| SOM2_1 | ADA12_1, C1QA_1, C1QB_1, CAMP_1, FA9_1, FA9_2, IBP4_3, LEP_1, SEPP1_1, SVEP1_1, TENX_2, TETN_1 |
| SOM2_2 | ADA12_1, C1QB_1, CRAC1_1, CRAC1_2, DPEP2_1, FA9_1, FA9_2, IBP4_3, LEP_1, TETN_1 |
| SPRL1_1 | ADA12_1, CAMP_2, IBP4_3, TETN_1 |
| SVEP1_1 | ATS13_1, CRAC1_2, CRAC1_3, ISM2_1, ISM2_2, NOTUM_2, PCD12_1 |
| TENX_1 | ATS13_1, IBP4_3, SVEP1_1, TETN_1 |
| TENX_2 | ADA12_1, FA5_2, FA9_1, IBP4_3, SEPP1_2, SVEP1_1, TETN_1 |
| TETN_1 | ATL4_1, ATS13_2, CADH5_1, CAMP_1, CAMP_2, CRAC1_2, CRAC1_3, DPEP2_1, DPEP2_2, ECM1_1, ECM1_2, EGLN_1, EGLN_2, FA5_2, FGFR1_1, GELS_2, KIT_1, KIT_2, MFAP5_1, MUC18_1, MUC18_2, PAEP_1, PAEP_2, PCD12_2, PROS_1, PROS_2, SEPP1_1, SEPP1_2, SVEP1_1, TETN_2 |
| TETN_2 | ATS13_2, FGFR1_1, GELS_2, MFAP5_1, PAEP_1, PROS_1, SVEP1_1 |
| TIE1_1 | IBP4_3 |
| TIMP1_1 | CAMP_2, TETN_1 |
| VTDB_1 | IBP4_3 |

TABLE 18

Analyte pairs in models containing InvParity for GABD 161-182

| Analyte1 | Analyte2 |
|---|---|
| A2GL_1 | IBP4_1 |
| AACT_1 | ADA12_1, CNTN1_1 |
| ADA12_1 | AMBP_1, AOC1_1, AOC1_2, C1QA_1, C1QA_2, C1QB_1, C1QC_1, C1QC_2, CRAC1_3, DEF1_2, EGLN_1, FA9_1, FA9_2, FGFR1_1, FGFR1_2, IGF1_1, ISM2_1, ISM2_2, KIT_1, LIRB5_1, MFAP5_1, NOTUM_1, NOTUM_2, PCD12_1, PRG4_2, PRL_1, PRL_2, PROS_2, RET4_1, SEPP1_1, SHBG_2, TETN_1, THRB_1, VGFR1_1 |
| AFAM_1 | AACT_1, CRIS3_2, ENPP2_1, FA9_2, LBP_2 |
| AFAM_2 | ADA12_1, B2MG_1, C1QA_2, C1QB_1, CBPN_1, CFAB_1, CNTN1_2, FA9_1, FA9_2, LBP_2, PRDX2_1, PRL_1, PRL_2, PSG9_2 |
| ALS_1 | ADA12_1, ANGT_1, C1QB_1, CD14_2, CHL1_1, CNTN1_2, CRIS3_2, IBP4_1, LBP_2, LEP_2, PEDF_2, PGRP2_1, TETN_2, VTDB_1, VTNC_1 |
| AMBP_1 | DEF1_1, ECM1_2, PCD12_1 |
| ANGT_1 | B2MG_1, C1QB_1, CD14_2, CRIS3_2, FA9_2, FETUA_1, FETUA_2, IBP2_1, PGRP2_1, PTGDS_1, THBG_1, VTDB_1 |
| ANT3_1 | IL1R1_1 |
| APOC3_1 | ADA12_1, B2MG_1, B2MG_2, C1QB_1, CRIS3_1, CRIS3_2, IBP4_2, IBP4_3, PRL_1, PRL_2, SOM2_2, SVEP1_1 |
| APOH_1 | B2MG_2, CD14_1, CNTN1_1, CO8A_1, CRIS3_2, KIT_2, LYAM1_1, PCD12_1, PGRP2_1, THBG_1 |
| ATL4_1 | PCD12_1 |
| B2MG_1 | ADA12_1, ATL4_1, C163A_1, C1QB_1, CD14_1, CHL1_1, CNTN1_1, CNTN1_2, CO5_1, CO8A_1, CRAC1_3, CRIS3_1, CRIS3_2, ENPP2_2, FA9_2, KIT_2, LYAM1_1, PCD12_1, SOM2_2, SVEP1_1, THBG_1, VTDB_1 |
| B2MG_2 | ATL4_1, BGH3_1, C163A_1, C1QB_2, C1QC_1, CBPN_1, CD14_2, CHL1_1, CLUS_2, CNTN1_1, CNTN1_2, CO8A_1, CO8B_1, CRAC1_1, CRAC1_2, CRIS3_2, DPEP2_2, ENPP2_2, FA11_2, FA9_2, FETUA_1, FETUA_2, GELS_1, HLACI_1, IBP4_1, IBP6_2, IGF2_1, IL1R1_1, ISM2_1, ITIH4_1, ITIH4_2, KIT_1, KIT_2, LBP_1, LIRB5_1, PAEP_2, PCD12_1, PCD12_2, PEDF_1, PEDF_2, |

TABLE 18-continued

Analyte pairs in models containing InvParity for GABD 161-182

| Analyte1 | Analyte2 |
|---|---|
| | PGRP2_1, PRDX2_1, PRG2_1, PSG2_1, PSG9_2, RET4_1, SHBG_2, SHBG_3, SOM2_2, SVEP1_1, TIE1_1, TIMP1_1, VTDB_1 |
| BGH3_1 | CD14_1, CD14_2, CO8A_1, ENPP2_1, FA9_1, IBP4_2, IBP4_3, LYAM1_1, VTNC_1 |
| C163A_1 | ATL4_1, CD14_1, CHL1_1, CNTN1_1, CO8A_1, CRIS3_1, EGLN_1, FA9_1, FA9_2, KIT_2, LYAM1_1, PCD12_1, PGRP2_1, PRDX2_1 |
| C1QA_1 | CNTN1_2, EGLN_1 |
| C1QA_2 | CNTN1_2, EGLN_1, TETN_2 |
| C1QB_1 | C1QC_1, C1QC_2, CAMP_2, ECM1_2, EGLN_1, FGFR1_1, IL1R1_1, ISM2_2, LEP_1, MFAP5_1, NOTUM_1, NOTUM_2, PCD12_1, PROS_2, PTGDS_1, SEPP1_1, SVEP1_1, TETN_2, VGFR1_1 |
| C1QB_2 | PCD12_1 |
| C1QB_3 | CD14_1, CNTN1_1, CO8A_1, CRIS3_2, FA9_1, FA9_2, LYAM1_1 |
| CADH5_2 | CNTN1_1 |
| CAH1_1 | C1QB_1, CRIS3_2, FA9_1, IBP4_3, LYAM1_1, PRDX2_1, TETN_2, VTDB_1, VTNC_2 |
| CATD_1 | ATL4_1, CHL1_1, CRIS3_2, FA9_2, GPX3_1, IBP2_1, KIT_2, NOTUM_1, PSG3_1, SVEP1_1, TETN_1, VTDB_1 |
| CATD_2 | C1QB_1, CD14_1, CNTN1_1, CO8A_1, FA9_2, LYAM1_1, VTDB_1 |
| CBPN_1 | C1QB_1, CRIS3_2, FA9_1, FA9_2 |
| CBPN_2 | C1QB_1, CRIS3_2, FA9_2, PCD12_1, PGRP2_1, PRDX2_1, VTDB_1 |
| CD14_1 | AMBP_1, ATL4_1, ATS13_2, C1QA_2, C1QB_1, C1QB_2, C1QC_1, CAMP_2, CFAB_1, CGB1_1, CGB1_2, CLUS_1, CLUS_2, CNTN1_1, CNTN1_2, CO5_1, CO5_2, CO8A_1, CO8B_1, CRAC1_2, CRAC1_3, CSH_1, DPEP2_2, ECM1_2, EGLN_1, EGLN_2, ENPP2_1, ENPP2_2, FA11_2, FA9_1, FA9_2, FBLN1_1, FBLN3_1, FETUA_1, FETUA_2, FGFR1_1, GPX3_1, HLACI_1, IBP2_1, IBP4_3, IBP6_1, IBP6_2, ISM2_1, ISM2_2, ITIH3_1, ITIH4_1, ITIH4_3, KIT_1, KNG1_2, LBP_1, LBP_2, LEP_1, LYAM1_1, NOTUM_1, PAEP_1, PAEP_2, PCD12_1, PCD12_2, PEDF_1, PEDF_2, PGRP2_1, PRDX2_1, PRL_1, PROS_2, PSG11_1, PSG2_1, PSG9_1, PSG9_2, PTGDS_1, PTGDS_2, RET4_1, SEPP1_1, SEPP1_2, SHBG_2, SHBG_3, SOM2_1, SOM2_2, SVEP1_1, TENX_1, TETN_2, TIE1_1, TIMP1_1, VTDB_1, VTNC_1 |
| CD14_2 | ADA12_1, ATL4_1, ATS13_2, C1QA_2, C1QB_1, CGB1_1, CGB1_2, CHL1_1, CLUS_1, CLUS_2, CNTN1_1, CNTN1_2, CO5_1, CO5_2, CO8A_1, CO8B_1, CRAC1_1, CRAC1_2, CRAC1_3, CRIS3_2, DPEP2_1, EGLN_2, FA11_2, FA9_1, FA9_2, FBLN3_1, GPX3_1, HLACI_1, IBP2_1, IBP3_2, IBP4_3, IBP6_2, IGF2_1, IL1R1_1, KIT_1, LBP_2, LEP_2, LYAM1_1, MFAP5_1, NOTUM_1, PAEP_1, PGRP2_1, PRDX2_1, PSG1_1, SEPP1_2, SOM2_1, SOM2_2, SVEP1_1, TETN_2, VTDB_1, VTNC_1 |
| CFAB_1 | ADA12_1, C1QA_2, CHL1_1, CRIS3_1, CRIS3_2, EGLN_1, ENPP2_2, FA9_1, GPX3_1, LYAM1_1, PCD12_1, PGRP2_1, VTNC_1 |
| CGB1_1 | ADA12_1, C1QB_1, FA9_2, TETN_1 |
| CGB1_2 | ADA12_1, C1QB_1, FA9_1, FA9_2, KIT_2, PCD12_1, PRG4_2, SVEP1_1, TETN_1, TETN_2 |
| CHL1_1 | ADA12_1, ANT3_1, AOC1_2, CNTN1_1, CNTN1_2, CO8B_1, CRIS3_1, CRIS3_2, DEF1_1, DEF1_2, ECM1_1, ECM1_2, ENPP2_1, FA11_2, FA9_1, HABP2_1, HLACI_1, IBP4_1, IBP6_1, INHBC_1, IPSP_1, ITIH4_2, LYAM1_1, PCD12_1, PEDF_1, PGRP2_1, PRDX2_1, PSG1_1, SEPP1_2, SOM2_1, SOM2_2, SVEP1_1, TENX_2, TETN_2, THBG_1, TIMP1_1, VTDB_1, VTNC_1 |
| CLUS_1 | C1QB_1, CNTN1_1, CRIS3_2, FA9_1, FA9_2, IBP4_3, SOM2_2, VTDB_1 |
| CLUS_2 | C1QB_1, CNTN1_1, CO8A_1, CRIS3_2, LYAM1_1, SOM2_1, THBG_1, VTDB_1 |
| CNTN1_1 | ATL4_1, CRAC1_1, CRAC1_2, CRAC1_3, DPEP2_1, DPEP2_2, ISM2_1, ISM2_2, MFAP5_1, NOTUM_1, NOTUM_2, PCD12_1, PCD12_2 |
| CNTN1_2 | ATL4_1, ECM1_2, PCD12_1, SVEP1_1 |
| CO5_1 | ADA12_1, C1QB_1, CNTN1_2, CO8A_1, CRIS3_2, ECM1_1, ECM1_2, EGLN_1, FA9_1, GPX3_1, HLACI_1, INHBC_1, KIT_2, LIRB5_1, LYAM1_1, PCD12_1, PGRP2_1, PRDX2_1, PTGDS_1, SVEP1_1, TENX_1, VTDB_1, VTNC_1 |
| CO5_2 | C1QA_2, C1QB_1, CNTN1_2, CO8A_1, CRIS3_1, CRIS3_2, FA9_1, FA9_2, LYAM1_1, PCD12_1, PGRP2_1, PRDX2_1, PSG1_1, SOM2_2, TETN_2 |
| CO6_1 | CO8A_1, CRIS3_2, EGLN_1, FA9_1, ITIH3_1, PGRP2_1, VTDB_1 |
| CO8A_1 | ADA12_1, AMBP_1, ATL4_1, C1QA_2, C1QB_1, C1QB_2, CGB1_1, CGB1_2, CNTN1_1, CNTN1_2, CRAC1_1, CRAC1_2, CRIS3_2, CSH_1, DEF1_2, DPEP2_1, DPEP2_2, ECM1_1, ECM1_2, EGLN_2, FA11_2, FA9_2, FBLN1_1, FBLN3_1, FETUA_1, FETUA_2, FGFR1_2, GELS_1, GPX3_1, HEMO_1, HLACI_1, IBP6_1, IBP6_2, ISM2_1, ISM2_2, ITIH4_1, ITIH4_3, KIT_2, LBP_1, LIRB5_1, LYAM1_1, MFAP5_1, NOTUM_1, PAEP_1, PAEP_2, PAPP1_1, PCD12_1, PCD12_2, PGRP2_1, PRDX2_1, PROS_1, PSG2_1, PSG9_1, PSG9_2, PTGDS_2, RET4_1, SHBG_1, SHBG_2, SHBG_3, SOM2_1, SOM2_2, TENX_1, TIE1_1, TIMP1_1, VTDB_1 |
| CO8B_1 | ADA12_1, AMBP_1, C1QB_1, CNTN1_1, CNTN1_2, CRIS3_1, CRIS3_2, FA9_2, IBP4_1, IBP4_2, LYAM1_1, PGRP2_1, SVEP1_1, TENX_1, TETN_1, VTDB_1, VTNC_1 |
| CRIS3_1 | CNTN1_1, CNTN1_2, EGLN_1, FA9_1, FA9_2, HABP2_1, IBP4_2, ITIH4_3, KIT_2, LEP_1, MUC18_2, PRDX2_1, PRG2_1, SOM2_2, SPRL1_1, SVEP1_1, TETN_1, TETN_2, VTNC_1 |

TABLE 18-continued

Analyte pairs in models containing InvParity for GABD 161-182

| Analyte1 | Analyte2 |
|---|---|
| CRIS3_2 | AACT_1, ADA12_1, AMBP_1, ATL4_1, ATS13_1, C1QB_1, C1QC_2, CADH5_1, CADH5_2, CNTN1_1, CNTN1_2, CRAC1_1, CRAC1_2, CRAC1_3, CSH_1, DPEP2_1, DPEP2_2, EGLN_1, FA11_2, FA5_1, FA9_1, FA9_2, FBLN1_1, FBLN3_1, FGFR1_1, GELS_1, GPX3_1, HABP2_1, IBP2_1, IBP3_1, IBP3_2, IBP4_2, IBP4_3, IGF2_1, IPSP_1, IPSP_2, ITIH3_1, ITIH4_3, KIT_1, KIT_2, KNG1_1, KNG1_2, LBP_1, LBP_2, LYAM1_1, NOTUM_1, PAEP_1, PAEP_2, PAPP1_1, PCD12_1, PEDF_1, PGRP2_1, PRDX2_1, PROS_1, PROS_2, PSG1_1, PSG2_1, PSG3_1, PTGDS_1, PTGDS_2, RET4_1, SHBG_1, SOM2_1, SOM2_2, SPRL1_1, SVEP1_1, TENX_1, TETN_1, TETN_2, THRB_1, VTDB_1, VTNC_1, VTNC_2 |
| CSH_1 | FA9_1, LYAM1_1 |
| CSH_2 | CNTN1_1, LYAM1_1 |
| DPEP2_1 | PCD12_1 |
| EGLN_1 | CNTN1_1, LEP_1, NOTUM_1, NOTUM_2, PRG4_1 |
| ENPP2_1 | C1QA_2, C1QB_1, FGFR1_2, IBP4_2, IBP4_3, INHBC_1, ITIH4_2, LIRB5_1, PCD12_1, VTDB_1, VTNC_1 |
| ENPP2_2 | AOC1_1, AOC1_2, C1QA_1, C1QA_2, C1QC_1, C1QC_2, CNTN1_2, FBLN1_1, IBP4_2, INHBC_1, ITIH4_2, LBP_2, LEP_1, NOTUM_1, NOTUM_2, PAPP1_1, PCD12_1, PGRP2_1, PRG2_1, PROS_2, PSG2_1, RET4_1, VGFR1_1, VTNC_1 |
| F13B_1 | FA9_1, FA9_2, PRDX2_1 |
| FA11_2 | CNTN1_1, TETN_2 |
| FA9_1 | AMBP_1, ANT3_1, ATL4_1, ATS13_2, C1QA_1, C1QA_2, C1QB_1, C1QB_2, C1QC_1, C1QC_2, CADH5_1, CADH5_2, CNTN1_1, CNTN1_2, CRAC1_1, CRAC1_2, CRAC1_3, DEF1_2, EGLN_1, FA11_2, FA9_2, FGFR1_2, GELS_1, IPSP_1, IPSP_2, ISM2_1, ISM2_2, KIT_1, KIT_2, LEP_1, NOTUM_1, NOTUM_2, PCD12_2, PRL_2, PROS_1, PTGDS_1, RET4_1, SEPP1_1, SEPP1_2, SHBG_2, SVEP1_1, TETN_1, TETN_2, TIMP1_1 |
| FA9_2 | AMBP_1, AOC1_1, AOC1_2, ATL4_1, ATS13_2, C1QA_1, C1QA_2, C1QC_1, C1QC_2, CAMP_1, CNTN1_2, CRAC1_2, DPEP2_1, DPEP2_2, ECM1_1, ECM1_2, EGLN_1, EGLN_2, FA11_2, FGFR1_2, IL1R1_1, IPSP_1, IPSP_2, ISM2_2, MUC18_1, PAPP2_1, PRL_1, PRL_2, PROS_2, PTGDS_1, RET4_1, SEPP1_1, SVEP1_1, TETN_1 |
| FBLN1_1 | CNTN1_1, CNTN1_2, FA9_1, FA9_2, HABP2_1, SOM2_1, VTNC_1 |
| FBLN3_1 | C1QB_1, CNTN1_1, IBP4_3 |
| FETUA_1 | C1QB_1, CNTN1_1, FA9_1, FA9_2, GELS_2, KIT_1, LYAM1_1, THBG_1, VTDB_1 |
| FETUA_2 | C1QB_1, CNTN1_1, FA9_2, GELS_2, LYAM1_1, VTDB_1, VTNC_1 |
| FGFR1_1 | CNTN1_1, CRAC1_3 |
| GELS_1 | ATL4_1, CNTN1_1, CNTN1_2, KIT_1 |
| GELS_2 | CNTN1_1, CNTN1_2 |
| GPX3_1 | ADA12_1, CNTN1_1, CNTN1_2, ECM1_2, FA9_1, FA9_2, IBP4_1, IBP4_3, IPSP_2, PCD12_1 |
| GPX3_2 | CNTN1_1, FA9_1, FA9_2 |
| HABP2_1 | C1QA_2, FA9_1, GPX3_1, IBP4_1, IBP6_2, ITIH4_2, LYAM1_1, PGRP2_1, PRG2_1, PSG3_1 |
| HEMO_1 | ADA12_1, IBP4_3, LBP_2, LYAM1_1 |
| HLACI_1 | AMBP_1, C1QB_1, FA9_2, GELS_1, IBP4_2, IBP4_3, LYAM1_1, PCD12_1, PGRP2_1, PRDX2_1, SOM2_2, VTDB_1 |
| IBP1_1 | CNTN1_1, CNTN1_2, FA9_1, SOM2_2, VTDB_1 |
| IBP2_1 | AMBP_1, C1QB_1, EGLN_1, FA9_1, FA9_2, IBP4_1, IBP4_3, IPSP_2, LBP_2, LEP_2, SOM2_1 |
| IBP3_1 | FA9_1, FA9_2, IBP4_1, IBP4_3, LYAM1_1 |
| IBP3_2 | FA9_2, LYAM1_1, TENX_1, VTDB_1 |
| IBP4_1 | ADA12_1, ANT3_1, AOC1_1, AOC1_2, ATL4_1, C1QB_1, CRAC1_3, EGLN_1, FA9_1, FA9_2, IPSP_1, IPSP_2, NOTUM_1, NOTUM_2, PCD12_1, SVEP1_1, VGFR1_1 |
| IBP4_2 | AMBP_1, ANT3_1, C1QA_2, CGB1_2, CNTN1_2, EGLN_1, FA5_2, FA9_2, GPX3_1, IBP4_1, ITIH4_2, KIT_1, LYAM1_1, PGRP2_1, PRDX2_1, PSG11_1, TETN_1, TETN_2, THBG_1 |
| IBP4_3 | ADA12_1, AOC1_2, ATL4_1, C1QB_1, CADH5_1, CGB1_1, CGB1_2, DEF1_1, FA9_2, FGFR1_1, IPSP_1, IPSP_2, KIT_1, NOTUM_1, PAEP_1, PCD12_1, PRL_2, SEPP1_1, SVEP1_1, TETN_1, TETN_2 |
| IBP6_1 | CNTN1_1, FA9_1, FA9_2, IBP4_3, LBP_2, LEP_1, LYAM1_1, TETN_2, VTDB_1 |
| IBP6_2 | ADA12_1, C1QB_1, FA9_2, IBP4_3, LBP_2, LYAM1_1, VTDB_1 |
| IGF1_1 | CNTN1_2, TETN_1, TETN_2 |
| IGF2_1 | CNTN1_1, FA9_2, IBP4_3, LBP_2, LYAM1_1, PRDX2_1, TETN_2, VTDB_1 |
| IL1R1_1 | CNTN1_1, EGLN_1, PCD12_1 |
| INHBC_1 | ADA12_1, AOC1_1, C1QA_1, C1QB_1, CGB1_1, CNTN1_2, FA9_2, IPSP_2, KIT_2, LYAM1_1, NOTUM_1, NOTUM_2, PGRP2_1, PRDX2_1, PRG2_1, PROS_2, PTGDS_2, SOM2_2, SPRL1_1, SVEP1_1, TETN_1, TETN_2, THRB_1, VTNC_1 |
| IPSP_1 | NOTUM_1, TETN_1 |
| IPSP_2 | ATL4_1 |
| ITIH3_1 | LYAM1_1, VTNC_1 |

TABLE 18-continued

Analyte pairs in models containing InvParity for GABD 161-182

| Analyte1 | Analyte2 |
| --- | --- |
| ITIH4_1 | ATL4_1, FA9_2, GPX3_1, LYAM1_1, PGRP2_1, SOM2_1, SOM2_2, VTDB_1, VTNC_1 |
| ITIH4_2 | CNTN1_1, FA9_2, IBP4_3, LBP_2, LYAM1_1, PGRP2_1, PRDX2_1, TETN_2, VTDB_1 |
| ITIH4_3 | C1QB_1, CNTN1_1, LYAM1_1, VTDB_1, VTNC_1 |
| KIT_1 | AOC1_2, CNTN1_2, FGFR1_1, PCD12_1, SVEP1_1 |
| KIT_2 | CNTN1_1, PCD12_1, SVEP1_1 |
| KNG1_1 | C1QB_1, FA9_1, LYAM1_1, PCD12_1, SOM2_2 |
| KNG1_2 | FA9_2, LBP_2, PGRP2_1 |
| LBP_1 | ADA12_1, CNTN1_1, FA9_1, FA9_2, LBP_2, LYAM1_1, PCD12_1 |
| LBP_2 | ADA12_1, AOC1_2, ATL4_1, C1QA_1, C1QB_1, CAMP_1, CGB1_1, CGB1_2, CNTN1_2, DEF1_1, EGLN_1, EGLN_2, FA11_2, FA9_2, FGFR1_1, GELS_2, IBP4_3, KIT_2, LEP_1, LYAM1_1, MUC18_2, PCD12_1, PEDF_1, PGRP2_1, PRDX2_1, PRG2_1, PRL_1, PRL_2, PROS_2, PSG2_1, SEPP1_2, SOM2_2, VTDB_1 |
| LIRB5_1 | C1QB_1, FA9_1 |
| LYAM1_1 | ADA12_1, ATS13_2, C1QA_1, C1QB_2, C1QC_1, C1QC_2, CGB1_1, CGB1_2, CNTN1_1, CNTN1_2, CRAC1_2, DEF1_1, DPEP2_1, DPEP2_2, ECM1_1, ECM1_2, EGLN_2, FA11_1, FA11_2, FGFR1_2, GELS_1, GPX3_1, IBP4_1, IBP4_3, IL1R1_1, ISM2_1, ISM2_2, KIT_1, LIRB5_1, MFAP5_1, NOTUM_1, PAEP_1, PAEP_2, PAPP1_1, PCD12_1, PCD12_2, PEDF_1, PEDF_2, PGRP2_1, PRG2_1, PROS_1, PSG1_1, PSG11_1, PSG2_1, PSG3_1, PSG9_1, PSG9_2, PTGDS_1, PTGDS_2, SEPP1_1, SHBG_1, SHBG_2, SHBG_3, SOM2_1, SOM2_2, TENX_2, TETN_1, TETN_2, THBG_1, TIE1_1, TIMP1_1, VGFR1_1, VTDB_1, VTNC_1 |
| NOTUM_1 | PCD12_1 |
| NOTUM_2 | PAPP2_1, PCD12_1 |
| PAEP_1 | CNTN1_1 |
| PAEP_2 | CNTN1_1 |
| PAPP1_1 | ADA12_1, ANT3_1, C1QA_2, C1QB_1, CNTN1_1, FA9_1, FA9_2, IBP4_1, IBP4_3, KIT_1, PRDX2_1, TETN_1, TIMP1_1, VTNC_1 |
| PCD12_1 | CRAC1_2 |
| PEDF_1 | FA9_1, IBP4_1, TENX_1, VTNC_1 |
| PEDF_2 | ADA12_1, FA9_1, SVEP1_1, THBG_1, VTDB_1 |
| PGRP2_1 | ADA12_1, AMBP_1, C1QA_2, C1QB_1, CADH5_2, CGB1_2, CNTN1_1, CNTN1_2, CRAC1_1, CRAC1_2, CRAC1_3, FA5_2, FA9_1, FA9_2, GELS_2, GPX3_1, IBP4_3, IPSP_2, LIRB5_1, PCD12_1, PRDX2_1, PROS_2, PSG1_1, PSG3_1, SEPP1_1, SOM2_1, SOM2_2, SPRL1_1, TETN_2, THBG_1, VTDB_1, VTNC_1 |
| PRDX2_1 | ADA12_1, AMBP_1, AOC1_1, C1QA_2, C1QC_2, CNTN1_2, CRAC1_3, DPEP2_2, ECM1_2, FA9_1, FA9_2, GPX3_1, IBP4_3, IL1R1_1, IPSP_1, THBG_1, VGFR1_1, VTDB_1 |
| PRG2_1 | ADA12_1, AMBP_1, C1QB_1, CNTN1_1, FA9_2, IBP4_1, KIT_1, PCD12_1, THRB_1, VTNC_1 |
| PRL_2 | C1QB_1, TETN_1 |
| PROS_1 | CNTN1_1 |
| PSG1_1 | ATL4_1, C1QB_1, FA9_1, FA9_2, IBP4_1, KIT_1, KIT_2, PCD12_1, TENX_1, TETN_2, VTDB_1 |
| PSG11_1 | ADA12_1, FA9_2, IBP4_3 |
| PSG2_1 | CNTN1_1, VTNC_1 |
| PSG3_1 | C1QB_1, FA9_1 |
| PSG9_1 | ADA12_1, CNTN1_1, FA9_1, THBG_1, VTNC_1 |
| PSG9_2 | C1QB_1, CNTN1_1, FA9_1, FA9_2 |
| PTGDS_2 | AMBP_1, FA9_1, FA9_2, IBP4_3, VTNC_1 |
| SHBG_1 | ADA12_1, FA9_1 |
| SHBG_3 | ADA12_1 |
| SOM2_1 | AOC1_1, C1QB_1, CRAC1_2, FA9_1, IL1R1_1, KIT_2, LEP_1, MFAP5_1, PCD12_1, SHBG_3, TENX_1, TENX_2, TETN_1, THBG_1, VTDB_1, VTNC_1 |
| SOM2_2 | C1QA_2, C1QB_1, CRAC1_2, FA9_1, FA9_2, GPX3_1, IBP4_2, IBP4_3, IL1R1_1, KIT_2, LEP_1, NOTUM_1, NOTUM_2, PCD12_1, SEPP1_2, TENX_1, TENX_2, TETN_1, TETN_2, THBG_1, VGFR1_1, VTDB_1 |
| SPRL1_1 | ADA12_1, C1QB_1, IBP4_3, VTNC_1 |
| SVEP1_1 | ISM2_1, ISM2_2, NOTUM_2 |
| TENX_1 | AOC1_2, C1QC_2, EGLN_1, FA5_2, FA9_1, FA9_2, IL1R1_1, ISM2_1, KIT_1, LIRB5_1, SVEP1_1, VTDB_1 |
| TENX_2 | AMBP_1, CNTN1_2, EGLN_1, FA9_1, FA9_2 |
| TETN_2 | ATL4_1, CNTN1_1, CNTN1_2, DPEP2_1, EGLN_1, FGFR1_1, NOTUM_1, PCD12_1, SVEP1_1 |
| THBG_1 | ADA12_1, C1QB_2, EGLN_1, FA9_1, GPX3_1, IBP4_3, IGF1_1, IL1R1_1, SHBG_2, SHBG_3, SVEP1_1, TETN_1, VTNC_2 |
| TIE1_1 | CNTN1_1, FA9_1, FA9_2 |
| TIMP1_1 | C1QB_1, CNTN1_2, KIT_1 |
| VGFR1_1 | MFAP5_1 |
| VTDB_1 | ADA12_1, ATS13_1, ATS13_2, C1QB_1, C1QC_1, C1QC_2, CAMP_2, CNTN1_1, CRAC1_3, EGLN_1, EGLN_2, FA11_2, FA9_1, FA9_2, FGFR1_1, FGFR1_2, GPX3_1, GPX3_2, IL1R1_1, IPSP_1, IPSP_2, KIT_1, KIT_2, |

TABLE 18-continued

Analyte pairs in models containing InvParity for GABD 161-182

| Analyte1 | Analyte2 |
|---|---|
| VTNC_1 | LIRB5_1, MFAP5_1, PAEP_1, PAEP_2, PCD12_1, PTGDS_1, RET4_1, SEPP1_1, SEPP1_2, SVEP1_1, TETN_2, TIMP1_1, VGFR1_1, VTNC_1 ADA12_1, AOC1_1, AOC1_2, C1QB_2, CADH5_1, CNTN1_2, CRAC1_2, CRAC1_3, DEF1_1, DEF1_2, DPEP2_1, EGLN_1, FA11_2, FGFR1_1, FGFR1_2, GELS_1, GELS_2, IBP4_1, IL1R1_1, ISM2_1, ISM2_2, MFAP5_1, NOTUM_1, NOTUM_2, PAEP_1, PCD12_1, PROS_1, SVEP1_1, VGFR1_1 |
| VTNC_2 | ADA12_1, IGF1_1, PRL_1, SVEP1_1 |

TABLE 19

Analyte pairs in models containing InvParity for GABD 168-189

| Analyte1 | Analyte2 |
|---|---|
| A2GL_1 | F13B_1, PCD12_1 |
| AACT_1 | CGB1_1, CGB1_2, CRAC1_2, FA11_1, FA9_1, FA9_2, GELS_2, KIT_2, PCD12_1, PCD12_2 |
| ADA12_1 | AMBP_1, C1QA_1, FA11_1, FA11_2, FA5_2, FA9_1, FA9_2, PCD12_1, PCD12_2, PRG4_1, PRG4_2, PROS_1, TETN_1 |
| AFAM_1 | CD14_1, CRIS3_2, PCD12_1 |
| AFAM_2 | FA9_2, PCD12_1 |
| ALS_1 | C1QB_1, CAMP_2, CD14_1, CD14_2, CHL1_1, CO8B_1, CRIS3_2, ECM1_1, ECM1_2, ENPP2_1, ENPP2_2, FA5_2, FA9_2, HABP2_1, IBP4_1, IBP4_2, IBP4_3, LBP_2, PCD12_1, VTDB_1 |
| AMBP_1 | EGLN_1, FA5_1, IPSP_1, PCD12_1, TETN_2 |
| ANGT_1 | AMBP_1, C1QB_1, CATD_1, CD14_1, CD14_2, CO8A_1, CRAC1_2, CRIS3_2, ECM1_1, FA9_2, GELS_1, HABP2_1, LEP_1, MUC18_1, PCD12_1, PCD12_2, SPRL1_1, TETN_1, VTDB_1 |
| ANT3_1 | PCD12_1 |
| AOC1_1 | PAPP2_1, PCD12_1 |
| AOC1_2 | CNTN1_2, PCD12_1 |
| APOC3_1 | AACT_1, ATS13_2, C1QB_1, C1QC_1, CATD_1, CD14_1, CO5_2, CO6_1, CO8B_1, CRAC1_2, CRIS3_1, CRIS3_2, ECM1_1, ECM1_2, ENPP2_2, F13B_1, FA9_1, FA9_2, FGFR1_1, GELS_1, GELS_2, IBP4_3, INHBC_1, IPSP_1, IPSP_2, ISM2_2, ITIH4_1, ITIH4_3, LBP_1, LBP_2, LEP_1, PED12_1, PEDF_2, PGRP_1, PRDX2_1, PSG1_1, PSG9_1, PSG9_2, PTGDS_2, SPRL1_1, TETN_1, TIMP1_1, VTDB_1 |
| APOH_1 | CD14_1, CO8A_1, ENPP2_2, FA9_1, PCD12_1, PCD12_2 |
| ATL4_1 | PCD12_1, PCD12_2 |
| ATS13_1 | PCD12_1, PCD12_2 |
| ATS13_2 | PCD12_1, PCD12_2 |
| B2MG_1 | CD14_1, CD14_2, CO8A_1, CO8B_1, ENPP2_2, FA9_1, FA9_2, IBP6_1, PCD12_1, PCD12_2 |
| B2MG_2 | CD14_1, CD14_2, CGB1_2, CHL1_1, ENPP2_2, FA9_1, HABP2_1, PCD12_1 |
| BGH3_1 | ATL4_1, F13B_1, FA9_1, PCD12_1 |
| C163A_1 | CD14_1, CO8A_1, CO8B_1, FA11_1, FA9_1, FA9_2, PCD12_1, PCD12_2 |
| C1QA_1 | PCD12_1, PCD12_2, PRG4_1, TETN_1 |
| C1QA_2 | PCD12_1, PCD12_2 |
| C1QB_1 | PCD12_1, PCD12_2 |
| C1QB_2 | PCD12_1, PCD12_2 |
| C1QB_3 | CO8A_1, CO8B_1, ENPP2_2, FA9_1, FA9_2, PCD12_1 |
| C1QC_1 | GELS_1, PCD12_1, PCD12_2 |
| C1QC_2 | PCD12_1 |
| CADH5_2 | PCD12_1 |
| CAH1_1 | CD14_1, FA9_1, FA9_2, PCD12_1 |
| CAMP_1 | ECM1_2, PCD12_1 |
| CAMP_2 | PCD12_1, PCD12_2 |
| CATD_1 | AACT_1, AOC1_2, CD14_1, CNTN1_2, CO8A_1, CO8B_1, CRAC1_2, CRIS3_2, ECM1_1, FA11_1, FA9_1, IBP2_1, INHBC_1, LEP_1, LYAM1_1, PCD12_1, PCD12_2, PEDF_2, PRG2_1, SPRL1_1, TETN_2, VGFR1_1, VTDB_1 |
| CATD_2 | CD14_1, CRAC1_2, FA9_1, PCD12_1, PCD12_2 |
| CBPN_1 | PCD12_1 |
| CBPN_2 | CD14_1, PCD12_1 |
| CD14_1 | AACT_1, ADA12_1, ANT3_1, AOC1_1, AOC1_2, ATL4_1, ATS13_1, ATS13_2, C1QA_1, C1QB_1, C1QB_2, C1QC_1, C1QC_2, CADH5_1, CADH5_2, CFAB_1, CGB1_2, CLUS_2, CNTN1_2, CO5_2, CO6_1, CO8A_1, CO8B_1, CRAC1_1, CRAC1_2, CRAC1_3, CRIS3_1, CRIS3_2, CSH_1, CSH_2, DEF1_1, DPEP2_1, DPEP2_2, ECM1_1, ECM1_2, EGLN_1, EGLN_2, ENPP2_1, ENPP2_2, F13B_1, FA11_1, FA5_1, FA5_2, FA9_1, FA9_2, FBLN1_1, FBLN3_1, FETUA_1, FETUA_2, FGFR1_1, FGFR1_2, GELS_1, GELS_2, GPX3_1, GPX3_2, HABP2_1, HEMO_1, HLACI_1, IBP1_1, IBP2_1, IBP3_1, IBP3_2, IBP4_3, IBP6_1, IBP6_2, IGF1_1, IGF2_1, INHBC_1, IPSP_1, IPSP_2, ISM2_1, ISM2_2, ITIH3_1, ITIH4_1, ITIH4_2, ITIH4_3, KIT_1, KIT_2, KNG1_1, |

TABLE 19-continued

Analyte pairs in models containing InvParity for GABD 168-189

| Analyte1 | Analyte2 |
|---|---|
| | KNG1_2, LBP_1, LBP_2, LEP_1, LEP_2, LIRB5_1, LYAM1_1, MFAP5_1, MUC18_1, NOTUM_2, PAEP_1, PAEP_2, PAPP2_1, PCD12_1, PCD12_2, PEDF_1, PEDF_2, PGRP2_1, PRDX2_1, PROS_1, PROS_2, PSG1_1, PSG11_1, PSG2_1, PSG3_1, PSG9_1, PTGDS_1, RET4_1, SEPP1_1, SEPP1_2, SHBG_1, SHBG_2, SOM2_1, SOM2_2, SVEP1_1, TETN_1, THBG_1, THRB_1, TIE1_1, TIMP1_1, VTDB_1, VTNC_1 |
| CD14_2 | AACT_1, ADA12_1, ATS13_2, CGB1_2, CHL1_1, CNTN1_1, CNTN1_2, CO8A_1, CO8B_1, CRAC1_1, CRAC1_2, CRIS3_1, CRIS3_2, ENPP2_1, ENPP2_2, FA9_1, FA9_2, FBLN1_1, HEMO_1, HLACI_1, IBP2_1, IBP3_1, IBP6_1, KIT_2, LYAM1_1, PAEP_1, PAPP2_1, PCD12_1, PCD12_2, PRDX2_1, PSG1_1, TETN_2, THBG_1, VTDB_1 |
| CFAB_1 | CO8A_1, CO8B_1, FA9_1, FA9_2, PCD12_1, PCD12_2 |
| CGB1_1 | AMBP_1, C1QA_1, FA9_1, FA9_2, ISM2_2, NOTUM_2, PCD12_1 |
| CGB1_2 | C1QC_1, FA9_2, ISM2_2, PAPP2_1, PCD12_1 |
| CHL1_1 | ADA12_1, ENPP2_1, ENPP2_2, F13B_1, FA11_1, FA9_1, FA9_2, FBLN1_1, IBP4_1, IBP4_2, IBP4_3, IBP6_1, INHBC_1, LBP_2, PCD12_1, PSG1_1 |
| CLUS_1 | PCD12_1 |
| CLUS_2 | CO8A_1, FA9_1, FA9_2, PCD12_1 |
| CNTN1_1 | PCD12_1, PCD12_2 |
| CNTN1_2 | PCD12_1, PCD12_2 |
| CO5_1 | CO8A_1, CRAC1_2, FA9_1, PCD12_1, PCD12_2 |
| CO5_2 | CO8B_1, FA11_1, FA9_1, PCD12_1, PCD12_2, RET4_1 |
| CO6_1 | CO8B_1, FA5_2, PCD12_1 |
| CO8A_1 | ADA12_1, AMBP_1, ANT3_1, ATS13_1, ATS13_2, CGB1_1, CGB1_2, CRAC1_3, CRIS3_1, CRIS3_2, DEF1_1, DEF1_2, EGLN_2, ENPP2_1, ENPP2_2, FA5_1, FA9_1, FA9_2, FETUA_1, FETUA_2, FGFR1_2, GPX3_1, GPX3_2, HLACI_1, IBP2_1, IBP4_1, IBP4_2, IGF2_1, INHBC_1, IPSP_2, ITIH4_1, KNG1_1, LBP_1, LEP_1, LEP_2, LIRB5_1, MFAP5_1, PAEP_1, PAEP_2, PCD12_1, PCD12_2, PEDF_1, PROS_2, PSG11_1, PSG3_1, PTGDS_1, SHBG_1, SHBG_2, SOM2_1, SOM2_2, SVEP1_1, TETN_2, THBG_1, THRB_1, TIE1_1, VTDB_1 |
| CO8B_1 | AACT_1, ANT3_1, ATS13_2, C1QA_1, C1QA_2, C1QC_1, CRAC1_1, CRAC1_2, CRAC1_3, CRIS3_1, CRIS3_2, CSH_1, EGLN_2, ENPP2_2, F13B_1, FA9_2, FBLN1_1, GELS_2, HLACI_1, IBP2_1, IBP4_1, IL1R1_1, INHBC_1, ISM2_1, ISM2_2, KNG1_1, LBP_1, LBP_2, LEP_1, LIRB5_1, MUC18_1, NOTUM_2, PCD12_1, PCD12_2, PEDF_1, PGRP2_1, PRDX2_1, PSG1_1, PSG3_1, SOM2_2, TENX_2, TETN_1, THBG_1, VTDB_1, VTNC_1 |
| CRIS3_1 | AACT_1, ECM1_1, ENPP2_2, FAS_2, FA9_1, GELS_1, HABP2_1, NOTUM_1, PCD12_1, PCD12_2, TENX_1, THBG_1, VTDB_1 |
| CRIS3_2 | AACT_1, ADA12_1, ECM1_1, ECM1_2, EGLN_1, F13B_1, FA11_1, FA11_2, FAS_2, FA9_1, FA9_2, HABP2_1, IBP4_1, KNG1_2, PCD12_1, PCD12_2, PROS_2, TETN_2, THBG_1, VTDB_1 |
| CSH_1 | FA9_1, PCD12_1, PCD12_2 |
| CSH_2 | PCD12_1 |
| DEF1_1 | PCD12_1, PCD12_2 |
| DEF1_2 | PCD12_1 |
| DPEP2_1 | PCD12_1, PCD12_2 |
| DPEP2_2 | PCD12_1, PCD12_2 |
| ECM1_1 | PAPP2_1, PCD12_1, PCD12_2, PRG4_1 |
| ECM1_2 | PCD12_1 |
| EGLN_1 | ECM1_1, PCD12_1, PCD12_2 |
| EGLN_2 | PCD12_1 |
| ENPP2_1 | C1QC_2, ECM1_2, F13B_1, FA5_2, FA9_2, IBP4_1, ITIH3_1, PCD12_1, PCD12_2, PEDF_1, SHBG_3, TETN_2, VGFR1_1 |
| ENPP2_2 | AACT_1, C1QA_1, C1QA_2, C1QB_1, CGB1_1, CGB1_2, CNTN1_2, CRAC1_1, CRAC1_2, ECM1_1, ECM1_2, F13B_1, FA11_1, FA11_2, FA5_1, FA5_2, FA9_2, GELS_1, GELS_2, GPX3_1, HABP2_1, IBP1_1, IBP3_1, IBP3_2, IBP4_1, IBP4_3, IBP6_1, IGF1_1, IGF2_1, INHBC_1, ISM2_2, ITIH3_3, ITIH4_1, KIT_2, KNG1_1, KNG1_2, LBP_2, LIRB5_1, MUC18_2, PAEP_1, PAEP_2, PAPP1_1, PCD12_1, PCD12_2, PEDF_1, PROS_2, PSG9_2, PTGDS_2, SEPP1_1, SEPP1_2, SHBG_1, SHBG_2, SHBG_3, TETN_2, VTDB_1, VTNC_2 |
| F13B_1 | ATS13_2, CGB1_2, CNTN1_2, CRAC1_2, FA9_1, FBLN1_1, LBP_2, PAPP2_1, PCD12_1, PSG1_1, VTDB_7 |
| FA11_1 | CRAC1_2, ECM1_1, EGLN_1, KIT_2, PCD12_1, TETN_2 |
| FA11_2 | IL1R1_1, PCD12_1, PCD12_2 |
| FA5_1 | PCD12_1 |
| FA5_2 | ATS13_2, PCD12_1, PCD12_2, PRG4_2, SVEP1_1 |
| FA9_1 | ANT3_1, ATS13_1, C1QA_1, C1QA_2, C1QB_1, C1QB_2, C1QC_1, C1QC_2, CADH5_2, CRAC1_1, CRAC1_2, CRAC1_3, DEF1_1, DPEP2_1, DPEP2_2, ECM1_1, EGLN_1, FA11_1, FA11_2, FA5_1, FA5_2, FA9_2, FGFR1_1, FGFR1_2, GELS_2, IGF1_1, ISM2_1, ISM2_2, KIT_1, KIT_2, LEP_1, LEP_2, MFAP5_1, MUC18_1, NOTUM_1, NOTUM_2, PAEP_2, PAPP2_1, PCD12_1, PCD12_2, PRL_2, PROS_1, PROS_2, RET4_1, SEPP1_1, SEPP1_2, SHBG_2, SVEP1_1, TETN_1, TETN_2, THRB_1, TIMP1_1 |

TABLE 19-continued

Analyte pairs in models containing InvParity for GABD 168-189

| Analyte1 | Analyte2 |
|---|---|
| FA9_2 | ANT3_1, AOC1_1, ATS13_1, C1QA_1, C1QA_2, C1QB_1, C1QB_2, DEF1_1, DPEP2_1, DPEP2_2, ECM1_1, EGLN_1, FA5_2, FGFR1_1, LEP_1, NOTUM_1, NOTUM_2, PAEP_1, PAEP_2, PAPP2_1, PCD12_1, PCD12_2, SEPP1_2, SVEP1_1, TETN_1, VGFR1_1 |
| FBLN1_1 | ADA12_1, CRAC1_1, HABP2_1, KNG1_1, PAPP2_1, PCD12_1, PCD12_2, PSG1_1, PSG3_1, SVEP1_1, VTDB_1 |
| FBLN3_1 | IBP4_3, PCD12_1, PCD12_2 |
| FETUA_1 | FA9_1, FA9_2, IBP6_1, PCD12_1, PCD12_2 |
| FETUA_2 | FA9_1, IBP6_1, PCD12_1, PCD12_2 |
| FGFR1_1 | CRAC1_3, PCD12_1, PCD12_2 |
| FGFR1_2 | PCD12_1, PCD12_2 |
| GELS_1 | PCD12_1, PCD12_2 |
| GELS_2 | PCD12_1, PCD12_2 |
| GPX3_1 | PCD12_1, PCD12_2 |
| GPX3_2 | FA9_1, FA9_2, PCD12_1, PCD12_2 |
| HABP2_1 | ADA12_1, AMBP_1, ATL4_1, C1QA_2, CGB1_1, CGB1_2, CNTN1_2, ECM1_1, ECM1_2, EGLN_1, FA5_2, FA9_1, GELS_1, GELS_2, HLACI_2, IBP4_1, IBP4_3, KNG1_2, MFAP5_1, NOTUM_1, PAPP1_1, PCD12_1, PEDF_1, PGRP2_1, PSG11_1, PSG3_1, PTGDS_2, SHBG_2, TETN_1, TETN_2, TIE1_1 |
| HEMO_1 | PCD12_1, PCD12_2, PEDF_1 |
| HLACI_1 | FA11_1, FA9_2, IBP4_1, IBP4_2, PCD12_1, VTNC_1 |
| IBP1_1 | FA9_2, PCD12_1, PCD12_2 |
| IBP2_1 | AACT_1, CNTN1_2, FA9_1, FA9_2, PCD12_1, PCD12_2 |
| IBP3_1 | FA11_1, FA9_1, IBP4_1, PCD12_1, PCD12_2 |
| IBP3_2 | FA9_1, PCD12_1, PCD12_2 |
| IBP4_1 | FA11_1, FA11_2, FA5_2, FA9_1, FA9_2, PCD12_1, PCD12_2 |
| IBP4_2 | ADA12_1, CRAC1_2, FA9_1, IGF1_1, PCD12_1, PCD12_2, TETN_1 |
| IBP4_3 | AOC1_2, CAMP_2, FA11_1, PCD12_1, PCD12_2, PRL_2 |
| IBP6_1 | ATS13_1, ATS13_2, CNTN1_2, DEF1_1, EGLN_2, FA9_1, GPX3_1, GPX3_2, KIT_2, LIRB5_1, PAEP_2, PCD12_1, PGRP2_1, PTGDS_1, SHBG_1, SHBG_2 |
| IBP6_2 | FA9_1, FA9_2, GELS_2, PCD12_1, PGRP2_1 |
| IGF1_1 | ECM1_1, ECM1_2, PCD12_1 |
| IGF2_1 | FA9_1, CD12_1, PCD12_2 |
| IL1R1_1 | PAPP2_1, PCD12_1 |
| INHBC_1 | ADA12_1, C1QA_2, CNTN1_2, CRAC1_3, ECM1_1, FA11_1, FA9_1, KIT_2, NOTUM_2, PCD12_1, PCD12_2, PGRP2_1, PSG9_2, TETN_1 |
| IPSP_1 | CRAC1_3, PCD12_1, PCD12_2, PRG4_2 |
| IPSP_2 | ATS13_1, ECM1_1, PCD12_1 |
| ISM2_1 | PAPP2_1, PCD12_1 |
| ISM2_2 | PAPP2_1, PCD12_1, PCD12_2 |
| ITIH3_1 | FA11_2, FA9_1, PCD12_1, PCD12_2, PRG4_1 |
| ITIH4_1 | FA11_1, FA11_2, FA9_2, PCD12_1, PCD12_2, PEDF_1, THBG_1, VTDB_1 |
| ITIH4_2 | CNTN1_2, PCD12_1, PCD12_2 |
| ITIH4_3 | CRAC1_3, FA9_2, ISM2_1, PCD12_1, PCD12_2 |
| KIT_1 | ECM1_1, PCD12_1 |
| KIT_2 | PAPP2_1, PCD12_1 |
| KNG1_1 | FA9_1, FA9_2, LBP_2, PCD12_1, PEDF_1 |
| KNG1_2 | FA9_1, FA9_2, PCD12_1 |
| LBP_1 | ATS13_2, FA9_1, PCD12_1, PCD12_2 |
| LBP_2 | ECM1_1, EGLN_1, FA11_1, VTDB_1 |
| LEP_1 | PCD12_1, PCD12_2 |
| LEP_2 | PCD12_1 |
| LIRB5_1 | FA9_1, FA9_2, PCD12_1, PCD12_2 |
| LYAM1_1 | ECM1_2, IBP4_1, PCD12_1, PRG4_1, PRG4_2, VTDB_1 |
| MFAP5_1 | PCD12_1 |
| MUC18_2 | PCD12_1 |
| NOTUM_1 | PCD12_1 |
| NOTUM_2 | PAPP2_1, PCD12_1 |
| PAEP_1 | PCD12_1 |
| PAEP_2 | PCD12_1, PCD12_2 |
| PAPP1_1 | FA9_1, PAPP2_1, PCD12_1, VTNC_1 |
| PAPP2_1 | PCD12_2 |
| PCD12_1 | CRAC1_1, CRAC1_2, CRAC1_3, PCD12_2, THRB_1 |
| PCD12_2 | CRAC1_1, CRAC1_2, CRAC1_3, THRB_1 |
| PEDF_1 | ADA12_1, ANT3_1, ATL4_1, ATS13_2, C1QB_2, CGB1_2, CNTN1_2, EGLN_1, FA9_1, IPSP_2, PCD12_1, PCD12_2, RET4_1, VTNC_1 |
| PEDF_2 | IPSP_2, PCD12_1, TETN_1, VTDB_1 |
| PGRP2_1 | CGB1_2, CNTN1_2, FA9_1, FA9_2, ISM2_1, KIT_1, PCD12_1, VTDB_1 |
| PRDX2_1 | AMBP_1, FA9_1, FA9_2, PCD12_1 |
| PRG2_1 | ADA12_1, FA9_1, PCD12_1 |
| PRG4_1 | PCD12_1, PCD12_2 |
| PRG4_2 | PCD12_1 |
| PRL_1 | PCD12_1 |
| PRL_2 | CNTN1_2, CRAC1_3, PCD12_1 |
| PROS_1 | PCD12_1 |
| PROS_2 | PCD12_1, PCD12_2 |

TABLE 19-continued

Analyte pairs in models containing InvParity for GABD 168-189

| Analyte1 | Analyte2 |
| --- | --- |
| PSG1_1 | AMBP_1, CRAC1_3, FA11_1, FA9_1, FA9_2, PCD12_1, PRG4_1, PSG9_1 |
| PSG11_1 | PCD12_1 |
| PSG2_1 | FA9_1, FA9_2, PCD12_1, PCD12_2 |
| PSG3_1 | FA11_1, FA9_1, PCD12_1 |
| PSG9_1 | ADA12_1, CGB1_1, CGB1_2, IBP4_1, IBP4_3, IGF1_1, KIT_2, PCD12_1, PCD12_2 |
| PSG9_2 | CRAC1_2, IBP4_1, PCD12_1, PCD12_2 |
| PTGDS_1 | PCD12_1 |
| PTGDS_2 | FA9_1, FA9_2, PCD12_1 |
| RET4_1 | PCD12_1 |
| SEPP1_1 | PCD12_1 |
| SEPP1_2 | PCD12_1 |
| SHBG_1 | FA9_1, PCD12_1, PCD12_2 |
| SHBG_2 | PCD12_1, PCD12_2 |
| SHBG_3 | AOC1_1, FA9_1, PCD12_1, PCD12_2 |
| SOM2_1 | FA9_1, PCD12_1, PCD12_2 |
| SOM2_2 | IPSP_2, PCD12_1 |
| SPRL1_1 | PCD12_1 |
| SVEP1_1 | CRAC1_2, PCD12_1, PCD12_2 |
| TENX_1 | ATL4_1, FA9_1, FA9_2, GELS_2, PCD12_1, PCD12_2 |
| TENX_2 | FA11_1, FA11_2, FA9_1, PCD12_1, PCD12_2, RET4_1 |
| TETN_1 | FA5_2, PAPP2_1, PCD12_1, PCD12_2 |
| TETN_2 | PCD12_1 |
| THBG_1 | ECM1_1, GELS_1, KIT_2, PCD12_1, PCD12_2, VTDB_1 |
| TIE1_1 | FA9_1, FA9_2, PCD12_1, PCD12_2 |
| TIMP1_1 | FA11_1, PCD12_1 |
| VGFR1_1 | PAPP2_1, PCD12_1 |
| VTDB_1 | AACT_1, ADA12_1, ATL4_1, ATS13_2, ECM1_2, EGLN_1, FA11_1, FA9_1, FA9_2, FGFR1_1, IBP4_3, KIT_1, PCD12_1, PCD12_2, PRL_2 |
| VTNC_1 | ADA12_1, ECM1_1, ECM1_2, FA9_1, FA9_2, ISM2_1, PAPP2_1, PCD12_1 |
| VTNC_2 | PCD12_1 |

TABLE 20

Analyte pairs in models containing InvParity for GABD 175-196

| Analyte1 | Analyte2 |
| --- | --- |
| A2GL_1 | ADA12_1, CD14_1 |
| AACT_1 | ADA12_1, PRG4_1 |
| ADA12_1 | AMBP_1, AOC1_2, ATL4_1, ATS13_2, C1QA_1, C1QA_2, C1QB_1, C1QC_1, CAMP_1, CRAC1_2, CRAC1_3, DEF1_1, DEF1_2, DPEP2_1, ECM1_1, EGLN_1, EGLN_2, FA11_1, FA11_2, FA5_1, FA5_2, GELS_2, IL1R1_1, IPSP_1, IPSP_2, ISM2_2, KIT_1, LEP_1, LEP_2, LIRB5_1, NOTUM_1, NOTUM_2, PAEP_1, PAEP_2, PAPP2_1, PCD12_1, PRL_1, PRL_2, PROS_1, PROS_2, SEPP1_2, SHBG_2, TETN_1, TETN_2, THRB_1, TIMP1_1 |
| AFAM_1 | AACT_1, DEF1_1, DEF1_2, FA5_2 |
| AFAM_2 | AMBP_1 |
| ALS_1 | CGB1_1, DEF1_1, FA5_1, ITIH3_1, TIE1_1 |
| AMBP_1 | FGFR1_1, FGFR1_2, IPSP_2, PAEP_1, SVEP1_1 |
| ANGT_1 | AACT_1, ADA12_1, AMBP_1, ANT3_1, ATL4_1, CAH1_1, CGB1_1, CGB1_2, FA5_2, PAPP2_1, PEDF_1, PRDX2_1, SVEP1_1 |
| APOC3_1 | ADA12_1 |
| B2MG_1 | ADA12_1, AMBP_1 |
| B2MG_2 | CD14_1 |
| BGH3_1 | ADA12_1 |
| C163A_1 | AACT_1, ADA12_1, ATL4_1, ATS13_1 |
| C1QA_2 | PAPP2_1 |
| C1QB_3 | ADA12_1 |
| CAH1_1 | CATD_2 |
| CATD_1 | ADA12_1 |
| CATD_2 | ADA12_1, FA5_2 |
| CBPN_2 | ADA12_1 |
| CD14_1 | AACT_1, ADA12_1, C1QA_2, C1QB_1, CGB1_1, DEF1_2, FA5_1, FA9_1, FGFR1_1, GELS_2, HABP2_1, IBP4_1, ITIH3_1, LIRB5_1, LYAM1_1, PAEP_1, PROS_2, SVEP1_1, VTNC_1 |
| CD14_2 | AACT_1, ADA12_1 |
| CGB1_1 | ADA12_1, ATL4_1, PAPP2_1, SVEP1_1 |
| CGB1_2 | ADA12_1, PAPP2_1 |
| CLUS_2 | AMBP_1 |
| CO5_1 | ADA12_1, ANT3_1, ECM1_2, EGLN_1, FA9_1, ITIH3_1, PAEP_1, PAEP_2, PCD12_1, SVEP1_1 |

TABLE 20-continued

Analyte pairs in models containing InvParity for GABD 175-196

| Analyte1 | Analyte2 |
|---|---|
| CO5_2 | ADA12_1, ATL4_1, FGFR1_1 |
| CO6_1 | ADA12_1, AMBP_1, GELS_1 |
| CO8A_1 | ADA12_1, CGB1_2, DEF1_1 |
| CO8B_1 | ADA12_1 |
| CRIS3_2 | ADA12_1 |
| DEF1_1 | CRAC1_3 |
| DEF1_2 | PAPP2_1 |
| ECM1_1 | SVEP1_1 |
| FA5_1 | SVEP1_1 |
| FA5_2 | ISM2_1, NOTUM_2, PCD12_1, SVEP1_1 |
| FA9_1 | KIT_1 |
| FA9_2 | KIT_1 |
| FBLN1_1 | ADA12_1, AMBP_1 |
| FBLN3_1 | ADA12_1, PAPP2_1 |
| GELS_1 | FA5_2 |
| HABP2_1 | ADA12_1, AMBP_1, FA5_1, IPSP_2 |
| IBP1_1 | ADA12_1 |
| IBP3_1 | ADA12_1 |
| IBP4_1 | ADA12_1, FA5_1 |
| IBP4_2 | ADA12_1 |
| IBP4_3 | ADA12_1, AMBP_1 |
| IBP6_1 | ADA12_1 |
| IBP6_2 | ADA12_1, AMBP_1 |
| INHBC_1 | PRG2_1 |
| IPSP_1 | SVEP1_1 |
| IPSP_2 | GELS_2, SVEP1_1 |
| ITIH3_1 | ADA12_1, PCD12_1 |
| ITIH4_1 | ADA12_1 |
| KNG1_1 | ADA12_1, AMBP_1, FA5_2, LIRB5_1, PAEP_2, PCD12_1 |
| LIRB5_1 | AMBP_1, FA5_2 |
| PAEP_1 | FA5_2, PAPP2_1 |
| PAEP_2 | FA5_2 |
| PAPP1_1 | ADA12_1 |
| PEDF_1 | ADA12_1, CAMP_1, CAMP_2, DEF1_2, SEPP1_2 |
| PEDF_2 | ADA12_1 |
| PGRP2_1 | ADA12_1, FA5_2, SVEP1_1 |
| PRG2_1 | ADA12_1 |
| PSG11_1 | ADA12_1 |
| PSG9_1 | ADA12_1, AMBP_1, SVEP1_1 |
| PTGDS_2 | ADA12_1 |
| SHBG_1 | ADA12_1, SVEP1_1 |
| SHBG_3 | ADA12_1 |
| SOM2_2 | ADA12_1 |
| SPRL1_1 | PAPP2_1 |
| SVEP1_1 | CRAC1_2, ISM2_1 |
| TENX_1 | PCD12_1 |
| TENX_2 | AMBP_1 |
| TETN_1 | FA5_2 |
| TETN_2 | FA5_2 |
| TIE1_1 | ADA12_1, CGB1_1 |
| VTDB_1 | ADA12_1, FA5_2 |
| VTNC_1 | FA9_2 |
| VTNC_2 | ADA12_1 |

TABLE 21

Analyte pairs in models containing InvParity for GABD 182-203

| Analyte1 | Analyte2 |
|---|---|
| A2GL_1 | AACT_1, ADA12_1, AFAM_2, ANGT_1, FA5_1, IPSP_2, KNG1_1, LBP_2, MUC18_1, PCD12_1, SOM2_1, SVEP1_1 |
| AACT_1 | ADA12_1, AMBP_1, AOC1_1, AOC1_2, ATS13_2, C1QA_1, C1QA_2, C1QB_2, CADH5_1, CADH5_2, CAMP_1, CAMP_2, CGB1_1, CGB1_2, CNTN1_2, CRAC1_1, CRAC1_2, CRAC1_3, DEF1_2, EGLN_2, FA11_2, FA5_1, FA5_2, FGFR1_1, GELS_1, GELS_2, GPX3_2, IL1R1_1, ISM2_2, KIT_1, KIT_2, LEP_1, LEP_2, LIRB5_1, MUC18_1, PAEP_1, PAPP2_1, PCD12_2, PRG4_1, PRG4_2, PRL_1, PROS_1, PROS_2, SEPP1_1, SEPP1_2, SHBG_2, SHBG_3, SVEP1_1, TETN_1, THRB_1 |
| ADA12_1 | AMBP_1, ANT3_1, AOC1_1, AOC1_2, ATL4_1, ATS13_1, ATS13_2, C1QA_1, C1QA_2, C1QB_1, C1QB_2, C1QC_1, C1QC_2, CADH5_1, CADH5_2, CAMP_1, CAMP_2, CNTN1_1, CNTN1_2, CRAC1_1, CRAC1_2, CRAC1_3, DEF1_1, DEF1_2, DPEP2_1, DPEP2_2, ECM1_1, ECM1_2, EGLN_1, |

TABLE 21-continued

Analyte pairs in models containing InvParity for GABD 182-203

| Analyte1 | Analyte2 |
|---|---|
| | EGLN_2, FA11_1, FA11_2, FA5_1, FA5_2, FA9_1, FA9_2, FGFR1_1, FGFR1_2, GELS_1, GELS_2, IGF1_1, IL1R1_1, IPSP_1, IPSP_2, ISM2_1, ISM2_2, KIT_1, KIT_2, LEP_1, LEP_2, LIRB5_1, MFAP5_1, MUC18_1, MUC18_2, NOTUM_1, NOTUM_2, PAEP_1, PAEP_2, PAPP2_1, PCD12_1, PCD12_2, PRG4_1, PRG4_2, PRL_1, PRL_2, PROS_1, PROS_2, PTGDS_1, RET4_1, SEPP1_1, SEPP1_2, SHBG_2, SVEP1_1, TETN_1, TETN_2, THRB_1, TIMP1_1, VGFR1_1 |
| AFAM_1 | AACT_1, ADA12_1, AFAM_2, CO5_1, SVEP1_1, TETN_2, VTNC_2 |
| AFAM_2 | AACT_1, ADA12_1, ALS_1, AMBP_1, ANGT_1, ANT3_1, AOC1_1, AOC1_2, APOH_1, ATL4_1, ATS13_1, ATS13_2, B2MG_2, BGH3_1, C1QA_1, C1QA_2, C1QB_1, C1QB_2, C1QB_3, C1QC_1, C1QC_2, CADH5_1, CADH5_2, CAH1_1, CAMP_1, CAMP_2, CATD_1, CATD_2, CBPN_1, CBPN_2, CD14_2, CGB1_1, CGB1_2, CHL1_1, CLUS_1, CNTN1_1, CO5_1, CO6_1, CO8A_1, CO8B_1, CRAC1_1, CRAC1_2, CRAC1_3, CRIS3_1, CRIS3_2, CSH_1, CSH_2, DEF1_1, DEF1_2, DPEP2_2, ECM1_1, ECM1_2, ENPP2_2, F13B_1, FA11_1, FA11_2, FA5_1, FBLN3_1, FETUA_1, FETUA_2, FGFR1_1, FGFR1_2, GELS_1, GELS_2, HLACI_1, IBP1_1, IBP3_1, IBP3_2, IBP4_1, IBP4_2, IBP4_3, IBP6_1, IBP6_2, IGF1_1, IGF2_1, IL1R1_1, ISM2_1, ISM2_2, ITIH3_1, ITIH4_1, ITIH4_2, ITIH4_3, KIT_1, KIT_2, KNG1_1, KNG1_2, LBP_1, LBP_2, LEP_1, LEP_2, LIRB5_1, LYAM1_1, MFAP5_1, MUC18_1, NOTUM_1, NOTUM_2, PAEP_1, PAEP_2, PAPP1_1, PAPP2_1, PCD12_1, PEDF_2, PRDX2_1, PRG2_1, PRG4_1, PRL_1, PRL_2, PROS_2, PSG1_1, PSG11_1, PSG2_1, PSG3_1, PSG9_1, PSG9_2, PTGDS_1, PTGDS_2, RET4_1, SEPP1_1, SEPP1_2, SHBG_1, SHBG_2, SHBG_3, SOM2_1, SOM2_2, SPRL1_1, SVEP1_1, TENX_1, TENX_2, TETN_2, THRB_1, TIMP1_1, VGFR1_1, VTDB_1, VTNC_1, VTNC_2 |
| ALS_1 | AACT_1, ADA12_1, SVEP1_1 |
| AMBP_1 | DEF1_1, DPEP2_1, DPEP2_2, ECM1_2, FA5_2, FGFR1_2, GELS_2, IPSP_1, IPSP_2, LEP_1, MUC18_1, MUC18_2, PAEP_1, PAPP2_1, PCD12_1, PRG4_1, PROS_2, PTGDS_1, SVEP1_1, TETN_1, THRB_1 |
| ANGT_1 | AACT_1, ADA12_1, AMBP_1, ANT3_1, C1QB_3, CAMP_1, CAMP_2, CATD_2, CBPN_1, CGB1_1, CO8B_1, CRAC1_1, CRIS3_2, DEF1_1, DPEP2_2, ECM1_2, FA5_1, FA5_2, FA9_1, FETUA_1, GELS_2, IBP1_1, IBP4_3, IPSP_1, IPSP_2, ITIH4_3, KIT_1, KNG1_1, LEP_1, MUC18_1, PAEP_1, PAPP1_1, PAPP2_1, PCD12_1, PRG4_1, PSG1_1, PSG2_1, PTGDS_2, SPRL1_1, SVEP1_1, TENX_1, TETN_1, VTDB_1, VTNC_1 |
| ANT3_1 | AMBP_1, FA5_1 |
| AOC1_1 | SVEP1_1 |
| APOC3_1 | AACT_1, ADA12_1, CD14_1, FA5_1, FA5_2, GELS_1, IBP6_2, IPSP_1, SEPP1_2, SVEP1_1 |
| APOH_1 | AACT_1, ADA12_1, SEPP1_2, SVEP1_1 |
| B2MG_1 | |
| B2MG_2 | ADA12_1, KNG1_2 |
| BGH3_1 | AACT_1, ADA12_1, CD14_1, FA5_1, SEPP1_2 |
| C163A_1 | ADA12_1 |
| C1QA_1 | FA5_1, GELS_1, SVEP1_1 |
| C1QA_2 | FA5_1, SVEP1_1 |
| C1QB_1 | FA5_1, SVEP1_1 |
| C1QB_2 | FA5_1 |
| C1QB_3 | AACT_1, ADA12_1, FA5_1, SVEP1_1 |
| C1QC_1 | AMBP_1, FA5_1 |
| C1QC_2 | FA5_1 |
| CAH1_1 | AACT_1, ADA12_1, FA5_1, SEPP1_2 |
| CAMP_1 | SVEP1_1 |
| CAMP_2 | DEF1_1, SVEP1_1 |
| CATD_1 | AACT_1, ADA12_1, CRAC1_3, FA5_1, IPSP_2, KNG1_2, SVEP1_1 |
| CATD_2 | AACT_1, ADA12_1, C1QA_1, CRAC1_3, FA5_1, IBP4_1, IPSP_1, IPSP_2, KNG1_2, PRG4_1, SVEP1_1 |
| CBPN_1 | ADA12_1, CD14_1, FA5_1 |
| CBPN_2 | AACT_1, ADA12_1, FA5_1 |
| CD14_1 | AACT_1, ADA12_1, ANT3_1, ATL4_1, C1QB_1, C1QC_2, CAMP_1, CAMP_2, CRAC1_1, CRAC1_2, DEF1_2, DPEP2_1, DPEP2_2, ECM1_2, EGLN_1, FA5_1, FA5_2, FA9_1, FGFR1_1, GELS_1, GELS_2, IBP4_1, IBP4_2, IBP4_3, IBP6_1, IBP6_2, IPSP_1, ISM2_2, ITIH4_3, KIT_1, KNG1_1, KNG1_2, LBP_1, LBP_2, LEP_1, LIRB5_1, MUC18_2, NOTUM_1, NOTUM_2, PAPP2_1, PEDF_1, PGRP2_1, PRG2_1, PRL_2, PSG1_1, PSG11_1, PSG2_1, PSG3_1, PTGDS_2, SEPP1_1, SEPP1_2, SOM2_2, SPRL1_1, SVEP1_1, TENX_2, TETN_1, TETN_2, THRB_1 |

TABLE 21-continued

Analyte pairs in models containing InvParity for GABD 182-203

| Analyte1 | Analyte2 |
| --- | --- |
| CD14_2 | ADA12_1, FA5_1, KNG1_2, LIRB5_1, SEPP1_2 |
| CFAB_1 | GELS_1 |
| CGB1_1 | ADA12_1, FA5_1 |
| CGB1_2 | ADA12_1, FA5_1 |
| CHL1_1 | AACT_1, ADA12_1 |
| CLUS_1 | AACT_1, ADA12_1, DEF1_2, FA5_1 |
| CLUS_2 | ADA12_1 |
| CO5_1 | AACT_1, ADA12_1, CRAC1_1, FA9_1, FGFR1_2, GELS_1, IBP1_1, IBP6_2, MUC18_1, PAPP1_1, SVEP1_1 |
| CO5_2 | ADA12_1, FGFR1_2, GELS_1, PAPP2_1, PRG4_1, PRG4_2 |
| CO6_1 | AACT_1, ADA12_1, FA5_1 |
| CO8A_1 | ADA12_1, SEPP1_2, SVEP1_1 |
| CO8B_1 | AACT_1, ADA12_1, GELS_1, KNG1_1, KNG1_2, LIRB5_1, PAEP_1 |
| CRIS3_1 | ADA12_1, FA5_1, SEPP1_2 |
| CRIS3_2 | ADA12_1, FA5_1, VTNC_2 |
| CSH_1 | AACT_1, ADA12_1, FA11_2, FA5_1, LBP_2, TENX_1 |
| CSH_2 | ADA12_1, FA5_1 |
| DEF1_1 | PRG4_1 |
| EGLN_1 | SEPP1_2 |
| EGLN_2 | SEPP1_2 |
| ENPP2_1 | AACT_1, ADA12_1, FA5_1, FA5_2, GELS_1, KNG1_1, MUC18_2 |
| ENPP2_2 | AACT_1, ADA12_1, FA5_1, SVEP1_1 |
| F13B_1 | AACT_1, ADA12_1, FA5_1, IPSP_1, IPSP_2, LBP_2, SEPP1_2, SVEP1_1 |
| FA11_1 | DPEP2_2, FA5_1, MUC18_1, SVEP1_1 |
| FA11_2 | DPEP2_2, FA5_1, MUC18_1, SVEP1_1 |
| FA5_1 | AOC1_1, AOC1_2, ATS13_1, CADH5_1, CADH5_2, CRAC1_1, CRAC1_2, CRAC1_3, DEF1_1, DEF1_2, DPEP2_1, ECM1_2, EGLN_2, IL1R1_1, ISM2_1, ISM2_2, LEP_2, MFAP5_1, MUC18_1, MUC18_2, NOTUM_1, NOTUM_2, PAPP2_1, PCD12_1, PCD12_2, PRG4_1, PRG4_2, SEPP1_1, SVEP1_1, THRB_1, VGFR1_1 |
| FA5_2 | CRAC1_1, CRAC1_2, SVEP1_1 |
| FA9_1 | AMBP_1, FA5_1 |
| FA9_2 | GELS_1 |
| FBLN1_1 | ADA12_1, AMBP_1, DEF1_1, FA5_1 |
| FBLN3_1 | AACT_1, ADA12_1, FA5_1 |
| FETUA_1 | AACT_1, ADA12_1, FA5_1 |
| FETUA_2 | AACT_1, ADA12_1, FA5_1, SVEP1_1 |
| FGFR1_1 | FA5_1 |
| FGFR1_2 | CRAC1_3, FA5_1, FA5_2 |
| GELS_1 | AOC1_1, DEF1_1, DEF1_2, ECM1_2, FA5_1, FA5_2, LEP_2, PCD12_1, PCD12_2, PRG4_1, PRG4_2, SEPP1_1 |
| GELS_2 | DEF1_1, ECM1_2, FA5_1, FA5_2, PRG4_2, SEPP1_2, SVEP1_1 |
| GPX3_1 | ADA12_1, FA5_1 |
| GPX3_2 | ADA12_1, FA5_1 |
| HABP2_1 | AACT_1, ADA12_1, GELS_1, GELS_2, LEP_1, PTGDS_1, SVEP1_1 |
| HEMO_1 | ADA12_1, SVEP1_1 |
| HLACI_1 | ADA12_1 |
| IBP1_1 | ADA12_1, FA5_1 |
| IBP2_1 | AACT_1, ADA12_1, FA5_1 |
| IBP3_1 | AACT_1, ADA12_1, GELS_2, IBP6_2, IL1R1_1, KNG1_2, LEP_1, PSG1_1, PTGDS_2, SVEP1_1, TETN_1 |
| IBP3_2 | AACT_1, ADA12_1, GELS_2, SVEP1_1 |
| IBP4_1 | ADA12_1, FA5_1, GELS_1, GELS_2, PRG4_1, SEPP1_2, SVEP1_1 |
| IBP4_2 | AACT_1, ADA12_1, FA5_1, KNG1_2, SVEP1_1 |
| IBP4_3 | ADA12_1, FA5_1, IPSP_2 |
| IBP6_1 | AACT_1, ADA12_1 |
| IBP6_2 | ADA12_1, AMBP_1, CRAC1_1, FA5_1, INHBC_1, KNG1_2, PEDF_2, PRG4_1, PRG4_2, VTNC_1 |
| IGF1_1 | FA5_1, GELS_1, SVEP1_1 |
| IGF2_1 | AACT_1, ADA12_1, FA5_1, SVEP1_1 |
| INHBC_1 | AACT_1, ADA12_1, FA5_1, GELS_1 |
| IPSP_1 | ATL4_1, CRAC1_1, CRAC1_2, CRAC1_3, FA5_1, GELS_2, PRG4_1, PRG4_2, SEPP1_2 |
| IPSP_2 | ATL4_1, CNTN1_1, CNTN1_2, CRAC1_1, CRAC1_3, DEF1_1, DEF1_2, ECM1_1, FA5_1, FA5_2, MUC18_1, PAEP_1, PRG4_1, SEPP1_2 |
| ITIH3_1 | ADA12_1, ANT3_1, IPSP_2, SVEP1_1 |
| ITIH4_1 | ADA12_1, AMBP_1, FA5_1, SVEP1_1 |
| ITIH4_2 | ADA12_1, FA5_1 |
| ITIH4_3 | AACT_1, ADA12_1, FA5_1, IPSP_2, KNG1_2, PRG4_1, SEPP1_2 |
| KIT_1 | FA5_1, SVEP1_1 |
| KIT_2 | FA5_1, PCD12_1, SVEP1_1 |
| KNG1_1 | AACT_1, ADA12_1, ANT3_1, C1QA_1, CRAC1_1, CRAC1_2, CRAC1_3, FA5_1, GELS_1, LIRB5_1, PCD12_1, SVEP1_1 |

TABLE 21-continued

Analyte pairs in models containing InvParity for GABD 182-203

| Analyte1 | Analyte2 |
|---|---|
| KNG1_2 | AACT_1, ADA12_1, ATL4_1, CRAC1_1, FA5_1, IL1R1_1, IPSP_1, KIT_2, LEP_1, LIRB5_1, PAPP1_1, PCD12_1, PRG2_1, PRG4_1, PSG1_1, PSG11_1, PSG9_1, SEPP1_1, SHBG_3, SPRL1_1, SVEP1_1, TETN_2 |
| LBP_1 | ADA12_1 |
| LBP_2 | AACT_1, ADA12_1, CADH5_2, CRAC1_1, FA11_1, FA5_1, FGFR1_2, GELS_1, PSG3_1, SVEP1_1 |
| LEP_1 | DEF1_1, PRG4_1, PRG4_2, SEPP1_2 |
| LIRB5_1 | AMBP_1, FA5_1, FA5_2, PAPP2_1, PRG4_1, PRL_1 |
| LYAM1_1 | AACT_1, ADA12_1, FA5_1 |
| MUC18_1 | PAPP2_1, SVEP1_1 |
| NOTUM_1 | PRG4_1 |
| PAEP_1 | DEF1_1, FA5_1 |
| PAEP_2 | FA5_1 |
| PAPP1_1 | AACT_1, ADA12_1, AMBP_1, FA5_1, KIT_2, SPRL1_1 |
| PCD12_2 | CRAC1_1 |
| PEDF_1 | ADA12_1, AMBP_1, FA5_1, SEPP1_2, SVEP1_1 |
| PEDF_2 | ADA12_1, GELS_1, SVEP1_1 |
| PGRP2_1 | AACT_1, ADA12_1, FA5_1 |
| PRDX2_1 | AACT_1, ADA12_1, FA5_1 |
| PRG2_1 | ADA12_1, FA5_1, SEPP1_2 |
| PRG4_1 | PAPP2_1, PCD12_1 |
| PRL_1 | AMBP_1, CRAC1_1, CRAC1_3, FA5_1, GELS_1, IPSP_1, IPSP_2, MUC18_1, PCD12_2, PRL_2, TETN_1 |
| PRL_2 | AMBP_1, GELS_1, IPSP_1 |
| PROS_2 | FA5_1 |
| PSG1_1 | AACT_1, ADA12_1, AMBP_1, FA5_1, SEPP1_2 |
| PSG11_1 | ADA12_1, FA5_1, FA5_2, SVEP1_1 |
| PSG2_1 | ADA12_1, AMBP_1, SVEP1_1, TENX_1 |
| PSG3_1 | ADA12_1 |
| PSG9_1 | AACT_1, ADA12_1, FA5_1 |
| PSG9_2 | ADA12_1, AMBP_1, VTDB_1 |
| PTGDS_2 | ADA12_1, FA5_1, GELS_1, SVEP1_1 |
| RET4_1 | FA5_1 |
| SEPP1_1 | PRG4_1, SVEP1_1 |
| SEPP1_2 | CAMP_1, CAMP_2, ISM2_2, PAPP2_1, SVEP1_1 |
| SHBG_1 | AACT_1, ADA12_1, FA5_1, SVEP1_1 |
| SHBG_2 | FA5_1, GELS_1 |
| SHBG_3 | ADA12_1, FA5_1, GELS_1, IPSP_2 |
| SOM2_1 | ADA12_1, FA5_1 |
| SOM2_2 | ADA12_1, FA5_1 |
| SPRL1_1 | ADA12_1, ANT3_1, GELS_1, SVEP1_1 |
| SVEP1_1 | ATL4_1, ATS13_2, CRAC1_3, PRG4_1, PRG4_2 |
| TENX_1 | AACT_1, ADA12_1, FA5_1, IBP4_1, IGF1_1, IPSP_2, LIRB5_1, PRG4_1, SEPP1_2, SVEP1_1 |
| TENX_2 | AACT_1, ADA12_1, AMBP_1, FA5_1, FA5_2, IBP4_1, PCD12_2, PRL_1, SEPP1_2 |
| TETN_1 | FA5_1, PRG4_1 |
| TETN_2 | FA5_1, PRG4_1, SVEP1_1 |
| THBG_1 | ADA12_1, GELS_1 |
| TIE1_1 | ADA12_1, FA5_1, GELS_1 |
| TIMP1_1 | FA5_1, SVEP1_1 |
| VTDB_1 | ADA12_1, ANT3_1, CRAC1_1, DEF1_2, FA5_1, IPSP_1, LIRB5_1, PAEP_1, PAEP_2, SVEP1_1 |
| VTNC_1 | AACT_1, ADA12_1, DEF1_1, GELS_1, IPSP_1, SVEP1_1 |
| VTNC_2 | AACT_1, ADA12_1, GELS_1, PCD12_1, SVEP1_1 |

Model 3: Overlapping GABD Windows, Parity 0, AACT Plus Analyte Pairs

Model 3 (TTB~ETB+AACT_EIGELYLPK (SEQ ID NO:129)+Analyte1+Analyte2) was run for 171 analytes and 28 log-transformed numeric clinical variables in all possible pairs, in overlapping three-week windows with an overlap of one week. All TERM samples were used (204 nulliparous subjects were TERM). Analytes were included not as a ratio (i.e. a reversal) to allow for different coefficients for each. AACT_EIGELYLPK (SEQ ID NO:129) was chosen as the 3rd analyte in exemplifying trivariate performance based on an initial scan showing strong performance for this analyte in women of Parity 0 with blood drawn in GA weeks 23-28 weeks. In particular, this model was applied to subjects with Parity 0 and late GAs at blood draw, in 3-week GA windows from $23^{0/7}$ to $25^{6/7}$, $24^{0/7}$ to $26^{6/7}$, $25^{0/7}$ to $27^{6/7}$, and $26^{0/7}$ to $28^{6/7}$. The performance metric was accuracy.

TABLE 22

Overlapping windows of GA at blood draw, the number of samples in each and the minimum, median and maximum accuracy in each window. Nomenclature: for example [161-182) means 161 ≤ GA at blood draw < 182.

| Windows | nTERM | min | med | max |
|---|---|---|---|---|
| [161-182) | 99 | 38.4 | 44.4 | 54.5 |
| [168-189) | 108 | 39.8 | 46.3 | 53.7 |
| [175-196) | 100 | 39.0 | 45.0 | 55.0 |
| [182-203) | 105 | 41.0 | 47.6 | 57.1 |

TABLE 23

Numerical clinical variables included in Model 3 assessments

| Factor | Definition |
|---|---|
| Bleeding | Bleeding in the second or third trimesters of the current pregnancy |
| BMI | Weight in kilograms over height in meters squared |
| cDM | History of diabetes pre-existing prior to the current pregnancy |
| Cervix | Cervical abnormalities or transvaginal cervical ultrasound in this pregnancy |
| cHTN | History of hypertension pre-existing prior to the current pregnancy |
| DM | Notation of gestational diabetes in the current pregnancy or history of pre-existing diabetes, with each assigned a distinct value |
| GABD | GA at blood draw as recorded by clinical staff |
| GABD. | GA at blood draw calculated from the dates of blood draw and estimated delivery |
| GDM | Notation of gestational diabetes in the current pregnancy |
| Gravidity. | Number of recorded current and prior pregnancies of any duration, calculated as Parity plus the number of spontaneous and therapeutic abortions and ectopic pregnancies |
| InvGravidity. | 1/(Gravidity + 0.5), a transform emphasizing differences between low Gravidities |
| InvParity. | 1/(Parity + 0.5), a transform emphasizing differences between low Parities |
| IPMLOS | Maternal length of stay in hospital for the current delivery |
| LABGAD | Day of GA week of blood draw as recorded by clinical staff |
| LABPGAW | GA week of blood draw as recorded by clinical staff |
| MAGE | Maternal age in years |
| MDHT | Maternal height in centimeters |
| MDHTC | Maternal height in inches |
| MDWT | Maternal weight in kilograms |
| MDWTC | Maternal weight in pounds |
| NdelComp | Number of adverse delivery complications recorded for the current delivery |
| NpregComp | Number of adverse pregnancy complications recorded for the current pregnancy |
| Parity. | Number of recorded prior pregnancies carried to 20 0/7 weeks' GA |
| PEspec | Notation of preeclampsia, pregnancy-induced or gestational hypertension in the current pregnancy, with each assigned a distinct value |
| PriorPTBvTerm | Difference between count of prior spontaneous preterm births and prior full-term births, with absence of obstetric history as a distinct value |
| PriorSPTB | Count of prior spontaneous preterm births |
| User | Number of substances used by the subject including tobacco and alcohol; opiates are counted doubly as the fetus also becomes dependent. |

TABLE 24

Analyte pairs in trianalyte models containing AACT for nulliparous women with gestational age at blood draws days 161-182

| Analyte1 | Analyte2 |
|---|---|
| A2GL_1 | ADA12_1, ALS_1, ANGT_1, ANT3_1, APOH_1, ATS13_1, CATD_1, CD14_1, CLUS_1, CNTN1_1, CO6_1, CRAC1_1, ENPP2_2, FA9_1, FETUA_1, IBP4_1, IBP4_3, IGF1_1, ISM2_1, ITIH4_1, LEP_2, MDHT., MUC18_2, NpregC, PRG2_1, PRG4_2, PRL_1, PRL_2, SEPP1_2, TENX_1, TETN_2, THRB_1, TIMP1_1, VTNC_2 |
| AACT_1 | FETUA_2, IBP4_1, MDHT. |
| ADA12_1 | A2GL_1, AFAM_2, ALS_1, AOC1_2, ATS13_2, CADH5_1, CD14_1, CLUS_1, CO5_2, CRAC1_1, FETUA_1, FETUA_2, IBP4_1, IBP4_3, IGF1_1, IGF2_1, IL1R1_1, InvGra, ISM2_1, ITIH4_2, LBP_1, LYAM1_1, MDHT., NOTUM_2, PAPP1_1, PAPP2_1, PRL_2, PSG1_1, SEPP1_1, SHBG_1, VGFR1_1, VTDB_1, VTNC_1, VTNC_2 |
| AFAM_1 | cHTN, FETUA_2, MDHT., MDWT., PRL_1 |
| AFAM_2 | ADA12_1, BMI, CNTN1_1, FETUA_2, LEP_1, MDWT., PEDF_2, PRL_1, PRL_2, SHBG_1, SHBG_3, SVEP1_1 |
| ALS_1 | A2GL_1, ADA12_1, Bleedi, cHTN, FETUA_1, ITIH4_2, MDWT., PRDX2_1 |
| AMBP_1 | FETUA_2, IBP4_1, MDHT. |
| ANGT_1 | A2GL_1, FETUA_2 |
| ANT3_1 | A2GL_1, cHTN, FETUA_2, IBP4_1, MDHT. |
| AOC1_1 | FETUA_2, MDHT. |
| AOC1_2 | ADA12_1, FETUA_2, IBP4_1 |
| APOC3_1 | FETUA_2, IBP4_1, MDHT. |
| APOH_1 | A2GL_1, FETUA_2, IBP4_1, MDHT., MDWT. |
| ATL4_1 | cHTN, FETUA_2, MDHT. |
| ATS13_1 | A2GL_1, FETUA_2, IBP4_1 |
| ATS13_2 | ADA12_1, FETUA_1, FETUA_2, IBP4_1, LBP_1, MDHT. |
| B2MG_1 | FETUA_2, ITIH4_2, MDHT., MUC18_1 |
| B2MG_2 | cHTN, FETUA_2, IBP4_1, MDHT. |
| BGH3_1 | cHTN, FETUA_2, IBP4_1, MDHT. |
| Bleedi | ALS_1, FETUA_2, MDHT., PAPP2_1 |
| BMI | AFAM_2, cHTN, CRAC1_1, FETUA_1, FETUA_2, MDHT., MDWT., MUC18_1, SEPP1_1, VTNC_1, VTNC_2 |
| C163A_1 | FETUA_2, IBP4_1, MDHT. |
| C1QA_1 | SEPP1_1 |
| C1QA_2 | FETUA_2, MDHT. |
| C1QB_1 | FETUA_2, IBP4_1 |
| C1QB_3 | FETUA_2 |
| C1QC_1 | FETUA_2, MDWT. |
| C1QC_2 | IBP4_1, LEP_1 |
| CADH5_1 | ADA12_1, PRG4_1, PRG4_2, VTNC_2 |

TABLE 24-continued

Analyte pairs in trianalyte models containing AACT for nulliparous women with gestational age at blood draws days 161-182

| Analyte1 | Analyte2 |
|---|---|
| CADH5_2 | FBLN1_1, PRL_1, SEPP1_1 |
| CAH1_1 | FETUA_2, MDHT. |
| CAMP_1 | cHTN, FETUA_1, FETUA_2 |
| CAMP_2 | FETUA_1, FETUA_2, IBP4_1 |
| CATD_1 | A2GL_1, FETUA_1, IBP4_1, LBP_1 |
| CATD_2 | FETUA_2, IBP4_1, MDHT. |
| CBPN_1 | FETUA_2, IBP4_1, MDHT. |
| CBPN_2 | FETUA_1, FETUA_2, MDHT. |
| CD14_1 | A2GL_1, ADA12_1, FETUA_2, IBP4_1 |
| CD14_2 | FETUA_2, IBP4_1, MDHT., PRL_2 |
| cDM | FETUA_2, IBP4_1, MDHT. |
| Cervix | cHTN, FETUA_2, IBP4_1, MDHT. |
| CFAB_1 | FETUA_2, IBP4_1, IGF1_1, MUC18_1 |
| CGB1_1 | FETUA_2 |
| CGB1_2 | FETUA_2, MDHT. |
| CHL1_1 | FETUA_2, IBP4_1, MDHT. |
| cHTN | AFAM_1, ALS_1, ANT3_1, ATL4_1, B2MG_2, BGH3_1, BMI, CAMP_1, Cervix, CNTN1_2, CO8B_1, CRAC1_3, CRIS3_2, ECM1_1, ENPP2_1, F13B_1, FBLN1_1, FBLN3_1, FETUA_1, FETUA_2, FGFR1_1, FGFR1_2, GELS_2, GPX3_1, HABP2_1, HEMO_1, IBP4_1, IBP4_2, IBP6_1, IGF1_1, InvGra, ITIH4_1, KNG1_1, LBP_1, LBP_2, LEP_1, MAGE, MDHT., MDWT., MUC18_1, NOTUM_1, PAEP_1, PAPP2_1, PEspec, PRDX2_1, PRG2_1, PRL_1, PRL_2, PROS_1, PROS_2, PSG2_1, PSG9_1, PSG9_2, SEPP1_1, SHBG_1, SVEP1_1, TENX_1, TIE1_1, VTNC_1 |
| CLUS_1 | A2GL_1, ADA12_1, FETUA_2, IBP4_1, MDWT. |
| CLUS_2 | FETUA_2, MDHT., MUC18_1 |
| CNTN1_1 | A2GL_1, AFAM_2, CRAC1_1, FETUA_1, FETUA_2, IBP4_1, IGF1_1, MDHT., PAPP2_1, PRL_2 |
| CNTN1_2 | cHTN, FETUA_2, IBP4_1, MDHT. |
| CO5_1 | FETUA_2, IBP4_1, MDHT. |
| CO5_2 | ADA12_1, IBP4_1, SEPP1_1 |
| CO6_1 | A2GL_1 |
| CO8A_1 | FETUA_2, MDHT. |
| CO8B_1 | cHTN, FETUA_2, IBP4_1, MDHT. |
| CRAC1_1 | A2GL_1, ADA12_1, BMI, CNTN1_1, FETUA_2, MDHT., MUC18_1, MUC18_2, SEPP1_1 |
| CRAC1_2 | FETUA_1, FETUA_2, ITIH4_2, MDHT., MUC18_1 |
| CRAC1_3 | cHTN, FETUA_2, IBP4_1, MDHT. |
| CRIS3_2 | cHTN |
| CSH_1 | FETUA_1, FETUA_2, IBP4_1, MDHT. |
| CSH_2 | FETUA_2, IBP4_1, MDHT. |
| DEF1_1 | FETUA_2, MDHT. |
| DEF1_2 | FETUA_2, IBP4_1, MDHT. |
| DM | FETUA_2, IBP4_1 |
| DPEP2_1 | FETUA_2, MDHT. |
| DPEP2_2 | FETUA_1, FETUA_2, IBP4_1, MDHT., MDWT. |
| ECM1_1 | cHTN, FETUA_2, MDHT. |
| ECM1_2 | FETUA_2, MDHT. |
| EGLN_1 | FETUA_2, IBP4_1, MAGE, MDHT., MUC18_1 |
| EGLN_2 | FETUA_2, IBP4_1 |
| ENPP2_1 | cHTN, FETUA_2, IBP4_1, MDHT. |
| ENPP2_2 | A2GL_1, FETUA_2, MDHT. |
| F13B_1 | cHTN, FETUA_2, MDHT. |
| FA11_1 | MDHT |
| FA11_2 | FA9_2 |
| FA5_1 | FETUA_2, MDHT. |
| FA5_2 | FETUA_1, FETUA_2, IBP4_1, IPMLOS, SHBG_1 |
| FA9_1 | A2GL_1, FETUA_1, FETUA_2, IBP4_1, MDWT. |
| FA9_2 | FA11_2, FETUA_1 |
| FBLN1_1 | CADH5_2, cHTN, FETUA_2, IBP4_1, IGF1_1, ITIH4_2, LBP_1, LBP_2, MDHT., MDWT., PEspec |
| FBLN3_1 | cHTN, MDHT. |
| FETUA_1 | A2GL_1, ADA12_1, ALS_1, ATS13_2, BMI, CAMP_1, CAMP_2, CATD_1, CBPN_2, cHTN, CNTN1_1, CRAC1_2, CSH_1, DPEP2_2, FA5_2, FA9_1, FA9_2, FETUA_2, IBP3_2, IBP4_1, IBP4_3, IGF1_1, ISM2_1, ITIH4_1, ITIH4_2, KIT_1, KIT_2, LBP_1, LBP_2, LEP_1, LYAM1_1, MAGE, MDHT., MDWT., MUC18_1, MUC18_2, NdelCo, PAPP2_1, PRG4_1, PRG4_2, PRL_1, PRL_2, PROS_2, PSG2_1, PSG9_1, PSG9_2, RET4_1, SEPP1_1, SOM2_2, TENX_1, THRE3_1, User |
| FETUA_2 | AACT_1, ADA12_1, AFAM_1, AFAM_2, AMBP_1, ANGT_1, ANT3_1, AOC1_1, AOC1_2, APOC3_1, APOH_1, ATL4_1, ATS13_1, ATS13_2, B2MG_1, B2MG_2, BGH3_1, Bleedi, BMI, C163A_1, C1QA_2, C1QB_1, C1QB_3, C1QC_1, CAH1_1, CAMP_1, CAMP_2, CATD_2, CBPN_1, CBPN_2, CD14_1, CD14_2, cDM, Cervix, CFAB_1, CGB1_1, CGB1_2, CHL1_1, cHTN, CLUS_1, CLUS_2, CNTN1_1, CNTN1_2, CO5_1, CO8A_1, CO8B_1, CRAC1_1, |

TABLE 24-continued

Analyte pairs in trianalyte models containing AACT for nulliparous
women with gestational age at blood draws days 161-182

| Analyte1 | Analyte2 |
|---|---|
| | CRAC1__2, CRAC1__3, CSH__1, CSH__2, DEF1__1, DEF1__2, DM, DPEP2__1, DPEP2__2, ECM1__1, ECM1__2, EGLN__1, EGLN__2, ENPP2__1, ENPP2__2, F13B__1, FA5__1, FA5__2, FA9__1, FBLN1__1, FETUA__1, GABD., GDM, GELS__1, GELS__2, GPX3__1, HABP2__1, HEMO__1, HLACI__1, IBP1__1, IBP4__1, IBP4__2, IBP4__3, IBP6__1, IGF1__1, IGF2__1, INHBC__1, InvGra, InvPar, IPSP__1, IPSP__2, ISM2__1, ISM2__2, ITIH3__1, ITIH4__1, ITIH4__2, ITIH4__3, KIT__1, KIT__2, KNG1__2, LBP__1, LBP__2, LYAM1__1, MAGE, MDHT., MDWT., MFAP5__1, MUC18__1, MUC18__2, NdelCo, NOTUM__1, NOTUM__2, NpregC, PAEP__1, PAEP__2, PAPP1__1, PCD12__1, PCD12__2, PEDF__1, PEDF__2, PEspec, PGRP2__1, PRG2__1, PriorP, PRL__1, PRL__2, PROS__1, PROS__2, PSG1__1, PSG11__1, PSG2__1, PSG3__1, PSG9__1, PSG9__2, PTGDS__1, RET4__1, SEPP1__1, SEPP1__2, SHBG__1, SHBG__3, SOM2__1, SPRL1__1, SVEP1__1, TENX__1, TENX__2, TIE1__1, TIMP1__1, User, VGFR1__1, VTDB__1, VTNC__1, VTNC__2 |
| FGFR1__1 | cHTN, MDHT. |
| FGFR1__2 | cHTN |
| GABD. | FETUA__2, IBP4__1, MDHT. |
| GDM | FETUA__2, IBP4__1, MDHT. |
| GELS__1 | FETUA__2 |
| GELS__2 | cHTN, FETUA__2, HEMO__1 |
| GPX3__1 | cHTN, FETUA__2, IBP4__1, MDHT. |
| GPX3__2 | IBP4__1 |
| HABP2__1 | cHTN, FETUA__2 |
| HEMO__1 | cHTN, FETUA__2, GELS__2, IBP4__1, SEPP1__1 |
| HLACI__1 | FETUA__2, MDWT., MUC18__1 |
| IBP1__1 | FETUA__2, MDHT. |
| IBP2__1 | IBP4__1 |
| IBP3__1 | MDHT., MUC18__1 |
| IBP3__2 | FETUA__1, MDHT. |
| IBP4__1 | A2GL__1, AACT__1, ADA12__1, AMBP__1, ANT3__1, AOC1__2, APOC3__1, APOH__1, ATS13__1, ATS13__2, B2MG__2, BGH3__1, C163A__1, C1QB__1, C1QC__2, CAMP__2, CATD__1, CATD__2, CBPN__1, CD14__1, CD14__2, cDM, Cervix, CFAB__1, CHL1__1, cHTN, CLUS__1, CNTN1__1, CNTN1__2, CO5__1, CO5__2, CO8B__1, CRAC1__3, CSH__1, CSH__2, DEF1__2, DM, DPEP2__2, EGLN__1, EGLN__2, ENPP2__1, FA5__2, FA9__1, FBLN1__1, FETUA__1, FETUA__2, GABD., GDM, GPX3__1, GPX3__2, HEMO__1, IBP2__1, IBP4__3, IBP6__1, IGF2__1, INHBC__1, InvPar, IPMLOS, ISM2__1, ITIH4__2, KNG1__1, LBP__1, LBP__2, LIRB5__1, LYAM1__1, MDHT., MDWT., NpregC, PAEP__1, PAEP__2, PEDF__1, PEDF__1, PEspec, PGRP2__1, PriorP, PROS__1, PROS__2, PSG3__1, PSG9__1, RET4__1, SEPP1__1, SEPP1__2, SHBG__1, SHBG__3, SOM2__1, TENX__1, TENX__2, TETN__2, THBG__1, TIE1__1, TIMP1__1 |
| IBP4__2 | cHTN, FETUA__2, MDHT., PRL__2 |
| IBP4__3 | A2GL__1, ADA12__1, FETUA__1, FETUA__2, IBP4__1 |
| IBP6__1 | cHTN, FETUA__2, IBP4__1, MUC18__1 |
| IBP6__2 | MDHT. |
| IGF1__1 | A2GL__1, ADA12__1, CFAB__1, cHTN, CNTN1__1, FBLN1__1, FETUA__1, FETUA__2, MDHT., MUC18__1, SVEP1__1 |
| IGF2__1 | ADA12__1, FETUA__2, IBP4__1, MDHT. |
| IL1R1__1 | ADA12__1, MDHT., MDWT., PRL__1, SHBG__1, SVEP1__1 |
| INHBC__1 | FETUA__2, IBP4__1, MDHT. |
| InvGra | ADA12__1, cHTN, FETUA__2 |
| InvPar | FETUA__2, IBP4__1, MDHT. |
| IPMLOS | FA5__2, IBP4__1, ITIH4__2 |
| IPSP__1 | FETUA__2 |
| IPSP__2 | FETUA__2, MDHT. |
| ISM2__1 | A2GL__1, ADA12__1, FETUA__1, FETUA__2, IBP4__1, MDHT., PRL__1, PRL__2 |
| ISM2__2 | FETUA__2, MDHT., PRL__1 |
| ITIH3__1 | FETUA__2, MDHT., PRL__2 |
| ITIH4__1 | A2GL__1, cHTN, FETUA__1, FETUA__2, MDHT., MDWT. |
| ITIH4__2 | ADA12__1, ALS__1, B2MG__1, CRAC1__2, FBLN1__1, FETUA__1, FETUA__2, IBP4__1, IPMLOS, MDHT., MUC18__1, PRG4__2, PRL__1, SEPP1__2, TENX__1 |
| ITIH4__3 | FETUA__2 |
| KIT__1 | FETUA__1, FETUA__2, MDHT. |
| KIT__2 | FETUA__1, FETUA__2, MDHT. |
| KNG1__1 | cHTN, IBP4__1, MDWT. |
| KNG1__2 | FETUA__2, MDHT. |
| LBP__1 | ADA12__1, ATS13__2, CATD__1, cHTN, FBLN1__1, FETUA__1, FETUA__2, IBP4__1, MDHT., MUC18__1, PRL__1, SEPP1__1, SHBG__1, SOM2__2 |
| LBP__2 | cHTN, FBLN1__1, FETUA__1, FETUA__2, IBP4__1, MDHT., SEPP1__1, SHBG__1, SOM2__2 |
| LEP__1 | AFAM__2, C1QC__2, cHTN, FETUA__1, LYAM1__1, MDHT., PRG4__2, SEPP1__1, VTNC__2 |
| LEP__2 | A2GL__1 |
| LIRB5__1 | IBP4__1, MUC18__1 |
| LYAM1__1 | ADA12__1, FETUA__1, FETUA__2, IBP4__1, LEP__1, MDHT., User |
| MAGE | cHTN, EGLN__1, FETUA__1, FETUA__2 |

TABLE 24-continued

Analyte pairs in trianalyte models containing AACT for nulliparous
women with gestational age at blood draws days 161-182

| Analyte1 | Analyte2 |
|---|---|
| MDHT. | A2GL_1, AACT_1, ADA12_1, AFAM_1, AMBP_1, ANT3_1, AOC1_1, APOC3_1, APOH_1, ATL4_1, ATS13_2, B2MG_1, B2MG_2, BGH3_1, Bleedi, BMI, C163A_1, C1QA_2, CAH1_1, CATD_2, CBPN_1, CBPN_2, CD14_2, cDM, Cervix, CGB1_2, CHL1_1, cHTN, CLUS_2, CNTN1_1, CNTN1_2, CO5_1, CO8A_1, CO8B_1, CRAC1_1, CRAC1_2, CRAC1_3, CSH_1, CSH_2, DEF1_1, DEF1_2, DPEP2_1, DPEP2_2, ECM1_1, ECM1_2, EGLN_1, ENPP2_1, ENPP2_2, F13B_1, FA5_1, FBLN1_1, FBLN3_1, FETUA_1, FETUA_2, FGFR1_1, GABD., GDM, GPX3_1, IBP1_1, IBP3_1, IBP3_2, IBP4_1, IBP4_2, IBP6_2, IGF1_1, IGF2_1, IL1R1_1, INHBC_1, InvPar, IPSP_2, ISM2_1, ISM2_2, ITIH3_1, ITIH4_1, ITIH4_2, KIT_1, KIT_2, KNG1_2, LBP_1, LBP_2, LEP_1, LYAM1_1, MDWT., MFAP5_1, NOTUM_1, NpregC, PAEP_1, PAEP_2, PAPP1_1, PAPP2_1, PCD12_1, PCD12_2, PEDF_1, PEDF_2, PGRP2_1, PRG2_1, PriorP, PRL_1, PRL_2, PROS_1, PROS_2, PSG1_1, PSG2_1, PSG3_1, PSG9_1, PSG9_2, PTGDS_1, SEPP1_1, SHBG_1, SHBG_3, SPRL1_1, SVEP1_1, TENX_1, TENX_2, TIE1_1, TIMP1_1, VGFR1_1, VTNC_1, VTNC_2 |
| MDWT. | AFAM_1, AFAM_2, ALS_1, APOH_1, BMI, C1QC_1, cHTN, CLUS_1, DPEP2_2, FA9_1, FBLN1_1, FETUA_1, FETUA_2, HLACI_1, IBP4_1, IL1R1_1, ITIH4_1, KNG1_1, MDHT., MUC18_1, NOTUM_1, PRG4_1, PRG4_2, PRL_2, PSG1_1, SEPP1_1, SEPP1_2, SHBG_1, VGFR1_1, VTNC_1, VTNC_2 |
| MFAP5_1 | FETUA_2, MDHT. |
| MUC18_1 | B2MG_1, BMI, CFAB_1, cHTN, CLUS_2, CRAC1_1, CRAC1_2, EGLN_1, FETUA_1, FETUA_2, HLACI_1, IBP3_1, IBP6_1, IGF1_1, ITIH4_2, LBP_1, LIRB5_1, MDWT., PAPP2_1, PEspec, PRG2_1, PROS_1, SEPP1_2, TENX_2, TIMP1_1 |
| MUC18_2 | A2GL_1, CRAC1_1, FETUA_1, FETUA_2, SHBG_1 |
| NdelCo | FETUA_1, FETUA_2 |
| NOTUM_1 | cHTN, FETUA_2, MDHT., MDWT. |
| NOTUM_2 | ADA12_1, FETUA_2, PRL_1 |
| NpregC | A2GL_1, FETUA_2, IBP4_1, MDHT. |
| PAEP_1 | cHTN, FETUA_2, IBP4_1, MDHT. |
| PAEP_2 | FETUA_2, IBP4_1, MDHT. |
| PAPP1_1 | ADA12_1, FETUA_2, MDHT. |
| PAPP2_1 | ADA12_1, Bleedi, cHTN, CNTN1_1, FETUA_1, MDHT., MUC18_1, PEDF_2, PEspec |
| PCD12_1 | FETUA_2, MDHT. |
| PCD12_2 | FETUA_2, MDHT. |
| PEDF_1 | FETUA_2, IBP4_1, MDHT., PRL_1, SEPP1_1 |
| PEDF_2 | AFAM_2, FETUA_2, IBP4_1, MDHT., PAPP2_1, SEPP1_1, VTNC_1 |
| PEspec | cHTN, FBLN1_1, FETUA_2, IBP4_1, MUC18_1, PAPP2_1, PRL_1 |
| PGRP2_1 | FETUA_2, IBP4_1, MDHT. |
| PRDX2_1 | ALS_1, cHTN, SEPP1_1 |
| PRG2_1 | A2GL_1, cHTN, FETUA_2, MDHT., MUC18_1 |
| PRG4_1 | CADH5_1, FETUA_1, MDWT. |
| PRG4_2 | A2GL_1, CADH5_1, FETUA_1, ITIH4_2, LEP_1, MDWT., SHBG_1 |
| PriorP | FETUA_2, IBP4_1, MDHT. |
| PRL_1 | A2GL_1, AFAM_1, AFAM_2, CADH5_2, cHTN, FETUA_1, FETUA_2, IL1R1_1, ISM2_1, ISM2_2, ITIH4_2, LBP_1, MDHT., NOTUM_2, PEDF_1, PEspec, TENX_1, VGFR1_1 |
| PRL_2 | A2GL_1, ADA12_1, AFAM_2, CD14_2, cHTN, CNTN1_1, FETUA_1, FETUA_2, IBP4_2, ISM2_1, ITIH3_1, MDHT., MDWT., PROS_1, TENX_1, VGFR1_1 |
| PROS_1 | cHTN, FETUA_2, IBP4_1, MDHT., MUC18_1, PRL_2 |
| PROS_2 | cHTN, FETUA_1, FETUA_2, IBP4_1, MDHT. |
| PSG1_1 | ADA12_1, FETUA_2, MDHT., MDWT. |
| PSG11_1 | FETUA_2 |
| PSG2_1 | cHTN, FETUA_1, FETUA_2, MDHT. |
| PSG3_1 | FETUA_2, IBP4_1, MDHT. |
| PSG9_1 | cHTN, FETUA_1, FETUA_2, IBP4_1, MDHT. |
| PSG9_2 | cHTN, FETUA_1, FETUA_2, MDHT. |
| PTGDS_1 | FETUA_2, MDHT. |
| RET4_1 | FETUA_1, FETUA_2, IBP4_1 |
| SEPP1_1 | ADA12_1, BMI, C1QA_1, CADH5_2, cHTN, CO5_2, CRAC1_1, FETUA_1, FETUA_2, HEMO_1, IBP4_1, LBP_1, LBP_2, LEP_1, MDHT., MDWT., PEDF_1, PEDF_2, PRDX2_1, SHBG_1, SHBG_3 |
| SEPP1_2 | A2GL_1, FETUA_2, IBP4_1, ITIH4_2, MDWT., MUC18_1 |
| SHBG_1 | ADA12_1, AFAM_2, cHTN, FA5_2, FETUA_2, IBP4_1, IL1R1_1, LBP_1, LBP_2, MDHT., MDWT., MUC18_2, PRG4_2, SEPP1_1, VGFR1_1, VTNC_1, VTNC_2 |
| SHBG_3 | AFAM_2, FETUA_2, IBP4_1, MDHT., SEPP1_1 |
| SOM2_1 | IBP4_1 |
| SOM2_2 | FETUA_1, FETUA_2, LBP_1, LBP_2 |
| SPRL1_1 | FETUA_2, MDHT. |
| SVEP1_1 | AFAM_2, cHTN, FETUA_2, IGF1_1, IL1R1_1, MDHT. |

TABLE 24-continued

Analyte pairs in trianalyte models containing AACT for nulliparous women with gestational age at blood draws days 161-182

| Analyte1 | Analyte2 |
|---|---|
| TENX_1 | A2GL_1, cHTN, FETUA_1, FETUA_2, IBP4_1, ITIH4_2, MDHT., PRL_1, PRL_2 |
| TENX_2 | FETUA_2, IBP4_1, MDHT., MUC18_1 |
| TETN_2 | A2GL_1, IBP4_1 |
| THBG_1 | IBP4_1 |
| THRB_1 | A2GL_1, FETUA_1 |
| TIE1_1 | cHTN, FETUA_2, IBP4_1, MDHT. |
| TIMP1_1 | A2GL_1, FETUA_2, IBP4_1, MDHT., MUC18_1 |
| User | FETUA_1, FETUA_2, LYAM1_1 |
| VGFR1_1 | ADA12_1, FETUA_2, MDHT., MDWT., PRL_1, PRL_2, SHBG_1 |
| VTDB_1 | ADA12_1, FETUA_2 |
| VTNC_1 | ADA12_1, BMI, cHTN, FETUA_2, MDHT., MDWT., PEDF_2, SHBG_1 |
| VTNC_2 | A2GL_1, ADA12_1, BMI, CADH5_1, FETUA_2, LEP_1, MDHT., MDWT., SHBG_1 |

TABLE 25

Analyte pairs in trianalyte models containing AACT for nulliparous women with gestational age at blood draws days 168-189

| Analyte1 | Analyte2 |
|---|---|
| A2GL_1 | CAH1_1, FETUA_2, PAEP_2, TENX_2 |
| AACT_1 | FETUA_2, IBP4_1, PAEP_1, PAEP_2 |
| ADA12_1 | AMBP_1, Bleedi, FETUA_2, IBP4_1, PAEP_1, PAEP_2, TENX_2 |
| AFAM_1 | ENPP2_2, FETUA_2, PAEP_1, TENX_2 |
| AFAM_2 | FETUA_2, TENX_2 |
| ALS_1 | FETUA_1, FETUA_2, ITIH4_2, ITIH4_3, PSG1_1, TENX_1, TENX_2 |
| AMBP_1 | ADA12_1, FETUA_2, IBP4_1, PRL_1, PRL_2 |
| ANGT_1 | DPEP2_1, FETUA_2, IBP4_1, PAEP_1, PAEP_2, PRL_2, VTNC_2 |
| ANT3_1 | FETUA_2, PRL_1, PRL_2 |
| AOC1_1 | IBP4_1, PAEP_1, PAEP_2 |
| AOC1_2 | IBP4_1 |
| APOC3_1 | IBP4_1, PAEP_1, PAEP_2 |
| APOH_1 | FETUA_2, IBP4_1, ITIH4_2, PAEP_2 |
| ATL4_1 | PAEP_1 |
| ATS13_1 | FETUA_2, IBP4_1, PAEP_1, PAEP_2 |
| ATS13_2 | FETUA_2, IBP4_1, PAEP_1, PAEP_2 |
| B2MG_1 | FETUA_2, ITIH4_2 |
| B2MG_2 | FETUA_2, ITIH4_2, ITIH4_3, PSG1_1 |
| BGH3_1 | PAEP_1, PAEP_2 |
| Bleedi | ADA12_1, PAEP_1 |
| BMI | FETUA_2, IBP4_1, ITIH4_2, KNG1_1, LBP_1, PAEP_2, RET4_1, VTNC_2 |
| C163A_1 | CLUS_1, FETUA_2, TENX_2 |
| C1QA_1 | CLUS_1, IBP4_1, IPSP_1, PAEP_1, PRL_1 |
| C1QA_2 | CBPN_2, FETUA_2, IBP4_1, IPSP_1, PAEP_1, PAEP_2 |
| C1QB_1 | IBP4_1, LEP_1, PAPP2_1, PSG9_1, PSG9_2 |
| C1QB_2 | PAEP_1, PAEP_2 |
| C1QB_3 | FETUA_2 |
| C1QC_1 | CBPN_2, IBP4_1 |
| C1QC_2 | DPEP2_2, IGF1_1, IPSP_1, ITIH4_2, PAPP2_1, SOM2_1, VTDB_1 |
| CADH5_2 | CBPN_1, FETUA_2 |
| CAH1_1 | A2GL_1, FETUA_1, IGF1_1, PGRP2_1, TENX_2 |
| CAMP_1 | PAEP_1, PAEP_2 |
| CAMP_2 | PAEP_1 |
| CATD_1 | FETUA_2, IBP4_1 |
| CATD_2 | FETUA_2, IBP4_1, PAEP_1 |
| CBPN_1 | CADH5_2, CLUS_1, ECM1_1, FETUA_1, FETUA_2, ITIH4_2, PEspec, TENX_1, TENX_2 |
| CBPN_2 | C1QA_2, C1QC_1, CLUS_1, FETUA_1, FETUA_2, LEP_1, MDWT., PAEP_1, PSG1_1, TENX_1, TENX_2 |
| CD14_1 | FETUA_2, IBP4_1, PRDX2_1 |
| cDM | FETUA_2, IBP4_1, PAEP_1, PAEP_2 |
| Cervix | FETUA_2, IBP4_1, ITIH4_2 |
| CFAB_1 | IBP4_1, ITIH4_3, LIRB5_1, PAEP_1, PAEP_2, PSG1_1, TENX_2 |
| CGB1_1 | FETUA_2, IBP4_1, PAEP_1, TENX_2 |
| CGB1_2 | FETUA_2, IBP4_1, TENX_2 |
| CHL1_1 | IBP4_1, PAEP_1 |
| cHTN | FETUA_2, IBP4_1, PAEP_1, PAEP_2 |
| CLUS_1 | C163A_1, C1QA_1, CBPN_1, CBPN_2, FETUA_1, FETUA_2, HEMO_1, IBP4_1, LIRB5_1, PRDX2_1, SPRL1_1, TENX_1, TIMP1_1 |
| CLUS_2 | FETUA_2, IBP4_1, PAEP_1, PAEP_2 |

TABLE 25-continued

Analyte pairs in trianalyte models containing AACT for nulliparous women with gestational age at blood draws days 168-189

| Analyte1 | Analyte2 |
|---|---|
| CNTN1__1 | PAEP__1, PAEP__2 |
| CNTN1__2 | FETUA__2, IBP4__1, PAEP__1 |
| CO5__1 | FETUA__2, IBP4__1, LIRB5__1 |
| CO5__2 | FETUA__2, IBP4__1, PAEP__1, PAEP__2 |
| CO6__1 | IBP4__1, PAEP__2 |
| CO8A__1 | FETUA__2, ITIH4__2, PRL__1, RET4__1 |
| CO8B__1 | FETUA__2, IBP4__1 |
| CRAC1__1 | FETUA__2 |
| CRAC1__2 | IBP4__1, PAEP__1, PAEP__2, TENX__2 |
| CRAC1__3 | FETUA__2, PAEP__1, PAEP__2 |
| CRIS3__1 | FETUA__2, IBP4__1, TENX__2 |
| CRIS3__2 | FETUA__2, IBP4__1, PAEP__1, PRL__1, PRL__2, TENX__2 |
| CSH__1 | FETUA__2, PRL__1 |
| CSH__2 | HEMO__1, PAEP__2 |
| DEF1__1 | FETUA__2 |
| DEF1__2 | FETUA__2, PAEP__2 |
| DM | IBP4__1, PAEP__1, PRL__1 |
| DPEP2__1 | ANGT__1, FETUA__2 |
| DPEP2__2 | C1QC__2, FETUA__2, RET4__1 |
| ECM1__1 | CBPN__1, FETUA__2, PRDX2__1, PRL__1, PRL__2, PSG1__1, TENX__2 |
| ECM1__2 | FETUA__2, PAEP__1 |
| EGLN__1 | IBP4__1, PAEP__2 |
| EGLN__2 | FETUA__2, GELS__2, PCD12__1, PSG1__1 |
| ENPP2__1 | FETUA__2, IBP4__1, PAEP__1 |
| ENPP2__2 | AFAM__1, FETUA__2, PRL__1 |
| F13B__1 | RET4__1 |
| FA11__1 | FETUA__2, IBP4__1, PRL__1, TENX__2 |
| FA11__2 | FETUA__2, LEP__1 |
| FA5__1 | FETUA__2, PAEP__1, RET4__1, TENX__2 |
| FA5__2 | IBP4__1 |
| FBLN1__1 | FETUA__2, IBP4__1 |
| FBLN3__1 | FETUA__2, IBP4__1, TENX__2 |
| FETUA__1 | ALS__1, CAH1__1, CBPN__1, CBPN__2, CLUS__1, FETUA__2, IBP4__3, ITIH4__3, PCD12__1, PRL__1, PRL__2, PSG1__1, PSG9__1, RET4__1 |
| FETUA__2 | A2GL__1, AACT__1, ADA12__1, AFAM__1, AFAM__2, ALS__1, AMBP__1, ANGT__1, ANT3__1, APOH__1, ATS13__1, ATS13__2, B2MG__1, B2MG__2, BMI, C163A__1, C1QA__2, C1QB__3, CADH5__2, CATD__1, CATD__2, CBPN__1, CBPN__2, CD14__1, cDM, Cervix, CGB1__1, CGB1__2, cHTN, CLUS__1, CLUS__2, CNTN1__2, CO5__1, CO5__2, CO8A__1, CO8B__1, CRAC1__1, CRAC1__3, CRIS3__1, CRIS3__2, CSH__1, DEF1__1, DEF1__2, DPEP2__1, DPEP2__2, ECM1__1, ECM1__2, EGLN__2, ENPP2__1, ENPP2__2, FA11__1, FA11__2, FA5__1, FBLN1__1, FBLN3__1, FETUA__1, GABD., GDM, GELS__1, GPX3__1, GPX3__2, HABP2__1, HEMO__1, HLACI__1, IBP2__1, IBP3__1, IBP3__2, IBP4__2, IBP4__3, IBP6__1, IBP6__2, IGF1__1, INHBC__1, InvGra, InvPar, IPMLOS, IPSP__1, IPSP__2, ITIH4__2, ITIH4__3, KIT__1, KIT__2, KNG1__1, KNG1__2, LBP__1, LBP__2, LEP__2, LYAM1__1, MDHT., MDWT., MFAP5__1, NdelCo, PAEP__1, PAEP__2, PCD12__1, PCD12__2, PEDF__2, PEspec, PGRP2__1, PriorP, PRL__1, PRL__2, PROS__1, PROS__2, PSG1__1, PSG11__1, PSG2__1, PSG3__1, PSG9__1, PSG9__2, PTGDS__1, PTGDS__2, RET4__1, SEPP1__1, SEPP1__2, SHBG__1, SHBG__3, SOM2__2, SPRL1__1, SVEP1__1, TENX3, TENX__2, TIMP1__1, User, VTDB__1 |
| FGFR1__2 | IBP4__1, LIRB5__1, PCD12__1 |
| GABD. | FETUA__2, IBP4__1, PAEP__1, PAEP__2 |
| GDM | FETUA__2, IBP4__1 |
| GELS__1 | FETUA__2, HEMO__1, PAEP__2 |
| GELS__2 | EGLN__2, HEMO__1, PAEP__1, TENX__2 |
| GPX3__1 | FETUA__2, IBP4__1, PAEP__2 |
| GPX3__2 | FETUA__2, HEMO__1, IBP4__1, PRL__1 |
| HABP2__1 | FETUA__2, IBP4__1, PAEP__1, PAEP__2 |
| HEMO__1 | CLUS__1, CSH__2, FETUA__2, GELS__1, GELS__2, GPX3__2, IBP4__1, KNG1__2, LIRB5__1, PAEP__1, PAPP1__1, PRG4__2, PSG9__1, TENX__2, VTNC__2 |
| HLACI__1 | FETUA__2, IBP4__1, PAEP__1, PAEP__2 |
| IBP1__1 | TENX__2 |
| IBP2__1 | FETUA__2, PAEP__1, PAEP__2 |
| IBP3__1 | FETUA__2, PAEP__1 |
| IBP3__2 | FETUA__2, IBP4__1, PAEP__2 |
| IBP4__1 | AACT__1, ADA12__1, AMBP__1, ANGT__1, AOC1__1, AOC1__2, APOC3__1, APOH__1, ATS13__1, ATS13__2, BMI, C1QA__1, C1QA__2, C1QB__1, C1QC__1, CATD__1, CATD__2, CD14__1, cDM, Cervix, CFAB__1, CGB1__1, CGB1__2, CHL1__1, cHTN, CLUS__1, CLUS__2, CNTN1__2, CO5__1, CO5__2, CO6__1, CO8B__1, CRAC1__2, CRIS3__1, CRIS3__2, DM, EGLN__1, ENPP2__1, FA11__1, FA5__2, FBLN1__1, FBLN3__1, FGFR1__2, GABD., GDM, GPX3__1, GPX3__2, HABP2__1, HEMO__1, HLACI__1, IBP3__2, IBP4__2, IBP4__3, IBP6__2, InvGra, InvPar, IPSP__2, ISM2__1, ISM2__2, ITIH3__1, ITIH4__2, KIT__1, KIT__2, KNG1__2, LBP__1, LEP__2, MDHT., MDWT., MFAP5__1, NOTUM__2, PAEP__1, PAEP__2, PAPP1__1, PAPP2__1, PCD12__2, PEDF__1, PEDF__2, PEspec, PGRP2__1, PriorP, |

TABLE 25-continued

Analyte pairs in trianalyte models containing AACT for nulliparous
women with gestational age at blood draws days 168-189

| Analyte1 | Analyte2 |
|---|---|
| | PROS_1, PROS_2, PSG2_1, PSG3_1, SEPP1_1, SHBG_1, SOM2_1, SVEP1_1, TETN_2, THRB_1, TIE1_1, TIMP1_1, User, VGFR1_1, VTDB_1 |
| IBP4_2 | FETUA_2, IBP4_1, PRL_1 |
| IBP4_3 | FETUA_1, FETUA_2, IBP4_1, ITIH4_2, PAEP_1 |
| IBP6_1 | FETUA_2, PAEP_1 |
| IBP6_2 | FETUA_2, IBP4_1, PAEP_1 |
| IGF1_1 | C1QC_2, CAH1_1, FETUA_2, ITIH4_2 |
| IL1R1_1 | PRL_1, PSG1_1 |
| INHBC_1 | FETUA_2, PAEP_1, PAEP_2 |
| InvGra | FETUA_2, IBP4_1, PAEP_2 |
| InvPar | FETUA_2, IBP4_1, PAEP_1, PAEP_2 |
| IPMLOS | FETUA_2, PEspec, TENX_2 |
| IPSP_1 | C1QA_1, C1QA_2, C1QC_2, FETUA_2 |
| IPSP_2 | FETUA_2, IBP4_1, PAEP_1, PAEP_2 |
| ISM2_1 | IBP4_1, PRL_1 |
| ISM2_2 | IBP4_1, PAEP_1, PAEP_2, PRL_1 |
| ITIH3_1 | IBP4_1, PAEP_1, PAEP_2 |
| ITIH4_2 | ALS_1, APOH_1, B2MG_1, B2MG_2, BMI, C1QC_2, CBPN_1, Cervix, CO8A_1, FETUA_2, IBP4_1, IBP4_3, IGF1_1, LBP_1, LIRB5_1, MDWT., PriorP, PRL_1, PRL_2, RET4_1, SEPP1_1, SEPP1_2, TENX_2 |
| ITIH4_3 | ALS_1, B2MG_2, CFAB_1, FETUA_1, FETUA_2, LEP_1, LIRB5_1, PAEP_1 |
| KIT_1 | FETUA_2, IBP4_1 |
| KIT_2 | FETUA_2, IBP4_1, LIRB5_1 |
| KNG1_1 | BMI, FETUA_2, MDWT., PAEP_1 |
| KNG1_2 | FETUA_2, HEMO_1, IBP4_1, PAEP_1, PRL_1 |
| LBP_1 | BMI, FETUA_2, IBP4_1, ITIH4_2 |
| LBP_2 | FETUA_2 |
| LEP_1 | C1QB_1, CBPN_2, FA11_2, ITIH4_3, LYAM1_1, PAEP_1, PSG1_1, RET4_1, TENX_1, TENX_2 |
| LEP_2 | FETUA_2, IBP4_1, PAEP_1, PAEP_2 |
| LIRB5_1 | CFAB_1, CLUS_1, CO5_1, FGFR1_2, HEMO_1, ITIH4_2, ITIH4_3, KIT_2, PEDF_1, PEspec, PRDX2_1, PROS_1, PROS_2 |
| LYAM1_1 | FETUA_2, LEP_1, TENX_2 |
| MDHT. | FETUA_2, IBP4_1 |
| MDWT. | CBPN_2, FETUA_2, IBP4_1, ITIH4_2, KNG1_1, RET4_1 |
| MFAP5_1 | FETUA_2, IBP4_1, PAEP_1, PAEP_2 |
| MUC18_1 | RET4_1 |
| NdelCo | FETUA_2, PAEP_2, TENX_2 |
| NOTUM_1 | PAEP_2 |
| NOTUM_2 | IBP4_1, PAEP_2 |
| PAEP_1 | AACT_1, ADA12_1, AFAM_1, ANGT_1, AOC1_1, APOC3_1, ATL4_1, ATS13_1, ATS13_2, BGH3_1, Bleedi, C1QA_1, C1QA_2, C1QB_2, CAMP_1, CAMP_2, CATD_2, CBPN_2, cDM, CFAB_1, CGB1_1, CHL1_1, cHTN, CLUS_2, CNTN1_1, CNTN1_2, CO5_2, CRAC1_2, CRAC1_3, CRIS3_2, DM, ECM1_2, ENPP2_1, FA5_1, FETUA_2, GABD., GELS_2, HABP2_1, HEMO_1, HLACI_1, IBP2_1, IBP3_1, IBP4_1, IBP4_3, IBP6_1, IBP6_2, INHBC_1, InvPar, IPSP_2, ISM2_2, ITIH3_1, ITIH4_3, KNG1_1, KNG1_2, LEP_1, LEP_2, MFAP5_1, PAEP_2, PAPP1_1, PAPP2_1, PCD12_2, PEDF_1, PEDF_2, PEspec, PGRP2_1, PRL_2, PSG9_2, PTGDS_1, PTGDS_2, SEPP1_1, SEPP1_2, SHBG_1, SHBG_3, SOM2_1, SVEP1_1, TENX_1, TENX_2, TIMP1_1, VGFR1_1, VTDB_1 |
| PAEP_2 | A2GL_1, AACT_1, ADA12_1, ANGT_1, AOC1_1, APOC3_1, APOH_1, ATS13_1, ATS13_2, BGH3_1, BMI, C1QA_2, C1QB_2, CAMP_1, cDM, CFAB_1, cHTN, CLUS_2, CNTN1_1, CO5_2, CO6_1, CRAC1_2, CRAC1_3, CSH_2, DEF1_2, EGLN_1, FETUA_2, GABD., GELS_1, GPX3_1, HABP2_1, HLACI_1, IBP2_1, IBP3_2, IBP4_1, INHBC_1, InvGra, InvPar, IPSP_2, ISM2_2, ITIH3_1, LEP_2, MFAP5_1, NdelCo, NOTUM_1, NOTUM_2, PAEP_1, PAPP1_1, PAPP2_1, PEDF_1, PEDF_2, PGRP2_1, PRG2_1, PRL_2, PSG2_1, PSG9_2, PTGDS_1, PTGDS_2, SEPP1_2, SHBG_1, SOM2_1, SPRL1_1, SVEP1_1, TENX_1, TENX_2, TIMP1_1, VGFR1_1, VTDB_1 |
| PAPP1_1 | HEMO_1, IBP4_1, PAEP_1, PAEP_2 |
| PAPP2_1 | C1QB_1, C1QC_2, IBP4_1, PAEP_1, PAEP_2, TENX_2 |
| PCD12_1 | EGLN_2, FETUA_1, FETUA_2, FGFR1_2, PRDX2_1, PRL_1, PRL_2, RET4_1, TENX_2, TIE1_1, User |
| PCD12_2 | FETUA_2, IBP4_1, PAEP_1, TENX_2 |
| PEDF_1 | IBP4_1, LIRB5_1, PAEP_1, PAEP_2 |
| PEDF_2 | FETUA_2, IBP4_1, PAEP_1, PAEP_2, RET4_1 |
| PEspec | CBPN_1, FETUA_2, IBP4_1, IPMLOS, LIRB5_1, PAEP_1, RET4_1, TENX_2 |
| PGRP2_1 | CAH1_1, FETUA_2, IBP4_1, PAEP_1, PAEP_2 |
| PRDX2_1 | CD14_1, CLUS_1, ECM1_1, LIRB5_1, PCD12_1, TENX_2 |
| PRG2_1 | PAEP_2 |
| PRG4_2 | HEMO_1 |
| PriorP | FETUA_2, IBP4_1, ITIH4_2 |
| PRL_1 | AMBP_1, ANT3_1, C1QA_1, CO8A_1, CRIS3_2, CSH_1, DM, ECM1_1, ENPP2_2, FA11_1, FETUA_1, FETUA_2, GPX3_2, IBP4_2, IL1R1_1, ISM2_1, |

TABLE 25-continued

Analyte pairs in trianalyte models containing AACT for nulliparous women with gestational age at blood draws days 168-189

| Analyte1 | Analyte2 |
| --- | --- |
| | ISM2__2, ITIH4__2, KNG1__2, PCD12__1, RET4__1, SHBG__3, SOM2__1, TENX__1, TENX__2, TIE1__1, TIMP1__1, VTNC__1 |
| PRL__2 | AMBP__1, ANGT__1, ANT3__1, CRIS3__2, ECM1__1, FETUA__1, FETUA__2, ITIH4__2, PAEP__1, PAEP__2, PCD12__1, SEPP1__1, TENX__1, TENX__2 |
| PROS__1 | FETUA__2, IBP4__1, LIRB5__1, RET4__1 |
| PROS__2 | FETUA__2, IBP4__1, LIRB5__1 |
| PSG1__1 | ALS__1, B2MG__2, CBPN__2, CFAB__1, ECM1__1, EGLN__2, FETUA__1, FETUA__2, IL1R1__1, LEP__1, RET4__1, SOM2__2, TENX__2, TIE1__1 |
| PSG11__1 | FETUA__2 |
| PSG2__1 | FETUA__2, IBP4__1, PAEP__2 |
| PSG3__1 | FETUA__2, IBP4__1, TENX__1 |
| PSG9__1 | C1QB__1, FETUA__1, FETUA__2, HEMO__1, TENX__2 |
| PSG9__2 | C1QB__1, FETUA__2, PAEP__1, PAEP__2, TENX__1, TENX__2, TIE1__1 |
| PTGDS__1 | FETUA__2, PAEP__1, PAEP__2 |
| PTGDS__2 | FETUA__2, PAEP__1, PAEP__2 |
| RET4__1 | BMI, CO8A__1, DPEP2__2, F13B__1, FA5__1, FETUA__1, FETUA__2, ITIH4__2, LEP__1, MDWT., MUC18__1, PCD12__1, PEDF__2, PEspec, PRL__1, PROS__1, PSG1__1, TENX__1, TIMP1__1, VTDB__1 |
| SEPP1__1 | FETUA__2, IBP4__1, ITIH4__2, PAEP__1, PRL__2, SPRL1__1 |
| SEPP1__2 | FETUA__2, ITIH4__2, PAEP__1, PAEP__2 |
| SHBG__1 | FETUA__2, IBP4__1, PAEP__1, PAEP__2 |
| SHBG__3 | FETUA__2, PAEP__1, PRL__1 |
| SOM2__1 | C1QC__2, IBP4__1, PAEP__1, PAEP__2, PRL__1 |
| SOM2__2 | FETUA__2, PSG1__1 |
| SPRL1__1 | CLUS__1, FETUA__2, PAEP__2, SEPP1__1, TENX__2 |
| SVEP1__1 | FETUA__2, IBP4__1, PAEP__1, PAEP__2 |
| TENX__1 | ALS__1, CBPN__1, CBPN__2, CLUS__1, FETUA__2, LEP__1, PAEP__1, PAEP__2, PRL__1, PRL__2, PSG3__1, PSG9__2, RET4__1 |
| TENX__2 | A2GL__1, ADA12__1, AFAM__1, AFAM__2, ALS__1, C163A__1, CAH1__1, CBPN__1, CBPN__2, CFAB__1, CGB1__1, CGB1__2, CRAC1__2, CRIS3__1, CRIS3__2, ECM1__1, FA11__1, FA5__1, FBLN3__1, FETUA__2, GELS__2, HEMO__1, IBP1__1, IPMLOS, ITIH4__2, LEP__1, LYAM1__1, NdelCo, PAEP__1, PAEP__2, PAPP2__1, PCD12__1, PCD12__2, PEspec, PRDX2__1, PRL__1, PRL__2, PSG1__1, PSG9__1, PSG9__2, SPRL1__1, TETN__2, VTNC__2 |
| TETN__2 | IBP4__1, TENX__2 |
| THRB__1 | IBP4__1 |
| TIE1__1 | IBP4__1, PCD12__1, PRL__1, PSG1__1, PSG9__2 |
| TIMP1__1 | CLUS__1, FETUA__2, IBP4__1, PAEP__1, PAEP__2, PRL__1, RET4__1 |
| User | FETUA__2, IBP4__1, PCD12__1 |
| VGFR1__1 | IBP4__1, PAEP__1, PAEP__2 |
| VTDB__1 | C1QC__2, FETUA__2, IBP4__1, PAEP__1, PAEP__2, RET4__1 |
| VTNC__1 | PRL__1 |
| VTNC__2 | ANGT__1, BMI, HEMO__1, TENX__2 |

TABLE 26

Analyte pairs in trianalyte models containing AACT for nulliparous women with gestational age at blood draws days 175-196

| Analyte1 | Analyte2 |
| --- | --- |
| A2GL__1 | ADA12__1, AFAM__1, AFAM__2, ALS__1, APOH__1, ATS13__2, B2MG__1, BMI, C1QB__1, C1QC__1, CBPN__2, CLUS__1, CO8B__1, CRAC1__3, CSH__2, FA11__1, FA11__2, FETUA__2, GELS__1, GELS__2, IBP2__1, IPMLOS, KNG1__1, LEP__1, LEP__2, MDHT., MDWT., NdelCo, PAEP__1, PAEP__2, PEDF__1, PSG9__1, PSG9__2, RET4__1, SEPP1__1, SEPP1__2, SOM2__1, SPRL1__1, TENX__1, TENX__2, TETN__1, TETN__2, TIMP1__1, VTDB__1, VTNC__2 |
| AACT__1 | KNG1__1, LEP__1, PAEP__1, PSG9__1, PSG9__2, RET4__1 |
| ADA12__1 | A2GL__1, AOC1__1, B2MG__1, C1QA__2, C1QC__1, CADH5__2, CATD__1, CGB1__1, CGB1__2, CO6__1, CRAC1__2, CRAC1__3, CRIS3__1, CSH__2, ECM1__1, ECM1__2, EGLN__2, FGFR1__2, ITIH4__2, KNG1__1, LEP__2, MDHT., PAEP__1, PAEP__2, PRG2__1, PROS__2, PSG9__1, PSG9__2, RET4__1, SEPP1__2, SOM2__2, TENX__1, VGFR1__1, VTDB__1 |
| AFAM__1 | A2GL__1, BMI, C1QA__1, C1QA__2, C1QB__1, C1QB__2, C1QC__1, C1QC__2, CGB1__1, CGB1__2, CRAC1__1, FETUA__1, IBP2__1, KIT__1, KIT__2, KNG1__1, LEP__2, MDWT., NpregC, PEDF__2, PRG2__1, PSG1__1, PSG9__1, PSG9__2, SEPP1__2, TENX__2 |
| AFAM__2 | A2GL__1, C1QA__2, C1QB__2, C1QC__1, ECM1__1, GELS__2, IBP2__1, KNG1__1, LEP__1, MDWT., PAEP__1, SEPP1__1, SHBG__3, TENX__1, TENX__2 |
| ALS__1 | A2GL__1, C1QC__1, GELS__2, PAEP__1, PEDF__1, TENX__1 |
| AMBP__1 | KNG1__1, LEP__1, LEP__2, PAEP__1, PSG9__2, RET4__1 |
| ANGT__1 | CSH__2, ECM1__1, GPX3__1, KNG1__1, PAEP__1, PAEP__2, RET4__1 |

TABLE 26-continued

Analyte pairs in trianalyte models containing AACT for nulliparous
women with gestational age at blood draws days 175-196

| Analyte1 | Analyte2 |
| --- | --- |
| ANT3__1 | GELS__2, KNG1__1, TENX__2 |
| AOC1__1 | ADA12__1, KNG1__1, LEP__1, PAEP__1, PEDF__1, PSG9__1, PSG9__2, RET4__1, VTDB__1 |
| AOC1__2 | GELS__2, KNG1__1, LEP__1, PSG9__2, RET4__1 |
| APOC3__1 | CO8B__1, KNG1__1, PAEP__1, SOM2__1 |
| APOH__1 | A2GL__1, BMI, CAMP__1, CAMP__2, GELS__2, IGF2__1, KNG1__1, LEP__1, MDWT., PAEP__1, PSG9__1, PSG9__2, RET4__1 |
| ATL4__1 | KNG1__1, LEP__1, PSG9__2, RET4__1 |
| ATS13__1 | CBPN__1, EGLN__2, KNG1__1, LEP__1, PAEP__1, PROS__2, PSG9__1, PSG9__2, RET4__1, SEPP1__1, SPRL1__1 |
| ATS13__2 | A2GL__1, C1QB__1, C1QB__2, CSH__2, IBP2__1, KNG1__1, LEP__1, LEP__2, PAEP__1, PAEP__2, PSG9__1, PSG9__2, TENX__1, VTDB__1 |
| B2MG__1 | A2GL__1, ADA12__1, CBPN__1, CD14__1, CGB1__1, CGB1__2, CRAC1__2, GELS__2, IBP2__1, KIT__1, MUC18__1, MUC18__2, PAEP__1, PRDX2__1, RET4__1, SVEP1__1 |
| B2MG__2 | GELS__2, KNG1__1, PAEP__1, PSG9__2, RET4__1 |
| BGH3__1 | GELS__2, KNG1__1, PAEP__1 |
| Bleedi | BMI, KNG1__1, LEP__2, PAEP__1, PROS__2, PSG9__2, RET4__1, VTDB__1 |
| BMI | A2GL__1, AFAM__1, APOH__1, Bleedi, C1QA__2, CBPN__1, cHTN, CO5__2, CO6__1, CSH__2, FETUA__1, FGFR1__2, IBP3__2, IL1R1__1, ITIH4__1, KIT__1, KNG1__1, KNG1__2, LEP__1, LEP__2, MDHT., MDWT., PCD12__1, PRG2__1, PSG9__1, PSG9__2, RET4__1, SEPP1__1, SHBG__3, SPRL1__1, THBG__1, VTDB__1 |
| C163A__1 | CO6__1, KNG1__1, LEP__1, PSG9__2 |
| C1QA__1 | AFAM__1, CGB1__2, CO6__1, KNG1__1, LEP__1, PEDF__1, PSG9__1, PSG9__2, RET4__1, SPRL1__1 |
| C1QA__2 | ADA12__1, AFAM__1, AFAM__2, BMI, ECM1__1, FA5__2, IBP1__1, LEP__1, PAEP__1, PSG9__2, RET4__1 |
| C1QB__1 | A2GL__1, AFAM__1, ATS13__2, C1QB__3, CBPN__1, CLUS__1, CRIS3__1, LEP__1, PSG9__1, RET4__1, TENX__2 |
| C1QB__2 | AFAM__1, AFAM__2, ATS13__2, CBPN__1, CRIS3__1, IBP2__1, LEP__1, PSG9__2, RET4__1 |
| C1QB__3 | C1QB__1, KNG1__1, LEP__1, PAEP__1, PSG9__1, PSG9__2, RET4__1 |
| C1QC__1 | A2GL__1, ADA12__1, AFAM__1, AFAM__2, ALS__1, CO6__1, ECM1__1, IGF2__1, KNG1__1, LEP__1, PSG9__1, PSG9__2, SPRL1__1, TENX__2 |
| C1QC__2 | AFAM__1, CGB1__1, GELS__2 |
| CADH5__2 | ADA12__1, FA5__2, GELS__2, IBP2__1, IBP3__2, IBP6__1, KNG1__1, PAEP__1, PAPP2__1, PRG4__2, PSG9__2, SVEP1__1, TENX__2 |
| CAH1__1 | KNG1__1, PAEP__1, PSG9__1, PSG9__2, RET4__1 |
| CAMP__1 | APOH__1, ECM1__1 |
| CAMP__2 | APOH__1, KNG1__1, PROS__2 |
| CATD__1 | ADA12__1, KNG1__1, LEP__1, PAEP__1, PSG1__1, PSG9__1, PSG9__2, RET4__1 |
| CATD__2 | CSH__2, GELS__2, IBP3__1, KNG1__1, LEP__1, PAEP__1, PAEP__2, PSG9__2 |
| CBPN__1 | ATS13__1, B2MG__1, BMI, C1QB__1, C1QB__2, ECM1__1, KNG1__1, LEP__1, MDWT., PAEP__1, PAEP__2, PSG9__1, PSG9__2, RET4__1 |
| CBPN__2 | A2GL__1, CSH__2, ECM1__1, KNG1__1, LEP__1, PAEP__1, PAEP__2, PSG9__1, PSG9__2, RET4__1 |
| CD14__1 | B2MG__1, KNG1__1, LEP__1, PAEP__1, PEDF__1, PSG9__1, PSG9__2 |
| CD14__2 | GELS__2, IBP3__1, KNG1__1, LEP__1, PAEP__1, RET4__1 |
| cDM | KNG1__1, LEP__1, PAEP__1, PSG9__1, PSG9__2, RET4__1 |
| Cervix | KNG1__1 |
| CFAB__1 | KNG1__1, PAEP__1 |
| CGB1__1 | ADA12__1, AFAM__1, B2MG__1, C1QC__2, CSH__2, ECM1__1, IBP3__2, KNG1__1, KNG1__2, PAEP__1, PAEP__2, PSG9__1, PSG9__2, SOM2__1, VTDB__1 |
| CGB1__2 | ADA12__1, AFAM__1, B2MG__1, C1QA__1, KNG1__1, PSG9__1, PSG9__2 |
| CHL1__1 | KNG1__1, LEP__1, PSG9__2 |
| cHTN | BMI, KNG1__1, MDWT., PAEP__1 |
| CLUS__1 | A2GL__1, C1QB__1, KNG1__1, LEP__1, PAEP__1 |
| CLUS__2 | KNG1__1, PAEP__1 |
| CNTN1__1 | KNG1__1, PAEP__1, PSG9__1, PSG9__2 |
| CNTN1__2 | KNG1__1, LEP__1, PAEP__1, PSG9__1, PSG9__2 |
| CO5__1 | GELS__2, KNG1__1, PAEP__1, PAEP__2, PSG9__1, PSG9__2, RET4__1 |
| CO5__2 | BMI, LEP__1, MDWT., PAEP__1, PSG9__1, PSG9__2, RET4__1 |
| CO6__1 | ADA12__1, BMI, C163A__1, C1QA__1, C1QC__1, ECM1__1, FETUA__1, LEP__1, PAEP__1, PAEP__2, PEDF__1, PSG9__1, PSG9__2, RET4__1, SOM2__1 |
| CO8A__1 | KNG1__1, PAEP__1, PSG9__2, RET4__1 |
| CO8B__1 | A2GL__1, APOC3__1, KNG1__1, KNG1__2, LEP__1, PAEP__1, PRG4__2, PSG9__2, VTDB__1 |
| CRAC1__1 | AFAM__1, KNG1__1, LEP__1, PAEP__1, PSG9__1, PSG9__2 |
| CRAC1__2 | ADA12__1, B2MG__1, KNG1__1, LEP__1, PAEP__1 |
| CRAC1__3 | A2GL__1, ADA12__1, GELS__2, KNG1__1, PAEP__1, PAEP__2 |
| CRIS3__1 | ADA12__1, C1QB__1, C1QB__2, ECM1__1, GELS__2, GPX3__1, KNG1__1, KNG1__2, LEP__1, LEP__2, MFAP5__1, PAEP__1, PAEP__2, PROS__2, PSG1__1, PSG9__1, PSG9__2, RET4__1, VTDB__1 |
| CRIS3__2 | ECM1__1, GELS__1, KNG1__1, LEP__1, PAEP__1, PEDF__1 |
| CSH__1 | KNG1__1, PAEP__1, PSG9__2, RET4__1 |

TABLE 26-continued

Analyte pairs in trianalyte models containing AACT for nulliparous
women with gestational age at blood draws days 175-196

| Analyte1 | Analyte2 |
|---|---|
| CSH_2 | A2GL_1, ADA12_1, ANGT_1, ATS13_2, BMI, CATD_2, CBPN_2, CGB1_1, ENPP2_1, GELS_2, IBP3_2, IGF2_1, KNG1_1, LEP_1, PROS_2, PSG9_2, SVEP1_1, TENX_2, THBG_1, VTDB_1 |
| DEF1_1 | KNG1_1, LEP_1, PSG9_2, VTDB_1 |
| DEF1_2 | KNG1_1, VTDB_1 |
| DM | KNG1_1, PAEP_1 |
| DPEP2_1 | KNG1_1, LEP_1, PAEP_1, PSG9_1, PSG9_2, RET4_1 |
| DPEP2_2 | KNG1_1, LEP_1, PAEP_1, PSG9_1, PSG9_2 |
| ECM1_1 | ADA12_1, AFAM_2, ANGT_1, C1QA_2, C1QC_1, CAMP_1, CBPN_1, CBPN_2, CGB1_1, CO6_1, CRIS3_1, CRIS3_2, FA5_2, FBLN1_1, GELS_2, GPX3_1, IBP3_2, IGF2_1, KNG1_1, LEP_1, LEP_2, PAEP_1, PAEP_2, PEDF_1, PRL_2, SEPP1_2, SPRL1_1, TENX_2, TIMP1_1 |
| ECM1_2 | ADA12_1, KNG1_1, LEP_1, PAEP_1 |
| EGLN_1 | KNG1_1, LEP_1, PSG9_2, RET4_1, TENX_1 |
| EGLN_2 | ADA12_1, ATS13_1, GPX3_1, KNG1_1, LEP_1, PAEP_1, PSG9_2 |
| ENPP2_1 | CSH_2, GELS_2, KNG1_1, LEP_1, PAEP_1, PSG9_1, PSG9_2, RET4_1 |
| ENPP2_2 | KNG1_1, LEP_1, PAEP_1, PSG9_1, PSG9_2, RET4_1 |
| F13B_1 | KNG1_1, PSG9_2, RET4_1 |
| FA11_1 | A2GL_1, IBP6_2, KNG1_1 |
| FA11_2 | A2GL_1, GELS_2, IBP6_2, PSG9_2, RET4_1 |
| FA5_1 | IBP3_1, KNG1_1, PAEP_1, PSG9_2 |
| FA5_2 | C1QA_2, CADH5_2, ECM1_1, GELS_2, KNG1_1, PAEP_1, PAEP_2, PSG9_1, PSG9_2, RET4_1 |
| FA9_1 | PEDF_1 |
| FA9_2 | KNG1_1, PAEP_1 |
| FBLN1_1 | ECM1_1, GELS_2, KNG1_1, PSG9_1, PSG9_2 |
| FBLN3_1 | GELS_2, KNG1_1, LEP_1, PAEP_1, PSG9_1, PSG9_2, RET4_1 |
| FETUA_1 | AFAM_1, BMI, CO6_1, IBP3_1, IBP3_2, IGF2_1, KNG1_1, KNG1_2, LEP_1, LEP_2, MDWT., PAEP_1, PSG9_2, RET4_1 |
| FETUA_2 | A2GL_1, KNG1_2, VTDB_1 |
| FGFR1_1 | GELS_2, KNG1_1, LEP_1, PAEP_1, PAEP_2, PSG9_1, PSG9_2, RET4_1, SEPP1_1 |
| FGFR1_2 | ADA12_1, BMI, GPX3_1, LEP_1, PAEP_1, PSG9_1, PSG9_2, RET4_1 |
| GABD. | KNG1_1, LEP_1, PAEP_1, PSG9_1, PSG9_2, RET4_1 |
| GDM | KNG1_1 |
| GELS_1 | A2GL_1, CRIS3_2, LEP_1, PAEP_1, PAEP_2, PRG4_2 |
| GELS_2 | A2GL_1, AFAM_2, ALS_1, ANT3_1, AOC1_2, APOH_1, B2MG_1, B2MG_2, BGH3_1, C1QC_2, CADH5_2, CATD_2, CD14_2, CO5_1, CRAC1_3, CRIS3_1, CSH_2, ECM1_1, ENPP2_1, FA11_2, FA5_2, FBLN1_1, FBLN3_1, FGFR1_1, HABP2_1, HEMO_1, HLACI_1, IBP1_1, IBP3_1, IBP3_2, IGF1_1, IGF2_1, InvGra, IPMLOS, ITIH4_3, KNG1_1, KNG1_2, LBP_1, LBP_2, LEP_1, LEP_2, MDWT., MFAP5_1, MUC18_1, NdelCo, PAEP_1, PAEP_2, PEDF_2, PRG4_1, PRG4_2, PriorP, PRL_2, PROS_1, PROS_2, PSG2_1, PSG3_1, PSG9_1, PSG9_2, SEPP1_2, SHBG_1, SPRL1_1, THRB_1, TIMP1_1, VTDB_1 |
| GPX3_1 | ANGT_1, CRIS3_1, ECM1_1, EGLN_2, FGFR1_2, IBP2_1, ITIH4_2, KIT_1, KNG1_1, LEP_1, NdelCo, PRG4_2, TETN_2, TFMP1_1, VTDB_1 |
| GPX3_2 | KNG1_1, LEP_1, PAEP_1, PSG9_1, PSG9_2, RET4_1 |
| HABP2_1 | GELS_2, KNG1_1, LEP_1, PAEP_1, PSG9_2 |
| HEMO_1 | GELS_2, HLACI_1, IBP3_1, IGF2_1, KIT_1, KIT_2, KNG1_1, PSG9_2, SEPP1_1, TENX_1 |
| HLACI_1 | GELS_2, HEMO_1, KNG1_1, LEP_1, PAEP_1, PSG9_2, RET4_1 |
| IBP1_1 | C1QA_2, GELS_2, LEP_1, TENX_1 |
| IBP2_1 | A2GL_1, AFAM_1, AFAM_2, ATS13_2, B2MG_1, C1QB_2, CADH5_2, GPX3_1, IBP3_1, IBP3_2, IGF2_1, KNG1_1, KNG1_2, LEP_1, PAEP_1, PCD12_1, PSG9_1, PSG9_2, RET4_1, TENX_1, VTDB_1 |
| IBP3_1 | CATD_2, CD14_2, FA5_1, FETUA_1, GELS_2, HEMO_1, IBP2_1, IBP6_2, KNG1_1, LYAM1_1, PAEP_1, PAEP_2, PEDF_1, PROS_2, SEPP1_1, TENX_1 |
| IBP3_2 | BMI, CADH5_2, CGB1_1, CSH_2, ECM1_1, FETUA_1, GELS_2, IBP2_1, IBP6_2, KNG1_1, LEP_1, LEP_2, MDWT., PAEP_1, PAEP_2, PEDF_1, TENX_1, TENX_2 |
| IBP4_1 | KNG1_1 |
| IBP4_2 | KNG1_1 |
| IBP4_3 | KNG1_1, PSG9_1, PSG9_2 |
| IBP6_1 | CADH5_2, KNG1_1, PEDF_1, RET4_1 |
| IBP6_2 | FA11_1, FA11_2, IBP3_1, IBP3_2, KNG1_1, PSG9_2, THRB_1, VTDB_1 |
| IGF1_1 | GELS_2, PAEP_1 |
| IGF2_1 | APOH_1, C1QC_1, CSH_2, ECM1_1, FETUA_1, GELS_2, HEMO_1, IBP2_1, KNG1_1, MDWT., PAEP_1, PEDF_1, PROS_2, PSG9_2, RET4_1 |
| IL1R1_1 | BMI, KNG1_1, PAEP_1, PSG9_2, RET4_1 |
| INHBC_1 | KNG1_1, PSG9_2, RET4_1, VTDB_1 |
| InvGra | GELS_2, KNG1_1, LEP_1, PAEP_2, PROS_2, PSG9_1, PSG9_2, RET4_1 |
| InvPar | KNG1_1, LEP_1, PAEP_1, PSG9_1, PSG9_2, RET4_1 |
| IPMLOS | A2GL_1, GELS_2, KNG1_1, PAEP_1, PSG9_2, RET4_1 |
| IPSP_1 | KNG1_1, LEP_1, PAEP_1, PSG9_1, PSG9_2, RET4_1 |
| IPSP_2 | KNG1_1, LEP_1, PAEP_1, PSG9_1, PSG9_2, RET4_1 |

TABLE 26-continued

Analyte pairs in trianalyte models containing AACT for nulliparous
women with gestational age at blood draws days 175-196

| Analyte1 | Analyte2 |
| --- | --- |
| ISM2__1 | KNG1__1, LEP__1, PAEP__1, PAEP__2, PSG9__1, PSG9__2, RET4__1 |
| ISM2__2 | KNG1__1, LEP__1, NOTUM__2, PAEP__1, PEDF__1, PSG9__1, PSG9__2, TENX__2 |
| ITIH3__1 | KNG1__1 |
| ITIH4__1 | BMI, KNG1__1, PSG9__2, RET4__1 |
| ITIH4__2 | ADA12__1, GPX3__1, KNG1__1, PAEP__1, PSG9__2, RET4__1, SEPP1__2 |
| ITIH4__3 | GELS__2, KNG1__1, LEP__1, PAEP__1, PEDF__1, PSG1__1 |
| KIT__1 | AFAM__1, B2MG__1, BMI, GPX3__1, HEMO__1, KNG1__1, LEP__1, PAEP__1, PAEP__2, PSG9__2, TENX__1 |
| KIT__2 | AFAM__1, HEMO__1, KNG1__1, PAEP__1, PAEP__2 |
| KNG1__1 | A2GL__1, AACT__1, ADA12__1, AFAM__1, AFAM__2, AMBP__1, ANGT__1, ANT3__1, AOC1__1, AOC1__2, APOC3__1, APOH__1, ATL4__1, ATS13__1, ATS13__2, B2MG__2, BGH3__1, Bleedi, BMI, C163A__1, C1QA__1, C1QB__3, C1QC__1, CADH5__1, CAH1__1, CAMP__2, CATD__1, CATD__2, CBPN__1, CBPN__2, CD14__1, CD14__2, cDM, Cervix, CFAB__1, CGB1__1, CGB1__2, CHL1__1, cHTN, CLUS__1, CLUS__2, CNTN1__1, CNTN1__2, CO5__1, CO8A__1, CO8B__1, CRAC1__1, CRAC1__2, CRAC1__3, CRIS3__1, CRIS3__2, CSH__1, CSH__2, DEF1__1, DEF1__2, DM, DPEP2__1, DPEP2__2, ECM1__1, ECM1__2, EGLN__1, EGLN__2, ENPP2__1, ENPP2__2, F13B__1, FA11__1, FA5__1, FA5__2, FA9__2, FBLN1__1, FBLN3__1, FETUA__1, FGFR1__1, GABD., GDM, GELS__2, GPX3__1, GPX3__2, HABP2__1, HEMO__1, HLACI__1, IBP2__1, IBP3__1, IBP3__2, IBP4__1, IBP4__2, IBP4__3, IBP6__1, IBP6__2, IGF2__1, IL1R1__1, INHBC__1, InvGra, InvPar, IPMLOS, IPSP__1, IPSP__2, ISM2__1, ISM2__2, ITIH3__1, ITIH4__1, ITIH4__2, ITIH4__3, KIT__1, KIT__2, KNG1__2, LBP__1, LBP__2, LEP__1, LEP__2, LIRB5__1, LYAM1__1, MAGE, MDHT., MDWT., MFAP5__1, MUC18__1, NdelCo, NOTUM__1, NOTUM__2, PAEP__1, PAEP__2, PAPP1__1, PAPP2__1, PCD12__1, PCD12__2, PEDF__2, PEspec, PGRP2__1, PRDX2__1, PRG2__1, PRG4__1, PRG4__2, PriorP, PRL__2, PROS__1, PROS__2, PSG11__1, PSG2__1, PSG3__1, PSG9__1, PSG9__2, PTGDS__1, PTGDS__2, RET4__1, SEPP1__1, SEPP1__2, SHBG__1, SHBG__3, SOM2__1, SOM2__2, SPRL1__1, TETN__1, TETN__2, THBG__1, THRB__1, TIE1__1, TIMP1__1, User, VGFR1__1, VTDB__1, VTNC__2 |
| KNG1__2 | BMI, CGB1__1, CO8B__1, CRIS3__1, FETUA__1, FETUA__2, GELS__2, IBP2__1, KNG1__1, LEP__1, MDWT., PAEP__1, PEDF__1, PROS__2 |
| LBP__1 | GELS__2, KNG1__1, LEP__1, TENX__2 |
| LBP__2 | GELS__2, KNG1__1 |
| LEP__1 | A2GL__1, AACT__1, AFAM__2, AMBP__1, AOC1__1, AOC1__2, APOH__1, ATL4__1, ATS13__1, ATS13__2, BMI, C163A__1, C1QA__1, C1QA__2, C1QB__1, C1QB__2, C1QB__3, C1QC__1, CATD__1, CATD__2, CBPN__1, CBPN__2, CD14__1, CD14__2, cDM, CHL1__1, CLUS__1, CNTN1__2, CO5__2, CO6__1, CO8B__1, CRAC1__1, CRAC1__2, CRIS3__1, CRIS3__2, CSH__2, DEF1__1, DPEP2__1, DPEP2__2, ECM1__1, ECM1__2, EGLN__1, EGLN__2, ENPP2__1, ENPP2__2, FBLN3__1, FETUA__1, FGFR1__1, FGFR1__2, GABD., GELS__1, GELS__2, GPX3__2, HABP2__1, HLACI__1, IBP1__1, IBP2__1, IBP3__2, InvGra, InvPar, IPSP__1, IPSP__2, ISM2__1, ISM2__2, ITIH4__3, KIT__1, KNG1__1, KNG1__2, LBP__1, LEP__2, LIRB5__1, LYAM1__1, MDHT., MDWT., NOTUM__1, PAEP__1, PAEP__2, PAPP2__1, PCD12__1, PEspec, PGRP2__1, PRG2__1, PRL__2, PROS__1, PROS__2, PSG11__1, PSG3__1, PSG9__1, PSG9__2, PTGDS__1, PTGDS__2, RET4__1, SEPP1__1, SHBG__1, SHBG__3, SOM2__2, SPRL1__1, TENX__1, TENX__2, TETN__1, TETN__2, THBG__1, THRB__1, User, VGFR1__1, VTDB__1, VTNC__1, VTNC__2 |
| LEP__2 | A2GL__1, ADA12__1, AFAM__1, AMBP__1, ATS13__2, Bleedi, BMI, CRIS3__1, ECM1__1, FETUA__1, GELS__2, IBP3__2, KNG1__1, LEP__1, PAEP__1, PCD12__1, PRL__1, PSG11__1, PSG9__1, PSG9__2, RET4__1, SEPP1__2, THRB__1, VTDB__1 |
| LIRB5__1 | KNG1__1, LEP__1 |
| LYAM1__1 | IBP3__1, KNG1__1, LEP__1, PAEP__1, PSG9__1, PSG9__2, RET4__1 |
| MAGE | KNG1__1, PAEP__1, PSG9__1, PSG9__2, RET4__1 |
| MDHT. | A2GL__1, ADA12__1, BMI, KNG1__1, LEP__1, MDWT., PAEP__1, PAEP__2, PSG9__2, RET4__1, SEPP1__2 |
| MDWT. | A2GL__1, AFAM__1, AFAM__2, APOH__1, BMI, CBPN__1, cHTN, CO5__2, FETUA__1, GELS__2, IBP3__2, IGF2__1, KNG1__1, KNG1__2, LEP__1, MDHT., PAEP__1, PAEP__2, PCD12__1, PRG4__2, PSG9__1, PSG9__2, RET4__1, SEPP1__1, SHBG__3, SPRL1__1, VTDB__1 |
| MFAP5__1 | CRIS3__1, GELS__2, KNG1__1, PAEP__1, PSG9__1, PSG9__2, RET4__1, TENX__1 |
| MUC18__1 | B2MG__1, GELS__2, KNG1__1, PSG9__2 |
| MUC18__2 | B2MG__1, PAEP__1 |
| NdelCo | A2GL__1, GELS__2, GPX3__1, KNG1__1, PAEP__1, PSG9__2 |
| NOTUM__1 | KNG1__1, LEP__1, PAEP__1, PSG9__1, PSG9__2 |
| NOTUM__2 | ISM2__2, KNG1__1, PAEP__1, PAEP__2, PSG9__1, PSG9__2, RET4__1 |
| NpregC | AFAM__1 |
| PAEP__1 | A2GL__1, AACT__1, ADA12__1, AFAM__2, ALS__1, AMBP__1, ANGT__1, AOC1__1, APOC3__1, APOH__1, ATS13__1, ATS13__2, B2MG__1, B2MG__2, BGH3__1, Bleedi, C1QA__2, C1QB__3, CADH5__2, CAH1__1, CATD__1, CATD__2, CBPN__1, CBPN__2, CD14__1, CD14__2, cDM, CFAB__1, CGB1__1, cHTN, CLUS__1, CLUS__2, CNTN1__1, CNTN1__2, CO5__1, CO5__2, CO6__1, CO8A__1, CO8B__1, CRAC1__1, CRAC1__2, CRAC1__3, CRIS3__1, CRIS3__2, CSH__1, DM, DPEP2__1, DPEP2__2, ECM1__1, ECM1__2, EGLN__2, ENPP2__1, ENPP2__2, FA5__1, FA5__2, FA9__2, FBLN3__1, FETUA__1, FGFR1__1, FGFR1__2, GABD., GELS__1, GELS__2, GPX3__2, |

TABLE 26-continued

Analyte pairs in trianalyte models containing AACT for nulliparous
women with gestational age at blood draws days 175-196

| Analyte1 | Analyte2 |
|---|---|
| | HABP2_1, HLACI_1, IBP2_1, IBP3_1, IBP3_2, IGF1_1, IGF2_1, IL1R1_1, InvPar, IPMLOS, IPSP_1, IPSP_2, ISM2_1, ISM2_2, ITIH4_2, ITIH4_3, KIT_1, KIT_2, KNG1_1, KNG1_2, LEP_1, LEP_2, LYAM1_1, MAGE, MDHT., MDWT., MFAP5_1, MUC18_2, NdelCo, NOTUM_1, NOTUM_2, PAPP1_1, PAPP2_1, PCD12_1, PCD12_2, PEDF_1, PEDF_2, PEspec, PRDX2_1, PRG2_1, PRG4_1, PRG4_2, PriorP, PROS_1, PROS_2, PSG2_1, PSG9_1, PSG9_2, PTGDS_2, SEPP1_1, SEPP1_2, SHBG_1, SHBG_3, SOM2_1, SOM2_2, SPRL1_1, TENX_1, TENX_2, TETN_1, TETN_2, THBG_1, THRB_1, TIMP1_1, User, VGFR1_1, VTDB_1, VTNC_2 |
| PAEP_2 | A2GL_1, ADA12_1, ANGT_1, ATS13_2, CATD_2, CBPN_1, CBPN_2, CGB1_1, CO5_1, CO6_1, CRAC1_3, CRIS3_1, ECM1_1, FA5_2, FGFR1_1, GELS_1, GELS_2, IBP3_1, IBP3_2, InvGra, ISM2_1, KIT_1, KIT_2, KNG1_1, LEP_1, MDHT., MDWT., NOTUM_2, PRG4_1, PRG4_2, PriorP, PROS_2, PSG2_1, SEPP1_2, SPRL1_1, TENX_1, TENX_2, TIMP1_1 |
| PAPP1_1 | KNG1_1, PAEP_1, PSG9_1, PSG9_2, RET4_1 |
| PAPP2_1 | CADH5_2, KNG1_1, LEP_1, PAEP_1, RET4_1 |
| PCD12_1 | BMI, IBP2_1, KNG1_1, LEP_1, LEP_2, MDWT., PAEP_1, PEDF_1, PSG9_2, RET4_1 |
| PCD12_2 | KNG1_1, PAEP_1, PSG9_1, PSG9_2, RET4_1 |
| PEDF_1 | A2GL_1, ALS_1, AOC1_1, C1QA_1, CD14_1, CO6_1, CRIS3_2, ECM1_1, FA9_1, IBP3_1, IBP3_2, IBP6_1, IGF2_1, ISM2_2, ITIH4_3, KNG1_2, PAEP_1, PCD12_1, PRG4_1, PRG4_2, PSG9_1, PSG9_2, PTGDS_2, RET4_1, SEPP1_2, TENX_1, User, VTDB_1 |
| PEDF_2 | AFAM_1, GELS_2, KNG1_1, PAEP_1, PSG9_1, PSG9_2, RET4_1 |
| PEspec | KNG1_1, LEP_1, PAEP_1, PSG9_1, PSG9_2, RET4_1 |
| PGRP2_1 | KNG1_1, LEP_1, PSG9_2 |
| PRDX2_1 | B2MG_1, KNG1_1, PAEP_1, PSG9_2, RET4_1 |
| PRG2_1 | ADA12_1, AFAM_1, BMI, KNG1_1, LEP_1, PAEP_1, PSG9_2, RET4_1 |
| PRG4_1 | GELS_2, KNG1_1, PAEP_1, PAEP_2, PEDF_1 |
| PRG4_2 | CADH5_2, CO8B_1, GELS_1, GELS_2, GPX3_1, KNG1_1, MDWT., PAEP_1, PAEP_2, PEDF_1, PROS_2, TIMP1_1 |
| PriorP | GELS_2, KNG1_1, PAEP_1, PAEP_2, PSG9_1, PSG9_2, RET4_1 |
| PRL_1 | LEP_2, PSG9_2, RET4_1 |
| PRL_2 | ECM1_1, GELS_2, KNG1_1, LEP_1, PSG9_1, PSG9_2 |
| PROS_1 | GELS_2, KNG1_1, LEP_1, PAEP_1, PSG9_1, PSG9_2 |
| PROS_2 | ADA12_1, ATS13_1, Bleedi, CAMP_2, CRIS3_1, CSH_2, GELS_2, IBP3_1, IGF2_1, InvGra, KNG1_1, KNG1_2, LEP_1, PAEP_1, PAEP_2, PRG4_2, PSG9_1, PSG9_2, RET4_1, SEPP1_2, THBG_1, VTDB_1 |
| PSG1_1 | AFAM_1, CATD_1, CRIS3_1, ITIH4_3 |
| PSG11_1 | KNG1_1, LEP_1, LEP_2, PSG9_1, PSG9_2, RET4_1 |
| PSG2_1 | GELS_2, KNG1_1, PAEP_1, PAEP_2, PSG9_1, PSG9_2, RET4_1 |
| PSG3_1 | GELS_2, KNG1_1, LEP_1, PSG9_1, PSG9_2, RET4_1 |
| PSG9_1 | A2GL_1, AACT_1, ADA12_1, AFAM_1, AOC1_1, APOH_1, ATS13_1, ATS13_2, BMI, C1QA_1, C1QB_1, C1QB_3, C1QC_1, CAH1_1, CATD_1, CBPN_1, CBPN_2, CD14_1, cDM, CGB1_1, CGB1_2, CNTN1_1, CNTN1_2, CO5_1, CO5_2, CO6_1, CRAC1_1, CRIS3_1, DPEP2_1, DPEP2_2, ENPP2_1, ENPP2_2, FA5_2, FBLN1_1, FBLN3_1, FGFR1_1, FGFR1_2, GABD., GELS_2, GPX3_2, IBP2_1, IBP4_3, InvGra, InvPar, IPSP_1, IPSP_2, ISM2_1, ISM2_2, KNG1_1, LEP_1, LEP_2, LYAM1_1, MAGE, MDWT., MFAP5_1, NOTUM_1, NOTUM_2, PAEP_1, PAPP1_1, PCD12_2, PEDF_1, PEDF_2, PEspec, PriorP, PRL_2, PROS_1, PROS_2, PSG11_1, PSG2_1, PSG3_1, PSG9_2, PTGDS_2, RET4_1, SHBG_1, SHBG_3, TENX_1, TENX_2, TETN_1, TETN_2, TIMP1_1, User, VGFR1_1 |
| PSG9_2 | A2GL_1, AACT_1, ADA12_1, AFAM_1, AMBP_1, AOC1_1, AOC1_2, APOH_1, ATL4_1, ATS13_1, ATS13_2, B2MG_2, Bleedi, BMI, C163A_1, C1QA_1, C1QA_2, C1QB_2, C1QB_3, C1QC_1, CADH5_2, CAH1_1, CATD_1, CATD_2, CBPN_1, CBPN_2, CD14_1, cDM, CGB1_1, CGB1_2, CHL1_1, CNTN1_1, CNTN1_2, CO5_1, CO5_2, CO6_1, CO8A_1, CO8B_1, CRAC1_1, CRIS3_1, CSH_1, CSH_2, DEF1_1, DPEP2_1, DPEP2_2, EGLN_1, EGLN_2, ENPP2_1, ENPP2_2, F13B_1, FA11_2, FA5_1, FA5_2, FBLN1_1, FBLN3_1, FETUA_1, FGFR1_1, FGFR1_2, GABD., GELS_2, GPX3_2, HABP2_1, HEMO_1, HLACI_1, IBP2_1, IBP4_3, IBP6_1, IGF2_1, IL1R1_1, INHBC_1, InvGra, InvPar, IPMLOS, IPSP_1, IPSP_2, ISM2_1, ISM2_2, ITIH4_1, ITIH4_2, KIT_1, KNG1_1, LEP_1, LEP_2, LYAM1_1, MAGE, MDHT., MDWT., MFAP5_1, MUC18_1, NdelCo, NOTUM_1, NOTUM_2, PAEP_1, PAPP1_1, PCD12_1, PCD12_2, PEDF_1, PEDF_2, PEspec, PGRP2_1, PRDX2_1, PRG2_1, PriorP, PRL_1, PRL_2, PROS_1, PROS_2, PSG11_1, PSG2_1, PSG3_1, PSG9_1, PTGDS_2, RET4_1, SEPP1_1, SHBG_1, SHBG_3, SOM2_1, SOM2_2, SPRL1_1, TENX_2, TETN_1, TETN_2, THRB_1, TIE1_1, TIMP1_1, User, VGFR1_1 |
| PTGDS_1 | KNG1_1, LEP_1 |
| PTGDS_2 | KNG1_1, LEP_1, PAEP_1, PEDF_1, PSG9_1, PSG9_2, RET4_1 |
| RET4_1 | A2GL_1, AACT_1, ADA12_1, AMBP_1, ANGT_1, AOC1_1, AOC1_2, APOH_1, ATL4_1, ATS13_1, B2MG_1, B2MG_2, Bleedi, BMI, C1QA_1, C1QA_2, C1QB_1, C1QB_2, C1QB_3, CAH1_1, CATD_1, CBPN_1, CBPN_2, CD14_2, cDM, CO5_1, CO5_2, CO6_1, CO8A_1, CRIS3_1, CSH_1, DPEP2_1, EGLN_1, |

TABLE 26-continued

Analyte pairs in trianalyte models containing AACT for nulliparous
women with gestational age at blood draws days 175-196

| Analyte1 | Analyte2 |
|---|---|
| | ENPP2_1, ENPP2_2, F13B_1, FA11_2, FA5_2, FBLN3_1, FETUA_1, FGFR1_1, FGFR1_2, GABD., GPX3_2, HLACI_1, IBP2_1, IBP6_1, IGF2_1, IL1R1_1, INHBC_1, InvGra, InvPar, IPMLOS, IPSP_1, IPSP_2, ISM2_1, ITIH4_1, ITIH4_2, KNG1_1, LEP_1, LEP_2, LYAM1_1, MAGE, MDHT., MDWT., MFAP5_1, NOTUM_2, PAPP1_1, PAPP2_1, PCD12_1, PCD12_2, PEDF_1, PEDF_2, PEspec, PRDX2_1, PRG2_1, PriorP, PRL_1, PROS_2, PSG11_1, PSG2_1, PSG3_1, PSG9_1, PSG9_2, PTGDS_2, SEPP1_1, SHBG_1, SHBG_3, SOM2_1, SPRL1_1, TENX_1, THBG_1, TIE1_1, TIMP1_1, User, VGFR1_1 |
| SEPP1_1 | A2GL_1, AFAM_2, ATS13_1, BMI, FGFR1_1, HEMO_1, IBP3_1, KNG1_1, LEP_1, MDWT., PAEP_1, PSG9_2, RET4_1 |
| SEPP1_2 | A2GL_1, ADA12_1, AFAM_1, ECM1_1, GELS_2, ITIH4_2, KNG1_1, LEP_2, MDHT., PAEP_1, PAEP_2, PEDF_1, PROS_2, VTDB_1 |
| SHBG_1 | GELS_2, KNG1_1, LEP_1, PAEP_1, PSG9_1, PSG9_2, RET4_1 |
| SHBG_3 | AFAM_2, BMI, KNG1_1, LEP_1, MDWT., PAEP_1, PSG9_1, PSG9_2, RET4_1 |
| SOM2_1 | A2GL_1, APOC3_1, CGB1_1, CO6_1, KNG1_1, PAEP_1, PSG9_2, RET4_1, TENX_2 |
| SOM2_2 | ADA12_1, KNG1_1, LEP_1, PAEP_1, PSG9_2 |
| SPRL1_1 | A2GL_1, ATS13_1, BMI, C1QA_1, C1QC_1, ECM1_1, GELS_2, KNG1_1, LEP_1, MDWT., PAEP_1, PAEP_2, PSG9_2, RET4_1, TENX_1 |
| SVEP1_1 | B2MG_1, CADH5_2, CSH_2 |
| TENX_1 | A2GL_1, ADA12_1, AFAM_2, ALS_1, ATS13_2, EGLN_1, HEMO_1, IBP1_1, IBP2_1, IBP3_1, IBP3_2, KIT_1, LEP_1, MFAP5_1, PAEP_1, PAEP_2, PEDF_1, PSG9_1, RET4_1, SPRL1_1 |
| TENX_2 | A2GL_1, AFAM_1, AFAM_2, ANT3_1, C1QB_1, C1QC_1, CADH5_2, CSH_2, ECM1_1, IBP3_2, ISM2_2, LBP_1, LEP_1, PAEP_1, PAEP_2, PSG9_1, PSG9_2, SOM2_1 |
| TETN_1 | A2GL_1, KNG1_1, LEP_1, PAEP_1, PSG9_1, PSG9_2, VTDB_1 |
| TETN_2 | A2GL_1, GPX3_1, KNG1_1, LEP_1, PAEP_1, PSG9_1, PSG9_2 |
| THBG_1 | BMI, CSH_2, KNG1_1, LEP_1, PAEP_1, PROS_2, RET4_1 |
| THRB_1 | GELS_2, IBP6_2, KNG1_1, LEP_1, LEP_2, PAEP_1, PSG9_2 |
| TIE1_1 | KNG1_1, PSG9_2, RET4_1 |
| TIMP1_1 | A2GL_1, ECM1_1, GELS_2, GPX3_1, KNG1_1, PAEP_1, PAEP_2, PRG4_2, PSG9_1, PSG9_2, RET4_1, VTDB_1 |
| User | KNG1_1, LEP_1, PAEP_1, PEDF_1, PSG9_1, PSG9_2, RET4_1 |
| VGFR1_1 | ADA12_1, KNG1_1, LEP_1, PAEP_1, PSG9_1, PSG9_2, RET4_1 |
| VTDB_1 | A2GL_1, ADA12_1, AOC1_1, ATS13_2, Bleedi, BMI, CGB1_1, CO8B_1, CRIS3_1, CSH_2, DEF1_1, DEF1_2, FETUA_2, GELS_2, GPX3_1, IBP2_1, IBP6_2, INHBC_1, KNG1_1, LEP_1, LEP_2, MDWT., PAEP_1, PEDF_1, PROS_2, SEPP1_2, TETN_1, TIMP1_1 |
| VTNC_1 | LEP_1 |
| VTNC_2 | A2GL_1, KNG1_1, LEP_1, PAEP_1 |

TABLE 27

Analyte pairs in trianalyte models containing AACT for nulliparous
women with gestational age at blood draws days 182-203

| Analyte1 | Analyte2 |
|---|---|
| A2GL_1 | AFAM_2, IBP6_1, PRG4_1, PRG4_2, PSG2_1, TENX_2 |
| AACT_1 | PAEP_1, PRG4_1, TENX_2 |
| ADA12_1 | AFAM_1, AFAM_2, AOC1_1, AOC1_2, ATL4_1, ATS13_1, B2MG_2, BMI, C1QA_2, C1QC_1, CAMP_1, CAMP_2, CATD_1, CBPN_2, Cervix, CGB1_1, CGB1_2, cHTN, CLUS_1, CRAC1_2, CRIS3_1, CRIS3_2, DEF1_1, DEF1_2, ECM1_1, FA9_1, FBLN3_1, GDM, IBP2_1, IBP6_1, IGF2_1, InvGra, IPMLOS, IPSP_2, ISM2_2, KIT_1, LEP_2, MDWT., MUC18_2, NdelCo, PAEP_1, PAEP_2, PAPP2_1, PEDF_1, PEDF_2, PRG2_1, PriorP, PROS_1, PSG2_1, PSG9_1, TIMP1_1, VTNC_2 |
| AFAM_1 | ADA12_1, AFAM_2, AOC1_2, ATL4_1, C1QA_2, C1QB_2, C1QC_1, C1QC_2, CD14_2, CGB1_1, CGB1_2, cHTN, CRIS3_2, DPEP2_2, FETUA_2, GELS_2, IBP2_1, IBP6_2, InvGra, KNG1_1, LEP_1, LEP_2, MDHT., NOTUM_1, PAEP_1, PAEP_2, PEspec, PRG2_1, PRG4_1, PSG1_1, PSG11_1, PSG3_1, PTGDS_2, SOM2_1, SOM2_2, TENX_1, TENX_2, THRB_1 |
| AFAM_2 | A2GL_1, ADA12_1, AFAM_1, AMBP_1, ANGT_1, ANT3_1, APOC3_1, ATL4_1, ATS13_1, BGH3_1, Bleedi, C1QA_2, C1QB_1, C1QB_2, C1QB_3, CADH5_1, CADH5_2, CAMP_1, CAMP_2, CATD_1, CBPN_1, CBPN_2, CD14_2, Cervix, CGB1_1, CGB1_2, CHL1_1, cHTN, CLUS_1, CNTN1_1, CNTN1_2, CO5_2, CO6_1, CO8A_1, CRAC1_1, CRAC1_2, CRAC1_3, CRIS3_1, CRIS3_2, CSH_1, DEF1_1, DEF1_2, DPEP2_1, DPEP2_2, ECM1_1, EGLN_2, FA5_1, FA9_2, FETUA_1, FETUA_2, GELS_1, GELS_2, HEMO_1, HLACI_1, IBP2_1, IBP3_1, IBP3_2, IBP6_1, IBP6_2, IGF1_1, IGF2_1, InvGra, IPSP_1, IPSP_2, ISM2_1, ISM2_2, ITIH4_2, ITIH4_3, KIT_1, KIT_2, KNG1_1, KNG1_2, LBP_1, LBP_2, |

TABLE 27-continued

Analyte pairs in trianalyte models containing AACT for nulliparous women with gestational age at blood draws days 182-203

| Analyte1 | Analyte2 |
|---|---|
| | LEP__2, LIRB5__1, MFAP5__1, MUC18__1, NdelCo, NOTUM__1, PAEP__1, PAEP__2, PAPP1__1, PAPP2__1, PCD12__1, PCD12__2, PEDF__1, PEDF__2, PEspec, PGRP2__1, PRDX2__1, PRG2__1, PRG4__1, PRG4__2, PriorP, PROS__1, PROS__2, PSG1__1, PSG11__1, PSG2__1, PSG3__1, PSG9__1, PTGDS__2, RET4__1, SOM2__1, SOM2__2, TENX__1, TENX__2, VTNC__1, VTNC__2 |
| ALS__1 | PAEP__1, PRG4__1, PRG4__2, TENX__2 |
| AMBP__1 | AFAM__2, BMI, PAEP__1, PRG4__1, TENX__2 |
| ANGT__1 | AFAM__2, APOH__1, CATD__1, CD14__2, cHTN, ECM1__1, IBP6__2, InvGra, IPSP__2, ITIH4__3, KIT__1, MDHT., PAEP__1, PAEP__2, PEDF__1, PEDF__2, PRG4__1, PRG4__2, PriorP, PSG9__1, SEPP1__1, TENX__1, TENX__2 |
| ANT3__1 | AFAM__2, ECM1__1, PRG4__1, PSG2__1, TENX__2 |
| AOC1__1 | ADA12__1, PAEP__1, PRG4__1, PRG4__2, TENX__2 |
| AOC1__2 | ADA12__1, AFAM__1, CLUS__1, PAEP__1, PRG4__1, PRG4__2, TENX__2 |
| APOC3__1 | AFAM__2, DEF1__1, PAEP__1, PAEP__2, PRG4__1, PSG1__1 |
| APOH__1 | ANGT__1, IBP6__2, IGF2__1, PAEP__1, PAEP__2, PEDF__1, PRG4__1, PRG4__2, TENX__2 |
| ATL4__1 | ADA12__1, AFAM__1, AFAM__2, BMI, CD14__2, Cervix, ENPP2__1, IBP3__2, IBP6__1, NdelCo, NpregC, PRG4__1, PRG4__2, SEPP1__2, TENX__2 |
| ATS13__1 | ADA12__1, AFAM__2, PAEP__1, PAEP__2, PRG4__1, TENX__2 |
| ATS13__2 | PAEP__1, PEDF__1, PRG4__1, PSG2__1, TENX__2, THRB__1 |
| B2MG__1 | IBP2__1, LEP__1, PAEP__1, PAEP__2, PSG2__1 |
| B2MG__2 | ADA12__1, PSG2__1 |
| BGH3__1 | AFAM__2, CLUS__1, IBP3__1, IBP3__2, PAEP__1, PAEP__2, PRG4__1, PRG4__2, PSG2__1, TENX__2 |
| Bleedi | AFAM__2, PAEP__1, PRG4__1, PRG4__2, TENX__2 |
| BMI | ADA12__1, AMBP__1, ATL4__1, C163A__1, CAMP__2, cHTN, CRIS3__1, CRIS3__2, F13B__1, FA5__1, FA5__2, FGFR1__1, FGFR1__2, HEMO__1, IBP2__1, IBP3__1, IBP3__2, IBP4__1, IBP6__1, IGF2__1, InvGra, IPSP__2, LEP__2, MDHT., MDWT., MFAP5__1, MUC18__2, NdelCo, PAPP2__1, PCD12__1, PRG4__2, PriorP, PSG2__1, PSG3__1, PSG9__1, PSG9__2, TENX__2, TETN__1, THRB__1, TIMP1__1 |
| C163A__1 | BMI, TENX__2 |
| C1QA__2 | ADA12__1, AFAM__2, CATD__2, Cervix, ECM1__1, IBP6__1, NpregC, PRG4__1, PRG4__2, RET4__1 |
| C1QB__1 | AFAM__2, FBLN3__1, PAEP__1, PRG4__1 |
| C1QB__2 | AFAM__1, AFAM__2, PRG4__1, RET4__1 |
| C1QB__3 | AFAM__2, C1QC__1, CLUS__1, NpregC, PAEP__1, PAEP__2, PRG4__1, PRG4__2, THRB__1 |
| C1QC__1 | ADA12__1, AFAM__1, C1QB__3, ECM1__1, FA11__2, IBP6__1, PRG4__1, PRG4__2, TENX__2 |
| C1QC__2 | AFAM__1, NpregC |
| CADH5__1 | AFAM__2, PAEP__1, PRG4__1, TENX__2 |
| CADH5__2 | AFAM__2, PAEP__1, PRG4__1, PSG2__1 |
| CAH1__1 | PAEP__1, PRG4__1 |
| CAMP__1 | ADA12__1, AFAM__2, ECM1__1, PSG2__1 |
| CAMP__2 | ADA12__1, AFAM__2, BMI, ECM1__1, IBP6__1, MDWT., PSG2__1 |
| CATD__1 | ADA12__1, AFAM__2, ANGT__1, IBP4__2, KNG1__2, PAEP__1, PAEP__2, PRG4__1, PSG2__1, TENX__2 |
| CATD__2 | C1QA__2, PAEP__1, PAEP__2, PRG4__1, PSG2__1 |
| CBPN__1 | AFAM__2, PAEP__1, PRG4__1, PRG4__2, PSG2__1 |
| CBPN__2 | ADA12__1, AFAM__2, Cervix, PSG2__1, TENX__2 |
| CD14__1 | CD14__2, CLUS__1, PAEP__1, PRG4__1, TENX__2 |
| CD14__2 | AFAM__1, AFAM__2, ANGT__1, ATL4__1, CD14__1, KNG1__1, PRG4__1, PRG4__2, PSG2__1, TENX__2, THRB__1 |
| cDM | PAEP__1, PRG4__1, PRG4__2, TENX__2 |
| Cervix | ADA12__1, AFAM__2, ATL4__1, C1QA__2, CBPN__2, CRAC1__2, KNG1__1, KNG1__2, MDWT., PAEP__1, PRG4__1, PSG11__1, PSG2__1, SEPP1__2, TENX__2, THRB__1 |
| CGB1__1 | ADA12__1, AFAM__1, AFAM__2, CGB1__2, CLUS__1, NdelCo, PRG4__1, PSG2__1 |
| CGB1__2 | ADA12__1, AFAM__1, AFAM__2, CGB1__1, PAEP__1, PRG4__1, TENX__2 |
| CHL1__1 | AFAM__2, PAEP__1, PRG4__1, PRG4__2, PSG2__1, TENX__2 |
| cHTN | ADA12__1, AFAM__1, AFAM__2, ANGT__1, BMI, PAEP__1, PRG4__1, PRG4__2, PSG2__1, TENX__2 |
| CLUS__1 | ADA12__1, AFAM__2, AOC1__2, BGH3__1, C1QB__3, CD14__1, CGB1__1, CRAC1__1, CRAC1__2, DEF1__1, DPEP2__2, FA5__2, FETUA__1, IBP2__1, IBP6__1, ISM2__2, KIT__2, MUC18__2, NOTUM__1, NOTUM__2, PAEP__1, PAEP__2, PCD12__1, PCD12__2, PRG2__1, PRG4__1, PRG4__2, PTGDS__2, TENX__2, TETN__1, TETN__2, VTNC__1, VTNC__2 |
| CLUS__2 | PRG4__1, THRB__1 |
| CNTN1__1 | AFAM__2, CRAC1__1, ECM1__1, PRG4__1 |
| CNTN1__2 | AFAM__2, PRG4__1, TENX__2 |
| CO5__1 | PRG4__1, TENX__2 |
| CO5__2 | AFAM__2, PSG11__1 |
| CO6__1 | AFAM__2, KNG1__1, PAEP__1, PRG4__1, PRG4__2, PSG2__1, TENX__2 |
| CO8A__1 | AFAM__2, PAEP__1, PRG4__1, TENX__2 |
| CO8B__1 | PAEP__1, PRG4__1, PSG9__1 |

TABLE 27-continued

Analyte pairs in trianalyte models containing AACT for nulliparous
women with gestational age at blood draws days 182-203

| Analyte1 | Analyte2 |
|---|---|
| CRAC1_1 | AFAM_2, CLUS_1, CNTN1_1, IBP3_2, InvGra, KNG1_1, LBP_1, LBP_2, LEP_2, PRG4_1, PriorP |
| CRAC1_2 | ADA12_1, AFAM_2, Cervix, CLUS_1, FBLN1_1, HEMO_1, PRG4_1, TENX_2, THRB_1, User |
| CRAC1_3 | AFAM_2, KNG1_1, PRG4_1, TENX_2 |
| CRIS3_1 | ADA12_1, AFAM_2, BMI, KNG1_1, PRG4_1, PSG2_1, PSG9_1, PSG9_2 |
| CRIS3_2 | ADA12_1, AFAM_1, AFAM_2, BMI, PRG4_1 |
| CSH_1 | AFAM_2, CSH_2, ECM1_1, PAEP_1, PRG4_1, PRG4_2, PSG2_1 |
| CSH_2 | CSH_1, PAEP_1, PRG4_1, PSG2_1, TENX_2 |
| DEF1_1 | ADA12_1, AFAM_2, APOC3_1, CLUS_1, IBP6_1, NpregC, PAEP_1, PRG4_1, PRG4_2, PSG2_1, TENX_2 |
| DEF1_2 | ADA12_1, AFAM_2, IBP6_1, KNG1_1, PRG4_1, TENX_2, THRB_1 |
| DM | KNG1_1, PAEP_1, PRG4_1, PSG1_1, PSG2_1 |
| DPEP2_1 | AFAM_2, PEDF_1, PRG4_1, PSG2_1 |
| DPEP2_2 | AFAM_1, AFAM_2, CLUS_1, ECM1_1, PAEP_1, PRG4_1, PSG2_1, THRB_1 |
| ECM1_1 | ADA12_1, AFAM_2, ANGT_1, ANT3_1, C1QA_2, C1QC_1, CAMP_1, CAMP_2, CNTN1_1, CSH_1, DPEP2_2, FA9_2, FBLN3_1, IBP3_1, IBP3_2, IBP6_1, InvGra, LBP_2, MDHT., PAEP_1, PAEP_2, PRG4_1, PRG4_2, PriorP, PSG11_1, PSG2_1, THRB_1 |
| ECM1_2 | PRG4_1 |
| EGLN_1 | PRG4_1, PSG2_1, TENX_2 |
| EGLN_2 | AFAM_2, PRG4_1, PSG2_1 |
| ENPP2_1 | ATL4_1, IBP6_2, PAEP_1, PRG4_1, PRG4_2, TENX_2 |
| ENPP2_2 | IBP6_2, PAEP_1, PRG4_1, PRG4_2, TENX_2 |
| F13B_1 | BMI, MDWT., PAEP_1, PRG4_1 |
| FA11_1 | IBP2_1, PAEP_1, PRG4_1, PSG2_1, TENX_2 |
| FA11_2 | C1QC_1, IBP2_1, PRG4_1, PRG4_2, PSG2_1 |
| FA5_1 | AFAM_2, BMI, PAEP_2, PRG4_1, TENX_2 |
| FA5_2 | BMI, CLUS_1, PRG4_1, PRG4_2, PSG2_1, TENX_2 |
| FA9_1 | ADA12_1, IBP3_2, PAEP_1, PRG4_1, PRG4_2, TENX_2, THRB_1 |
| FA9_2 | AFAM_2, ECM1_1, IBP6_2, PAEP_1, PRG4_1, PRG4_2 |
| FBLN1_1 | CRAC1_2, IBP3_2, TENX_2 |
| FBLN3_1 | ADA12_1, C1QB_1, ECM1_1, GDM, IBP6_1, NpregC, PAEP_1, PEDF_1, PRG4_1, PRG4_2 |
| FETUA_1 | AFAM_2, CLUS_1, PAEP_1, PRG4_1, PSG2_1, TENX_2 |
| FETUA_2 | AFAM_1, AFAM_2, IBP3_2, PRG4_1, PSG2_1 |
| FGFR1_1 | BMI, PRG4_1, PRG4_2, TENX_2 |
| FGFR1_2 | BMI, PRG4_1, PSG2_1 |
| GABD. | PAEP_1, PRG4_1, TENX_2 |
| GDM | ADA12_1, FBLN3_1, KNG1_1, PRG4_1, PSG1_1, PSG2_1, TENX_2 |
| GELS_1 | AFAM_2, PRG4_1, PSG9_1, PSG9_2 |
| GELS_2 | AFAM_1, AFAM_2, IBP3_2, PAEP_1, PRG4_1, PRG4_2, PSG2_1, TETN_2 |
| GPX3_1 | IBP6_1, IGF2_1, PRG4_1, PRG4_2, PSG2_1, PSG9_1, TENX_2 |
| GPX3_2 | PRG4_1 |
| HABP2_1 | PSG11_1 |
| HEMO_1 | AFAM_2, BMI, CRAC1_2, PRG4_1, PSG2_1 |
| HLACI_1 | AFAM_2, PRG4_1, PRG4_2 |
| IBP1_1 | PAEP_1, PRG4_1, TENX_2 |
| IBP2_1 | ADA12_1, AFAM_1, AFAM_2, B2MG_1, BMI, CLUS_1, FA11_1, FA11_2, IGF2_1, MUC18_2, PAEP_1, PRG4_1, PSG2_1, SEPP1_2 |
| IBP3_1 | AFAM_2, BGH3_1, BMI, ECM1_1, IBP6_2, MDWT., PAEP_1, PEDF_1, PRG4_1, PSG9_1, TENX_2, User |
| IBP3_2 | AFAM_2, ATL4_1, BGH3_1, BMI, CRAC1_1, ECM1_1, FA9_1, FBLN1_1, FETUA_2, GELS_2, IBP6_2, KNG1_1, PAEP_1, PAEP_2, PEDF_1, PSG11_1, TENX_1, TENX_2, THRB_1 |
| IBP4_1 | BMI, PRG4_1, TENX_2 |
| IBP4_2 | CATD_1, NpregC, PRG4_1, PSG9_2 |
| IBP4_3 | PRG4_1, PRG4_2 |
| IBP6_1 | A2GL_1, ADA12_1, AFAM_2, ATL4_1, BMI, C1QA_2, C1QC_1, CAMP_2, CLUS_1, DEF1_1, DEF1_2, ECM1_1, FBLN3_1, GPX3_1, IBP6_2, IGF2_1, InvGra, MDWT., PAEP_1, PEDF_1, PRG4_1, PRG4_2, PriorP, PSG2_1, PSG9_1, TENX_1, TENX_2, User |
| IBP6_2 | AFAM_1, AFAM_2, ANGT_1, APOH_1, ENPP2_1, ENPP2_2, FA9_2, IBP3_1, IBP3_2, IBP6_1, KNG1_1, LBP_1, LBP_2, NpregC, PRG4_1, PRG4_2, PSG2_1, PTGDS_2, SEPP1_2, TENX_2, THBG_1, THRB_1 |
| IGF1_1 | AFAM_2, PAEP_1, PRG4_1, TENX_2 |
| IGF2_1 | ADA12_1, AFAM_2, APOH_1, BMI, GPX3_1, IBP2_1, IBP6_1, KNG1_1, MDWT., MUC18_2, PAEP_1, PAEP_2, PEDF_1, PSG11_1, RET4_1, TENX_1, TENX_2, THRB_1, VTNC_1 |
| IL1R1_1 | PAEP_1, PRG4_1 |
| INHBC_1 | PAEP_1, PRG4_1, PSG2_1 |
| InvGra | ADA12_1, AFAM_1, AFAM_2, ANGT_1, BMI, CRAC1_1, ECM1_1, IBP6_1, KNG1_1, PAEP_1, PRG4_1, PRG4_2, TENX_2 |
| InvPar | PAEP_1, PRG4_1, TENX_2 |
| IPMLOS | ADA12_1, PRG4_1, PSG2_1, TENX_2 |

TABLE 27-continued

Analyte pairs in trianalyte models containing AACT for nulliparous
women with gestational age at blood draws days 182-203

| Analyte1 | Analyte2 |
|---|---|
| IPSP__1 | AFAM__2, PAEP__1, PRG4__1, PRG4__2, TENX__2 |
| IPSP__2 | ADA12__1, AFAM__2, ANGT__1, BMI, PAEP__1, PRG4__1, PRG4__2, PSG2__1 |
| ISM2__1 | AFAM__2, ISM2__2, KNG1__1, PAEP__1, PRG4__1 |
| ISM2__2 | ADA12__1, AFAM__2, CLUS__1, ISM2__1, PAEP__1, PRG4__1, PRG4__2, PSG2__1, TENX__2 |
| ITIH3__1 | PRG4__1 |
| ITIH4__1 | PRG4__1 |
| ITIH4__2 | AFAM__2, PAEP__1, PRG4__1, TENX__2 |
| ITIH4__3 | AFAM__2, ANGT__1, PAEP__1, PRG4__1, TENX__2 |
| KIT__1 | ADA12__1, AFAM__2, ANGT__1, PRG4__1, PRG4__2, TENX__2 |
| KIT__2 | AFAM__2, CLUS__1, PAEP__1, PRG4__1, TENX__2 |
| KNG1__1 | AFAM__1, AFAM__2, CD14__2, Cervix, CO6__1, CRAC1__1, CRAC1__3, CRIS3__1, DEF1__2, DM, GDM, IBP3__2, IBP6__2, IGF2__1, InvGra, ISM2__1, PAEP__1, PRG4__1, PriorP, PSG9__1, TIE1__1, VTNC__1 |
| KNG1__2 | AFAM__2, CATD__1, Cervix, PEDF__1, PRG4__1, TENX__2 |
| LBP__1 | AFAM__2, CRAC1__1, IBP6__2, PAEP__1, PRG4__1, THRB__1 |
| LBP__2 | AFAM__2, CRAC1__1, ECM1__1, IBP6__2, PAEP__1, PRG4__1, PRG4__2, PSG11__1, THRB__1 |
| LEP__1 | AFAM__1, B2MG__1 |
| LEP__2 | ADA12__1, AFAM__1, AFAM__2, BMI, CRAC1__1, PAEP__1, PRG4__1, PRG4__2, TENX__2 |
| LIRB5__1 | AFAM__2, PRG4__1, PRG4__2, TENX__2 |
| LYAM1__1 | PAEP__1, PRG4__1, TENX__2 |
| MAGE | PRG4__1, TENX__2 |
| MDHT. | AFAM__1, ANGT__1, BMI, ECM1__1, PAEP__1, PRG4__1, SEPP1__2, TENX__2 |
| MDWT. | ADA12__1, BMI, CAMP__2, Cervix, F13B__1, IBP3__1, IBP6__1, IGF2__1, MUC18__2, PRG4__1, PSG2__1, PSG9__2, SEPP1__2, THRB__1 |
| MFAP5__1 | AFAM__2, BMI, PRG4__1, TENX__1, TENX__2 |
| MUC18__1 | AFAM__2, PAEP__1, PRG4__1, PRG4__2, PSG2__1, TENX__2 |
| MUC18__2 | ADA12__1, BMI, CLUS__1, IBP2__1, IGF2__1, MDWT., PRG4__1, PSG2__1, RET4__1, SEPP1__2, TENX__2 |
| NdelCo | ADA12__1, AFAM__2, ATL4__1, BMI, CGB1__1, PRG4__1, PRG4__2, PSG11__1, PSG2__1, TENX__2 |
| NOTUM__1 | AFAM__1, AFAM__2, CLUS__1, PAEP__1, PRG4__1, PSG2__1, TENX__2 |
| NOTUM__2 | CLUS__1, PAEP__1, PRG4__1, TENX__2 |
| NpregC | ATL4__1, C1QA__2, C1QB__3, C1QC__2, DEF1__1, FBLN3__1, IBP4__2, IBP6__2, PAEP__1, PEDF__1, PRG4__1, PRG4__2, PSG11__1, PSG2__1, THRB__1, TIMP1__1 |
| PAEP__1 | AACT__1, ADA12__1, AFAM__1, AFAM__2, ALS__1, AMBP__1, ANGT__1, AOC1__1, AOC1__2, APOC3__1, APOH__1, ATS13__1, ATS13__2, B2MG__1, BGH3__1, Bleedi, C1QB__1, C1QB__3, CADH5__1, CADH5__2, CAH1__1, CATD__1, CATD__2, CBPN__1, CD14__1, cDM, Cervix, CGB1__2, CHL1__1, cHTN, CLUS__1, CO6__1, CO8A__1, CO8B__1, CSH__1, CSH__2, DEF1__1, DM, DPEP2__2, ECM1__1, ENPP2__1, ENPP2__2, F13B__1, FA11__1, FA9__1, FA9__2, FBLN3__1, FETUA__1, GABD., GELS__2, IBP1__1, IBP2__1, IBP3__1, IBP3__2, IBP6__1, IGF1__1, IGF2__1, IL1R1__1, INHBC__1, InvGra, InvPar, IPSP__1, IPSP__2, ISM2__1, ISM2__2, ITIH4__2, ITIH4__3, KIT__2, KNG1__1, LBP__1, LBP__2, LEP__2, LYAM1__1, MDHT., MUC18__1, NOTUM__1, NOTUM__2, NpregC, PAEP__2, PCD12__1, PCD12__2, PEDF__2, PRDX2__1, PRG2__1, PRG4__1, PRG4__2, PriorP, PROS__1, PSG2__1, PSG3__1, PSG9__1, PSG9__2, PTGDS__2, RET4__1, SEPP1__2, SOM2__1, TENX__1, TENX__2, TETN__1, TETN__2, THRB__1, User, VGFR1__1, VTDB__1, VTNC__1, VTNC__2 |
| PAEP__2 | ADA12__1, AFAM__1, AFAM__2, ANGT__1, APOC3__1, APOH__1, ATS13__1, B2MG__1, BGH3__1, C1QB__3, CATD__1, CATD__2, CLUS__1, ECM1__1, FA5__1, IBP3__2, IGF2__1, PAEP__1, PRG4__1, PRG4__2, PSG2__1, PSG9__2, RET4__1, SEPP1__1, TENX__2, THRB__1 |
| PAPP1__1 | AFAM__2, PRG4__1 |
| PAPP2__1 | ADA12__1, AFAM__2, BMI, PRG4__1, PSG2__1 |
| PCD12__1 | AFAM__2, BMI, CLUS__1, PAEP__1, PRG4__1, TENX__2, THRB__1 |
| PCD12__2 | AFAM__2, CLUS__1, PAEP__1, PRG4__1 |
| PEDF__1 | ADA12__1, AFAM__2, ANGT__1, APOH__1, ATS13__2, DPEP2__1, FBLN3__1, IBP3__1, IBP3__2, IBP6__1, IGF2__1, KNG1__2, NpregC, PRG4__1, PRG4__2, PSG2__1, THRB__1, TIMP1__1 |
| PEDF__2 | ADA12__1, AFAM__2, ANGT__1, PAEP__1, PRG4__1 |
| PEspec | AFAM__1, AFAM__2, PRG4__1, PSG2__1, TENX__2 |
| PGRP2__1 | AFAM__2, PRG4__1, PSG2__1, TENX__2 |
| PRDX2__1 | AFAM__2, PAEP__1, PRG4__1, TENX__2 |
| PRG2__1 | ADA12__1, AFAM__1, AFAM__2, CLUS__1, PAEP__1, PRG4__1, PRG4__2, PSG2__1, TENX__2 |
| PRG4__1 | A2GL__1, AACT__1, AFAM__1, AFAM__2, ALS__1, AMBP__1, ANGT__1, ANT3__1, AOC1__1, AOC1__2, APOC3__1, APOH__1, ATL4__1, ATS13__1, ATS13__2, BGH3__1, Bleedi, BMI, C1QA__2, C1QB__1, C1QB__2, C1QB__3, C1QC__1, CADH5__1, CADH5__2, CAH1__1, CATD__1, CATD__2, CBPN__1, CD14__1, CD14__2, cDM, Cervix, CGB1__1, CGB1__2, CHL1__1, cHTN, CLUS__1, CLUS__2, CNTN1__1, CNTN1__2, CO5__1, CO6__1, CO8A__1, CO8B__1, CRAC1__1, CRAC1__2, CRAC1__3, CRIS3__1, CRIS3__2, CSH__1, CSH__2, DEF1__1, DEF1__2, DM, DPEP2__1, DPEP2__2, ECM1__1, ECM1__2, EGLN__1, EGLN__2, ENPP2__1, ENPP2__2, |

TABLE 27-continued

Analyte pairs in trianalyte models containing AACT for nulliparous
women with gestational age at blood draws days 182-203

| Analyte1 | Analyte2 |
|---|---|
|  | F13B__1, FA11__1, FA11__2, FA5__1, FA5__2, FA9__1, FA9__2, FBLN3__1, FETUA__1, FETUA__2, FGFR1__1, FGFR1__2, GABD., GDM, GELS__1, GELS__2, GPX3__1, GPX3__2, HEMO__1, HLACI__1, IBP1__1, IBP2__1, IBP3__1, IBP4__1, IBP4__2, IBP4__3, IBP6__1, IBP6__2, IGF1__1, IL1R1__1, INHBC__1, InvGra, InvPar, IPMLOS, IPSP__1, IPSP__2, ISM2__1, ISM2__2, ITIH3__1, ITIH4__1, ITIH4__2, ITIH4__3, KIT__1, KIT__2, KNG1__1, KNG1__2, LBP__1, LBP__2, LEP__2, LIRB5__1, LYAM1__1, MAGE, MDHT, MDWT., MFAP5__1, MUC18__1, MUC18__2, NdelCo, NOTUM__1, NOTUM__2, NpregC, PAEP__1, PAEP__2, PAPP1__1, PAPP2__1, PCD12__1, PCD12__2, PEDF__1, PEDF__2, PEspec, PGRP2__1, PRDX2__1, PRG2__1, PRG4__2, PriorP, PRL__1, PRL__2, PROS__1, PROS__2, PSG1__1, PSG11__1, PSG2__1, PSG3__1, PSG9__1, PSG9__2, PTGDS__1, PTGDS__2, RET4__1, SEPP1__1, SEPP1__2, SHBG__1, SHBG__3, SOM2__1, SOM2__2, SPRL1__1, SVEP1__1, TENX__1, TENX__2, TETN__1, TETN__2, THBG__1, THRB__1, TIE1__1, TIMP1__1, User, VGFR1__1, VTNC__1, VTNC__2 |
| PRG4__2 | A2GL__1, AFAM__2, ALS__1, ANGT__1, AOC1__1, AOC1__2, APOH__1, ATL4__1, BGH3__1, Bleedi, C1QA__2, C1QB__3, C1QC__1, CBPN__2, CD14__2, cDM, CHL1__1, cHTN, CLUS__1, CO6__1, CSH__1, DEF1__1, ECM1__1, ENPP2__1, ENPP2__2, FA11__2, FA5__2, FA9__1, FA9__2, FBLN3__1, FGFR1__1, GELS__2, GPX3__1, HLACI__1, IBP4__3, IBP6__1, IBP6__2, InvGra, IPSP__1, IPSP__2, ISM2__2, KIT__1, LBP__2, LEP__2, LIRB5__1, MUC18__1, NdelCo, NpregC, PAEP__1, PAEP__2, PEDF__1, PRG2__1, PRG4__1, PriorP, PRL__2, PSG11__1, SEPP1__2, SOM2__1, SVEP1__1, TENX__1, TENX__2, TETN__1, TETN__2, THRB__1, VTNC__1, VTNC__2 |
| PriorP | ADA12__1, AFAM__2, ANGT__1, BMI, CRAC1__1, ECM1__1, IBP6__1, KNG1__1, PAEP__1, PRG4__1, PRG4__2, TENX__2 |
| PRL__1 | PRG4__1, TENX__2 |
| PRL__2 | PRG4__1, PRG4__2, TENX__2 |
| PROS__1 | ADA12__1, AFAM__2, PAEP__1, PRG4__1, TENX__2 |
| PROS__2 | AFAM__2, PRG4__1, TENX__2 |
| PSG1__1 | AFAM__1, AFAM__2, APOC3__1, DM, GDM, PRG4__1, PSG9__2, TENX__1 |
| PSG11__1 | AFAM__1, AFAM__2, Cervix, CO5__2, ECM1__1, HABP2__1, IBP3__2, IGF2__1, LBP__2, NdelCo, NpregC, PRG4__1, PRG4__2, PSG2__1, PSG9__1, SEPP1__1 |
| PSG2__1 | A2GL__1, ADA12__1, AFAM__2, ANT3__1, ATS13__2, B2MG__1, B2MG__2, BGH3__1, BMI, CADH5__2, CAMP__1, CAMP__2, CATD__1, CATD__2, CBPN__1, CBPN__2, CD14__2, Cervix, CGB1__1, CHL1__1, cHTN, CO6__1, CRIS3__1, CSH__1, CSH__2, DEF1__1, DM, DPEP2__1, DPEP2__2, ECM1__1, EGLN__1, EGLN__2, FA11__1, FA11__2, FA5__2, FETUA__1, FETUA__2, FGFR1__2, GDM, GELS__2, GPX3__1, HEMO__1, IBP2__1, IBP6__1, IBP6__2, INHBC__1, IPMLOS, IPSP__2, ISM2__2, MDWT., MUC18__1, MUC18__2, NdelCo, NOTUM__1, NpregC, PAEP__1, PAEP__2, PAPP1__1, PEDF__1, PEspec, PGRP2__1, PRG2__1, PRG4__1, PSG11__1, PSG9__1, PSG9__2, RET4__1, SOM2__1, SOM2__2, SVEP1__1, TENX__1, THRB__1, TIMP1__1, User, VTNC__1 |
| PSG3__1 | AFAM__1, AFAM__2, BMI, PAEP__1, PRG4__1, TENX__2 |
| PSG9__1 | ADA12__1, AFAM__2, ANGT__1, BMI, CO8B__1, CRIS3__1, GELS__1, GPX3__1, IBP3__1, IBP6__1, KNG1__1, PAEP__1, PRG4__1, PSG11__1, PSG2__1, PSG9__2, SOM2__2, TENX__2 |
| PSG9__2 | BMI, CRIS3__1, GELS__1, IBP4__2, MDWT., PAEP__1, PAEP__2, PRG4__1, PSG1__1, PSG2__1, PSG9__1, SOM2__2, TENX__2 |
| PTGDS__1 | PRG4__1 |
| PTGDS__2 | AFAM__1, AFAM__2, CLUS__1, IBP6__2, PAEP__1, PRG4__1, TENX__2 |
| RET4__1 | AFAM__2, C1QA__2, C1QB__2, IGF2__1, MUC18__2, PAEP__1, PAEP__2, PRG4__1, PSG2__1, TENX__2 |
| SEPP1__1 | ANGT__1, PAEP__2, PRG4__1, PSG11__1, TENX__2 |
| SEPP1__2 | ATL4__1, Cervix, IBP2__1, IBP6__2, MDHT., MDWT., MUC18__2, PAEP__1, PRG4__1, PRG4__2, SHBG__3, THRB__1 |
| SHBG__1 | PRG4__1, TENX__2 |
| SHBG__3 | PRG4__1, SEPP1__2, TENX__2 |
| SOM2__1 | AFAM__1, AFAM__2, PAEP__1, PRG4__1, PRG4__2, PSG2__1 |
| SOM2__2 | AFAM__1, AFAM__2, PRG4__1, PSG2__1, PSG9__1, PSG9__2 |
| SPRL1__1 | PRG4__1 |
| SVEP1__1 | PRG4__1, PRG4__2, PSG2__1 |
| TENX__1 | AFAM__1, AFAM__2, ANGT__1, IBP3__2, IBP6__1, IGF2__1, MFAP5__1, PAEP__1, PRG4__1, PRG4__2, PSG1__1, PSG2__1, TENX__2 |
| TENX__2 | A2GL__1, AACT__1, AFAM__1, AFAM__2, ALS__1, AMBP__1, ANGT__1, ANT3__1, AOC1__1, AOC1__2, APOH__1, ATL4__1, ATS13__1, ATS13__2, BGH3__1, Bleedi, BMI, C163A__1, C1QC__1, CADH5__1, CATD__1, CBPN__2, CD14__1, CD14__2, cDM, Cervix, CGB1__2, CHL1__1, cHTN, CLUS__1, CNTN1__2, CO5__1, CO6__1, CO8A__1, CRAC1__2, CRAC1__3, CSH__2, DEF1__1, DEF1__2, EGLN__1, ENPP2__1, ENPP2__2, FA11__1, FA5__1, FA5__2, FA9__1, FBLN1__1, FETUA__1, FGFR1__1, GABD., GDM, GPX3__1, IBP1__1, IBP3__1, IBP3__2, IBP4__1, IBP6__1, IBP6__2, IGF1__1, IGF2__1, InvGra, InvPar, IPMLOS, IPSP__1, ISM2__2, ITIH4__2, ITIH4__3, KIT__1, KIT__2, KNG1__2, LEP__2, LIRB5__1, LYAM1__1, MAGE, MDHT., MFAP5__1, MUC18__1, MUC18__2, NdelCo, NOTUM__1, NOTUM__2, PAEP__1, PAEP__2, PCD12__1, PEspec, PGRP2__1, PRDX2__1, PRG2__1, PRG4__1, PRG4__2, PriorP, PRL__1, PRL__2, PROS__1, PROS__2, PSG3__1, PSG9__1, PSG9__2, PTGDS__2, |

TABLE 27-continued

Analyte pairs in trianalyte models containing AACT for nulliparous women with gestational age at blood draws days 182-203

| Analyte1 | Analyte2 |
|---|---|
| | RET4_1, SEPP1_1, SHBG_1, SHBG_3, TENX_1, TETN_1, TETN_2, THBG_1, THRB_1, TIE1_1, VGFR1_1, VTNC_1 |
| TETN_1 | BMI, CLUS_1, PAEP_1, PRG4_1, PRG4_2, TENX_2 |
| TETN_2 | CLUS_1, GELS_2, PAEP_1, PRG4_1, PRG4_2, TENX_2 |
| THBG_1 | IBP6_2, PRG4_1, TENX_2, THRB_1 |
| THRB_1 | AFAM_1, ATS13_2, BMI, C1QB_3, CD14_2, Cervix, CLUS_2, CRAC1_2, DEF1_2, DPEP2_2, ECM1_1, FA9_1, IBP3_2, IBP6_2, IGF2_1, LBP_1, LBP_2, MDWT., NpregC, PAEP_1, PAEP_2, PCD12_1, PEDF_1, PRG4_1, PRG4_2, PSG2_1, SEPP1_2, TENX_2, THBG_1, User |
| TIE1_1 | KNG1_1, PRG4_1, TENX_2 |
| TIMP1_1 | ADA12_1, BMI, NpregC, PEDF_1, PRG4_1, PSG2_1 |
| User | CRAC1_2, IBP3_1, IBP6_1, PAEP_1, PRG4_1, PSG2_1, THRB_1 |
| VGFR1_1 | PAEP_1, PRG4_1, TENX_2 |
| VTDB_1 | PAEP_1 |
| VTNC_1 | AFAM_2, CLUS_1, IGF2_1, KNG1_1, PAEP_1, PRG4_1, PRG4_2, PSG2_1, TENX_2 |
| VTNC_2 | ADA12_1, AFAM_2, CLUS_1, PAEP_1, PRG4_1, PRG4_2 |

TABLE 28

Analytes and corresponding abbreviations

| Analyte | SEQ ID NO: | Abbrev | Protein name |
|---|---|---|---|
| A2GL_DLLLPQPDLR | 29 | A2GL_1 | Leucine-rich alpha-2-glycoprotein |
| AACT_EIGELYLPK | 129 | AACT_1 | Alpha-1-antichymotrypsin |
| ADA12_FGEGGSTDSGPIR | 84 | ADA12_1 | Disintegrin and metalloproteinase domain-containing protein 12 |
| AFAM_DADPDTFFAK | 41 | AFAM_1 | Afamin |
| AFAM_HFQNLGK | 39 | AFAM_2 | Afamin |
| ALS_IRPHTFTGLSGLR | 67 | ALS_1 | Insulin-like growth factor-binding protein complex acid labile subunit |
| AMBP_EILLQDFR | 168 | AMBP_1 | Protein AMBP |
| ANGT_DPTFIPAPIQAK | 20 | ANGT_1 | Angiotensinogen |
| ANT3_TSDQIHEFFAK | 96 | ANT3_1 | Antithrombin-III |
| AOC1_AVHSFLWSK | 120 | AOC1_1 | Amiloride-sensitive amine oxidase [copper-containing] |
| AOC1_DNGPNYVQR | 121 | AOC1_2 | Amiloride-sensitive amine oxidase [copper-containing] |
| APOC3_GWVTDGFSSLK | 3 | APOC3_1 | Apolipoprotein C-III |
| APOH_ATVVYQGER | 22 | APOH_1 | Beta-2-glycoprotein 1 |
| ATL4_ILWIPAGALR | 134 | ATL4_1 | ADAMTS-like protein 4 |
| ATS13_SLVELTPIAAVHGR | 135 | ATS13_1 | A disintegrin and metalloproteinase with thrombospondin motifs 13 |
| ATS13_YGSQLAPETFYR | 136 | ATS13_2 | A disintegrin and metalloproteinase with thrombospondin motifs 13 |
| B2MG_VEHSDLSFSK | 14 | B2MG_1 | Beta-2-microglobulin |
| B2MG_VNHVTLSQPK | 6 | B2MG_2 | Beta-2-microglobulin |
| BGH3_LTLLAPLNSVFK | 73 | BGH3_1 | Transforming growth factor-beta-induced protein ig-h3 |
| C163A_INPASLDK | 75 | C163A_1 | Scavenger receptor cysteine-rich type 1 protein M130 |
| C1QA_DQPRPAFSAIR | 86 | C1QA_1 | Complement C1q subcomponent subunit A |

TABLE 28-continued

Analytes and corresponding abbreviations

| Analyte | SEQ ID NO: | Abbrev | Protein name |
|---|---|---|---|
| C1QA_SLGFCDTTNK | 87 | C1QA_2 | Complement C1q subcomponent subunit A |
| C1QB_IAFSATR | 137 | C1Q6_1 | Complement C1q subcomponent subunit B |
| C1QB_LEQGENVFLQATDK | 88 | C1Q6_2 | Complement C1q subcomponent subunit B |
| C1QB_VPGLYYFTYHASSR | 32 | C1Q6_3 | Complement C1q subcomponent subunit B |
| C1QC_FNAVLTNPQGDYDTSTGK | 89 | C1QC_1 | Complement C1q subcomponent subunit C |
| C1QC_TNQVNSGGVLLR | 90 | C1QC_2 | Complement C1q subcomponent subunit C |
| CADH5_YEIVVEAR | 97 | CADH5_1 | Cadherin-5 |
| CADH5_YTFVVPEDTR | 98 | CADH5_2 | Cadherin-5 |
| CAH1_GGPFSDSYR | 138 | CAH1_1 | Carbonic anhydrase 1 |
| CAMP_AIDGINQR | 93 | CAMP_1 | Cathelicidin antimicrobial peptide |
| CAMP_SSDANLYR | 139 | CAMP_2 | Cathelicidin antimicrobial peptide |
| CATD_VGFAEAAR | 1 | CATD_1 | Cathepsin D |
| CATD_VSTLPAITLK | 2 | CATD_2 | Cathepsin D |
| CBPN_EALIQFLEQVHQGIK | 55 | CBPN_1 | Carboxypeptidase N catalytic chain |
| CBPN_NNANGVDLNR | 42 | CBPN_2 | Carboxypeptidase N catalytic chain |
| CD14_LTVGAAQVPAQLLVGALR | 13 | CD14_1 | Monocyte differentiation antigen CD14 |
| CD14_SWLAELQQWLKPGLK | 8 | CD14_2 | Monocyte differentiation antigen CD14 |
| CFAB_YGLVTYATYPK | 23 | CFAB_1 | Complement factor B |
| CGB1_GVNPVVSYAVALSCQCALCR | 140 | CGB1_1 | Choriogonadotropin subunit beta variant 1 |
| CGB1_VLQGVLPALPQVVCNYR | 141 | CGB1_2 | Choriogonadotropin subunit beta variant 1 |
| CHL1_VIAVNEVGR | 66 | CHL1_1 | Neural cell adhesion molecule L1-like protein |
| CLUS_ASSIIDELFQDR | 34 | CLUS_1 | Clusterin |
| CLUS_LFDSDPITVTVPVEVSR | 56 | CLUS_2 | Clusterin |
| CNTN1_FIPLIPIPER | 99 | CNTN1_1 | Contactin-1 |
| CNTN1_TTKPYPADIVVQFK | 142 | CNTN1_2 | Contactin-1 |
| CO5_TLLPVSKPEIR | 17 | CO5_1 | Complement C5 |
| CO5_VFQFLEK | 10 | CO5_2 | Complement C5 |
| CO6_ALNHLPLEYNSALYSR | 37 | CO6_1 | Complement component C6 |
| CO8A_SLLQPNK | 31 | CO8A_1 | Complement component C8 alpha chain |
| CO8B_QALEEFQK | 28 | CO8B_1 | Complement component C8 beta chain |
| CRAC1_GVALADFNR | 143 | CRAC1_1 | Cartilage acidic protein 1 |
| CRAC1_GVASLFAGR | 144 | CRAC1_2 | Cartilage acidic protein 1 |
| CRAC1_LVNIAVDER | 145 | CRAC1_3 | Cartilage acidic protein 1 |
| CRIS3_AVSPPAR | 72 | CRIS3_1 | Cysteine-rich secretory protein 3 |
| CRIS3_YEDLYSNCK | 70 | CRIS3_2 | Cysteine-rich secretory protein 3 |
| CSH_AHQLAIDTYQEFEETYIPK | 33 | CSH_1 | Chorionic somatomammotropin hormone 1 |
| CSH_ISLLUESWLEPVR | 43 | CSH_2 | Chorionic somatomammotropin hormone 1 |

TABLE 28-continued

Analytes and corresponding abbreviations

| Analyte | SEQ ID NO: | Abbrev | Protein name |
|---|---|---|---|
| DEF1_IPACIAGER | 146 | DEF1_1 | Neutrophil defensin 1 |
| DEF1_YGTCIYQGR | 147 | DEF1_2 | Neutrophil defensin 1 |
| DPEP2_ALEVSQAPVIFSHSAAR | 101 | DPEP2_1 | Dipeptidase 2 |
| DPEP2_LTLEQIDLIR | 95 | DPEP2_2 | Dipeptidase 2 |
| ECM1_ELLALIQLER | 148 | ECM1_1 | Extracellular matrix protein 1 |
| ECM1_LLPAQLPAEK | 103 | ECM1_2 | Extracellular matrix protein 1 |
| EGLN_GPITSAAELNDPQSILLR | 118 | EGLN_1 | Endoglin |
| EGLN_TQILEWAAER | 149 | EGLN_2 | Endoglin |
| ENPP2_TEFLSNYLTNVDDITLVPGTLGR | 25 | ENPP2_1 | Ectonucleotide pyrophosphatase/phosphodiesterase family member 2 |
| ENPP2_TYLHTYESEI | 18 | ENPP2_2 | Ectonucleotide pyrophosphatase/phosphodiesterase family member 2 |
| F13B_GDTYPAELYITGSILR | 46 | F13B_1 | Coagulation factor XIII B chain |
| FA11_DSVTETLPR | 150 | FA11_1 | Coagulation factor XI |
| FA11_TAAISGYSFK | 151 | FA11_2 | Coagulation factor XI |
| FA5_AEVDDVIQVR | 152 | FA5_1 | Coagulation factor V |
| FA5_LSEGASYLDHTFPAEK | 153 | FA5_2 | Coagulation factor V |
| FA9_FGSGYVSGWGR | 112 | FA9_1 | Coagulation factor IX |
| FA9_SALVLQYLR | 113 | FA9_2 | Coagulation factor IX |
| FBLN1_TGYYFDGISR | 79 | FBLN1_1 | Fibulin-1 |
| FBLN3_IPSNPSHR | 47 | FBLN3_1 | EGF-containing fibulin-like extracellular matrix protein 1 |
| FETUA_FSVVYAK | 50 | FETUA_1 | Alpha-2-HS-glycoprotein |
| FETUA_HTLNQIDEVK | 51 | FETUA_2 | Alpha-2-HS-glycoprotein |
| FGFR1_IGPDNLPYVQILK | 154 | FGFR1_1 | Fibroblast growth factor receptor 1 |
| FGFR1_VYSDPQPHIQWLK | 155 | FGFR1_2 | Fibroblast growth factor receptor 1 |
| GELS_AQPVQVAEGSEPDGFWEALGGK | 107 | GELS_1 | Gelsolin |
| GELS_TASDFITK | 102 | GELS_2 | Gelsolin |
| GPX3_QEPGENSEILPTLK | 110 | GPX3_1 | Glutathione peroxidase 3 |
| GPX3_YVRPGGGFVPNFQLFEK | 156 | GPX3_2 | Glutathione peroxidase 3 |
| HABP2_FLNWIK | 48 | HABP2_1 | Hyaluronan-binding protein 2 |
| HEMO_NFPSPVDAAFR | 26 | HEMO_1 | Hemopexin |
| HLACI_WAAVVVPSGEEQR | 83 | HLACI_1 | HLA class I histocompatibility antigen, Cw-2 alpha chain |
| IBP1_VVESLAK | 81 | IBP1_1 | Insulin-like growth factor-binding protein 1 |
| IBP2_LIQGAPTIR | 35 | IBP2_1 | Insulin-like growth factor-binding protein 2 |
| IBP3_FLNVLSPR | 63 | IBP3_1 | Insulin-like growth factor-binding protein 3 |
| IBP3_YGQPLPGYTTK | 64 | IBP3_2 | Insulin-like growth factor-binding protein 3 |
| IBP4_Q.CHPALDGQR | 111 | IBP4_1 | Insulin-like growth factor-binding protein 4 |
| IBP4_QCHPALDGQR | 4 | IBP4_2 | Insulin-like growth factor-binding protein 4 |

TABLE 28-continued

Analytes and corresponding abbreviations

| Analyte | SEQ ID NO: | Abbrev | Protein name |
|---|---|---|---|
| IBP4_QCHPALDGQR.2 | 85 | IBP4_3 | Insulin-like growth factor-binding protein 4 |
| IBP6_GAQTLYVPNCDHR | 40 | IBP6_1 | Insulin-like growth factor-binding protein 6 |
| IBP6_HLDSVLQQLQTEVYR | 15 | IBP6_2 | Insulin-like growth factor-binding protein 6 |
| IGF1_GFYFNKPTGYGSSSR | 115 | IGF1_1 | Insulin-like growth factor I |
| IGF2_GIVEECCFR | 68 | IGF2_1 | Insulin-like growth factor II |
| IL1R1_LWFVPAK | 157 | IL1R1_1 | Interleukin-1 receptor type 1 |
| INHBC_LDFHFSSDR | 9 | INHBC_1 | Inhibin beta C chain |
| IPSP_AVVEVDESGTR | 158 | IPSP_1 | Plasma serine protease inhibitor |
| IPSP_DFTFDLYR | 159 | IPSP_2 | Plasma serine protease inhibitor |
| ISM2_FDTTPWILCK | 160 | ISM2_1 | Isthmin-2 |
| ISM2_TRPCGYGCTATETR | 125 | ISM2_2 | Isthmin-2 |
| ITIH3_ALDLSLK | 16 | ITIH3_1 | Inter-alpha-trypsin inhibitor heavy chain H3 |
| ITIH4_ILDDLSPR | 30 | ITIH4_1 | Inter-alpha-trypsin inhibitor heavy chain H4 |
| ITIH4_NPLVWVHASPEHVVVTR | 45 | ITIH4_2 | Inter-alpha-trypsin inhibitor heavy chain H4 |
| ITIH4_QLGLPGPPDVPDHAAYHPF | 82 | ITIH4_3 | Inter-alpha-trypsin inhibitor heavy chain H4 |
| KIT_LCLHCSVDQEGK | 161 | KIT_1 | Mast/stem cell growth factor receptor Kit |
| KIT_YVSELHLTR | 162 | KIT_2 | Mast/stem cell growth factor receptor Kit |
| KNG1_DIPTNSPELEETLTHTITK | 27 | KNG1_1 | Kininogen-1 |
| KNG1_QVVAGLNFR | 11 | KNG1_2 | Kininogen-1 |
| LBP_ITGFLKPGK | 12 | LBP_1 | Lipopolysaccharide-binding protein |
| LBP_ITLPDFTGDLR | 21 | LBP_2 | Lipopolysaccharide-binding protein |
| LEP_DLLHVLAFSK | 91 | LEP_1 | Leptin |
| LEP_VTGLDFIPGLHPILTLSK | 163 | LEP_2 | Leptin |
| LIRB5_KPSLLIPQGSVVAR | 164 | LIRB5_1 | Leukocyte immunoglobulin-like receptor subfamily B member 5 |
| LYAM1_SYYWIGIR | 65 | LYAM1_1 | L-selectin |
| MFAP5_LYSVHRPVK | 124 | MFAP5_1 | Microfibrillar-associated protein 5 |
| MUC18_EVTVPVFYPTEK | 122 | MUC18_1 | Cell surface glycoprotein MUC18 |
| MUC18_GATLALTQVTPQDER | 165 | MUC18_2 | Cell surface glycoprotein MUC18 |
| NOTUM_GLADSGWELDNK | 126 | NOTUM_1 | Palmitoleoyl-protein carboxylesterase NOTUM |
| NOTUM_LYIQNLGR | 166 | NOTUM_2 | Palmitoleoyl-protein carboxylesterase NOTUM |
| PAEP_HLWYLLDLK | 116 | PAEP_1 | Glycodelin |
| PAEP_VHITSLLPTPEDNLEIVLHR | 117 | PAEP_2 | Glycodelin |
| PAPP1_DIPHWLNPTR | 77 | PAPP1_1 | Pappalysin-1 |
| PAPP2_LLLRPEVLAEIPR | 127 | PAPP2_1 | Pappalysin-2 |
| PCD12_AHDADLGINGK | 94 | PCD12_1 | Protocadherin-12 |
| PCD12_YQVSEEVPSGTVIGK | 128 | PCD12_2 | Protocadherin-12 |
| PEDF_LQSLFDSPDFSK | 24 | PEDF_1 | Pigment epithelium-derived factor |

TABLE 28-continued

Analytes and corresponding abbreviations

| Analyte | SEQ ID NO: | Abbrev | Protein name |
|---|---|---|---|
| PEDF_TVQAVLTVPK | 44 | PEDF_2 | Pigment epithelium-derived factor |
| PGRP2_AGLLRPDYALLGHR | 69 | PGRP2_1 | N-acetylmuramoyl-L-alanine amidase |
| PRDX2_GLFIIDGK | 167 | PRDX2_1 | Peroxiredoxin-2 |
| PRG2_WNFAYWAAHQPWSR | 78 | PRG2_1 | Bone marrow proteoglycan |
| PRG4_GLPNVVTSAISLPNIR | 168 | PRG4_1 | Proteoglycan 4 |
| PRG4_ITEVWGIPSPIDTVFTR | 133 | PRG4_2 | Proteoglycan 4 |
| PRL_LSAYYNLLHCLR | 169 | PRL_1 | Prolactin |
| PRL_SWNEPLYHLVTEVR | 170 | PRL_2 | Prolactin |
| PROS_FSAEFDFR | 104 | PROS_1 | Vitamin K-dependent protein S |
| PROS_SQDILLSVENTVIYR | 171 | PROS_2 | Vitamin K-dependent protein S |
| PSG1_FQLPGQK | 80 | PSG1_1 | Pregnancy-specific beta-1-glycoprotein 1 |
| PSG11_LFIPQITPK | 57 | PSG11_1 | Pregnancy-specific beta-1-glycoprotein 11 |
| PSG2_IHPSYTNYR | 52 | PSG2_1 | Pregnancy-specific beta-1-glycoprotein 2 |
| PSG3_VSAPSGTGHLPGLNPL | 76 | PSG3_1 | Pregnancy-specific beta-1-glycoprotein 3 |
| PSG9_DVLLLVHNLPQNLPGYFWYK | 59 | PSG9_1 | Pregnancy-specific beta-1-glycoprotein 9 |
| PSG9_LFIPQITR | 58 | PSG9_2 | Pregnancy-specific beta-1-glycoprotein 9 |
| PTGDS_AQGFTEDTIVFLPQTDK | 92 | PTGDS_1 | Prostaglandin-H2 D-isomerase |
| PTGDS_GPGEDFR | 53 | PTGDS_2 | Prostaglandin-H2 D-isomerase |
| RET4_YWGVASFLQK | 172 | RET4_1 | Retinol-binding protein 4 |
| SEPP1_LVYHLGLPFSFLTFPYVEEAIK | 123 | SEPP1_1 | Selenoprotein P |
| SEPP1_VSLATVDK | 132 | SEPP1_2 | Selenoprotein P |
| SHBG_IALGGLLFPASNLR | 74 | SHBG_1 | Sex hormone-binding globulin |
| SHBG_IALGGLLFPASNLR.1 | 174 | SHBG_2 | Sex hormone-binding globulin |
| SHBG_IALGGLLFPASNLR.2 | 100 | SHBG_3 | Sex hormone-binding globulin |
| SOM2_CSH_NYGLLYCFR | 108 | SOM2_1 | Growth hormone variant |
| SOM2_CSH_SVEGSCGF | 109 | SOM2_2 | Growth hormone variant |
| SPRL1_VLTHSELAPLR | 62 | SPRL1_1 | SPARC-like protein 1 |
| SVEP1_LLSDFPVVPTATR | 105 | SVEP1_1 | Sushi, von Willebrand factor type A, EGF and pentraxin domain-containing protein 1 |
| TENX_LNWEAPPGAFDSFLLR | 61 | TENX_1 | Tenascin-X |
| TENX_LSQLSVTDVTTSSLR | 60 | TENX_2 | Tenascin-X |
| TETN_CFLAFTQTK | 131 | TETN_1 | Tetranectin |
| TETN_LDTLAQEVALLK | 106 | TETN_2 | Tetranectin |
| THBG_AVLHIGEK | 49 | THBG_1 | Thyroxine-binding globulin |
| THRB_ELLESYIDGR | 173 | THRB_1 | Prothrombin |
| TIE1_VSWSLPLVPGPLVGDGELLR | 71 | TIE1_1 | Tyrosine-protein kinase receptor Tie-1 |
| TIMP1_HLACLPR | 114 | TIMP1_1 | Metalloproteinase inhibitor 1 |

TABLE 28-continued

Analytes and corresponding abbreviations

| Analyte | SEQ ID NO: | Abbrev | Protein name |
|---|---|---|---|
| VGFR1_YLAVPTSK | 119 | VGFR1_1 | Vascular endothelial growth factor receptor 1 |
| VTDB_ELPEHTVK | 36 | VTDB_1 | Vitamin D-binding protein |
| VTNC_GQYCYELDEK | 7 | VTNC_1 | Vitronectin |
| VTNC_VDTVDPPYPR | 5 | VTNC_2 | Vitronectin |

What is claimed is:

1. A method of detecting a reversal value for a pair of isolated biomarkers in a biological sample collected from a pregnant human female, the method comprising:
   (a) obtaining the biological sample;
   (b) detecting the presence or amount of the pair of isolated biomarkers in said biological sample; and
   (c) measuring in said biological sample a reversal value for said pair of isolated biomarkers;
   wherein detecting comprises subjecting the sample to a proteomics work-flow comprised of mass spectrometry (MS) quantification,
   wherein the biological sample is selected from whole blood, plasma, and serum, and
   wherein the pair of isolated biomarkers is selected from the group consisting of
      (i) Disintegrin and metalloproteinase domain-containing protein 12 (ADA12) and Glycodelin (PAEP),
      (ii) PAEP and Prosteoglycan 4 (PRG4),
      (iii) Insulin-like growth factor-binding protein 4 (IBP4) and PAEP,
      (iv) Alpha-2-HS-glycoprotein (FETUA) and IBP4,
      (v) ADA12 and Cysteine-rich secretory protein 3 (CRIS3),
      (vi) Component 5 (CO5) and ADA12,
      (vii) Afamin (AFAM) and Alpha-1-antichymotrypsin (AACT),
      (viii) Insulin-like growth factor-binding protein complex acid labile subunit (ALS) and Protocadherin-12 (PCD12),
      (ix) Vitronectin (VTNC) and PCD12,
      (x) CRIS3 and Tetranectin (TETN),
      (xi) Beta-2-microglobulin (B2MG) and Fibroblast Growth Factor Receptor 1 (FGFR1),
      (xii) Gelsolin (GELS) and FGFR1, and
      (xiii) Leukocyte immunoglobulin-like receptor subfamily B member 5 (LIRB5) and Coagulation factor IX (FA9).

2. The method of claim 1, wherein the pregnant female is carrying a fetus that is between 18 0/7 weeks and 22 6/7 weeks of gestation at the time the biological sample is collected.

3. The method of claim 1, wherein the pregnant female is carrying a fetus that is between 23 0/7 weeks and 28 6/7 weeks of gestation at the time the biological sample is collected.

4. The method of claim 1, wherein said pregnant human female is nulliparous.

5. The method of claim 1, further comprising measuring AACT Alpha-1-antichymotripsin (ACCT).

6. The method of claim 1, wherein the biological sample is serum.

7. The method of claim 1, wherein said method further comprises subjecting the biological sample to an assay that utilizes a capture agent.

8. The method of claim 7, wherein said capture agent is selected from the group consisting of an antibody, antibody fragment, small molecule or variant thereof.

9. The method of claim 7, wherein said assay is selected from the group consisting of enzyme immunoassay (EIA), enzyme-linked immunosorbent assay (ELISA), and radio-immunoassay (MA).

10. The method of claim 1, wherein said MS is selected from the group consisting of matrix-assisted laser desorption/ionization time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)n (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS; APCI-(MS)n; ion mobility spectrometry (IMS); inductively coupled plasma mass spectrometry (ICP-MS) atmospheric pressure photoionization mass spectrometry (APPI-MS), APPI-MS/MS; and APPI-(MS)n.

11. The method of claim 1, wherein said MS comprises affinity-capture MS (AC-MS), co-immunoprecipitation-mass spectrometry (co-IP MS), liquid chromatography-mass spectrometry (LC-MS), multiple reaction monitoring (MRM) or selected reaction monitoring (SRM).

12. The method of claim 1, wherein:
   (a) the pair of isolated biomarkers comprising AACT comprises a peptide fragment comprising the amino acid sequence EIGELYLPK (SEQ ID NO:129);
   (b) the pair of isolated biomarkers comprising ADA12 comprises a peptide fragment comprising the amino acid sequence FGFGGSTDSGPIR (SEQ ID NO:84);
   (c) the pair of isolated biomarkers comprising AFAM comprises a peptide fragment comprising the amino acid sequence HFQNLGK (SEQ ID NO:39);
   (d) the pair of isolated biomarkers comprising ALS comprises a peptide fragment comprising the amino acid sequence IRPHTFTGLSGLR (SEQ ID NO:67);
   (e) the pair of isolated biomarkers comprising B2MG comprises a peptide fragment comprising the amino acid sequence VEHSDLSFSK (SEQ ID NO:14);

(f) the pair of isolated biomarkers comprising CO5 comprises a peptide fragment comprising the amino acid sequence TLLPVSKPEIR (SEQ ID NO:17);

(g) the pair of isolated biomarkers comprising CRIS3 comprises a peptide fragment comprising the amino acid sequence YEDLYSNCK (SEQ ID NO:70);

(h) the pair of isolated biomarkers comprising FA9 comprises a peptide fragment comprising the amino acid sequence SALVLQYLR (SEQ ID NO:113);

(i) the pair of isolated biomarkers comprising FETUA comprises a peptide fragment comprising the amino acid sequence FSVVYAK (SEQ ID NO:50);

(j) the pair of isolated biomarkers comprising FGFR1 comprises a peptide fragment comprising the amino acid sequence IGPDNLPYVQILK (SEQ ID NO:154);

(k) the pair of isolated biomarkers comprising GELS comprises a peptide fragment comprising the amino acid sequence TASDFITK (SEQ ID NO:102);

(l) the pair of isolated biomarkers comprising IBP4 comprises a peptide fragment comprising the amino acid sequence Q.CHPALDGQR (SEQ ID NO:111);

(m) the pair of isolated biomarkers comprising LIRB5 comprises a peptide fragment comprising the amino acid sequence KPSLLIPQGSVVAR (SEQ ID NO:164);

(n) the pair of isolated biomarkers comprising PAEP comprises a peptide fragment comprising the amino acid sequence HLWYLLDLK (SEQ ID NO:116);

(o) the pair of isolated biomarkers comprising PCD12 comprises a peptide fragment comprising the amino acid sequence AHDADLGINGK (SEQ ID NO:94);

(p) the pair of isolated biomarkers comprising PRG4 comprises a peptide fragment comprising the amino acid sequence GLPNVVTSAISLPNIR (SEQ ID NO:168);

(q) the pair of isolated biomarkers comprising TETN comprises a peptide fragment comprising the amino acid sequence LDTLAQEVALLK (SEQ ID NO:106); or (r) the pair of isolated biomarkers comprising VTNC comprises a peptide fragment comprising the amino acid sequence GQYCYELDEK (SEQ ID NO:7).

13. The method of claim 5, wherein measuring AACT comprises measuring a peptide fragment comprising the amino acid sequence EIGELYLPK (SEQ ID NO:129).

\* \* \* \* \*

SEQUENCE LISTING

<160> NUMBER OF SEQ ID NOS: 174

<210> SEQ ID NO 1
<211> LENGTH: 8
<212> TYPE: PRT
<213> ORGANISM: Homo sapiens

<400> SEQUENCE: 1

Val Gly Phe Ala Glu Ala Ala Arg
1               5

<210> SEQ ID NO 2
<211> LENGTH: 10
<212> TYPE: PRT
<213> ORGANISM: Homo sapiens

<400> SEQUENCE: 2

Val Ser Thr Leu Pro Ala Ile Thr Leu Lys
1               5                   10

<210> SEQ ID NO 3
<211> LENGTH: 11
<212> TYPE: PRT
<213> ORGANISM: Homo sapiens

<400> SEQUENCE: 3

Gly Trp Val Thr Asp Gly Phe Ser Ser Leu Lys
1               5                   10

<210> SEQ ID NO 4
<211> LENGTH: 10
<212> TYPE: PRT
<213> ORGANISM: Homo sapiens

<400> SEQUENCE: 4

Gln Cys His Pro Ala Leu Asp Gly Gln Arg
1               5                   10

<210> SEQ ID NO 5
<211> LENGTH: 10
<212> TYPE: PRT
<213> ORGANISM: Homo sapiens

<400> SEQUENCE: 5

Val Asp Thr Val Asp Pro Pro Tyr Pro Arg
1               5                   10

<210> SEQ ID NO 6

-continued

```
<211> LENGTH: 10
<212> TYPE: PRT
<213> ORGANISM: Homo sapiens

<400> SEQUENCE: 6

Val Asn His Val Thr Leu Ser Gln Pro Lys
1               5                   10

<210> SEQ ID NO 7
<211> LENGTH: 10
<212> TYPE: PRT
<213> ORGANISM: Homo sapiens

<400> SEQUENCE: 7

Gly Gln Tyr Cys Tyr Glu Leu Asp Glu Lys
1               5                   10

<210> SEQ ID NO 8
<211> LENGTH: 15
<212> TYPE: PRT
<213> ORGANISM: Homo sapiens

<400> SEQUENCE: 8

Ser Trp Leu Ala Glu Leu Gln Gln Trp Leu Lys Pro Gly Leu Lys
1               5                   10                  15

<210> SEQ ID NO 9
<211> LENGTH: 9
<212> TYPE: PRT
<213> ORGANISM: Homo sapiens

<400> SEQUENCE: 9

Leu Asp Phe His Phe Ser Ser Asp Arg
1               5

<210> SEQ ID NO 10
<211> LENGTH: 7
<212> TYPE: PRT
<213> ORGANISM: Homo sapiens

<400> SEQUENCE: 10

Val Phe Gln Phe Leu Glu Lys
1               5

<210> SEQ ID NO 11
<211> LENGTH: 9
<212> TYPE: PRT
<213> ORGANISM: Homo sapiens

<400> SEQUENCE: 11

Gln Val Val Ala Gly Leu Asn Phe Arg
1               5

<210> SEQ ID NO 12
<211> LENGTH: 9
<212> TYPE: PRT
<213> ORGANISM: Homo sapiens

<400> SEQUENCE: 12

Ile Thr Gly Phe Leu Lys Pro Gly Lys
1               5

<210> SEQ ID NO 13
<211> LENGTH: 18
<212> TYPE: PRT
```

<213> ORGANISM: Homo sapiens

<400> SEQUENCE: 13

Leu Thr Val Gly Ala Ala Gln Val Pro Ala Gln Leu Leu Val Gly Ala
1               5                   10                  15
Leu Arg

<210> SEQ ID NO 14
<211> LENGTH: 10
<212> TYPE: PRT
<213> ORGANISM: Homo sapiens

<400> SEQUENCE: 14

Val Glu His Ser Asp Leu Ser Phe Ser Lys
1               5                   10

<210> SEQ ID NO 15
<211> LENGTH: 15
<212> TYPE: PRT
<213> ORGANISM: Homo sapiens

<400> SEQUENCE: 15

His Leu Asp Ser Val Leu Gln Gln Leu Gln Thr Glu Val Tyr Arg
1               5                   10                  15

<210> SEQ ID NO 16
<211> LENGTH: 7
<212> TYPE: PRT
<213> ORGANISM: Homo sapiens

<400> SEQUENCE: 16

Ala Leu Asp Leu Ser Leu Lys
1               5

<210> SEQ ID NO 17
<211> LENGTH: 11
<212> TYPE: PRT
<213> ORGANISM: Homo sapiens

<400> SEQUENCE: 17

Thr Leu Leu Pro Val Ser Lys Pro Glu Ile Arg
1               5                   10

<210> SEQ ID NO 18
<211> LENGTH: 10
<212> TYPE: PRT
<213> ORGANISM: Homo sapiens

<400> SEQUENCE: 18

Thr Tyr Leu His Thr Tyr Glu Ser Glu Ile
1               5                   10

<210> SEQ ID NO 19
<211> LENGTH: 8
<212> TYPE: PRT
<213> ORGANISM: Homo sapiens

<400> SEQUENCE: 19

Ser Val Glu Gly Ser Cys Gly Phe
1               5

<210> SEQ ID NO 20
<211> LENGTH: 12
<212> TYPE: PRT

<213> ORGANISM: Homo sapiens

<400> SEQUENCE: 20

Asp Pro Thr Phe Ile Pro Ala Pro Ile Gln Ala Lys
1               5                   10

<210> SEQ ID NO 21
<211> LENGTH: 11
<212> TYPE: PRT
<213> ORGANISM: Homo sapiens

<400> SEQUENCE: 21

Ile Thr Leu Pro Asp Phe Thr Gly Asp Leu Arg
1               5                   10

<210> SEQ ID NO 22
<211> LENGTH: 9
<212> TYPE: PRT
<213> ORGANISM: Homo sapiens

<400> SEQUENCE: 22

Ala Thr Val Val Tyr Gln Gly Glu Arg
1               5

<210> SEQ ID NO 23
<211> LENGTH: 11
<212> TYPE: PRT
<213> ORGANISM: Homo sapiens

<400> SEQUENCE: 23

Tyr Gly Leu Val Thr Tyr Ala Thr Tyr Pro Lys
1               5                   10

<210> SEQ ID NO 24
<211> LENGTH: 12
<212> TYPE: PRT
<213> ORGANISM: Homo sapiens

<400> SEQUENCE: 24

Leu Gln Ser Leu Phe Asp Ser Pro Asp Phe Ser Lys
1               5                   10

<210> SEQ ID NO 25
<211> LENGTH: 23
<212> TYPE: PRT
<213> ORGANISM: Homo sapiens

<400> SEQUENCE: 25

Thr Glu Phe Leu Ser Asn Tyr Leu Thr Asn Val Asp Asp Ile Thr Leu
1               5                   10                  15

Val Pro Gly Thr Leu Gly Arg
            20

<210> SEQ ID NO 26
<211> LENGTH: 11
<212> TYPE: PRT
<213> ORGANISM: Homo sapiens

<400> SEQUENCE: 26

Asn Phe Pro Ser Pro Val Asp Ala Ala Phe Arg
1               5                   10

<210> SEQ ID NO 27
<211> LENGTH: 19

```
<212> TYPE: PRT
<213> ORGANISM: Homo sapiens

<400> SEQUENCE: 27

Asp Ile Pro Thr Asn Ser Pro Glu Leu Glu Glu Thr Leu Thr His Thr
1               5                   10                  15
Ile Thr Lys

<210> SEQ ID NO 28
<211> LENGTH: 8
<212> TYPE: PRT
<213> ORGANISM: Homo sapiens

<400> SEQUENCE: 28

Gln Ala Leu Glu Glu Phe Gln Lys
1               5

<210> SEQ ID NO 29
<211> LENGTH: 10
<212> TYPE: PRT
<213> ORGANISM: Homo sapiens

<400> SEQUENCE: 29

Asp Leu Leu Leu Pro Gln Pro Asp Leu Arg
1               5                   10

<210> SEQ ID NO 30
<211> LENGTH: 8
<212> TYPE: PRT
<213> ORGANISM: Homo sapiens

<400> SEQUENCE: 30

Ile Leu Asp Asp Leu Ser Pro Arg
1               5

<210> SEQ ID NO 31
<211> LENGTH: 7
<212> TYPE: PRT
<213> ORGANISM: Homo sapiens

<400> SEQUENCE: 31

Ser Leu Leu Gln Pro Asn Lys
1               5

<210> SEQ ID NO 32
<211> LENGTH: 14
<212> TYPE: PRT
<213> ORGANISM: Homo sapiens

<400> SEQUENCE: 32

Val Pro Gly Leu Tyr Tyr Phe Thr Tyr His Ala Ser Ser Arg
1               5                   10

<210> SEQ ID NO 33
<211> LENGTH: 19
<212> TYPE: PRT
<213> ORGANISM: Homo sapiens

<400> SEQUENCE: 33

Ala His Gln Leu Ala Ile Asp Thr Tyr Gln Glu Phe Glu Glu Thr Tyr
1               5                   10                  15
Ile Pro Lys
```

```
<210> SEQ ID NO 34
<211> LENGTH: 12
<212> TYPE: PRT
<213> ORGANISM: Homo sapiens

<400> SEQUENCE: 34

Ala Ser Ser Ile Ile Asp Glu Leu Phe Gln Asp Arg
1               5                   10

<210> SEQ ID NO 35
<211> LENGTH: 9
<212> TYPE: PRT
<213> ORGANISM: Homo sapiens

<400> SEQUENCE: 35

Leu Ile Gln Gly Ala Pro Thr Ile Arg
1               5

<210> SEQ ID NO 36
<211> LENGTH: 8
<212> TYPE: PRT
<213> ORGANISM: Homo sapiens

<400> SEQUENCE: 36

Glu Leu Pro Glu His Thr Val Lys
1               5

<210> SEQ ID NO 37
<211> LENGTH: 16
<212> TYPE: PRT
<213> ORGANISM: Homo sapiens

<400> SEQUENCE: 37

Ala Leu Asn His Leu Pro Leu Glu Tyr Asn Ser Ala Leu Tyr Ser Arg
1               5                   10                  15

<210> SEQ ID NO 38
<211> LENGTH: 9
<212> TYPE: PRT
<213> ORGANISM: Homo sapiens

<400> SEQUENCE: 38

Asn Tyr Gly Leu Leu Tyr Cys Phe Arg
1               5

<210> SEQ ID NO 39
<211> LENGTH: 7
<212> TYPE: PRT
<213> ORGANISM: Homo sapiens

<400> SEQUENCE: 39

His Phe Gln Asn Leu Gly Lys
1               5

<210> SEQ ID NO 40
<211> LENGTH: 13
<212> TYPE: PRT
<213> ORGANISM: Homo sapiens

<400> SEQUENCE: 40

Gly Ala Gln Thr Leu Tyr Val Pro Asn Cys Asp His Arg
1               5                   10

<210> SEQ ID NO 41
<211> LENGTH: 10
```

-continued

```
<212> TYPE: PRT
<213> ORGANISM: Homo sapiens

<400> SEQUENCE: 41

Asp Ala Asp Pro Asp Thr Phe Phe Ala Lys
1               5                   10

<210> SEQ ID NO 42
<211> LENGTH: 10
<212> TYPE: PRT
<213> ORGANISM: Homo sapiens

<400> SEQUENCE: 42

Asn Asn Ala Asn Gly Val Asp Leu Asn Arg
1               5                   10

<210> SEQ ID NO 43
<211> LENGTH: 14
<212> TYPE: PRT
<213> ORGANISM: Homo sapiens

<400> SEQUENCE: 43

Ile Ser Leu Leu Leu Ile Glu Ser Trp Leu Glu Pro Val Arg
1               5                   10

<210> SEQ ID NO 44
<211> LENGTH: 10
<212> TYPE: PRT
<213> ORGANISM: Homo sapiens

<400> SEQUENCE: 44

Thr Val Gln Ala Val Leu Thr Val Pro Lys
1               5                   10

<210> SEQ ID NO 45
<211> LENGTH: 17
<212> TYPE: PRT
<213> ORGANISM: Homo sapiens

<400> SEQUENCE: 45

Asn Pro Leu Val Trp Val His Ala Ser Pro Glu His Val Val Thr
1               5                   10                  15

Arg

<210> SEQ ID NO 46
<211> LENGTH: 16
<212> TYPE: PRT
<213> ORGANISM: Homo sapiens

<400> SEQUENCE: 46

Gly Asp Thr Tyr Pro Ala Glu Leu Tyr Ile Thr Gly Ser Ile Leu Arg
1               5                   10                  15

<210> SEQ ID NO 47
<211> LENGTH: 8
<212> TYPE: PRT
<213> ORGANISM: Homo sapiens

<400> SEQUENCE: 47

Ile Pro Ser Asn Pro Ser His Arg
1               5

<210> SEQ ID NO 48
<211> LENGTH: 6
```

<212> TYPE: PRT
<213> ORGANISM: Homo sapiens

<400> SEQUENCE: 48

Phe Leu Asn Trp Ile Lys
1               5

<210> SEQ ID NO 49
<211> LENGTH: 8
<212> TYPE: PRT
<213> ORGANISM: Homo sapiens

<400> SEQUENCE: 49

Ala Val Leu His Ile Gly Glu Lys
1               5

<210> SEQ ID NO 50
<211> LENGTH: 7
<212> TYPE: PRT
<213> ORGANISM: Homo sapiens

<400> SEQUENCE: 50

Phe Ser Val Val Tyr Ala Lys
1               5

<210> SEQ ID NO 51
<211> LENGTH: 10
<212> TYPE: PRT
<213> ORGANISM: Homo sapiens

<400> SEQUENCE: 51

His Thr Leu Asn Gln Ile Asp Glu Val Lys
1               5                   10

<210> SEQ ID NO 52
<211> LENGTH: 9
<212> TYPE: PRT
<213> ORGANISM: Homo sapiens

<400> SEQUENCE: 52

Ile His Pro Ser Tyr Thr Asn Tyr Arg
1               5

<210> SEQ ID NO 53
<211> LENGTH: 7
<212> TYPE: PRT
<213> ORGANISM: Homo sapiens

<400> SEQUENCE: 53

Gly Pro Gly Glu Asp Phe Arg
1               5

<210> SEQ ID NO 54
<211> LENGTH: 12
<212> TYPE: PRT
<213> ORGANISM: Homo sapiens

<400> SEQUENCE: 54

Gly Leu Gly Glu Ile Ser Ala Ala Ser Glu Phe Lys
1               5                   10

<210> SEQ ID NO 55
<211> LENGTH: 15
<212> TYPE: PRT
<213> ORGANISM: Homo sapiens

<400> SEQUENCE: 55

Glu Ala Leu Ile Gln Phe Leu Glu Gln Val His Gln Gly Ile Lys
1               5                   10                  15

<210> SEQ ID NO 56
<211> LENGTH: 17
<212> TYPE: PRT
<213> ORGANISM: Homo sapiens

<400> SEQUENCE: 56

Leu Phe Asp Ser Asp Pro Ile Thr Val Thr Val Pro Val Glu Val Ser
1               5                   10                  15

Arg

<210> SEQ ID NO 57
<211> LENGTH: 9
<212> TYPE: PRT
<213> ORGANISM: Homo sapiens

<400> SEQUENCE: 57

Leu Phe Ile Pro Gln Ile Thr Pro Lys
1               5

<210> SEQ ID NO 58
<211> LENGTH: 8
<212> TYPE: PRT
<213> ORGANISM: Homo sapiens

<400> SEQUENCE: 58

Leu Phe Ile Pro Gln Ile Thr Arg
1               5

<210> SEQ ID NO 59
<211> LENGTH: 20
<212> TYPE: PRT
<213> ORGANISM: Homo sapiens

<400> SEQUENCE: 59

Asp Val Leu Leu Leu Val His Asn Leu Pro Gln Asn Leu Pro Gly Tyr
1               5                   10                  15

Phe Trp Tyr Lys
            20

<210> SEQ ID NO 60
<211> LENGTH: 15
<212> TYPE: PRT
<213> ORGANISM: Homo sapiens

<400> SEQUENCE: 60

Leu Ser Gln Leu Ser Val Thr Asp Val Thr Thr Ser Ser Leu Arg
1               5                   10                  15

<210> SEQ ID NO 61
<211> LENGTH: 16
<212> TYPE: PRT
<213> ORGANISM: Homo sapiens

<400> SEQUENCE: 61

Leu Asn Trp Glu Ala Pro Pro Gly Ala Phe Asp Ser Phe Leu Leu Arg
1               5                   10                  15

<210> SEQ ID NO 62

-continued

```
<211> LENGTH: 11
<212> TYPE: PRT
<213> ORGANISM: Homo sapiens

<400> SEQUENCE: 62

Val Leu Thr His Ser Glu Leu Ala Pro Leu Arg
1               5                   10

<210> SEQ ID NO 63
<211> LENGTH: 8
<212> TYPE: PRT
<213> ORGANISM: Homo sapiens

<400> SEQUENCE: 63

Phe Leu Asn Val Leu Ser Pro Arg
1               5

<210> SEQ ID NO 64
<211> LENGTH: 11
<212> TYPE: PRT
<213> ORGANISM: Homo sapiens

<400> SEQUENCE: 64

Tyr Gly Gln Pro Leu Pro Gly Tyr Thr Thr Lys
1               5                   10

<210> SEQ ID NO 65
<211> LENGTH: 8
<212> TYPE: PRT
<213> ORGANISM: Homo sapiens

<400> SEQUENCE: 65

Ser Tyr Tyr Trp Ile Gly Ile Arg
1               5

<210> SEQ ID NO 66
<211> LENGTH: 9
<212> TYPE: PRT
<213> ORGANISM: Homo sapiens

<400> SEQUENCE: 66

Val Ile Ala Val Asn Glu Val Gly Arg
1               5

<210> SEQ ID NO 67
<211> LENGTH: 13
<212> TYPE: PRT
<213> ORGANISM: Homo sapiens

<400> SEQUENCE: 67

Ile Arg Pro His Thr Phe Thr Gly Leu Ser Gly Leu Arg
1               5                   10

<210> SEQ ID NO 68
<211> LENGTH: 9
<212> TYPE: PRT
<213> ORGANISM: Homo sapiens

<400> SEQUENCE: 68

Gly Ile Val Glu Glu Cys Cys Phe Arg
1               5

<210> SEQ ID NO 69
<211> LENGTH: 14
<212> TYPE: PRT
```

<213> ORGANISM: Homo sapiens

<400> SEQUENCE: 69

Ala Gly Leu Leu Arg Pro Asp Tyr Ala Leu Leu Gly His Arg
1               5                   10

<210> SEQ ID NO 70
<211> LENGTH: 9
<212> TYPE: PRT
<213> ORGANISM: Homo sapiens

<400> SEQUENCE: 70

Tyr Glu Asp Leu Tyr Ser Asn Cys Lys
1               5

<210> SEQ ID NO 71
<211> LENGTH: 20
<212> TYPE: PRT
<213> ORGANISM: Homo sapiens

<400> SEQUENCE: 71

Val Ser Trp Ser Leu Pro Leu Val Pro Gly Pro Leu Val Gly Asp Gly
1               5                   10                  15

Phe Leu Leu Arg
            20

<210> SEQ ID NO 72
<211> LENGTH: 7
<212> TYPE: PRT
<213> ORGANISM: Homo sapiens

<400> SEQUENCE: 72

Ala Val Ser Pro Pro Ala Arg
1               5

<210> SEQ ID NO 73
<211> LENGTH: 12
<212> TYPE: PRT
<213> ORGANISM: Homo sapiens

<400> SEQUENCE: 73

Leu Thr Leu Leu Ala Pro Leu Asn Ser Val Phe Lys
1               5                   10

<210> SEQ ID NO 74
<211> LENGTH: 14
<212> TYPE: PRT
<213> ORGANISM: Homo sapiens

<400> SEQUENCE: 74

Ile Ala Leu Gly Gly Leu Leu Phe Pro Ala Ser Asn Leu Arg
1               5                   10

<210> SEQ ID NO 75
<211> LENGTH: 8
<212> TYPE: PRT
<213> ORGANISM: Homo sapiens

<400> SEQUENCE: 75

Ile Asn Pro Ala Ser Leu Asp Lys
1               5

<210> SEQ ID NO 76
<211> LENGTH: 16

```
<212> TYPE: PRT
<213> ORGANISM: Homo sapiens

<400> SEQUENCE: 76

Val Ser Ala Pro Ser Gly Thr Gly His Leu Pro Gly Leu Asn Pro Leu
1               5                   10                  15

<210> SEQ ID NO 77
<211> LENGTH: 10
<212> TYPE: PRT
<213> ORGANISM: Homo sapiens

<400> SEQUENCE: 77

Asp Ile Pro His Trp Leu Asn Pro Thr Arg
1               5                   10

<210> SEQ ID NO 78
<211> LENGTH: 14
<212> TYPE: PRT
<213> ORGANISM: Homo sapiens

<400> SEQUENCE: 78

Trp Asn Phe Ala Tyr Trp Ala Ala His Gln Pro Trp Ser Arg
1               5                   10

<210> SEQ ID NO 79
<211> LENGTH: 10
<212> TYPE: PRT
<213> ORGANISM: Homo sapiens

<400> SEQUENCE: 79

Thr Gly Tyr Tyr Phe Asp Gly Ile Ser Arg
1               5                   10

<210> SEQ ID NO 80
<211> LENGTH: 7
<212> TYPE: PRT
<213> ORGANISM: Homo sapiens

<400> SEQUENCE: 80

Phe Gln Leu Pro Gly Gln Lys
1               5

<210> SEQ ID NO 81
<211> LENGTH: 7
<212> TYPE: PRT
<213> ORGANISM: Homo sapiens

<400> SEQUENCE: 81

Val Val Glu Ser Leu Ala Lys
1               5

<210> SEQ ID NO 82
<211> LENGTH: 19
<212> TYPE: PRT
<213> ORGANISM: Homo sapiens

<400> SEQUENCE: 82

Gln Leu Gly Leu Pro Gly Pro Pro Asp Val Pro Asp His Ala Ala Tyr
1               5                   10                  15

His Pro Phe

<210> SEQ ID NO 83
<211> LENGTH: 13
```

```
<212> TYPE: PRT
<213> ORGANISM: Homo sapiens

<400> SEQUENCE: 83

Trp Ala Ala Val Val Pro Ser Gly Glu Glu Gln Arg
1               5                   10

<210> SEQ ID NO 84
<211> LENGTH: 13
<212> TYPE: PRT
<213> ORGANISM: Homo sapiens

<400> SEQUENCE: 84

Phe Gly Phe Gly Gly Ser Thr Asp Ser Gly Pro Ile Arg
1               5                   10

<210> SEQ ID NO 85
<211> LENGTH: 10
<212> TYPE: PRT
<213> ORGANISM: Homo sapiens

<400> SEQUENCE: 85

Gln Cys His Pro Ala Leu Asp Gly Gln Arg
1               5                   10

<210> SEQ ID NO 86
<211> LENGTH: 11
<212> TYPE: PRT
<213> ORGANISM: Homo sapiens

<400> SEQUENCE: 86

Asp Gln Pro Arg Pro Ala Phe Ser Ala Ile Arg
1               5                   10

<210> SEQ ID NO 87
<211> LENGTH: 10
<212> TYPE: PRT
<213> ORGANISM: Homo sapiens

<400> SEQUENCE: 87

Ser Leu Gly Phe Cys Asp Thr Thr Asn Lys
1               5                   10

<210> SEQ ID NO 88
<211> LENGTH: 14
<212> TYPE: PRT
<213> ORGANISM: Homo sapiens

<400> SEQUENCE: 88

Leu Glu Gln Gly Glu Asn Val Phe Leu Gln Ala Thr Asp Lys
1               5                   10

<210> SEQ ID NO 89
<211> LENGTH: 18
<212> TYPE: PRT
<213> ORGANISM: Homo sapiens

<400> SEQUENCE: 89

Phe Asn Ala Val Leu Thr Asn Pro Gln Gly Asp Tyr Asp Thr Ser Thr
1               5                   10                  15

Gly Lys

<210> SEQ ID NO 90
<211> LENGTH: 12
```

<212> TYPE: PRT
<213> ORGANISM: Homo sapiens

<400> SEQUENCE: 90

Thr Asn Gln Val Asn Ser Gly Gly Val Leu Leu Arg
1               5                   10

<210> SEQ ID NO 91
<211> LENGTH: 10
<212> TYPE: PRT
<213> ORGANISM: Homo sapiens

<400> SEQUENCE: 91

Asp Leu Leu His Val Leu Ala Phe Ser Lys
1               5                   10

<210> SEQ ID NO 92
<211> LENGTH: 17
<212> TYPE: PRT
<213> ORGANISM: Homo sapiens

<400> SEQUENCE: 92

Ala Gln Gly Phe Thr Glu Asp Thr Ile Val Phe Leu Pro Gln Thr Asp
1               5                   10                  15

Lys

<210> SEQ ID NO 93
<211> LENGTH: 8
<212> TYPE: PRT
<213> ORGANISM: Homo sapiens

<400> SEQUENCE: 93

Ala Ile Asp Gly Ile Asn Gln Arg
1               5

<210> SEQ ID NO 94
<211> LENGTH: 11
<212> TYPE: PRT
<213> ORGANISM: Homo sapiens

<400> SEQUENCE: 94

Ala His Asp Ala Asp Leu Gly Ile Asn Gly Lys
1               5                   10

<210> SEQ ID NO 95
<211> LENGTH: 10
<212> TYPE: PRT
<213> ORGANISM: Homo sapiens

<400> SEQUENCE: 95

Leu Thr Leu Glu Gln Ile Asp Leu Ile Arg
1               5                   10

<210> SEQ ID NO 96
<211> LENGTH: 11
<212> TYPE: PRT
<213> ORGANISM: Homo sapiens

<400> SEQUENCE: 96

Thr Ser Asp Gln Ile His Phe Phe Phe Ala Lys
1               5                   10

<210> SEQ ID NO 97
<211> LENGTH: 8

-continued

```
<212> TYPE: PRT
<213> ORGANISM: Homo sapiens

<400> SEQUENCE: 97

Tyr Glu Ile Val Val Glu Ala Arg
1               5

<210> SEQ ID NO 98
<211> LENGTH: 10
<212> TYPE: PRT
<213> ORGANISM: Homo sapiens

<400> SEQUENCE: 98

Tyr Thr Phe Val Val Pro Glu Asp Thr Arg
1               5                   10

<210> SEQ ID NO 99
<211> LENGTH: 10
<212> TYPE: PRT
<213> ORGANISM: Homo sapiens

<400> SEQUENCE: 99

Phe Ile Pro Leu Ile Pro Ile Pro Glu Arg
1               5                   10

<210> SEQ ID NO 100
<211> LENGTH: 14
<212> TYPE: PRT
<213> ORGANISM: Homo sapiens

<400> SEQUENCE: 100

Ile Ala Leu Gly Gly Leu Leu Phe Pro Ala Ser Asn Leu Arg
1               5                   10

<210> SEQ ID NO 101
<211> LENGTH: 17
<212> TYPE: PRT
<213> ORGANISM: Homo sapiens

<400> SEQUENCE: 101

Ala Leu Glu Val Ser Gln Ala Pro Val Ile Phe Ser His Ser Ala Ala
1               5                   10                  15
Arg

<210> SEQ ID NO 102
<211> LENGTH: 8
<212> TYPE: PRT
<213> ORGANISM: Homo sapiens

<400> SEQUENCE: 102

Thr Ala Ser Asp Phe Ile Thr Lys
1               5

<210> SEQ ID NO 103
<211> LENGTH: 10
<212> TYPE: PRT
<213> ORGANISM: Homo sapiens

<400> SEQUENCE: 103

Leu Leu Pro Ala Gln Leu Pro Ala Glu Lys
1               5                   10

<210> SEQ ID NO 104
<211> LENGTH: 8
```

```
<212> TYPE: PRT
<213> ORGANISM: Homo sapiens

<400> SEQUENCE: 104

Phe Ser Ala Glu Phe Asp Phe Arg
1               5

<210> SEQ ID NO 105
<211> LENGTH: 13
<212> TYPE: PRT
<213> ORGANISM: Homo sapiens

<400> SEQUENCE: 105

Leu Leu Ser Asp Phe Pro Val Val Pro Thr Ala Thr Arg
1               5                   10

<210> SEQ ID NO 106
<211> LENGTH: 12
<212> TYPE: PRT
<213> ORGANISM: Homo sapiens

<400> SEQUENCE: 106

Leu Asp Thr Leu Ala Gln Glu Val Ala Leu Leu Lys
1               5                   10

<210> SEQ ID NO 107
<211> LENGTH: 22
<212> TYPE: PRT
<213> ORGANISM: Homo sapiens

<400> SEQUENCE: 107

Ala Gln Pro Val Gln Val Ala Glu Gly Ser Glu Pro Asp Gly Phe Trp
1               5                   10                  15

Glu Ala Leu Gly Gly Lys
            20

<210> SEQ ID NO 108
<211> LENGTH: 9
<212> TYPE: PRT
<213> ORGANISM: Homo sapiens

<400> SEQUENCE: 108

Asn Tyr Gly Leu Leu Tyr Cys Phe Arg
1               5

<210> SEQ ID NO 109
<211> LENGTH: 8
<212> TYPE: PRT
<213> ORGANISM: Homo sapiens

<400> SEQUENCE: 109

Ser Val Glu Gly Ser Cys Gly Phe
1               5

<210> SEQ ID NO 110
<211> LENGTH: 14
<212> TYPE: PRT
<213> ORGANISM: Homo sapiens

<400> SEQUENCE: 110

Gln Glu Pro Gly Glu Asn Ser Glu Ile Leu Pro Thr Leu Lys
1               5                   10

<210> SEQ ID NO 111
```

```
<211> LENGTH: 10
<212> TYPE: PRT
<213> ORGANISM: Homo sapiens

<400> SEQUENCE: 111

Gln Cys His Pro Ala Leu Asp Gly Gln Arg
1               5                   10

<210> SEQ ID NO 112
<211> LENGTH: 11
<212> TYPE: PRT
<213> ORGANISM: Homo sapiens

<400> SEQUENCE: 112

Phe Gly Ser Gly Tyr Val Ser Gly Trp Gly Arg
1               5                   10

<210> SEQ ID NO 113
<211> LENGTH: 9
<212> TYPE: PRT
<213> ORGANISM: Homo sapiens

<400> SEQUENCE: 113

Ser Ala Leu Val Leu Gln Tyr Leu Arg
1               5

<210> SEQ ID NO 114
<211> LENGTH: 7
<212> TYPE: PRT
<213> ORGANISM: Homo sapiens

<400> SEQUENCE: 114

His Leu Ala Cys Leu Pro Arg
1               5

<210> SEQ ID NO 115
<211> LENGTH: 15
<212> TYPE: PRT
<213> ORGANISM: Homo sapiens

<400> SEQUENCE: 115

Gly Phe Tyr Phe Asn Lys Pro Thr Gly Tyr Gly Ser Ser Ser Arg
1               5                   10                  15

<210> SEQ ID NO 116
<211> LENGTH: 9
<212> TYPE: PRT
<213> ORGANISM: Homo sapiens

<400> SEQUENCE: 116

His Leu Trp Tyr Leu Leu Asp Leu Lys
1               5

<210> SEQ ID NO 117
<211> LENGTH: 20
<212> TYPE: PRT
<213> ORGANISM: Homo sapiens

<400> SEQUENCE: 117

Val His Ile Thr Ser Leu Leu Pro Thr Pro Glu Asp Asn Leu Glu Ile
1               5                   10                  15

Val Leu His Arg
            20
```

```
<210> SEQ ID NO 118
<211> LENGTH: 18
<212> TYPE: PRT
<213> ORGANISM: Homo sapiens

<400> SEQUENCE: 118

Gly Pro Ile Thr Ser Ala Ala Glu Leu Asn Asp Pro Gln Ser Ile Leu
1               5                   10                  15

Leu Arg

<210> SEQ ID NO 119
<211> LENGTH: 8
<212> TYPE: PRT
<213> ORGANISM: Homo sapiens

<400> SEQUENCE: 119

Tyr Leu Ala Val Pro Thr Ser Lys
1               5

<210> SEQ ID NO 120
<211> LENGTH: 9
<212> TYPE: PRT
<213> ORGANISM: Homo sapiens

<400> SEQUENCE: 120

Ala Val His Ser Phe Leu Trp Ser Lys
1               5

<210> SEQ ID NO 121
<211> LENGTH: 9
<212> TYPE: PRT
<213> ORGANISM: Homo sapiens

<400> SEQUENCE: 121

Asp Asn Gly Pro Asn Tyr Val Gln Arg
1               5

<210> SEQ ID NO 122
<211> LENGTH: 12
<212> TYPE: PRT
<213> ORGANISM: Homo sapiens

<400> SEQUENCE: 122

Glu Val Thr Val Pro Val Phe Tyr Pro Thr Glu Lys
1               5                   10

<210> SEQ ID NO 123
<211> LENGTH: 22
<212> TYPE: PRT
<213> ORGANISM: Homo sapiens

<400> SEQUENCE: 123

Leu Val Tyr His Leu Gly Leu Pro Phe Ser Phe Leu Thr Phe Pro Tyr
1               5                   10                  15

Val Glu Glu Ala Ile Lys
            20

<210> SEQ ID NO 124
<211> LENGTH: 9
<212> TYPE: PRT
<213> ORGANISM: Homo sapiens
```

<400> SEQUENCE: 124

Leu Tyr Ser Val His Arg Pro Val Lys
1               5

<210> SEQ ID NO 125
<211> LENGTH: 14
<212> TYPE: PRT
<213> ORGANISM: Homo sapiens

<400> SEQUENCE: 125

Thr Arg Pro Cys Gly Tyr Gly Cys Thr Ala Thr Glu Thr Arg
1               5                   10

<210> SEQ ID NO 126
<211> LENGTH: 12
<212> TYPE: PRT
<213> ORGANISM: Homo sapiens

<400> SEQUENCE: 126

Gly Leu Ala Asp Ser Gly Trp Phe Leu Asp Asn Lys
1               5                   10

<210> SEQ ID NO 127
<211> LENGTH: 13
<212> TYPE: PRT
<213> ORGANISM: Homo sapiens

<400> SEQUENCE: 127

Leu Leu Leu Arg Pro Glu Val Leu Ala Glu Ile Pro Arg
1               5                   10

<210> SEQ ID NO 128
<211> LENGTH: 15
<212> TYPE: PRT
<213> ORGANISM: Homo sapiens

<400> SEQUENCE: 128

Tyr Gln Val Ser Glu Glu Val Pro Ser Gly Thr Val Ile Gly Lys
1               5                   10                  15

<210> SEQ ID NO 129
<211> LENGTH: 9
<212> TYPE: PRT
<213> ORGANISM: Homo sapiens

<400> SEQUENCE: 129

Glu Ile Gly Glu Leu Tyr Leu Pro Lys
1               5

<210> SEQ ID NO 130
<211> LENGTH: 8
<212> TYPE: PRT
<213> ORGANISM: Homo sapiens

<400> SEQUENCE: 130

Glu Thr Leu Leu Gln Asp Phe Arg
1               5

<210> SEQ ID NO 131
<211> LENGTH: 9
<212> TYPE: PRT
<213> ORGANISM: Homo sapiens

<400> SEQUENCE: 131

Cys Phe Leu Ala Phe Thr Gln Thr Lys
1               5

<210> SEQ ID NO 132
<211> LENGTH: 8
<212> TYPE: PRT
<213> ORGANISM: Homo sapiens

<400> SEQUENCE: 132

Val Ser Leu Ala Thr Val Asp Lys
1               5

<210> SEQ ID NO 133
<211> LENGTH: 17
<212> TYPE: PRT
<213> ORGANISM: Homo sapiens

<400> SEQUENCE: 133

Ile Thr Glu Val Trp Gly Ile Pro Ser Pro Ile Asp Thr Val Phe Thr
1               5                   10                  15

Arg

<210> SEQ ID NO 134
<211> LENGTH: 10
<212> TYPE: PRT
<213> ORGANISM: Homo sapiens

<400> SEQUENCE: 134

Ile Leu Trp Ile Pro Ala Gly Ala Leu Arg
1               5                   10

<210> SEQ ID NO 135
<211> LENGTH: 14
<212> TYPE: PRT
<213> ORGANISM: Homo sapiens

<400> SEQUENCE: 135

Ser Leu Val Glu Leu Thr Pro Ile Ala Ala Val His Gly Arg
1               5                   10

<210> SEQ ID NO 136
<211> LENGTH: 12
<212> TYPE: PRT
<213> ORGANISM: Homo sapiens

<400> SEQUENCE: 136

Tyr Gly Ser Gln Leu Ala Pro Glu Thr Phe Tyr Arg
1               5                   10

<210> SEQ ID NO 137
<211> LENGTH: 7
<212> TYPE: PRT
<213> ORGANISM: Homo sapiens

<400> SEQUENCE: 137

Ile Ala Phe Ser Ala Thr Arg
1               5

<210> SEQ ID NO 138
<211> LENGTH: 9
<212> TYPE: PRT
<213> ORGANISM: Homo sapiens

```
<400> SEQUENCE: 138

Gly Gly Pro Phe Ser Asp Ser Tyr Arg
1               5

<210> SEQ ID NO 139
<211> LENGTH: 8
<212> TYPE: PRT
<213> ORGANISM: Homo sapiens

<400> SEQUENCE: 139

Ser Ser Asp Ala Asn Leu Tyr Arg
1               5

<210> SEQ ID NO 140
<211> LENGTH: 20
<212> TYPE: PRT
<213> ORGANISM: Homo sapiens

<400> SEQUENCE: 140

Gly Val Asn Pro Val Val Ser Tyr Ala Val Ala Leu Ser Cys Gln Cys
1               5                   10                  15

Ala Leu Cys Arg
            20

<210> SEQ ID NO 141
<211> LENGTH: 17
<212> TYPE: PRT
<213> ORGANISM: Homo sapiens

<400> SEQUENCE: 141

Val Leu Gln Gly Val Leu Pro Ala Leu Pro Gln Val Val Cys Asn Tyr
1               5                   10                  15

Arg

<210> SEQ ID NO 142
<211> LENGTH: 14
<212> TYPE: PRT
<213> ORGANISM: Homo sapiens

<400> SEQUENCE: 142

Thr Thr Lys Pro Tyr Pro Ala Asp Ile Val Val Gln Phe Lys
1               5                   10

<210> SEQ ID NO 143
<211> LENGTH: 9
<212> TYPE: PRT
<213> ORGANISM: Homo sapiens

<400> SEQUENCE: 143

Gly Val Ala Leu Ala Asp Phe Asn Arg
1               5

<210> SEQ ID NO 144
<211> LENGTH: 9
<212> TYPE: PRT
<213> ORGANISM: Homo sapiens

<400> SEQUENCE: 144

Gly Val Ala Ser Leu Phe Ala Gly Arg
1               5

<210> SEQ ID NO 145
```

```
<211> LENGTH: 9
<212> TYPE: PRT
<213> ORGANISM: Homo sapiens

<400> SEQUENCE: 145

Leu Val Asn Ile Ala Val Asp Glu Arg
1               5

<210> SEQ ID NO 146
<211> LENGTH: 9
<212> TYPE: PRT
<213> ORGANISM: Homo sapiens

<400> SEQUENCE: 146

Ile Pro Ala Cys Ile Ala Gly Glu Arg
1               5

<210> SEQ ID NO 147
<211> LENGTH: 9
<212> TYPE: PRT
<213> ORGANISM: Homo sapiens

<400> SEQUENCE: 147

Tyr Gly Thr Cys Ile Tyr Gln Gly Arg
1               5

<210> SEQ ID NO 148
<211> LENGTH: 10
<212> TYPE: PRT
<213> ORGANISM: Homo sapiens

<400> SEQUENCE: 148

Glu Leu Leu Ala Leu Ile Gln Leu Glu Arg
1               5                   10

<210> SEQ ID NO 149
<211> LENGTH: 10
<212> TYPE: PRT
<213> ORGANISM: Homo sapiens

<400> SEQUENCE: 149

Thr Gln Ile Leu Glu Trp Ala Ala Glu Arg
1               5                   10

<210> SEQ ID NO 150
<211> LENGTH: 9
<212> TYPE: PRT
<213> ORGANISM: Homo sapiens

<400> SEQUENCE: 150

Asp Ser Val Thr Glu Thr Leu Pro Arg
1               5

<210> SEQ ID NO 151
<211> LENGTH: 10
<212> TYPE: PRT
<213> ORGANISM: Homo sapiens

<400> SEQUENCE: 151

Thr Ala Ala Ile Ser Gly Tyr Ser Phe Lys
1               5                   10

<210> SEQ ID NO 152
<211> LENGTH: 10
<212> TYPE: PRT
```

<213> ORGANISM: Homo sapiens

<400> SEQUENCE: 152

Ala Glu Val Asp Asp Val Ile Gln Val Arg
1               5                   10

<210> SEQ ID NO 153
<211> LENGTH: 16
<212> TYPE: PRT
<213> ORGANISM: Homo sapiens

<400> SEQUENCE: 153

Leu Ser Glu Gly Ala Ser Tyr Leu Asp His Thr Phe Pro Ala Glu Lys
1               5                   10                  15

<210> SEQ ID NO 154
<211> LENGTH: 13
<212> TYPE: PRT
<213> ORGANISM: Homo sapiens

<400> SEQUENCE: 154

Ile Gly Pro Asp Asn Leu Pro Tyr Val Gln Ile Leu Lys
1               5                   10

<210> SEQ ID NO 155
<211> LENGTH: 13
<212> TYPE: PRT
<213> ORGANISM: Homo sapiens

<400> SEQUENCE: 155

Val Tyr Ser Asp Pro Gln Pro His Ile Gln Trp Leu Lys
1               5                   10

<210> SEQ ID NO 156
<211> LENGTH: 17
<212> TYPE: PRT
<213> ORGANISM: Homo sapiens

<400> SEQUENCE: 156

Tyr Val Arg Pro Gly Gly Gly Phe Val Pro Asn Phe Gln Leu Phe Glu
1               5                   10                  15

Lys

<210> SEQ ID NO 157
<211> LENGTH: 7
<212> TYPE: PRT
<213> ORGANISM: Homo sapiens

<400> SEQUENCE: 157

Leu Trp Phe Val Pro Ala Lys
1               5

<210> SEQ ID NO 158
<211> LENGTH: 11
<212> TYPE: PRT
<213> ORGANISM: Homo sapiens

<400> SEQUENCE: 158

Ala Val Val Glu Val Asp Glu Ser Gly Thr Arg
1               5                   10

<210> SEQ ID NO 159
<211> LENGTH: 8
<212> TYPE: PRT

<213> ORGANISM: Homo sapiens

<400> SEQUENCE: 159

Asp Phe Thr Phe Asp Leu Tyr Arg
1               5

<210> SEQ ID NO 160
<211> LENGTH: 10
<212> TYPE: PRT
<213> ORGANISM: Homo sapiens

<400> SEQUENCE: 160

Phe Asp Thr Thr Pro Trp Ile Leu Cys Lys
1               5                   10

<210> SEQ ID NO 161
<211> LENGTH: 12
<212> TYPE: PRT
<213> ORGANISM: Homo sapiens

<400> SEQUENCE: 161

Leu Cys Leu His Cys Ser Val Asp Gln Glu Gly Lys
1               5                   10

<210> SEQ ID NO 162
<211> LENGTH: 9
<212> TYPE: PRT
<213> ORGANISM: Homo sapiens

<400> SEQUENCE: 162

Tyr Val Ser Glu Leu His Leu Thr Arg
1               5

<210> SEQ ID NO 163
<211> LENGTH: 18
<212> TYPE: PRT
<213> ORGANISM: Homo sapiens

<400> SEQUENCE: 163

Val Thr Gly Leu Asp Phe Ile Pro Gly Leu His Pro Ile Leu Thr Leu
1               5                   10                  15

Ser Lys

<210> SEQ ID NO 164
<211> LENGTH: 14
<212> TYPE: PRT
<213> ORGANISM: Homo sapiens

<400> SEQUENCE: 164

Lys Pro Ser Leu Leu Ile Pro Gln Gly Ser Val Val Ala Arg
1               5                   10

<210> SEQ ID NO 165
<211> LENGTH: 15
<212> TYPE: PRT
<213> ORGANISM: Homo sapiens

<400> SEQUENCE: 165

Gly Ala Thr Leu Ala Leu Thr Gln Val Thr Pro Gln Asp Glu Arg
1               5                   10                  15

<210> SEQ ID NO 166
<211> LENGTH: 8
<212> TYPE: PRT

<213> ORGANISM: Homo sapiens

<400> SEQUENCE: 166

Leu Tyr Ile Gln Asn Leu Gly Arg
1               5

<210> SEQ ID NO 167
<211> LENGTH: 8
<212> TYPE: PRT
<213> ORGANISM: Homo sapiens

<400> SEQUENCE: 167

Gly Leu Phe Ile Ile Asp Gly Lys
1               5

<210> SEQ ID NO 168
<211> LENGTH: 16
<212> TYPE: PRT
<213> ORGANISM: Homo sapiens

<400> SEQUENCE: 168

Gly Leu Pro Asn Val Val Thr Ser Ala Ile Ser Leu Pro Asn Ile Arg
1               5                   10                  15

<210> SEQ ID NO 169
<211> LENGTH: 12
<212> TYPE: PRT
<213> ORGANISM: Homo sapiens

<400> SEQUENCE: 169

Leu Ser Ala Tyr Tyr Asn Leu Leu His Cys Leu Arg
1               5                   10

<210> SEQ ID NO 170
<211> LENGTH: 14
<212> TYPE: PRT
<213> ORGANISM: Homo sapiens

<400> SEQUENCE: 170

Ser Trp Asn Glu Pro Leu Tyr His Leu Val Thr Glu Val Arg
1               5                   10

<210> SEQ ID NO 171
<211> LENGTH: 15
<212> TYPE: PRT
<213> ORGANISM: Homo sapiens

<400> SEQUENCE: 171

Ser Gln Asp Ile Leu Leu Ser Val Glu Asn Thr Val Ile Tyr Arg
1               5                   10                  15

<210> SEQ ID NO 172
<211> LENGTH: 10
<212> TYPE: PRT
<213> ORGANISM: Homo sapiens

<400> SEQUENCE: 172

Tyr Trp Gly Val Ala Ser Phe Leu Gln Lys
1               5                   10

<210> SEQ ID NO 173
<211> LENGTH: 10
<212> TYPE: PRT
<213> ORGANISM: Homo sapiens

```
<400> SEQUENCE: 173

Glu Leu Leu Glu Ser Tyr Ile Asp Gly Arg
1               5                   10

<210> SEQ ID NO 174
<211> LENGTH: 14
<212> TYPE: PRT
<213> ORGANISM: Homo sapiens

<400> SEQUENCE: 174

Ile Ala Leu Gly Gly Leu Leu Phe Pro Ala Ser Asn Leu Arg
1               5                   10
```